United States Patent [19]

Akama et al.

[11] Patent Number: 5,539,112
[45] Date of Patent: Jul. 23, 1996

[54] 5-AMINOFLAVONE DERIVATIVES

[75] Inventors: Tsutomu Akama, Shizuoka-ken; Shun-ichi Ikeda, Numazu; Yasushi Shida, Mishima; Masaji Kasai, Fujisawa; Hiroyuki Ishida, Shizuoka-ken; Uichiro Kimura, Fukuoka; Katsushige Gomi, Susono; Hiromitsu Saito, Kawasaki; Kimihisa Ueno, Shizuoka-ken, all of Japan

[73] Assignee: Kyowa Hakko Kogyo Co., Ltd., Tokyo, Japan

[21] Appl. No.: 464,093

[22] Filed: Jun. 5, 1995

Related U.S. Application Data

[63] Continuation-in-part of Ser. No. 288,301, Aug. 10, 1994, abandoned, which is a continuation-in-part of Ser. No. 206,264, Mar. 7, 1994, abandoned, which is a continuation of Ser. No. 14,696, Feb. 8, 1993, abandoned.

[30] Foreign Application Priority Data

Feb. 14, 1992 [JP] Japan .................... 4-028113
Aug. 11, 1993 [JP] Japan .................... 5-199310
Aug. 18, 1993 [JP] Japan .................... 5-204356
Feb. 6, 1995 [JP] Japan .................... 7-017741

[51] Int. Cl.$^6$ .................... C07D 311/30; C07D 413/12
[52] U.S. Cl. .................... 544/151; 544/376; 546/196; 548/311.4; 548/454; 548/525; 549/403
[58] Field of Search .................... 544/151; 548/311.4; 549/403

[56] References Cited

FOREIGN PATENT DOCUMENTS

| 0233105 | 8/1987 | European Pat. Off. |
| 0374789 | 6/1990 | European Pat. Off. |
| 0556720 | 8/1993 | European Pat. Off. |
| 138277 | 5/1990 | Japan . |
| 1461777 | 1/1977 | United Kingdom . |

OTHER PUBLICATIONS

Chemical Abstracts, vol. 113 (1990) 171775n.
Chemical Abstracts, vol. 41, 120 (1947) (Abstract of Iyer et al Proc. Ind. Acad. Sci., vol. 23A (1946) 278:82.).
Eiden et al., Arch. Pharm., vol. 322 (1989) 589:92.
Joshi et al., Ind. J. Chem., vol. 1 (1963) 477:9.
Patent Abstracts of Japan, vol. 14, No. 377 (Aug. 1990) (C-748).
Indian Journal of Chemistry, vol. 1, No. 11 (Nov. 1963) 477:79.
Chemical Abstracts, vol. 119, No. 1 (Jul. 1993).
Chemical Abstracts, vol. 115, No. 21 (Nov. 1995) 22831q.

*Primary Examiner*—Robert W. Ramsuer
*Attorney, Agent, or Firm*—Fitzpatrick Cella Harper & Scinto

[57] ABSTRACT

5-Aminoflavone derivatives represented by the formula (I):

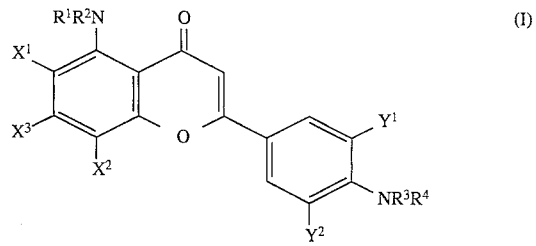

wherein $R^1$, $R^2$, $R^3$ and $R^4$ are the same or different and represent hydrogen, substituted or unsubstituted lower alkyl, lower alkenyl, halogen-substituted or unsubstituted lower alkanoyl or lower alkoxycarbonyl, $X^1$, $X^2$, $Y^1$ and $Y^2$ are the same or different and represent hydrogen, halogen or lower alkyl, at least one of $X^1$ and $X^2$ represents halogen or lower alkyl, $X^3$ represents hydrogen, substituted or unsubstituted lower alkyl, lower alkenyl, lower alkynyl, halogen, hydroxy, substituted or unsubstituted lower alkoxy, $NR^5R^6$ (wherein $R^5$ and $R^6$ are the same or different and represent hydrogen, or substituted or unsubstituted lower alkyl, or $R^5$ and $R^6$ are taken together to form a heterocyclic group containing the nitrogen atom in the ring), lower alkylthio, lower alkylsulfinyl, lower alkylsulfonyl, carboxy, lower alkoxycarbonyl, lower alkanoyl, adizo, cyano, substituted or unsubstituted carbamoyl or lower alkylthiothiocarbonyl: or pharmaceutically acceptable salts thereof.

19 Claims, No Drawings

5-AMINOFLAVONE DERIVATIVES

This application is a continuation-in-part application of application of Ser. No. 08/288,301 filed Aug. 10, 1994 now abandoned, which is a continuation-in-part application of application of Ser. No. 08/206,264 filed Mar. 7, 1994 now abandoned, which is a continuation application of Ser. No. 08/014,696 filed Feb. 8, 1993 now abandoned.

FIELD OF THE INVENTION

The present invention relates to novel 5-aminoflavone derivatives possessing antibacterial activity, anti-estrogenic activity and antitumor activity.

BACKGROUND OF THE INVENTION

As derivatives having an amino group at 5-position and a fluorine atom at 8-position of flavone (2-phenyl-4H-1-benzopyran-4-one), there are disclosed compounds possessing anti-cellular activity (Chem. Absts., 113, 171775n (1990)). However, the compounds do not have an amino group at 4'-position and no embodiments thereof are disclosed. As derivatives having amino groups at 5-position and 4'-position, there are disclosed compounds possessing anti-cellular activity (EP-A-374789). However, the compounds have no fluorine atom at 6-position and 8-position and have no substituents at 7-position.

As other derivatives having an amino group at 5-position, there are disclosed compounds having a hydroxyl group at 6-position (Chem. Abst., 41, 120f (1947)), compounds having an alkoxy group at 3-position with antiviral activity (EP-A-233105), compounds having anti-allergy activity and the like (GB-A-1461777) and compounds having a methyl group at 7-position [Arch. Pharm. (Weinheim), 322, 589 (1989)]. Further, there are disclosed derivatives having halogen atoms at 6- and/or 8-position and an amino group at 4'-position (Indian J. Chem., 1, 477 (1963)). However, anti-cellular activity of the above compounds is not known.

Further, anti-estrogenic activity is not known in the respective flavone derivatives described above.

OBJECTS OF THE INVENTION

The main object of the present invention is to provide novel 5-aminoflavone derivatives possessing antibacterial activity, anti-estrogenic activity and antitumor activity.

This object as well as other objects and advantages of the present invention will become apparent to those skilled in the art from the following description.

SUMMARY OF THE INVENTION

According to the present invention, there are provided 5-aminoflavone derivatives represented by the formula (I):

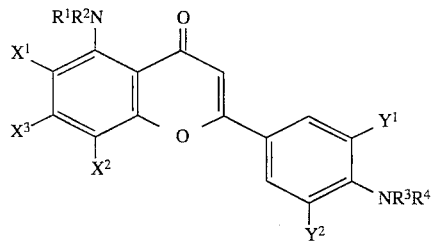

wherein $R^1$ $R^2$ $R^3$ and $R^4$ are the same or different and represent hydrogen, substituted or unsubstituted lower alkyl, lower alkenyl, halogen-substituted or unsubstituted lower alkanoyl or lower alkoxycarbonyl, $X^1$, $X^2$, $Y^1$ and $Y^2$ are the same or different and represent hydrogen, halogen or lower alkyl, at least one of $X^1$ and $X^2$ represents halogen or lower alkyl, $X^3$ represents hydrogen, substituted or unsubstituted lower alkyl, lower alkenyl, lower alkynyl, halogen, hydroxy, substituted or unsubstituted lower alkoxy, $NR^5R^6$ (wherein $R^5$ and $R^6$ are the same or different and represent hydrogen, substituted or unsubstituted lower alkyl, or $R^5$ and $R^6$ are taken together to form a heterocyclic group containing the nitrogen atom in the ring), lower alkylthio, lower alkylsulfinyl, lower alkylsulfonyl, carboxy, lower alkoxycarbonyl, lower alkanoyl, azido, cyano, substituted or unsubstituted carbamoyl or lower alkylthiothiocarbonyl (hereinafter referred to as compound (I); a compound having another number corresponds to the compound represented by the formula of the same number; compounds (IA), (IB), (Ia), (Ib) and the like mean to be included in compound (I)): or pharmaceutically acceptable salts thereof.

The 5-aminoflavone derivatives of the present invention have antibacterial activity, anti-estrogenic activity and antitumor activity.

DETAILED DESCRIPTION OF THE INVENTION

In the definition of the respective groups in the formula (I), examples of the lower alkyl are straight or branched alkyls having 1 to 8 carbon atoms, for example, methyl, ethyl, propyl, isopropyl, butyl, isobutyl, sec-butyl, tert-butyl, pentyl, isopentyl, neopentyl, hexyl, isohexyl, heptyl, isoheptyl, octyl and the like. Examples of the lower alkenyl are straight or branched alkenyls having 2 to 6 carbon atoms, for example, vinyl, allyl, methacryl, crotyl, 3-butenyl, pentenyl, hexenyl and the like. Examples of the lower alkynyl are alkynyls having 2 to 6 carbon atoms, for example, ethynyl, propynyl, butynyl, pentynyl, hexynyl and the like. Halogen represents fluorine, chlorine, bromine and iodine. Examples of the heterocyclic group are pyrrolidinyl, piperidyl, piperidino, morpholinyl, morpholino, substituted or unsubstituted piperazinyl and the like. The substituted piperazinyl has the same or different 1 to 2 substituents, for example, lower alkyl and the like. The lower alkyl is the same as defined above. Examples of the lower alkanoyl are straight or branched alkanoyls having 1 to 7 carbon atoms, for example, formyl, acetyl, propionyl, butanoyl, pentanoyl, pivaloyl, hexanoyl, heptanoyl and the like. The alkyl moiety of the lower alkoxy, lower alkylthio, lower alkylsulfinyl, lower alkylsulfonyl, lower alkoxycarbonyl and lower alkylthiothiocarbonyl is the same as defined for the above lower alkyl. The substituted lower alkyl and substituted lower alkoxy have the same or different 1 to 3 substituents, for example, halogen, hydroxy, substituted or unsubstituted lower alkoxy, substituted or unsubstituted lower alkanoyloxy, substituted or unsubstituted lower alkoxycarbonyloxy, $R^9R^{10}NCO_2$ (wherein $R^9$ and $R^{10}$ are the same as defined for the above $R^5$ and $R^6$), hydroxysulfonyloxy, $NR^{11}R^{12}$ (wherein $R^{11}$ and $R^{12}$ are the same as defined for the above $R^5$ and $R^6$) and the like. Examples of the substituents in the substituted lower alkoxy, substituted lower alkanoyloxy and substituted lower alkoxycarbonyloxy are halogen, hydroxy, lower alkoxy, lower alkoxycarbonyl, lower alkanoyloxy, lower alkenyl, $NR^{13}R^{14}$ (wherein $R^{13}$ and $R^{14}$ are the same as defined for the above $R^5$ and $R^6$) and the like [Halogen, the alkyl moiety of the lower alkoxy and the lower alkoxycarbonyl, the alkanoyl moiety of the lower alkanoyloxy, and the lower alkenyl are the same as defined above]. Halogen, the alkyl moiety of the lower alkoxy and the lower alkoxycarbonyloxy, and the alkanoyl moiety of the lower alkanoyloxy are the same as defined above. Examples of the halogen-substituted lower alkanoyl are lower alkanoyls having the same or different 1 to 6 substituents independently selected from the members of the above-defined halogen, for example, trifluoroacetyl and the like. The substituted carbamoyl has the same or different 1 to 2 substituents, for example, lower alkyl and the like. The lower alkyl is the same as defined above.

As pharmaceutically acceptable salts of compound (I), there are pharmaceutically acceptable acid or base addition salts, for example, inorganic acid salts such as hydrochloride, hydrobromide, sulfate, phosphate and the like and organic acid salts such as methanesulfonate, oxalate, acetate, malonate, succinate, fumarate, maleate, tartrate, citrate and the like as well as base addition salts such as sodium salt, potassium salt and the like.

Then, a process for producing compound (I) is explained below.

In addition, in the process described below, when the defined groups may be changed under the process conditions or are not suitable for the process, such the inconvenience can be avoided by a method usually used in organic synthetic chemistry, for example, protection and deprotection of functional groups and the like.

Preparation 1

Compound (Ia) which is compound (I) wherein $X^1$ and/or $X^2$ are hydrogen, chlorine, bromine or iodine can be prepared according to the following Scheme.

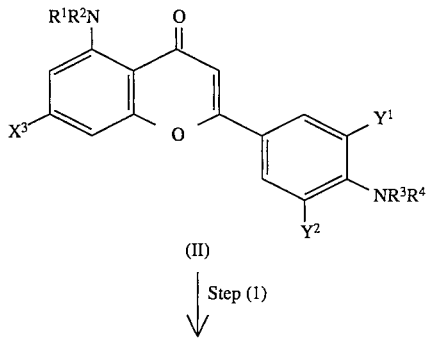

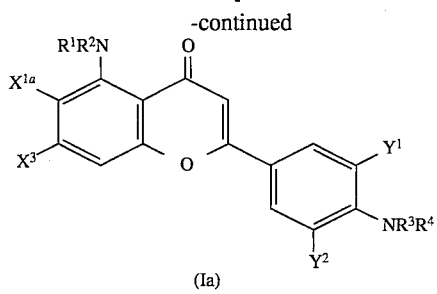

wherein $X^{1a}$ and $X^{2a}$ represent hydrogen, chlorine, bromine or iodine provided that $X^{1a}$ and $X^{2a}$ are not concurrently hydrogen, and $R^1$, $R^2$, $R^3$, $R^4$, $X^3$, $Y^1$ and $Y^2$ are the same as defined above.

Step (1)

Compound (Ia) is prepared by reacting compound (II) obtained by the known method (EP-A-384789) or modified method thereof with a halogenating agent such as chlorine, bromine, iodine, N-chlorosuccinimide, N-bromosuccinimide, N-iodosuccinimide and the like in acetic acid or dioxane. The reaction is carried out at room temperature to the boiling point of the solvent. The reaction completes in 1 to 20 hours.

Preparation 2

Compound (Ib) which is compound (I) wherein $X^1$ and/or $X^2$ are fluorine and $X^3$ is hydrogen can be prepared according to the following Scheme.

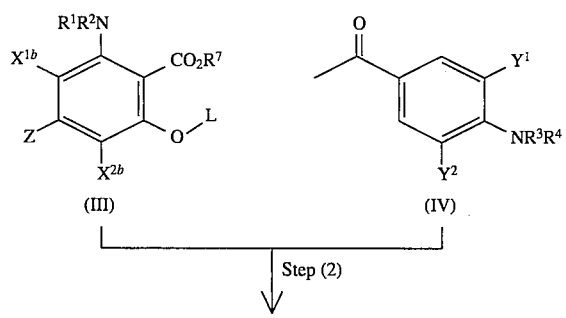

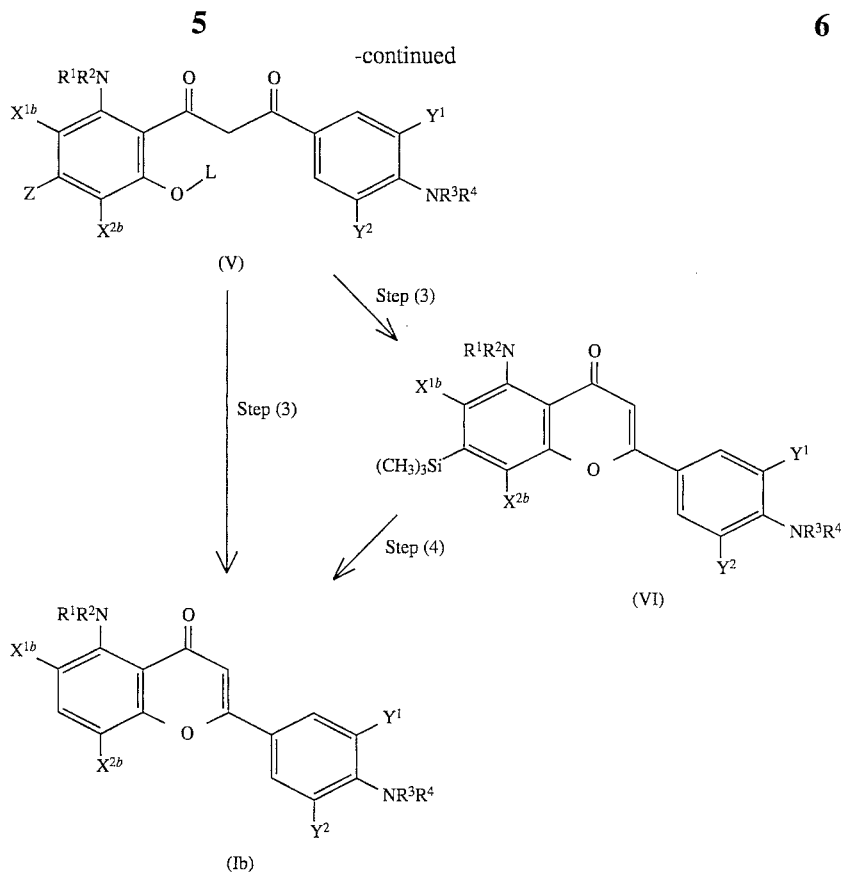

wherein $X^{1b}$ and $X^{2b}$ represent hydrogen or fluorine provided that $X^{1b}$ and $X^{2b}$ are not concurrently hydrogen, $R^7$ represents lower alkyl, Z represents hydrogen or trimethylsilyl, L represents a protecting group for hydroxy, and $R^1$, $R^2$, $R^3$, $R^4$, $Y^1$ and $Y^2$ are the same as defined above.

Lower alkyl is the same as defined for the above alkyl, and examples of L are tetrahydropyranyl, methoxymethyl and the like.

Step (2)

Compound (V) can be obtained by condensing compound (III) prepared by Reference Examples 1 to 5 with compound (IV) in the presence of 1 to 3 equivalents of a base in an inert solvent. As bases, sodium hydride, potassium hydride, sodium methoxide, sodium ethoxide, potassium tert-butoxide and the like are used. As suitable inert solvents, ethers such as tetrahydrofuran, dioxane and the like, alcohols such as methanol, ethanol and the like, toluene and dimethylformamide and the like are used. They can be used sole or in combination with each other. The reaction is normally carried out under warming, preferably at 40° C. to the boiling point of the solvent employed. The reaction normally completes in 1 to 12 hours.

Step (3)

When Z in compound (III) is hydrogen, compound (Ib) can be obtained by treating compound (V) prepared in Step (2) with hydrochloric acid or sulfuric acid at a concentration of 0.1 to 2N in a lower alcohol such as methanol, ethanol and the like, ether such as dioxane, tetrahydrofuran and the like or acetic acid at 0° to 50° C. for 5 to 12 hours to carry out deprotection and cyclization at the same time.

Step (4)

When Z in compound (III) is trimethylsilyl, compound (Ib) can be obtained by treating compound (VI) prepared by the same procedures as those in the above Step (3) with 1 to 2 equivalents of tetrabutylammonium fluoride in tetrahydrofuran at 0° C. to room temperature for 0.5 to 12 hours to carry out desilylation.

Preparation 3

Compound (Ic) which is compound (I) wherein $R^1$, $R^2$, $R^3$ and $R^4$ are hydrogen and $X^1$ and $X^2$ are fluorine can be prepared by the following Scheme.

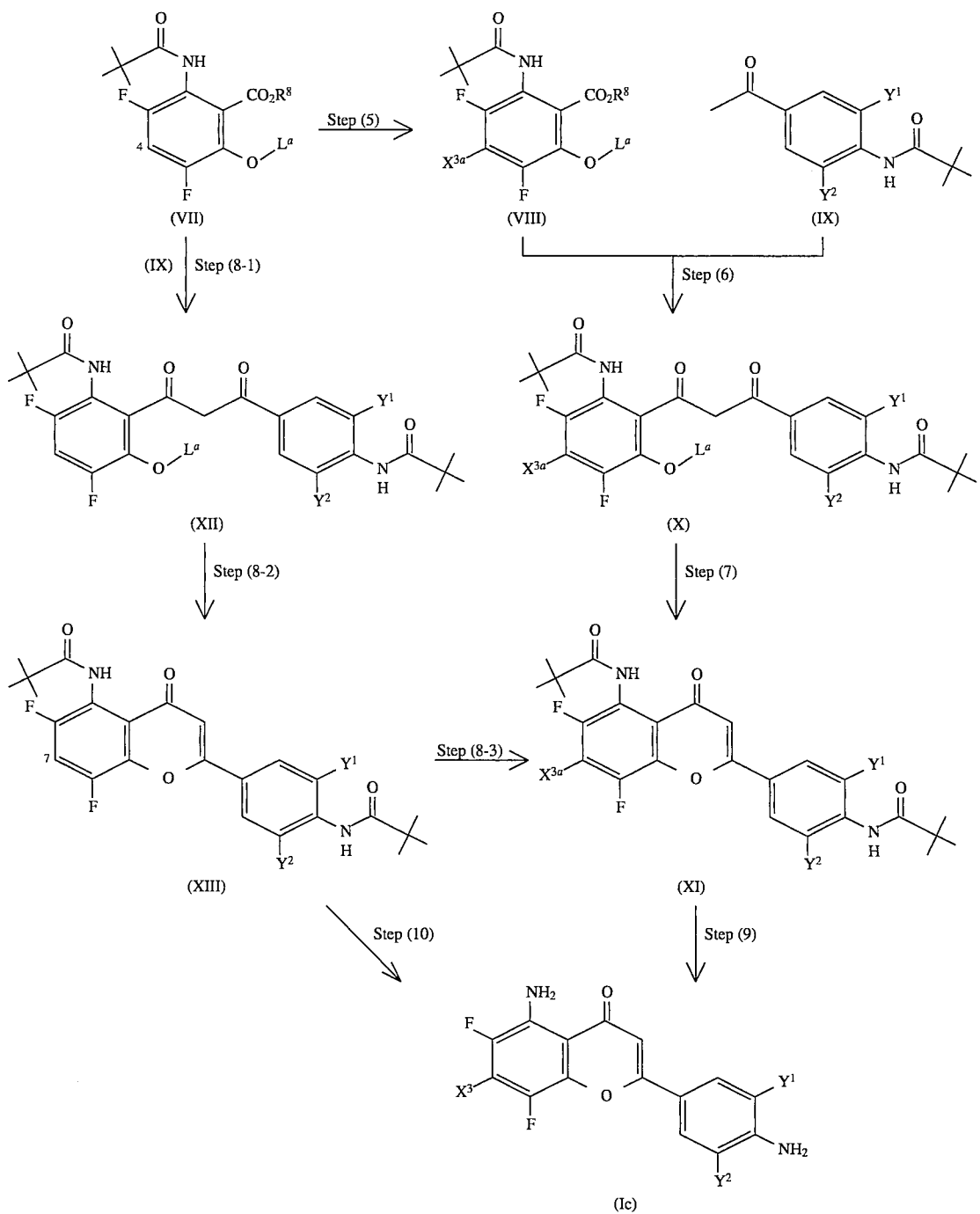

wherein $R^8$ represents lower alkyl, $L^a$ represents a protecting group for hydroxy, $X^{3a}$ represents the other groups than hydrogen, as defined for $X^3$, and $X^3$, $Y^1$ and $Y^2$ are the same as defined above.

The lower alkyl is the same as defined above. Examples of $L^a$ are tetrahydropyranyl, methoxymethyl and the like.

Step (5)

Compound (VIII) is prepared by lithiating 4-position of compound (VII) obtained according to the method described in Reference Example 4 or modified method thereof, then reacting the lithiated compound with 1 to 10 equivalents of an electrophile. Examples of a base used in the lithiation are lithium diisopropylamide, sec-butyllithium, tert-butyllithium and the like. Examples of a solvent used in the lithiation are tetrahydrofuran, ether, dimethoxyethane and the like. Examples of the electrophile are alkyl halides such as iodomethane, iodoethane, bromoethane, 1-iodobutane, 1-iodohexane and the like, N-chlorosuccinimide, N-bromosuccinimide, dialkyl disulfides such as dimethyl disulfide and the like, 1,2-dibromoethane, bromine, trimethoxyborane, carbon dioxide, carbon disulfide, ethyl chloroformate, p-toluenesulfonyl adize, p-toluenesulfonyl cyanide, aldehydes such as acetaldehyde and the like, dimethylformamide and the like. The reaction is carried out by lithiation at $-78°$ to 0° C., preferably at −60° C. or below for 0.5 to 3 hours, adding an electrophile and, if necessary, allowing to raise the temperature between 0° C. and room temperature. The reaction completes in 0.1 to 1 hours. When trimethoxyborane is used as an electrophile, a hydroxyl group can be introduced by later treatment with acetic acid and hydrogen peroxide. When dimethylformamide is used as an electrophile, a formyl group is introduced. This formyl group can be converted to a hydroxymethyl group using a reducing agent such as sodium borohydride and the like in methanol or ethanol. When a hydroxyl group is present as a substituent (hydroxyl group, hydroxymethyl group and the like), the hydroxyl group is desirably used in the next step after it is protected with a protecting group stable under the basic conditions, for example, tetrahydropyranyl group, trialkylsilyl group and the like according to the conventional method. When carbon disulfide is used as an electrophile, iodomethane is added thereto to give a dithiocarbonic acid ester which can be converted to a trifluoromethyl group according to the method described in the literature [Chem. Lett., 827 (1992)].

Step (6)

Compound (X) is prepared by condensing compound (VIII) with compound (IX) obtained by the method described in Reference Examples 6 to 9 in the presence of 3 to 5 equivalents of a base in an inert solvent. Examples of the base are sodium hydride, potassium hydride, sodium methoxide, sodium ethoxide, potassium tert-butoxide and the like. As the suitable inert solvent, ethers such as tetrahydrofuran, dioxane and the like, alcohols such as methanol, ethanol and the like, toluene, dimethylformamide and the like are used sole or in combination with each other. The reaction is carried out normally at an elevated temperature, preferably at 40° C. to the boiling point of the solvent employed. The reaction completes in 1 to 12 hours.

Step (7)

Compound (XI) is prepared by treating compound (X) with 1 to 6 N hydrochloric acid or sulfuric acid in a solvent such as an alcohol, for example, methanol, ethanol and the like, an ether, for example, dioxane, tetrahydrofuran and the like, or acetic acid at 0° to 50° C. for 0.5 to 12 hours to deprotect a protecting group $L^a$ and cyclize the deprotected compound.

Step (8)

Alternatively, compound (XI) is prepared by the following method. Compound (XII) is prepared starting from compound (VII) and compound (IX) according to Step (6). According to Step (7), compound (XII) is converted into compound (XIII) which is finally subjected to Step (5) to give compound (XI). When compound (XII) has the low solubility in the solvent, hexamethylphosphoric triamide and the like can be added to aid the dissolution.

Step (9)

Compound (Ica) which is compound (Ic) wherein $X^3$ is any other group than hydrogen, as defined for $X^3$ is prepared by depivaloylation by reacting compound (XI) with an acid such as hydrochloric acid, hydrobromic acid, sulfuric acid and the like in, if necessary, a lower alcohol such as methanol, ethanol and the like, an ether such as dioxane, tetrahydrofuran and the like, or acetic acid at room temperature to 100° C. or at the boiling point of the solvent employed for 0.1 to 10 hours.

Step (10)

Compound (Icb) which is compound (Ic) wherein $X^3$ is hydrogen can be obtained by depivaloylating compound (XIII) under the same conditions as those in Step (9).

At this stage, a part of compounds (XI) obtained in Step (7) or Step (8) may be modified at the substituent $X^{3a}$ and thereafter subjected to Step (9) to give a new derivative (Ic).

For example, compound (XIa) which is compound (XI) wherein $X^{3a}$ is an amino group is prepared by reacting compound (XIb) which is compound (XI) wherein $X^{3a}$ is azido with 1 to 10 equivalents of triphenylphosphine in an inert solvent such as tetrahydrofuran, ethyl acetate, acetonitrile and the like at 0° C. to the boiling point of the solvent for 1 to 12 hours, and then adding dilute hydrochloric acid thereto to react them at room temperature for 1 to 12 hours, or reacting compound (XIb) with 1 to 10 equivalents of sodium borohydride and water in a lower alcohol such as methanol, ethanol and the like.

Compound (XIc) which is compound (XI) wherein $X^{3a}$ is dialkylamino is prepared by reacting compound (XIa) and an equivalent amount to an excess amount of alkyl halide such as iodomethane, iodoethane, bromoethane, chloroethane and the like in the presence of an excess amount of a base in an inert solvent. Examples of the base are sodium hydride, potassium hydride, sodium carbonate, potassium carbonate and the like. Examples of the inert solvent are dimethylformamide, dimethyl sulfoxide, tetrahydrofuran, diethyl ether, dioxane, acetone and the like.

Compound (XId) which is compound (XI) wherein $X^{3a}$ is monoalkyl (acetyl) amino is prepared by reacting an amino group of compound (XIa) with acetic anhydride in pyridine, if necessary, in the presence of a catalytic amount of N,N-dimethylaminopyridine to give an acetamide which is alkylated under the same conditions as those for obtaining compound (XIc). An acetyl group is hydrolyzed in the next Step (9).

Compound (XIe) which is compound (XI) wherein $X^{3a}$ is a cyclic amino group such as piperazinyl and the like is prepared by reacting compound (XIf) which is compound (XI) wherein $X^{3a}$ is bromine with an excess amount of corresponding cyclic amine in an inert solvent such as dimethyl sulfoxide, dimethylformamide and the like at room temperature to the boiling point of the solvent employed, preferably at 80° to 120° C., for 1 to 24 hours.

Compound (XIg) which is compound (XI) wherein $X^{3a}$ is substituted or unsubstituted lower alkoxy is prepared by alkylating compound (XIh) which is compound (XI) wherein $X^{3a}$ is hydroxy under the same conditions as those for obtaining compound (XIc).

Compound (XIi) which is compound (XI) wherein $X^{3a}$ is lower alkylsulfinyl or lower alkylsulfonyl is prepared by treating compound (XIj) which is compound (XI) wherein $X^{3a}$ is lower alkylthio with an equivalent amount to an excess amount of an oxidizing agent in an inert solvent. As the inert solvent, a halogenated solvent such as dichloromethane, 1,2-dichloroethane and the like are preferably used. As the oxidizing agent, m-chloroperbenzoic acid is preferably used. The reaction is carried out at 0° C. to room temperature and completes in 0.5 to 12 hours.

Compound (XIk) which is compound (XI) wherein $X^{3a}$ is lower alkanoyl is prepared by treating compound (XIm) which is compound (XI) wherein $X^{3a}$ is corresponding 1-hydroxyalkyl with an equivalent amount to an excess amount of an oxidizing agent in an inert solvent. As the inert solvent, an aromatic hydrocarbon such as toluene, benzene and the like, a halogenated solvent such as dichloromethane, 1,2-dichloroethane and the like are used. As the oxidizing agent, manganese dioxide is preferably used. The reaction is carried out at room temperature to the boiling point of the solvent employed and completes in 0.5 to 24 hours.

Compound (XIn) which is compound (XI) wherein $X^{3a}$ is lower alkynyl is prepared by reacting compound (XIf) with an acetylene derivative. For example, compound (XIn) wherein X is ethynyl is prepared by coupling compound (XIf) with trimethylsilylacetylene in the presence of a base in an inert solvent using 0.01 to 0.3 equivalents of a palladium catalyst. As the inert solvent, dimethylformamide, toluene and the like are used. As the base, triethylamine, diethylamine and the like are used. In some cases, the base is also used as the solvent. Examples of the palladium catalyst are palladium catalysts having a ligand such as triphenylphosphine and the like. If necessary, palladium catalysts are used after ligand exchange in the reaction system. The reaction is carried out at room temperature to the boiling point of the solvent employed and completes in 0.5 to 24 hours.

Compound (XIo) which is compound (XI) wherein $X^{3a}$ is substituted or unsubstituted aminoalkyl is prepared by converting a hydroxyl group of compound (XIp) which is compound (XI) wherein $X^{3a}$ is hydroxyalkyl to leaving group, followed by substitution with various amines. For example, compound (XIp) is first reacted with 1 to 10 equivalents of methanesulfonyl chloride or p-toluenesulfonyl chloride in the presence of a base in an inert solvent to give a corresponding sulfonate or chlorinated compound. As the inert solvent, dimethylformamide, dichloromethane and the like are used. As the base, triethylamine, pyridine and the like are used. In some cases, the base is also used as the solvent. The reaction is carried out at 0° C. to room temperature and completes in 0.1 to 2 hours. The resulting sulfonate or chlorinated compound may be reacted with various amines in an inert solvent, if necessary, in the presence of a base to give compound (XIo). As the inert solvent, dimethylformamide, dimethyl sulfoxide, dichloromethane and the like are used. As the base, triethylamine, potassium carbonate, sodium carbonate and the like are used. The amine may be used at an equivalent amount to a largely excess amount, if necessary, in the form of a solution or salt. The reaction is carried out at 0° C. to the boiling point of the solvent employed, preferably at 0° C., to room temperature and completes in 0.1 to 24 hours.

Compound (XIq) which is compound (XI) wherein $X^{3a}$ is lower alkoxyalkyl is prepared by reacting a sulfonate or chlorinated compound of the above compound (XIp) with a lower alcohol which is also used as a solvent, such as methanol, ethanol and the like. The reaction is carried out at room temperature to the boiling point of the solvent, preferably at 50° to 100° C., and completes in 1 to 48 hours.

Compound (XIr) which is compound (XI) wherein $X^{3a}$ is substituted lower alkoxyalkyl is prepared by reacting a sulfonate or chlorinated compound of the above compound (XIp) with a sodium salt of a substituted lower alcohol in an inert solvent. As the inert solvent, dimethylformamide, dimethyl sulfoxide and the like are used. The reaction is carried out at 0° C. to room temperature, and completes in 0.5 to 12 hours.

A part of the resulting compound (Ic) may be used as a synthetic intermediate to give a new derivative (Ic).

Compound (Icaa) which is compound (Ic) wherein $X^3$ is carboxy is prepared by treating compound (Icab) which is compound (Ic) wherein $X^3$ is alkoxycarbonyl with an aqueous alkali solution in a solvent. As the solvent, inert water-miscible solvents, for example, a lower alcohol such as methanol, ethanol and the like, dioxane, tetrahydrofuran and the like are used sole or in combination with each other. An example of the aqueous alkali solution is a 1 to 10N aqueous solution of sodium hydroxide, potassium hydroxide or the like. The reaction is carried out at 0° C. to the boiling point of the solvent employed, preferably at 40° to 60° C., and completes in 0.5 to 12 hours.

Compound (Icac) which is compound (Ic) wherein $X^3$ is carbamoyl is prepared by reacting compound (Icab) with ammonia in a lower alcohol such as methanol, ethanol and the like. The reaction is carried out at room temperature or, if necessary, under heating in a sealed tube and completes in 1 to 7 days.

Compound (Icad) which is compound (Ic) wherein $X^3$ is cyano is prepared by dehydrating compound (Icac) with phosphorus oxychloride, thionyl chloride or the like, if necessary, in an inert solvent at 0° C. to the boiling point of the solvent employed, preferably at room temperature. Examples of the inert solvent are dimethylformamide, dichloromethane, pyridine and the like.

Compound (Icae) which is compound (Ic) wherein $X^3$ is substituted or unsubstituted lower alkanoyloxyalkyl is prepared by heating compound (Icaf) which is compound (Ic) wherein $X^3$ is hydroxyalkyl in a solvent of a lower fatty acid corresponding to a substituted or unsubstituted lower alkanoyl moiety in the presence of concentrated sulfuric acid. Concentrated sulfuric acid is preferably used at a concentration of 1 to 18N in a solvent. The reaction is carried out at room temperature to the boiling point of the solvent employed, preferably at 50° to 100° C., and completes in 0.1 to 10 hours. Alternatively, compound (XIp) having a protected group may be used as a starting compound. In this case, depivaloylation and esterification proceed simultaneously under the same conditions to give compound (Icae).

Compound (Icag) which is compound (Ic) wherein $X^3$ is hydroxysulfonyloxyalkyl is prepared by treating compound (Icaf) with concentrated sulfuric acid at 50° to 100° C. for 0.1 to 10 hours. Compound (XIp) having a protected group may be used as a starting compound as described above. In this case, depivaloylation and esterification proceed simultaneously under the same conditions to give compound (Icag).

Compound (Icah) which is compound (Ic) wherein $X^3$ is formyl is prepared by treating compound (Icaf-1) which is compound (Icaf) wherein $X^3$ is hydroxymethyl with 10 to 50 equivalents of an oxidizing agent in an inert solvent. Examples of the inert solvent are an aromatic hydrocarbon such as toluene, benzene and the like, halogenated solvent such as dichloromethane, 1,2-dichloroethane and the like, and ethyl acetate and the like. As the oxidizing agent, manganese dioxide is preferably used. The reaction is carried out at room temperature to the boiling point of the solvent employed, preferably at the boiling point of the solvent, and completes in 1 to 48 hours.

Compound (Icaj) which is compound (Ic) wherein $X^3$ is substituted or unsubstituted lower alkoxycarbonyloxyalkyl is prepared by reacting compound (Icaf) with 1 to 5 equivalents of a compound represented by $(R^{15}OCO)_2O$ (wherein $R^{15}$ represents substituted or unsubstituted lower alkyl. The substituted or unsubstituted lower alkyl is the same as defined above) in a solvent, if necessary, in the presence of 0.1 to 1 equivalent of dimethylaminopyridine. As the solvent, pyridine and the like are used. The reaction is carried out at 0° C. to room temperature, and completes in 1 to 10 hours.
Preparation 4
Compounds (Id) to (If) which fall in compound (I) wherein $R^1$ and/or $R^2$ is substituted or unsubstituted lower alkyl, $R^3$ and $R^4$ are hydrogen and $X^1$ and $X^2$ are fluorine are prepared using compound (Ic) as a starting compound according to the following Scheme.
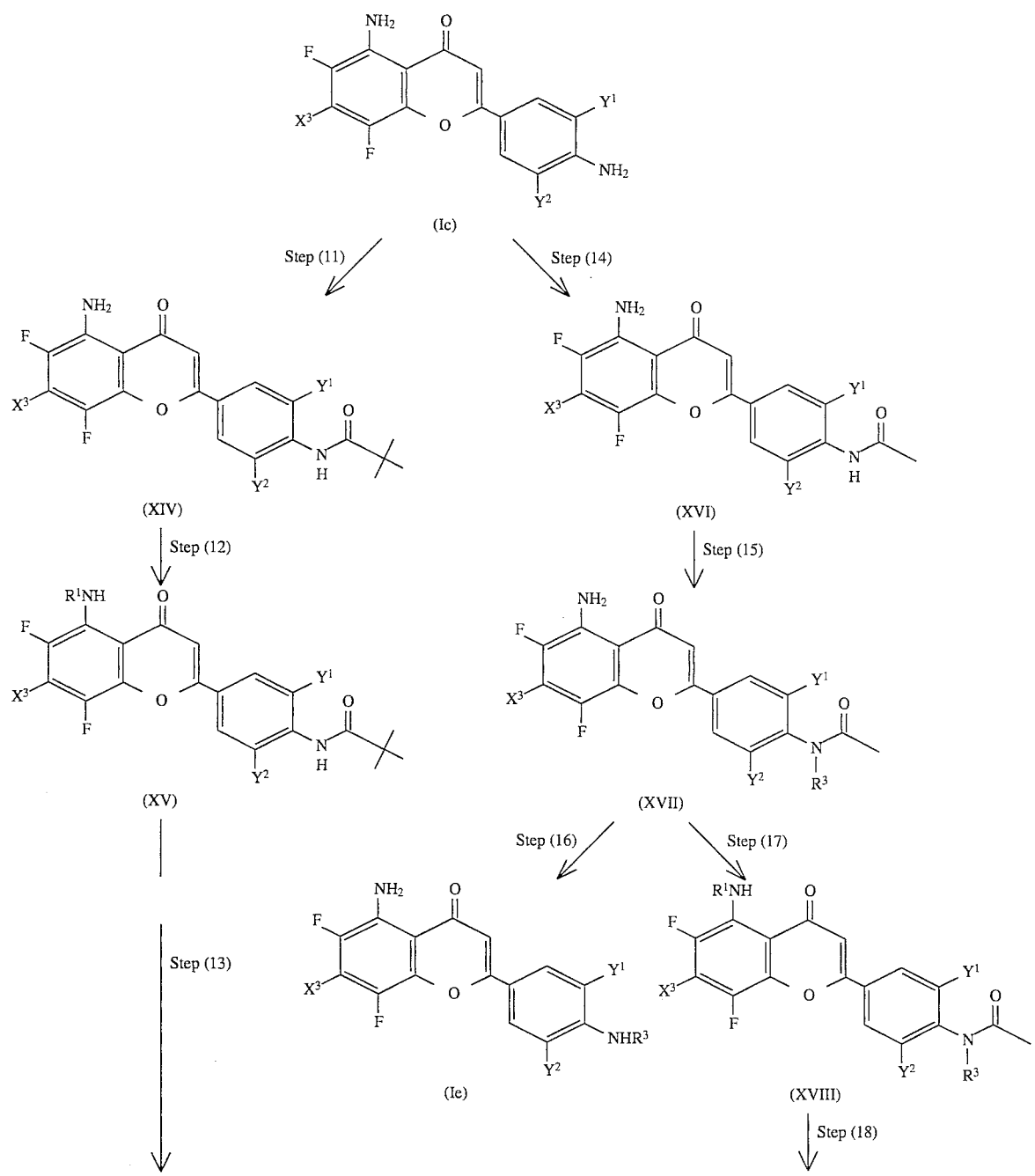

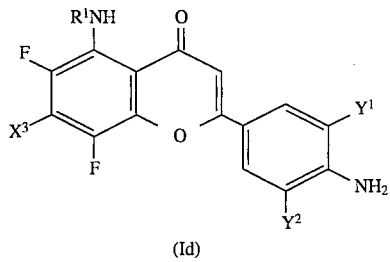

(Id)

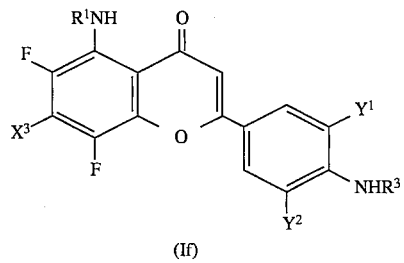

(If)

wherein $R^1$, $R^3$, $X^3$, $Y^1$ and $Y^2$ are the same as defined above.

Preparation of compound (Id) which is compound (I) wherein $R^1$ is substituted or unsubstituted lower alkyl and $R^3$ is hydrogen:

Step (11)

Compound (XIV) is prepared by reacting compound (Ic) with an equivalent amount to a slightly excess amount of pivaloyl chloride in an inert solvent in the presence of a base. Examples of the inert solvent are dichloromethane, 1,2-dichloroethane, dimethylformamide, tetrahydrofuran and the like. As the base, pyridine, triethylamine, diisopropylethylamine and the like are used. In some cases, the base is used also as the solvent. The reaction is carried out at 0° C. to room temperature and completes n 0.1 to 12 hours.

Step (12)

Compound (XV) is prepared by reacting compound (XIV) with 1 to 10 equivalents of an alkyl halide such as iodomethane, iodoethane, bromoethane, chloroethane, 1-iodopropane, 1-iodobutane, 1-iodopentane, 1-iodohexane, 1-iodoheptane and the like in an inert solvent in the presence of an equivalent amount to an excess amount of a base. As the base, sodium hydride, potassium hydride, sodium carbonate, potassium carbonate and the like are used. As the inert solvent, dimethylformamide, dimethyl sulfoxide, tetrahydro,utah, dioxane and the like are used. The reaction is carried out at 0° C. to the boiling point of the solvent employed and completes in 1 to 12 hours.

Step (13)

Compound (Id) is prepared by depivaloylating compound (XV) under the same conditions as those in Step (9).

Preparation of compound (Ie) which is compound (I) wherein $R^1$ is hydrogen and $R^3$ is substituted or unsubstituted lower alkyl:

Step (14)

Compound (XVI) is prepared by reacting compound (Ic) with an equivalent amount to a slightly excess amount of an acetylating agent in an inert solvent in the presence of a base. As the acetylating agent, acetic anhydride, acetyl chloride and the like are preferably used. As the inert solvent, dichloromethane, 1,2-dichloroethane, dimethylformamide, tetrahydrofuran, methanol, ethanol and the like are used. As the base, pyridine, triethylamine, diisopropylethylamine and the like are used. In some cases, the base is used also as a solvent. The reaction is carried out at 0° to 50° C. and completes in 1 to 48 hours.

Step (15)

Compound (XVII) is prepared by reacting compound (XVI) with 1 to 10 equivalents of an alkyl halide such as iodomethane, iodoethane, bromoethane, chloroethane, 1-iodopropane, 1-iodobutane, 1-iodopentane, 1-iodohexane, 1-iodoheptane and the like in an inert solvent in the presence of an equivalent amount to a slightly excess amount of a base. As the base, sodium hydride, potassium hydride, sodium carbonate, potassium carbonate and the like are used. As the inert solvent, dimethylformamide, dimethyl sulfoxide, tetrahydrofuran, dioxane and the like are used. The reaction is carried out at 0° C. to the boiling point of the solvent employed and completes in 1 to 12 hours.

Step (16)

Compound (Ie) is prepared by deacetylating compound (XvII) under the same conditions as those in Step (9).

Preparation of compound (If) which is compound (I) wherein $R^1$ and $R^3$ are substituted or unsubstituted lower alkyl:

Step (17)

Compound (XVIII) is prepared by alkylating compound (XVII) under the same conditions as those in Step (12).

Step (18)

Compound (If) is prepared by deacetylating compound (XVIII) under the same conditions as those in Step (9).

Preparation 5

Compound ((Icai) which is compound (Ic) wherein $R^1$, $R^2$, $R^3$ and $R^4$ are hydrogen and $X^1$, $X^2$ and $X^3$ are fluorine is prepared according to the following Scheme.

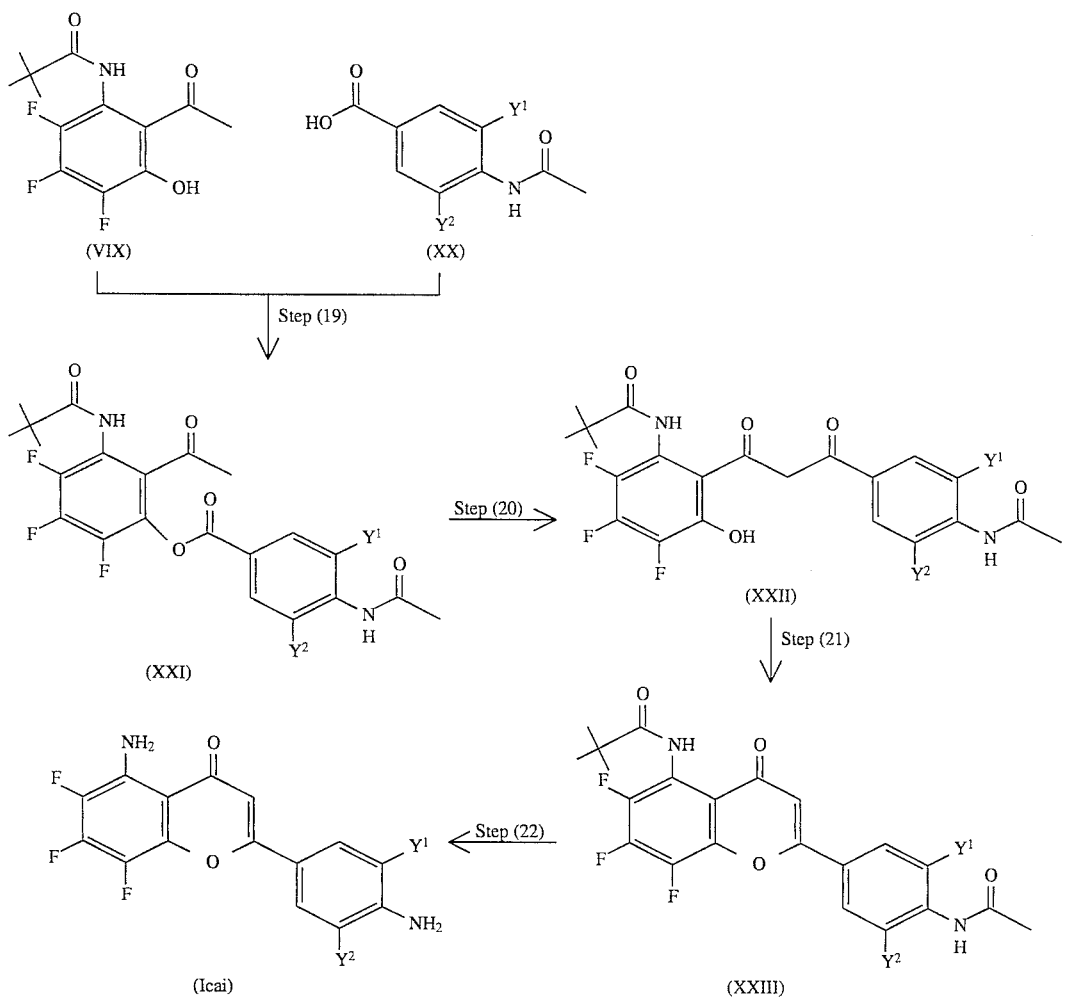

wherein $Y^1$ and $Y^2$ are the same as defined above.

Step (19)

Compound (XXI) is prepared by condensing compound (XIX) obtained by the method described in Reference Example 11 with 1 to 5 equivalents of a reactive derivative, for example, an acid chloride or acid anhydride of compound (XX) obtaied by the method described in Reference Example 12 in an inert solvent in the presence of 1 to 5 equivalents of a base, or by reacting compound (XIX) with 1 to 5 equivalents of compound (XX) in an inert solvent in the presence of a suitable condensing agent. As the base, sodium hydride, potassium hydride, triethylamine, pyridine and the like are used. As the inert solvent, tetrahydrofuran, dioxane, dimethylformamide, dichloromethane, pyridine and the like are used sole or in combination with each other. As the condensing agent, trifluoroacetic anhydride, dicyclohexylcarbodiimide, 2-chloro-1-methylpyridinium iodide and the like are used. The reaction is carried out normally at 0° to 30° C. and completes in 0.5 to 10 hours.

Step (20)

Compound (XXII) is prepared by subjecting compound (XXI) to the rearrangement reaction in an inert solvent in the presence of a base. As the base, sodium hydride, potassium hydride, potassium tert-butoxide and the like are used. As the inert solvent, tetrahydrofuran, dimethyl sulfoxide, dioxane, diethyl ether and the like are used. The reaction is carried out normally at 0° to 30° C. and completes in 1 to 10 hours.

Step (21)

Compound (XXIII) is prepared by cyclizing compound (XXII) under the same conditions as those in Step (7).

Step (22)

Compound (Ici) is prepared by deprotecting compound (XXIII) under the same conditions as those in Step (9).

Preparation 6

Compound (Icak) which is compound (Ic) wherein $X^3$ is $R^9R^{10}NCO_2$-substituted lower alkyl can be prepared by the following Scheme.

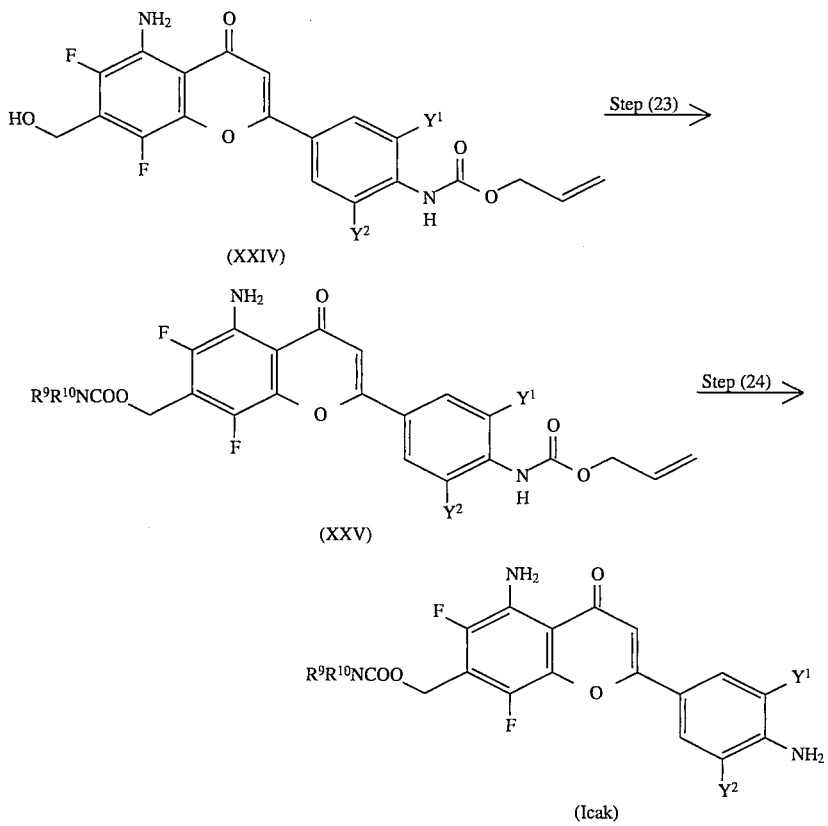

wherein $R^9$, $R^{10}$, $Y^1$ and $Y^2$ are the same as defined above

Step (23)

Compound (XXV) is prepared by reacting compound (XXIV) obtained by the method described in Reference Example or modified method thereof with 1 to 5 equivalents of p-nitrophenyl chloroformate in the presence of 2 to 5 equivalents of a base in a solvent to give a carnonate, then adding an amine represented by $R^9R^{10}NH$ (wherein $R^9$ and $R^{10}$ are the same as defined above). As the solvent, methylene chloride, dichloroethane, dimethylformamide and the like are used. As the base, triethylamine, diisopropylethylamine, pyridine, dimethylaminopyridine and the like are used. The reaction is carried out at 0° C. to room temperature, and completes in 1 to 10 hours.

Step (24)

Compound (Icak) is prepared by treating compound (XXV) with 1 to 10 equivalents of formic acid-triethylamine in the presence of 0.01 to 0.2 equivalent of tetrakis(triphenylphosphine)palladium in a solvent. As the solvent, tetrahydrofuran and the like are used. The reaction is carried out at 0° C. to room temperature, and completes in to 10 hours.

Preparation 7

Compound (Icae) can also be prepared by the following Scheme.

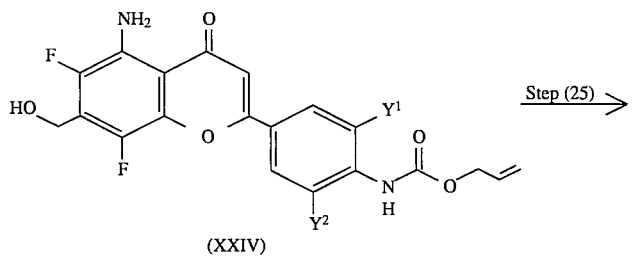

-continued

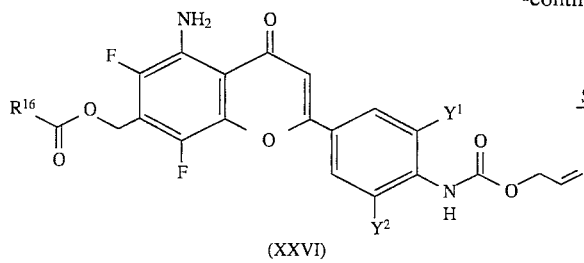

(XXVI)

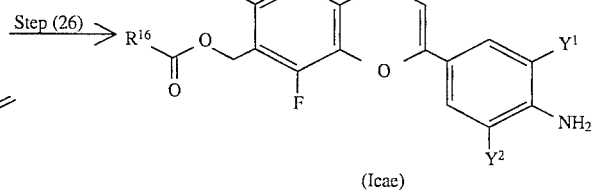

(Icae)

wherein $R^{16}$ represents substituted or unsubstituted lower alkyl. The substituted or unsubstituted lower alkyl is the same as defined above.

Step (25)

Compound (XXVI) is prepared by reacting compound (XXIV) obtained by the method described in Reference Example 13 or modified method thereof with 1 to 20 equivalents of a corresponding carboxylic acid or a reactive derivative thereof in the presence of 1 to 20 equivalents of a condensing agent or a base in an inert solvent. Examples of the reactive derivative of the carboxylic acid are acid halides such as an acid chloride and an acid bromide, acid anhydrides, active esters such as a p-nitrophenyl ester and an N-oxysuccinimide. As the inert solvent, methylene chloride, dichloroethane, toluene, dimethylformamide and the like are used. As the condensing agent, N,N'-carbonyldiimidazole, dicyclohexyl carbodiimide, 2-chloro-N-methylpyridinium iodide and the like are used. As the base, tertially amines such as pyridine, triethylamine and the like, potassium carbonate, sodium carbonate, sodium hydride and the like are used. The reaction is carried out at 0° C. to the boiling point of the solvent employed, preferably at room temperature to 80° C., and completes in one hour to one week.

Step (26)

Compound (Icae) is prepared by treating compound (XXVI) with formic acid-triethylamine under the same conditions as those in Step (24).

Some compounds thus obtained can be used as an intermediate to prepare novel derivatives (I).

For example, when compound (Ig) which is compound (I) wherein 5-position is an amino group ($R^1=R^2=H$) is desired, it can be obtained by hydrolyzing compound (I) wherein $R^1$and/or $R^1$ are lower alkanoyl according to a conventional method. For example, when $R^1$ or $R^2$ is pivaloyl, compound (Ig) can be obtained by reacting the compound with an acid such as hydrochloric acid, hydrobromic acid, sulfuric acid and the like, if necessary, in a lower alcohol or a water-miscible inert solvent at 0° C. to the boiling point of the solvent, normally, for 0.1 to 10 hours. As lower alcohols, those described in Step (2) are used. As water-miscible inert solvents, tetrahydrofuran, dioxane, dimethoxyethane, acetic acid and the like are used. The acid is used at 0.1 to 10N in an amount of 0.1 to 10 times volume relative to that of the solvent.

When compound (Ih) which is compound (I) wherein 4'-position is an amino group ($R^3=R^4=H$) is desired, it can be obtained by starting from compound (I) wherein $R^3$ and/or $R^4$ are lower alkanoyl under the almost same conditions as those for compound (Ig).

Compound (Ii) which is compound (I) wherein one of $R^3$ and $R^4$ is hydrogen and the other is substituted or unsubstituted lower alkyl or lower alkenyl can be obtained by reacting compound (I) wherein one of $R^3$ and $R^4$ is hydrogen and the other is acetyl, tert-butoxycarbonyl or the like with 1 to 20 equivalents of a substituted or unsubstituted lower alkyl or lower alkenyl halide (referred to as alkyl halide hereinafter) in the presence of an equivalent amount to an excess amount of a base in an inert solvent at room temperature to 120° C. for 1 to 24 hours and removing acetyl, tert-butoxycarbonyl or the like. Halogen in alkyl halide represents chlorine, bromine or iodine. When halogen is chlorine or bromine, the reaction is promoted, in some cases, using as a catalyst from 0.05 to 1 equivalents of sodium iodide or potassium iodide. As bases, sodium hydride, potassium hydride, sodium carbonate, potassium carbonate and the like are used. As inert solvents, dimethylformamide, dimethyl sulfoxide, tetrahydrofuran, dioxane and the like are used. Then, compound (Ii) can be obtained by treating the product with an acid such as hydrochloric acid, trifluoroacetic acid and the like in a lower alcohol or a water-miscible inert solvent at 0° C. to the boiling point of the solvent, normally, for 0.1 to 10 hours. As lower alcohols, those described in Step (3) are used. As inert solvents which are miscible with water, tetrahydrofuran, dioxane, acetic acid and the like are used. The acid is used at 0.1 to 10N in an amount of 0.1 to 10 times volume relative to that of the solvent.

Compound (Ij) which is compound (I) wherein $R^1$ or $R^2$ is substituted or unsubstituted lower alkyl or lower alkenyl can be obtained by starting from compound (Ig) and an alkyl halide according to the same procedures as those in the process for producing the above compound (Ii).

Compound (Ik) which is compound (I) wherein $R^1$ or $R^2$ is lower alkanoyl can be obtained by reacting the corresponding compound (Ig) and the corresponding lower aliphatic carboxylic acid or the reactive derivative of the carboxylic acid such as an acid anhydride, acid chloride, acid bromide and the like, if necessary, in the presence of a base. As bases, triethylamine, pyridine, dimethylaminopyridine, sodium carbonate, potassium carbonate and the like are used. As solvents for the reaction, dimethylformamide, dimethyl sulfoxide, tetrahydrofuran, dioxane and the like are used. Alternatively, carboxylic acid or the reactive derivative thereof may be used also as a solvent. The reaction completes in 0.5 to 10 hours at 0° C. to the boiling point of the solvent or carboxylic acid or the reactive derivative thereof employed.

Compound (Im) which is compound (I) wherein $R^3$ or $R^4$ is lower alkanoyl can be obtained by starting from compound (I) wherein $R^3$ and $R^4$ are hydrogen under the almost same conditions as those for the above compound (Ik).

Compound (In) which is compound (I) wherein $R^3$ or $R^4$ is amino-substituted alkyl can be obtained by reacting compound (Ii) wherein $R^3$ or $R^4$ is the corresponding phthalimido-substituted alkyl with hydrazine monohydrate in an inert solvent at 0° C. to the boiling point of the solvent. As inert solvents, lower alcohols such as methanol, ethanol and the like, dimethylformamide, chloroform and the like are used. They may be used sole or in combination with each other. Hydrazine monohydrate is used in an amount of 1 to 20 equivalents relative to that of compound (Ii). Normally, the reaction completes in 0.1 to 5 hours.

Alternatively, compound (In) can also be obtained by reacting compound (Ii) wherein $R^3$ or $R^4$ are the corresponding chlorine, bromine or iodine-substituted alkyl with 1 to 10 equivalents of sodium azide in dimethylformamide at room temperature to 70° C. to give an azide, reacting the azide with 1 to 10 equivalents of triphenylphosphine, and then hydrolyzing the resulting product. The reaction is carried out in tetrahydrofuran, ethyl acetate, acetonitrile and the like at room temperature. The reaction completes in 1 to 40 hours.

Compound (Io) which is compound (I) wherein $R^1$ or $R^2$ is amino-substituted alkyl can be obtained from compound (Ij) wherein $R^1$ or $R^2$ is the corresponding phthalimido, chlorine, bromine or iodine-substituted alkyl under the almost same conditions as those for compound (In).

Compound (Ip) which is compound (I) wherein $R^3$ or $R^4$ is dialkyl or nitrogen-containing heterocyclic group-substituted alkyl can be obtained by reacting compound (Ii) wherein the corresponding groups are chlorine, bromine or iodine-substituted alkyl with 1 to 10 equivalents of a dialkylamine or nitrogen-containing heterocycle such as pyrrolidine, morpholine, imidazole and the like, if necessary, in the presence of 1 to 5 equivalents of a base. As inert solvents, dimethylformamide, tetrahydrofuran and the like are used. As bases, sodium hydride, potassium carbonate and the like are used. The reaction completes in 1 to 20 hours at 0° C. to the boiling point of the solvent.

Compound (Iq) which is compound (I) wherein $R^1$ or $R^2$ is dialkyl or nitrogen-containing heterocycle group-substituted alkyl can be obtained from compound (Ij) wherein $R^1$ or $R^2$ is the corresponding chlorine, bromine or iodine-substituted alkyl under the almost same conditions as those for compound (Ip).

Compound (It) which is compound (I) wherein one of $R^3$ and $R^4$ is hydrogen and the other is lower alkoxycarbonyl can be obtained by starting from compound (I) wherein one of $R^3$ and $R^4$ is hydrogen and the other is acetyl according to the known method [J. Chem. Soc. Chem. Commun., 1317 (1985)].

Compound (Icaea) which is compound (Icae) wherein the substituent of the substituted lower alkanoyloxyalkyl as $X^3$ is $NR^{11}R^{12}$ (wherein $R^{11}$ and $R^{12}$ are the same as defined above) can be obtained by reacting compound (Icaeb) which is compound (Icae) wherein the substituent of the substituted lower alkanoyloxyalkyl as $X^3$ is halogen (wherein halogen is the same as defined above) with 1 to 10 equivalents of an amine represented by $R^{11}R^{12}NH$ (wherein $R^{11}$ and $R^{12}$ are the same as defined above) in an inert solvent, if necessary, in the presence of a base. As the inert solvent, dimethylformamide, dimethyl sulfoxide, tetrahydrofuran, dioxane and the like are used. As the base, triethylamine, diisopropylethylamine, pyridine, dimethylaminopyridine, potassium carbonate, sodium carbonate and the like are used. The reaction is carried out at 0° to 100° C., preferably at 50° to 70° C., and completes in 1 to 10 hours.

Compound (I) having desired functional groups at desired positions can be obtained by appropriately combining the above-described processes with each other.

Intermediates and final compounds in the above processes can be isolated and purified by purifying methods normally used in organic synthetic chemistry, for example, filtration, extraction, washing, drying, concentration, recrystallization, and various chromatographies and the like. In addition, intermediates may be subjected to the subsequent step without purification.

When the product is synthesized in the salted form, the salted compound can be subjected to known purification or isolation processes to give the salted product. If the product is synthesized in the unsalted form, to obtain a salt for compound (I), it can be converted into a salt by, for example, dissolving or suspending it in an appropriate organic solvent and adding an appropriate acid or base.

Compound (I) and salts thereof can also be present in the form of addition products to water or various solvents. Such addition products are also included within the scope of the present invention.

Particular compounds (I) of the present invention are shown in Table 1.

TABLE 1

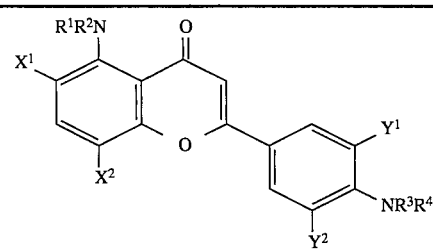

| Compound No. | NR$^1$R$^2$ | NR$^3$R$^4$ | X$^1$ | X$^2$ | Y$^1$ | Y$^2$ |
| --- | --- | --- | --- | --- | --- | --- |
| 1 | NH$_2$ | NH$_2$ | Cl | H | H | H |
| 2 | NH$_2$ | NH$_2$ | H | Cl | H | H |
| 3 | NH$_2$ | NH$_2$ | Cl | Cl | H | H |
| 4 | NH$_2$ | NH$_2$ | Br | H | H | H |
| 5 | NH$_2$ | NH$_2$ | H | Br | H | H |
| 6 | NH$_2$ | NH$_2$ | Br | Br | H | H |
| 7 | NHCOC(CH$_3$)$_3$ | NHCOC(CH$_3$)$_3$ | F | H | H | H |
| 8 | NH$_2$ | NH$_2$ | F | H | H | H |
| 9 | NHCOC(CH$_3$)$_3$ | NHCOC(CH$_3$)$_3$ | H | F | H | H |

TABLE 1-continued

| | | | | | | |
|---|---|---|---|---|---|---|
| 10 | NH$_2$ | NH$_2$ | H | F | H | H |
| 11 | NHCOC(CH$_3$)$_3$ | NHCOC(CH$_3$)$_3$ | F | F | H | H |
| 12 | NH$_2$ | NH$_2$ | F | F | H | H |
| 13 | NH$_2$ | NHCOCH$_3$ | F | H | H | H |
| 14 | NH$_2$ | N(COCH$_3$)(CH$_2$)$_3$Pht | F | H | H | H |
| 15 | NH$_2$ | NH(CH$_2$)$_3$Pht | F | H | H | H |
| 16 | NH$_2$ | NH(CH$_2$)$_3$NH$_2$ | F | H | H | H |
| 17 | NH$_2$ | NHCOCH$_3$ | H | F | H | H |
| 18 | NH$_2$ | N(COCH$_3$)(CH$_2$)$_3$Pht | H | F | H | H |
| 19 | NH$_2$ | NH(CH$_2$)$_3$Pht | H | F | H | H |
| 20 | NH$_2$ | NH(CH$_2$)$_3$NH$_2$ | H | F | H | H |
| 21 | NH$_2$ | NHCOCH$_3$ | F | F | H | H |
| 22 | NH$_2$ | N(COCH$_3$)(CH$_2$)$_3$Pht | F | F | H | H |
| 23 | NH$_2$ | NH(CH$_2$)$_3$Pht | F | F | H | H |
| 24 | NH$_2$ | NH(CH$_2$)$_3$NH$_2$ | F | F | H | H |
| 25 | NHCOC(CH$_3$)$_3$ | NHCOC(CH$_3$)$_3$ | F | F | F | H |
| 26 | NH$_2$ | NH$_2$ | F | F | F | H |
| 27 | NH$_2$ | NHCOCH$_3$ | F | F | F | H |
| 28 | NH$_2$ | N(COCH$_3$)(CH$_2$)$_3$Pht | F | F | F | H |
| 29 | NH$_2$ | NH(CH$_2$)$_3$Pht | F | F | F | H |
| 30 | NH$_2$ | NH(CH$_2$)$_3$NH$_2$ | F | F | F | H |
| 31 | NH(CH$_2$)$_5$CH$_3$ | N(COCH$_3$)(CH$_2$)$_3$Pht | F | F | F | H |
| 32 | NH(CH$_2$)$_5$CH$_3$ | NH(CH$_2$)$_3$Pht | F | F | F | H |
| 33 | NH(CH$_2$)$_5$CH$_3$ | NH(CH$_2$)$_3$NH$_2$ | F | F | F | H |
| 34 | NH$_2$ | NH$_2$ | F | F | F | F |
| 35 | NH$_2$ | NH$_2$ | F | F | Cl | Cl |
| 36 | NH$_2$ | NH$_2$ | F | F | Br | Br |
| 37 | NH$_2$ | NHCH$_3$ | F | F | F | H |
| 38 | NH$_2$ | N(CH$_3$)$_2$ | F | F | F | H |
| 39 | NH$_2$ | NH(CH$_2$)$_2$OCH$_3$ | F | F | F | H |
| 40 | NH$_2$ | NH(CH$_2$)$_2$N(CH$_3$)$_2$ | F | F | F | H |
| 41 | NH$_2$ | NH(CH$_2$)$_2$N⟨pyrrolidinyl⟩ | F | F | F | H |
| 42 | NH$_2$ | NH(CH$_2$)$_2$N⟨morpholinyl⟩ | F | F | F | H |
| 43 | NH$_2$ | NH(CH$_2$)$_2$SCH$_3$ | F | F | F | H |
| 44 | NH$_2$ | NHCH$_2$CO$_2$CH$_2$CH$_3$ | F | F | F | H |
| 45 | NH$_2$ | NHCH$_2$CO$_2$Na | F | F | F | H |
| 46 | NH$_2$ | NH(CH$_2$)$_3$OCH$_3$ | F | F | F | H |
| 47 | NH$_2$ | NH(CH$_2$)$_3$N(CH$_3$)$_2$ | F | F | F | H |
| 48 | NH$_2$ | NH(CH$_2$)$_3$N⟨pyrrolidinyl⟩ | F | F | F | H |
| 49 | NH$_2$ | NH(CH$_2$)$_3$SCH$_3$ | F | F | F | H |
| 50 | NH$_2$ | NH(CH$_2$)$_3$N⟨imidazolyl⟩ | F | F | F | H |
| 51 | NH$_2$ | NHCO$_2$C(CH$_3$)$_3$ | F | F | F | H |
| 52 | NH$_2$ | NH(CH$_2$)$_6$N⟨imidazolyl⟩ | F | F | F | H |
| 53 | NH$_2$ | NH(CH$_2$)$_6$N(CH$_3$)$_2$ | F | F | F | H |
| 54 | NH$_2$ | NH(CH$_2$)$_6$N⟨pyrrolidinyl⟩ | F | F | F | H |

TABLE 1-continued

| | | | | | | |
|---|---|---|---|---|---|---|
| 55 | $NH_2$ | $NH(CH_2)_6N\underset{\_\_\_}{\diagup\diagdown}O$ | F | F | F | H |
| 56 | $NH_2$ | $NH(CH_2)_5CO_2CH_2CH_3$ | F | F | F | H |
| 57 | $NH_2$ | $NH(CH_2)_5CO_2Na$ | F | F | F | H |
| 58 | $NH(CH_2)_5CH_3$ | $N(CH_3)_2$ | F | F | F | H |
| 59 | $NH(CH_2)_6Br$ | $N(CH_3)_2$ | F | F | F | H |
| 60 | $NH(CH_2)_6OH$ | $N(CH_3)_2$ | F | F | F | H |
| 61 | $NH(CH_2)_6OCH_3$ | $N(CH_3)_2$ | F | F | F | H |
| 62 | $NH(CH_2)_6N(CH_3)_2$ | $N(CH_3)_2$ | F | F | F | H |
| 63 | $NH(CH_2)_6N\underset{\_\_\_}{\diagup\diagdown}$ | $N(CH_3)_2$ | F | F | F | H |
| 64 | $NH(CH_2)_6N\diagup\diagdown_N$ | $N(CH_3)_2$ | F | F | F | H |
| 65 | $NH(CH_2)_6NH_2$ | $N(CH_3)_2$ | F | F | F | H |
| 66 | $NH(CH_2)_4CH_3$ | $NH_2$ | F | F | F | H |
| 67 | $NH(CH_2)_5CH_3$ | $NH_2$ | F | F | F | H |
| 68 | $NH(CH_2)_6CH_3$ | $NH_2$ | F | F | F | H |
| 69 | $NH(CH_2)_4CH(Cl)CH_3$ | $NH_2$ | F | F | F | H |
| 70 | $NH(CH_2)_2CH(CH_3)_2$ | $NH_2$ | F | F | F | H |
| 71 | $NH(CH_2)_3CH(CH_3)_2$ | $NH_2$ | F | F | F | H |
| 72 | $NH(CH_2)_3NH_2$ | $NH_2$ | F | F | F | H |
| 73 | $NH(CH_2)_4NH_2$ | $NH_2$ | F | F | F | H |
| 74 | $NH(CH_2)_5CH_3$ | $NHCH_2CO_2CH_2CH_3$ | F | F | F | H |
| 75 | $NH(CH_2)_5CH_3$ | $NHCH_2CO_2H$ | F | F | F | H |
| 76 | $NH(CH_2)_3CH=CH_2$ | $NHCH_3$ | F | F | F | H |
| 77 | $NH(CH_2)_4CH=CH_2$ | $NHCH_3$ | F | F | F | H |
| 78 | $NH(CH_2)_3OCH_3$ | $NHCH_3$ | F | F | F | H |
| 79 | $NH(CH_2)_4CH_3$ | $NH(CH_2)_3NH_2$ | F | F | F | H |

In Table 1, Pht represents 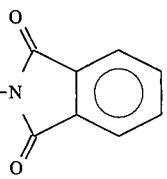

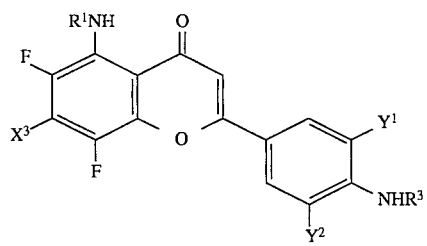

| Compound No. | $R^1$ | $R^3$ | $X^3$ | $Y^1$ | $Y^2$ |
|---|---|---|---|---|---|
| 80 | H | H | $CH_3$ | F | H |
| 81 | H | H | $CH_2CH_3$ | F | H |
| 82 | H | H | $(CH_2)_3CH_3$ | F | H |
| 83 | H | H | $(CH_2)_5CH_3$ | F | H |
| 84 | H | H | Cl | F | H |
| 85 | H | H | Br | F | H |
| 86 | H | H | OH | F | H |
| 87 | H | H | $OCH_3$ | F | H |
| 88 | H | H | $O(CH_2)_2N(CH_3)_2$ | F | H |
| 89 | H | H | $SCH_3$ | F | H |
| 90 | H | H | $SOCH_3$ | F | H |
| 91 | H | H | $SO_2CH_3$ | F | H |
| 92 | H | H | $CO_2CH_2CH_3$ | F | H |
| 93 | H | H | $CO_2H$ | F | H |
| 94 | H | H | $N_3$ | F | H |
| 95 | H | H | $NH_2$ | F | H |

TABLE 1-continued

| | | | | | |
|---|---|---|---|---|---|
| 96 | H | H | N(CH$_3$)$_2$ | F | H |
| 97 | H | H | NH(CH$_2$)$_3$N(CH$_3$)$_2$ | F | H |
| 98 | H | H | N⟨⟩N—CH$_3$ | F | H |
| 99 | H | H | CH(OH)CH$_3$ | F | H |
| 100 | H | H | CH=CH$_2$ | F | H |
| 101 | H | H | COCH$_3$ | F | H |
| 102 | CH$_3$ | H | N(CH$_3$)$_2$ | F | H |
| 103 | H | H | CH$_3$ | Cl | H |
| 104 | H | H | CH$_3$ | Cl | Cl |
| 105 | H | H | CH$_3$ | CH$_2$CH$_3$ | H |
| 106 | H | H | NH$_2$ | Cl | Cl |
| 107 | (CH$_2$)$_5$CH$_3$ | H | CH$_3$ | F | H |
| 108 | (CH$_2$)$_6$CH$_3$ | H | CH$_3$ | F | H |
| 109 | (CH$_2$)$_4$CH$_3$ | (CH$_2$)$_2$CH$_3$ | CH$_3$ | F | H |
| 110 | (CH$_2$)$_4$CH$_3$ | (CH$_2$)$_3$CH$_3$ | CH$_3$ | F | H |
| 111 | (CH$_2$)$_4$CH$_3$ | (CH$_2$)$_4$CH$_3$ | CH$_3$ | F | H |
| 112 | H | H | C≡CH | F | H |
| 113 | H | (CH$_2$)$_2$CH(CH$_3$)$_2$ | F | F | H |
| 114 | (CH$_2$)$_2$CH(CH$_3$)$_2$ | H | CH$_3$ | F | H |
| 115 | (CH$_2$)$_3$CH(CH$_3$)$_2$ | H | CH$_3$ | F | H |
| 116 | (CH$_2$)$_3$N(CH$_3$)$_2$ | H | CH$_3$ | F | H |
| 117 | (CH$_2$)$_3$N(CH$_2$CH$_3$)$_2$ | H | CH$_3$ | F | H |
| 118 | H | H | CH$_2$OH | F | H |
| 119 | H | H | CH$_2$OSO$_3$H | F | H |
| 120 | H | H | CH$_2$NH$_2$ | F | H |
| 121 | H | H | CH$_2$N(CH$_3$)$_2$ | F | H |
| 122 | H | H | CH$_2$OCH$_3$ | F | H |
| 123 | H | H | CH$_2$OCOCH$_3$ | F | H |
| 124 | H | H | CH$_2$OCOCH$_2$CH$_3$ | F | H |
| 125 | H | H | CH$_2$OCO(CH$_2$)$_4$CH$_3$ | F | H |

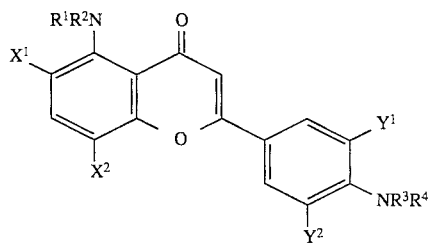

| Compound No. | NR$^1$R$^2$ | NR$^3$R$^4$ | X$^1$ | X$^2$ | Y$^1$ | Y$^2$ |
|---|---|---|---|---|---|---|
| 126 | NH(CH$_2$)$_3$CH$_3$ | NH(CH$_2$)$_3$NH$_2$ | F | F | F | H |
| 127 | NH(CH$_2$)$_4$CH$_3$ | NH(CH$_2$)$_3$N(CH$_3$)$_2$ | F | F | F | H |
| 128 | NH(CH$_2$)$_2$CH(CH$_3$)$_2$ | NH(CH$_2$)$_3$N(CH$_3$)$_2$ | F | F | F | H |
| 129 | NH(CH$_2$)$_3$N⟨imidazole⟩ | NH$_2$ | F | F | F | H |
| 130 | NH(CH$_2$)$_3$N(CH$_3$)$_2$ | NH$_2$ | F | F | F | H |
| 131 | NH(CH$_2$)$_3$N(CH$_2$CH$_3$)$_2$ | NH$_2$ | F | F | F | H |
| 132 | NH(CH$_2$)$_3$N⟨pyrrolidine⟩ | NH$_2$ | F | F | F | H |
| 133 | NH(CH$_2$)$_3$N⟨⟩NCH$_3$ | NH$_2$ | F | F | F | H |

TABLE 1-continued

| 134 | NH(CH₂)₃N〔morpholine〕 | NH₂ | F | F | F | H |
| 135 | NH(CH₂)₄N(CH₃)₂ | NH₂ | F | F | F | H |
| 136 | NH(CH₂)₄CH(CH₃)₂ | NH₂ | F | F | F | H |
| 137 | NH(CH₂)₂CH=C(CH₃)₂ | NH₂ | F | F | F | H |
| 138 | NH(CH₂)₃C(OH)(CH₃)₂ | NH₂ | F | F | F | H |
| 139 | NH(CH₂)₅N(CH₃)₂ | NH₂ | F | F | F | H |
| 140 | NHCH₂CO₂H | NH₂ | F | F | F | H |
| 141 | NH(CH₂)₃CO₂H | NH₂ | F | F | F | H |

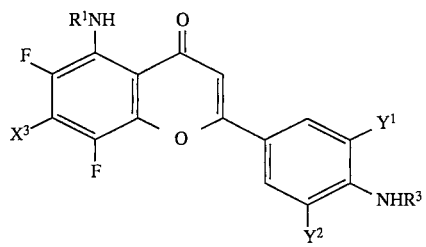

| Compound No. | R¹ | R³ | X³ | Y¹ | Y² |
|---|---|---|---|---|---|
| 142 | H | H | CH₂N〔N-methylpiperazine〕N—CH₃ | F | H |
| 143 | H | H | CH₂N〔morpholine〕O | F | H |
| 144 | H | H | CH₂NH(CH₂)₂CH₃ | F | H |
| 145 | H | H | CH₂NH(CH₂)₅CH₃ | F | H |
| 146 | H | H | CH₂NH(CH₂)₂N(CH₃)₂ | F | H |
| 147 | H | H | CH₂NH(CH₂)₂OH | F | H |
| 148 | H | H | CH₂N((CH₂)₂OH)₂ | F | H |
| 149 | H | H | CH₂NHCH(CH₂OH)₂ | F | H |
| 150 | H | H | CH₂O(CH₂)₂CH₃ | F | H |
| 151 | H | H | CH₂O(CH₂)₅CH₃ | F | H |
| 152 | H | H | CH₂O(CH₂)₃CH(CH₃)₂ | F | H |
| 153 | H | H | CH₂O(CH₂)₂N(CH₃)₂ | F | H |
| 154 | H | H | CH₂O(CH₂)₃N(CH₃)₂ | F | H |
| 155 | H | H | CH₂OCO(CH₂)₂CH(CH₃)₂ | F | H |

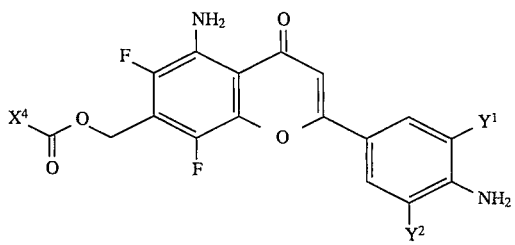

| Compound No. | X⁴ | Y¹ | Y² |
|---|---|---|---|
| 156 | N(CH₂CH₃)₂ | F | H |
| 157 | N〔N-methylpiperazine〕N—CH₃ | F | H |
| 158 | NH(CH₂)₂N(CH₃)₂ | F | H |
| 159 | CH₂Cl | F | H |

TABLE 1-continued

| | | | |
|---|---|---|---|
| 160 | (CH$_2$)$_2$Br | F | H |
| 161 | CH$_2$N(CH$_3$)$_2$ | F | H |
| 162 | (CH$_2$)$_2$N(CH$_3$)$_2$ | F | H |
| 163 | (CH$_2$)$_3$N(CH$_3$)$_2$ | F | H |
| 164 | CH$_2$N–(piperidinyl) | F | H |
| 165 | CH$_2$N–(4-methylpiperazinyl) N—CH$_3$ | F | H |
| 166 | CH$_2$N–(morpholinyl) O | F | H |
| 167 | CH$_2$N–(4-hydroxypiperidinyl)—OH | F | H |
| 168 | CH$_2$N(CH$_3$)(CH$_2$)$_2$N(CH$_3$)$_2$ | F | H |
| 169 | CH$_2$NHCH$_2$COOCH$_3$ | F | H |
| 170 | OCH$_2$CH=CH$_2$ | F | H |
| 171 | CH$_2$Cl | Cl | Cl |
| 172 | CH$_2$N(CH$_3$)$_2$ | Cl | Cl |

Anti-estrogenic activity of compound (I) can be demonstrated by the antagonism against the increase in uterus weight of an immature mouse treated with estradiol. Oral administration of compound (I) significantly inhibits the increase in the uterus weight observed in an estradiol-treated group, this confirming the anti-estrogenic activity. On the other hand, a known anti-estrogenic agent, tamoxifen, has the weak anti-estrogenic activity and this is due to its partial agonist action. Tamoxifen rather significantly increases the weight of the uterus in an estradiol-untreated group. Compound (I) is an anti-estrogenic agent possessing the uterus weight-decreasing activity even in an estradiol-untreated group. In addition, compound (I) inhibits the growth of human mammary cancer cells in the medium in a microplate and inhibits the growth of human mammary cancers transplanted to a nude mouse.

The compound possessing such the bioactivity is useful not only for treatment of the same symptoms as those for which tamoxifen is useful, for example, mammary cancer, non-ovulatory sterility or paramenia but also for treatment of the symptoms for which tamoxifen is not useful, for example, endometriosis or endometrial cancer.

Then, the activity of the representative compounds (I) is shown by experiments.

Test 1

Antibacterial activity

Antibacterial activity of compound (I) against *Bacillus subtilis* #10107 [Minimum Inhibition Concentration(MIC; μg/ml)] is shown in Table 2. Minimum Inhibition Concentration was determined by agar dilution method at pH 7.0.

TABLE 2

| Compound No. | MIC (μg/ml) |
|---|---|
| 16 | 5.2 |
| 24 | 2.6 |
| 88 | 52.1 |
| 97 | 52.1 |
| 101 | 13.0 |
| 116 | 13.0 |
| 117 | 13.0 |
| 120 | 3.26 |
| 130 | 52.1 |
| 131 | 52.1 |
| 132 | 104.2 |
| 133 | 104.2 |
| 139 | 104.2 |
| 158 | 83.3 |
| 161 | 26.0 |
| 162 | 104.2 |
| 163 | 104.2 |

Test 2

The effect against the increase in uterus weight of immature mouse

Immature female BALB/c mice, 4 weeks age, were divided into two groups and 50 μg of estradiol was subcutaneously administered to the animals of one group in the chest. The test compounds were repeatedly administered orally to each group (8 animals per group) for three days since the date of estradiol administration. After four days, the uteri were isolated and the weight thereof was measured.

The results are shown in Table 3. In Table 2, "estradiol (−)" represents an estradiol-untreated group and "estradiol (+)" represents an estradiol-treated group.

TABLE 3

| Compound No. | Dose (mg/kg) | Estradiol | Weight of uterus (mg) |
|---|---|---|---|
| Untreated | — | − | 24 |
| 80 | 50 | − | 17 |
| Tamoxifen | 5 | − | 49 |
| Untreated | — | + | 49 |
| 80 | 50 | + | 38 |
| Tamoxifen | 5 | + | 47 |

Test 3

Human uterine cervix carcinoma (HeLaS$_3$) growth inhibition test

Each 0.1 ml of HeLaS$_3$ cells which had been prepared to $3 \times 10^4$/ml using a medium (referred to as Medium A hereinafter) consisted of MEM medium, 2 mM glutamine and 10% bovine fetal serum was distributed in each well of 96 well-microtiter plate. The plate was cultured at 37° C. for 20 hours in a $CO_2$ gas incubator, each 0.05 ml of samples (test compounds) which had been appropriately diluted with Medium A was added thereto and the mixture was cultured at 37° C. for 72 hours in a $CO_2$ gas incubator. Supernatant was removed, each 0.1 ml of Medium A containing 0.02% neutral red was added to the residue, the mixture was cultured at 37° C. for 1 hour in a $CO_2$ gas incubator and the cells were stained. Supernatant was removed and the residue was washed once with saline. Then, the pigment was extracted with 0.001N hydrochloric acid/30% ethanol and the absorbance at 550 nm was measured with a microplatereader. Sample concentration (IC$_{50}$) at which the growth of cell is inhibited by 50% was calculated by comparing the absorbance of non-treated cells and that of cells treated with predetermined concentration of sample.

The results are shown in Table 4.

TABLE 4

| Compound No. | IC$_{50}$ (μM) | Compound No. | IC$_{50}$ (μM) |
|---|---|---|---|
| 2 | 3.2 | 63 | 7.0 |
| 3 | 33 | 64 | 3.0 |
| 5 | 6.1 | 65 | 7.0 |
| 10 | 21 | 67 | 9.4 |
| 12 | 10 | 71 | 12 |
| 16 | 5.8 | 74 | 12 |
| 20 | 9.3 | 75 | 16 |
| 24 | 3.4 | 77 | 11 |
| 26 | 26 | 79 | 7.5 |
| 30 | 14 | 126 | 6.1 |
| 38 | 12 | 130 | 6.6 |
| 41 | 5.0 | 131 | 6.5 |
| 52 | 4.4 | 132 | 6.4 |
| 53 | 6.8 | 135 | 6.4 |
| 54 | 6.1 | 136 | 9.2 |
| 55 | 11 | 137 | 6.3 |
| 62 | 7.1 | 139 | 6.5 |

Test 4

Human mammary cancer MCF-7 cell growth inhibition test

Each 0.1 ml of MCF-7 cells which had been prepared to $5 \times 10^4$/ml using a medium (referred to as Medium B hereinafter) prepared by adding 10% bovine fetal serum, $10^{-8}$M estradiol (manufactured by Sigma), 100 units/ml penicillin and 100 μg/ml streptomycin to RPMI1640 medium was distributed in each well of 96 well-microtiter plate. The plate was cultured at 37° C. for 20 hours in a $CO_2$ gas incubator, each 0.05 ml of samples (test compound) which had been appropriately diluted with Medium B was added thereto and the mixture was cultured at 37° C. for 72 hours in a $CO_2$ gas incubator. Supernatant was removed, each 0.1 ml of Medium B containing 0.02% neutral red was added to the residue, the mixture was cultured at 37° C. for 1 hour in a $CO_2$ gas incubator and the cells were stained by neutral red dye. Supernatant was removed and the residue was washed once with a physiological saline. Then, the dye was extracted with 0.001N hydrochloric acid/30% ethanol and the absorbance at 550 nm was determined with a microplatereader. Sample concentration (IC$_{50}$) at which the growth of cell is inhibited by 50% was calculated by comparing the absorbance of non-treated cells and sample-treated cells.

The results are shown in Table 5.

TABLE 5

| Compound No. | IC$_{50}$ (μM) | Compound No. | IC$_{50}$ (μM) |
|---|---|---|---|
| 2 | 0.37 | 92 | 1.4 |
| 3 | 22 | 95 | 0.0077 |
| 6 | 27 | 96 | 0.039 |
| 8 | 0.14 | 103 | 0.092 |
| 10 | 0.25 | 105 | 0.065 |
| 20 | 0.094 | 113 | 0.22 |
| 30 | 0.039 | 118 | 0.062 |
| 35 | 0.17 | 120 | 0.026 |
| 36 | 0.61 | 121 | 0.072 |
| 40 | 0.23 | 122 | 0.046 |
| 42 | 6.1 | 123 | 0.026 |
| 44 | 0.36 | 126 | 0.086 |
| 46 | 0.11 | 130 | 0.19 |
| 52 | 2.0 | 132 | 0.95 |
| 53 | 6.2 | 135 | 0.13 |
| 54 | 5.9 | 137 | 0.082 |
| 56 | 0.91 | 139 | 0.23 |
| 57 | 0.73 | 140 | 0.86 |
| 58 | 0.34 | 141 | 0.60 |
| 60 | 0.34 | 156 | 0.35 |
| 61 | 0.63 | 157 | 0.23 |
| 69 | 6.0 | 161 | 0.026 |
| 74 | 9.2 | 162 | 0.019 |
| 80 | 0.013 | 163 | 0.029 |
| 81 | 0.13 | 164 | 0.033 |
| 84 | 0.21 | 165 | 0.087 |
| 85 | 0.16 | 166 | 0.017 |
| 87 | 0.10 | 167 | 0.018 |
| 88 | 1.4 | 169 | 0.013 |
| 89 | 0.19 | 170 | 0.081 |
| 90 | 2.5 | Tamoxifen | 23 |

Test 5

Antitumor effects against estrogen-dependent human mammary cancer MCF-7

The tumor fragment (2 mm×2 mm×2 mm) of human hormone dependent mammary cancer MCF-7 was transplanted subcutaneously in the flank of female BALB/c-nu/nu mouse (Nihon Crea), 7 to 9 weeks age. For promoting the growth of tumor, 12.5 μg of estradiol propionate was intramuscularlly administered in the femoral region total two times, on the date of transplantation and two weeks after transplantation. 3 to 4 Weeks after transplantation, mice of the tumor volume 25 to 200 mm$^3$ were selected, and the test compounds were orally administered repeatedly to the groups (5 animals per group) for 5 days per a week, for total two weeks. In addition, estradiol propionate was administered again on the date of initial administration of the test compounds. Length and width of the tumor were determined every day, and the tumor volumes were calculated by means of ellipsoid approximation according to the following equation:

$$\text{Tumor volume (mm}^3) = \{\text{Length (mm)} \times [\text{Width (mm)}]^2\}/2$$

The tumor volume at initial administration ($V_o$) and on the day of judgement (V) was calculated, and the tumor growth rate ($V/V_o$) was calculated. T/C value was obtained as the ratio of $V/V_o$ value of treated group relative to that of control group.

The results are shown in Table 6.

TABLE 6

| Compound No. | Dose (mg/kg) | T/C | Judgement Date (Day) |
|---|---|---|---|
| 26 | 50 | 0.067 | 15 |
| 30 | 100 | 0.027 | 17 |
| 71 | 25 | 0.078 | 22 |
| 71 | 50 | 0.034 | 17 |
| 71 | 100 | 0.018 | 17 |
| 80 | 50 | 0.064 | 18 |
| 85 | 50 | 0.54 | 21 |
| 88 | 50 | 0.42 | 15 |
| 95 | 12.5 | 0.18 | 22 |
| 118 | 50 | 0.016 | 14 |
| 120 | 50 | 0.011 | 18 |
| 123 | 25 | 0.061 | 14 |
| 129 | 50 | 0.13 | 21 |
| 129 | 100 | 0.089 | 18 |
| 130 | 50 | 0.18 | 25 |
| 130 | 100 | 0.092 | 21 |
| 131 | 50 | 0.010 | 17 |
| 135 | 50 | 0.081 | 17 |
| 137 | 50 | 0.20 | 15 |
| 139 | 50 | 0.31 | 15 |
| 161 | 25 | 0.012 | 15, 17 |
| 162 | 25 | 0.041 | 18 |
| 163 | 25 | 0.15 | 14 |
| 164 | 25 | 0.042 | 14 |
| 165 | 25 | 0.070 | 14 |
| 166 | 25 | 0.044 | 18 |
| 167 | 25 | 0.035 | 18 |
| 168 | 25 | 0.022 | 24 |
| 169 | 25 | 0.013 | 25 |
| Tamoxifen | 5 | 0.25 | 22 |

Test 6

Antitumor effects against estrogen-dependent human mammary cancer MCF-7

The tumor fragment (2 mm×2 mm×2 mm) of human hormone dependent mammary cancer MCF-7 was transplanted subcutaneously in the flank of female BALB/c-nu/nu mouse (Nihon Crea), 7–9 weeks age. For promoting the growth of tumor, 12.5 μg of estradiol was intramuscularlly administered three times in the femoral region on the date of transplantation and 7 and 14 days after transplantation. 7 Days after transplantation, mice of the tumor volume 10–100 mm³ were selected, and test compounds were orally administered repeatedly for five days per a week, for four weeks, at five animals per group. Length and width of the tumor were determined every day, and the tumor volumes were calculated by means of ellipsoid approximation according to the above equation. The tumor volume at initial administration ($V_o$) and on the day of judgement (V) was calculated, and the tumor growth rate ($V/V_o$) was calculated. T/C value was obtained as the ratio of $V/V_o$ value of treated group relative to that of control group.

The results are shown in Table 7

TABLE 7

| Compound No. | Dose (mg/kg) | T/C | Judgement Date (Day) |
|---|---|---|---|
| 12 | 6.3 | 0.45 | 22 |
| 26 | 26 | 0.45 | 29 |

Test 7

Antitumor effects against estrogen-dependent human mammary cancer Br-10

The tumor fragment (2 mm×2 mm×2 mm) of human hormone dependent mammary cancer Br-10 was transplanted subcutaneously in the flank of female BALB/c-nu/nu mouse (Nihon Crea), 7 to 9 weeks age. For promoting the growth of tumor, 12.5 μg of estradiol propionete was intramuscularlly administered in the femoral region total two times, on the date of transplantation and two weeks after transplantation. 3 to 4 Weeks after transplantation, mice of the tumor volume 30 to 150 mm³ were selected, and the test compounds were orally administered repeatedly to the groups (5 animals per group) for 5 days per a week, for total two to four weeks. Estradiol propionate was additionally administered on the date of initial administration of the test compounds and 14 days after the administration. Length and width of the tumor were determined every day, and the tumor volumes were calculated by means of ellipsoid approximation according to the above equation. The tumor volume at initial administration ($V_o$) and on the day of judgement (V) was calculated, and the tumor growth rate ($V/V_o$) was calculated. T/C value was obtained as the ratio of $V/V_o$ value of treated group relative to that of control group.

The results are shown in Table 8.

TABLE 8

| Compound No. | Dose (mg/kg) | T/C | Judgement Date (Day) |
|---|---|---|---|
| 80 | 25 | 0.12 | 18 |
| 95 | 12.5 | 0.24 | 18 |
| 96 | 25 | 0.22 | 18 |
| Tamoxifen | 5 | 0.58 | 25 |

Test 8

The effect against the increase in uterus weight of immature mouse

Inmature female BALB/c mice, 9 weeks age, were divided into two groups (6 animals per group). The test compounds were repeatedly administered orally to one group for four days. After five days, the uteri were isolated and the weight thereof was measured.

The results are shown in Table 9.

TABLE 9

| Compound No. | Dose (mg/kg) | Weight of uterus (mg) |
|---|---|---|
| Untreated | — | 106 |
| 161 | 25 | 67 |

The following Examples and Reference Examples further illustrate the present invention in detail but are not to be construed to limit the scope thereof.

Physicochemical data on respective compounds in the following Examples and Reference Examples were determined using the apparatus:

| IR | Nihon Bunko IR-810 |
|---|---|
|  | HORIBA FT-200 |
| $^1$H NMR | JEOL JNM-GX270 (270 MHz) |
|  | JEOL JNM-EX270 (270 MHz) |
|  | HITACHI R-90H (90 MHz) |
| MS | JEOL JMS-D300 |
|  | JEOL JMS-SX102 |
|  | SHIMAZU QP-1000 |

EXAMPLE 1

5-Amino-2-(4-aminophenyl)-6-chloro-4H-1-benzopyran-4-one (Compound 1)

2.0 g (7.93 mmol) of 5-amino-2-(4-aminophenyl)-4H-1-benzopyran-4-one (EP-A-374789) was dissolved in 50 ml of dioxane, 1.06 g (7.93 mmol) of N-chlorosuccinimide was added and the mixture was stirred under heating at reflux for 19 hours. The reaction solution was concentrated under reduced pressure, and the residue was extracted with ethyl acetate. The extract was washed with an aqueous saturated solution of sodium chloride and dried over anhydrous sodium sulfate. The ethyl acetate layer was concentrated under reduced pressure and the residue was purified by silica gel column chromatography (chloroform:acetone=4:1) to give 710 mg (31%) of crude product. Further recrystallization from chloroform/methanol afforded 415 mg (18%) of Compound 1.

IR (KBr) ν (cm$^{-1}$) 3404, 1642, 1597, 1546, 1444, 1395, 1304, 829

NMR (270 MHz, DMSO-d$_6$) δ (ppm) 6.00 (2H, brs), 6.58 (1H, s), 6.67 (2H, d, J=8.9), 6.75 (1H, d, J=8.9), 7.54 (1H, d, J=8.4), 7.73 (2H, d, J=8.9)

MS (M/Z) 286/288 (M$^+$)

Molecular formula $C_{15}H_{11}ClN_2O_2$=286

EXAMPLE 2

5-Amino-2-(4-aminophenyl)-8-chloro-4H-1-benzopyran-4-one (Compound 2)

2.0 g (7.93 mmol) of 5-amino-2-(4-aminophenyl)-4H-1-benzopyran-4-one (EP-A-374789) was dissolved in 50 ml of dioxane, 1.59 g (11.9 mmol) of N-chlorosuccinimide was added and the mixture was stirred under heating at reflux for 5 hours. The reaction solution was extracted with ethyl acetate, and the extract was washed with an aqueous saturated solution of sodium chloride and dried over anhydrous sodium sulfate. The ethyl acetate layer was concentrated under reduced pressure and the residue was purified by silica gel column chromatography (chloroform: acetone=4:1) to give 0.61 g (27%) of crude product. Further recrystallization from chloroform/methanol afforded 266 mg (12%) of Compound 2.

IR (KBr) ν (cm$^{-1}$) 3436, 3308, 1640, 1580, 1544, 1471, 1396, 1186, 822

NMR (270 MHz, DMSO-d$_6$) δ (ppm) 6.52 (1H, d, J=8.9), 6.58 (2H, d, J=8.4), 6.68 (1H, s), 6.75 (2H, brs), 7.42 (1H, d, J=8.9), 7.75 (2H, d, J=8.4)

MS (M/Z) 286/288 (M$^+$)

Molecular formula $C_{15}H_{11}ClN_2O_2$=286

EXAMPLE 3

5-Amino-2-(4-aminophenyl)-6,8-dichloro-4H-1-benzopyran-4-one (Compound 3)

0.94 g (3.73 mmol) of 5-amino-2-(4-aminophenyl)-4H-1-benzopyran-4-one (EP-A-374789) was suspended in 50 ml of acetic acid, 24.0 g of 2.73% chlorine/acetic acid solution (chlorine: 9.23 mmol) was added and the mixture was stirred at room temperature for 18 hours. The reaction solution was poured into water, and the mixture was extracted with a mixed solution of chloroform and methanol. The extract was washed with an aqueous saturated solution of sodium bicarbonate and an aqueous saturated solution of sodium chloride and dried over anhydrous sodium sulfate. The organic layer was concentrated under reduced pressure and the residue was purified by silica gel column chromatography (chloroform:acetone=4:1) to give 375 mg (30%) of crude product. Further recrystallization from chloroform/methanol afforded 218 mg (18%) of Compound 3.

IR (KBr) ν (cm$^{-1}$) 3454, 3300, 1627, 1607, 1536, 1514, 1444, 1393, 1296, 1250, 1187, 1129, 823

NMR (270 MHz, DMSO-d$_6$) δ (ppm) 6.07 (2H, brs), 6.08 (1H, s), 6.68 (2H, d, J=9.4), 7.76 (1H, s), 7.76 (2H, d, J=8.9)

MS (M/Z) 320/322/324 (M$^+$)

Molecular formula $C_{15}H_{10}Cl_2N_2O_2$=321

EXAMPLE 4

5-Amino-2-(4-aminophenyl)-6-bromo-4H-1-benzopyran-4-one (Compound 4)

2.50 g (11.9 mmol) of 5-amino-2-(4-aminophenyl)-4H-1-benzopyran-4-one (EP-A-374789) was dissolved in 75 ml of dioxane, 1.86 g (13.1 mmol) of N-bromosuccinimide was added and the mixture was stirred at room temperature for 2 hours. The reaction solution was concentrated under reduced pressure, and the residue was extracted with a mixed solution of chloroform and methanol. The extract was washed with an aqueous saturated solution of sodium chloride and dried over anhydrous sodium sulfate. The organic layer was concentrated under reduced pressure and the residue was purified by silica gel column chromatography (chloroform:acetone=40:1) to give 170 mg (4.3%) of Compound 4.

IR (KBr) ν (cm$^{-1}$) 3344, 1627, 1582, 1544, 1536, 1388, 1185, 823

NMR (270 MHz, DMSO-d$_6$) δ (ppm) 6.01 (2H, brs), 6.49 (1H, d, J=8.9), 6.57 (1H, s), 6.67 (2H, d, J=8.1), 7.52 (1H, d, J=8.9), 7.58 (2H, brs), 7.77 (2H, d, J=8.4)

MS (M/Z) 330/332 (M$^+$)

Molecular formula $C_{15}H_{11}BrN_2O_2$=331

EXAMPLE 5

5-Amino-2-(4-aminophenyl)-8-bromo-4H-1-benzopyran-4-one (Compound 5)

2.50 g (11.9 mmol) of 5-amino-2-(4-aminophenyl)-4H-1-benzopyran-4-one (EP-A-374789) was dissolved in 75 ml of dioxane, 1.86 g (13.1 mmol) of N-bromosuccinimide was added and the mixture was stirred at room temperature for 2 hours. The reaction solution was concentrated under reduced pressure, and the residue was extracted with a mixed solution of chloroform and methanol. The extract was washed with an aqueous saturated solution of sodium chloride and dried over anhydrous sodium sulfate. The organic layer was concentrated under reduced pressure and the residue was purified by silica gel column chromatography (chloroform/acetone=40:1) to give 767 mg (20%) of Compound 5.

IR (KBr) ν (cm$^{-1}$) 3340, 1625, 1581, 1536, 1515, 1388, 1323, 1250, 1185, 824

NMR (270 MHz, DMSO-d$_6$) δ (ppm) 6.00 (2H, brs), 6.50 (1H, dd, J=8.9), 6.58 (1H, s), 7.52 (1H, d, J=8.9), 7.55 (2H, brs), 7.68 (2H, d, J=8.9), 7.78 (2H, d, J=8.4)

MS (M/Z) 330/332 (M$^+$)

Molecular formula C$_{15}$H$_{11}$BrN$_2$O$_2$=331

EXAMPLE 6

5-Amino-2-(4-aminophenyl)-6,8-dibromo-4H-1-benzopyran-4-one (Compound 6)

2.0 g (5.8 mmol) of 5-amino-2-(4-aminophenyl)-4H-1-benzopyran-4-one (EP-A-374789) was suspended in 100 ml of acetic acid, 0.45 ml (8.7 mmol) of bromine was added and the mixture was stirred at room temperature for 18. hours. The formed insoluble matters were collected by filtration and triturated with methanol to give 1.23 g (51%) of hydrobromide of Compound 6.

IR (KBr) ν (cm$^{-1}$) 3380, 1621, 1587, 1545, 1515, 1482, 1417, 1285, 1186

NMR (270 MHz, DMSO-d$_6$) δ (ppm) 6.05 (2H, brs), 6.68 (1H, s), 6.69 (2H, d, J=8.8), 7.79 (2H, d, J=8.6), 7.97 (1H, s)

MS (M/Z) 408/410/412 (M$^+$)

Molecular formula C$_{15}$H$_{10}$Br$_2$N$_2$O$_2$=410

EXAMPLE 7

6-Fluoro-5-pivaloylamino-2-(4-pivaloylaminophenyl)-1-4H-benzopyran-4-one (Compound 7)

A solution of 32.2 g of ethyl 2-(N-ethoxycarbonyl-N-pivaloylamino)-3-fluoro-6-methoxymethoxybenzoate obtained in Reference Example 1 and 17.6 g of 4'-pivaloylaminoacetophenone dissolved in 300 ml of dioxane was added dropwise to a suspension of 6.44 g of sodium hydride (60% oil dispersion) in 100 ml of dioxane over 30 minutes under heating at reflux and the mixture was heated at reflux for additional 30 minutes. The reaction solution was cooled, water was added, and the aqueous layer was washed with n-hexane and extracted with ethyl acetate. The ethyl acetate layer was washed with an aqueous saturated solution of sodium chloride, dried over anhydrous sodium sulfate and subjected to silica gel column chromatography (n-hexane-:ethyl acetate=2:1-1:1) to give 25.2 g (63%) of 1,3-diketone.

25.2 g of the resulting 1,3-diketone was dissolved in 300 ml of ethanol, 60 ml of concentrated hydrochloric acid was added and the mixture was stirred at room temperature for 1 hour. Then, 300 ml of water was added and the precipitated crystals were collected by filtration to give Compound 7.

NMR (90 MHz, CDCl$_3$) δ (ppm) 1.37 (9H, s), 1.42 (9H, s), 6.61 (1H, s), 7.11 (1H, dd, J=9.2, 4.2), 7.31 (1H, t, J=9.5), 7.50 (2H, d, J=9.0), 7.68 (2H, d, J=9.0), 8.08 (1H, brs), 10.9 (1H, brs)

MS (M/Z) 438 (M$^+$)

Molecular formula C25H$_{27}$FN$_2$O$_4$=438

EXAMPLE 8

5-Amino-2-(4-aminophenyl)-6-fluoro-4H-1-benzopyran-4-one (Compound 8)

Compound 7 obtained in Example 7 was dissolved in ml of dioxane, 210 ml of concentrated hydrochloric acid was added and the mixture was heated at reflux for 2.5 hours. The reaction solution was cooled on ice and the precipitated crystals were collected by filtration to give 9.08 g (total of hydrochloride of Compound 8.

IR (KBr) ν (cm$^{-1}$) 3425, 3310, 1619, 1595, 1561, 1554, 1485, 1394, 1298, 1248, 1187, 824

NMR (270 MHz, DMSO-d$_6$) δ (ppm) 6.00 (2H, brs), 6.43 (2H, dd, J=8.9, 3.5), 6.54 (1H, s), 6.67 (2H, d, J=7.9), 7.19 (2H, brs), 7.34 (1H, t, J=9.9), 7.69 (2H, d, J=8.4)

MS (M/Z) 270 (M$^+$)

Molecular formula C$_{15}$H$_{11}$FN$_2$O$_2$=270

EXAMPLE 9

8-Fluoro-5-pivaloylamino-2-(4-pivaloylaminophenyl)-H-1-benzopyran-4-one (Compound 9)

A solution of 15.6 g of ethyl 6-(N-ethoxycarbonyl-N-pivaloylamino)-3-fluoro-2-methoxymethoxybenzoate obtained in Reference Example 2 and 7.71 g of 4'-pivaloylaminoacetophenone dissolved in 150 ml of dioxane was added dropwise to a suspension of 3.13 g of sodium hydride (60% oil dispersion) in 40 ml of dioxane over 30 minutes under heating at reflux and the mixture was heated at reflux for additional 30 minutes. 1.56 g of sodium hydride (60% oil dispersion) was added thereto and the mixture was heated at reflux for additional 1 hour. The reaction solution was cooled, water was added, and the aqueous layer was washed with n-hexane and extracted with ethyl acetate. The ethyl acetate layer was washed with an aqueous saturated solution of sodium chloride, dried over anhydrous sodium sulfate and subjected to silica gel column chromatography (n-hexane-:ethyl acetate) to give 15.0 g (85%) of 1,3-diketone.

15.0 g of the resulting 1,3-diketone was dissolved in 100 ml of ethanol, 20 ml of concentrated hydrochloric acid was added and the mixture was stirred at room temperature for 2 hours. The reaction solution was cooled on ice, 100 ml of water was added and the precipitated crystals were collected by filtration to give 9.49 g (72%) of Compound 9.

NMR (90 MHz, CDCl$_3$) δ (ppm) 1.35 (9H, s), 1.38 (9H, s), 6.72 (1H,s), 7.42 (1H, t, J=9.7), 7.52 (1H, brs), 7.72 (2H, d, J=9.0), 7.92 (2H, d, J=9.0), 8.68 (1H, dd, J=9.3, 4.3), 12.5 (1H, brs)

MS (M/Z) 438 (M$^+$)

Molecular formula C$_{25}$H$_{27}$FN$_2$O$_4$=438

EXAMPLE 10

5-Amino-2-(4-aminophenyl)-8-fluoro-4H-1-benzopyran-4-one (Compound 10)

9.48 g of Compound 9 was dissolved in 140 ml of dioxane, 60 ml of concentrated hydrochloric acid was added and the mixture was heated at reflux for 4 hours. The reaction solution was cooled on ice and adjusted to pH 7 by addition of a 10N aqueous solution of sodium hydroxide thereto, water was added, and the precipitated crystals were collected by filtration and triturated with ether to give 5.28 g (91%) of Compound 10.

IR (KBr) ν (cm$^{-1}$) 3480, 3342, 1641, 1552, 1478, 1446, 1187, 819

NMR (270 MHz, DMSO-d$_6$) δ (ppm) 5.97 (2H, brs), 6.51 (1H, s), 6.65 (2H, d, J=8.9), 6.67 (1H, dd, J=9.2, 3.7), 7.25 (2H, brs), 7.37 (1H, dd, J=11.4, 9.4), 7.72 (2H, d, J=8.4)

MS (M/Z) 270 (M$^+$)

Molecular formula C$_{15}$H$_{11}$FN$_2$O$_2$=270

EXAMPLE 11

6,8-Difluoro-5-pivaloylamino-2-(4-pivaloylaminophenyl)-4H-1-benzopyran-4-one (Compound 11)

A solution of 10.6 g of ethyl 3,5-difluoro-6-(N-ethoxycarbonyl-N-pivaloylamino)-2-methoxymethoxybenzoate obtained in Reference Example 3 and 2.09 g of 4'-pivaloylaminoacetophenone dissolved in 40 ml of dioxane was added dropwise to a suspension of 1.27 g of sodium hydride (60% oil dispersion) in 20 ml of dioxane over 30 minutes under heating at reflux and the mixture was heated at reflux for additional 20 minutes. 424 mg of sodium hydride (60% oil dispersion) was added and the mixture was heated at reflux for additional 1 hour. The reaction solution was cooled, water was added, and the aqueous layer was washed with n-hexane and extracted with ethyl acetate. The ethyl acetate layer was washed with an aqueous saturated solution of sodium chloride, dried over anhydrous sodium sulfate and subjected to silica gel column chromatography (n-hexane:ethyl acetate=2:1) to give 2.53 g (46%) of 1,3-diketone.

2.53 g of the resulting 1,3-diketone was dissolved in 50 ml of ethanol, 10 ml of concentrated hydrochloric acid was added and the mixture was stirred at room temperature for 1.5 hours. The reaction solution was cooled on ice and the precipitated crystals were collected by filtration to give 1.42 g (64%) of Compound 11.

NMR (90 MHz, $CDCl_3$) δ (ppm) 1.37 (9H, s), 1.41 (9H, s), 7.12 (1H, t, J=10), 7.53 (2H, d, J=8.8), 7.73 (2H, d, J=8.8), 8.13 (1H, brs), 10.46 (1H, brs)

MS (M/Z) 456 ($M^+$)

Molecular formula $C_{25}H_{26}F_2N_2O_4$=456

EXAMPLE 12

5-Amino-2-(4-aminophenyl)-6,8-difluoro-4H-1-benzopyran-4-one (Compound 12)

1.42 g of Compound 11 was dissolved in 84 ml of dioxane, 36 ml of concentrated hydrochloric acid was added and the mixture was heated at reflux for 3 hours. The reaction solution was cooled on ice and the precipitated crystals were collected by filtration to give 579 mg (57%) of Compound 12.

IR (KBr) ν ($cm^{-1}$) 1653, 1562, 1515, 1483, 1395, 1309, 1121, 985, 832

NMR (270 MHz, DMSO-$d_6$) δ (ppm) 6.05 (2H, brs), 6.58 (1H, s), 6.68 (2H, d, J=8.9), 7.03 (2H, brs), 7.67 (1H, t, J=10.9), 7.71 (2H, d, J=8.9)

MS (M/Z) 288 ($M^+$)

Molecular formula $C_{15}H_{10}F_2N_2O_2$=288

EXAMPLE 13

2-(4-Acetylaminiophenyl)-5-amino-6-fluoro-4H-1-benzopyran-4-one (Compound 13)

10.8 g of Compound 8 was dissolved in 100 ml of pyridine, the solution was cooled to −20° C., 3.78 ml of acetic anhydride was added and the mixture was stirred for 2.3 hours while raising the temperature to room temperature gradually. Then, the reaction solution was poured into 200 ml of ice water, and the precipitated crystals were collected by filtration and triturated with ether to give 10.8 g (86%) of Compound 13.

NMR (90 MHz, DMSO-$d_6$) δ (ppm) 2.10 (3H, s), 6.5–6.8 (1H, m), 6.70 (1H, s), 7.23 (2H, brs), 7.38 (1H, t, J=10), 10.2 (1H, brs)

MS (M/Z) 312 ($M^+$)

Molecular formula $C_{17}H_{13}FN_2O_3$=312

EXAMPLE 14

2-[4-[N-Acetyl-N-(3-phthalimidopropyl)amino]phenyl]-5-amino-6-fluoro-4H-1-benzopyran-4-one (Compound 14)

10.8 g of Compound 13 was dissolved in 150 ml of dimethylformamide, 1.38 g of sodium hydride (60% oil dispersion), 9.28 g of N-(3-bromopropyl)phthalimide and 1.04 g of sodium iodide were added thereto under ice-cooling and the mixture was stirred at room temperature for 1.5 hours. Additional 1.38 g of sodium hydride (60% oil dispersion) and 9.28 g of N-(3-bromopropyl)phthalimide were added thereto and the mixture was stirred at room temperature for 2.3 hours. An aqueous solution of ammonium chloride was added to the reaction solution, the solvent was distilled off under reduced pressure and the residue was extracted once with chloroform. The chloroform layer was washed with an aqueous saturated solution of sodium chloride, and dried over anhydrous sodium sulfate, and the solvent was distilled off under reduced pressure. The residue was subjected to silica gel column chromatography (chloroform:methanol=60:1-40:1) to give 9.98 g (58%) of Compound 14.

NMR (90 MHz, $CDCl_3$) δ (ppm) 1.91 (2H, quint., J=7.3), 1.91 (3H, s), 3.74 (2H, t, J=7.5), 3.87 (2H, t, J=7.0), 6.49 (2H, brs), 6.61 (1H, s), 6.64 (1H, dd, J=10.1, 3.7), 7.24 (1H, t, J=9.0), 7.40 (2H, d, J=8.6), 7.6–7.9 (4H, m), 7.94 (2H, d, J=8.8)

MS (M/Z) 499 ($M^+$)

Molecular formula $C_{28}H_{22}FN_3O_5$=499

EXAMPLE 15

5-Amino-6-fluoro-2-[4-[(3-phthalimidopropyl)amino]phenyl]-4H-1-benzopyran-4-one (Compound 15)

6.0 g of Compound 14 was dissolved in 90 ml of dioxane, 60 ml of concentrated hydrochloric acid was added and the mixture was heated at reflux for 5 hours. The reaction solution was cooled on ice and adjusted to pH 7.5 by addition of a 10N aqueous solution of sodium hydroxide thereto, water was further added, and the precipitated crystals were collected by filtration to give 4.78 g (87%) of Compound 15.

NMR (90 MHz, DMSO-$d_6$) δ (ppm) 1.92 (2H, quint., J=6.6), 3.0–3.3 (2H, m), 3.71 (2H, t, J=6.9), 6.4–6.7 (3H, m), 6.51 (1H, s), 7.36 (1H, t, J=9.5), 7.6–7.9 (6H, m)

MS (M/Z) 457 ($M^+$)

Molecular formula $C_{26}H_{20}FN_3O_4$=457

EXAMPLE 16

5-Amino-2-[4-[(3-aminopropyl)amino]phenyl]-6-fluoro-4-H-1-benzopyran-4-one (Compound 16)

4.78 g of Compound 15 was dissolved in 200 ml of a mixed solvent of dimethylformamide and methanol (1:1), 5.07 ml of hydrazine monohydrate was added and the mixture was stirred at 50–60° C. for 1 hour. The reaction solution was concentrated under reduced pressure, the residue was subjected to silica gel column chromatography (chloroform:methanol :aqueous ammonia=9:1:1) to give Compound 16 which was dissolved in ethanol, a 5.5N hydrochloric acid- isopropylalcohol solution was added, isopropyl ether was added, and the precipitated crystals were collected by filtration to give 2.69 g (64%) of hydrochloride of Compound 16.

IR (KBr) ν (cm$^{-1}$) 3448, 3318, 1646, 1562, 1478, 1445, 1019

NMR (270 MHz, DMSO-d$_6$) δ (ppm) 1.90 (2H, quint., J=6.9), 2.52 (2H, m), 3.24 (2H, t, J=6.9), 6.56 (1H, s), 6.68 (1H, dd, J=8.9, 3.5), 6.77 (2H, d, J=8.4), 7.38 (1H, dd, J=11.4, 8.9), 7.80 (2H, d, J=8.9), 8.13 (2H, brs)

MS (M/Z) 327 (M$^+$)

Molecular formula C$_{18}$H$_{18}$FN$_3$O$_2$=327

EXAMPLE 17

2-(4-Acetylaminophenyl)-5-amino-8-fluroro-4H-1-benzopyran-4-one (Compound 17)

5.28 g of Compound 10 was dissolved in 50 ml of pyridine, the solution was cooled to −10° C., 1.85 ml of acetic anhydride was added and the mixture was stirred for 2.3 hours while raising the temperature to room temperature gradually. Then, the reaction solution was poured into 200 ml of ice water, and the precipitated crystals were collected by filtration and triturated with ether to give 5.42 g (90%) of Compound 17.

NMR (90 MHz, DMSO-d$_6$) δ (ppm) 2.09 (3H, s), 6.47 (1H, dd, J=9.2, 3.7), 6.76 (1H, s), 7.37 (1H, dd, J=10.8, 9.2), 7.76 (2H, d, J=9.0), 7.95 (2H, d, J=8.6)

MS (M/Z) 312 (M$^+$)

Molecular formula C$_{17}$H$_{13}$FN$_2$O$_3$=312

EXAMPLE 18

2-[4-[N-Acetyl-N-(3-phthalimidopropyl)amino]phenyl]-5-amino-8-fluoro-4H-1-benzopyran-4-one (Compound 18)

5.42 g of Compound 17 was dissolved in 80 ml of dimethylformamide, 695 mg of sodium hydride (60% oil dispersion), 5.60 g of N-(3-bromopropyl)phthalimide and 0.52 g of sodium iodide were added thereto under ice-cooling and the mixture was stirred at room temperature for 2 hours. Additional 695 mg of sodium hydride (60% oil dispersion) and 5.60 g of N-(3-bromopropyl)phthalimide were added thereto and the mixture was stirred at room temperature for 3 hours. An aqueous solution of ammonium chloride was added to the reaction solution, the solvent was distilled off under reduced pressure and the residue was extracted once with chloroform. The chloroform layer was washed with an aqueous saturated solution of sodium chloride, and dried over anhydrous sodium sulfate, and the solvent was distilled off under reduced pressure. The residue was subjected to silica gel column chromatography (chloroform:methanol=80:1-70:1) to give 5.81 g (67%) of Compound 18.

NMR (90 MHz, CDCl$_3$) δ (ppm) 1.7–2.1 (2H, m), 1.91 (3H, S), 3.4–4.0 (m, 4H), 6.37 (1H, dd, J=9.0.3.5), 6.65 (1H, s), 7.22 (1H, dd, J=10.3, 9.0), 7.40 (2H, d, J=8.6), 7.5–7.9 (4H, m), 7.98 (2H, d, J=8.6)

MS (M/Z) 499 (M$^+$)

Molecular formula C$_{28}$H$_{22}$FN$_3$O$_5$=499

EXAMPLE 19

5-Amino-8-fluoro-2-[4-[(3-phthalimidopropyl)amino]phenyl]-4H-1-benzopyran-4-one (Compound 19)

5.78 g of Compound 18 was dissolved in 90 ml of dioxane, 60 ml of concentrated hydrochloric acid was added and the mixture was heated at reflux for 4 hours. The reaction solution was cooled on ice and adjusted to pH 7 by addition of a 10N aqueous solution of sodium hydroxide thereto, water was further added, and the precipitated crystals were collected by filtration to give 4.23 g (80%) of Compound 19.

NMR (90 MHz, DMSO-d$_6$) δ (ppm) 1.92 (2H, quint., J=6.4), 3.0–3.4 (2H, m), 3.71 (2H, t, J=7.3), 6.43 (1H, dd, J=9.1, 3.8), 6.68 (2H, d, J=9.0), 7.34 (1H, dd, J=10.6, 9.1), 7.73 (2H, d, J=8.8), 7.84 (4H, brs)

MS (M/Z) 457 (M$^+$)

Molecular formula C$_{26}$H$_{20}$FN$_3$O$_4$=457

EXAMPLE 20

5-Amino-2-[4-[(3-aminopropyl)amino]phenyl]-8-fluoro-4H-1-benzopyran-4-one (Compound 20)

4.22 g of Compound 19 was dissolved in 200 ml of a mixed solvent of dimethylformamide and methanol (1:1), 9.0 ml of hydrazine monohydrate was added and the mixture was stirred at 50–60° C. for 20 minutes. The reaction solution was concentrated under reduced pressure, the residue was subjected to silica gel column chromatography (chloroform:methanol:aqueous ammonia=9:1:1) to give Compound 20 which was dissolved in ethanol, a 5.5N hydrochloric acid-isopropylalcohol solution was added, and the precipitated crystals were collected by filtration to give 1.47 g (40%) of Compound 20.

IR (KBr) ν (cm$^{-1}$) 1632, 1608, 1384, 1254. 1194, 824

NMR (270 MHz, DMSO-d$_6$) δ (ppm) 1.88 (2H, quint., J=6.9), 2.90 (2H, m), 3.23 (2H, t, J=6.9), 6.49 (1H, dd, J=9.2, 3.7), 6.61 (1H, s), 6.75 (2H, d, J=8.9), 7.37 (1H, t, J=9.9), 7.77 (2H, d, J=8.4), 8.06 (2H, brs)

MS (M/Z) 327 (M$^+$)

Molecular formula C$_{18}$H$_{18}$FN$_3$O$_2$=327

EXAMPLE 21

2-(4-Acetylamino)phenyl-5-amino-6,8-difluoro-4H-1-benzopyran-4-one (Compound 21)

720 mg of Compound 12 was dissolved in 10 ml of pyridine, the solution was cooled on ice, 0.24 ml of acetic anhydride was added and the mixture was stirred at 0° C. for 40 minutes. Then, the reaction solution was added to 20 ml of ice water, and the precipitated crystals were collected by filtration to give 696 mg (84%) of Compound 21.

NMR (90 MHz, DMSO-d$_6$) δ (ppm) 2.09 (3H, s), 6.79 (1H, s), 7.03 (2H, brs), 7.70 (1H, t, J=11.4), 7.75 (2H, d, J=9.9), 7.95 (2H, d, J=8.8), 10.2 (1H, brs)

MS (M/Z) 330

Molecular formula C$_7$H$_{12}$F$_2$N$_2$O$_3$=330

EXAMPLE 22

5-Amino-2-[4-[N-acetyl-N-(3-phthalimidopropyl)amino]phenyl]-6,8-difluoro-4H-1-benzopyran-4-one (Compound 22)

690 mg of Compound 21 was dissolved in 10 ml of dimethylformamide, 83.6 mg of sodium hydride (60% oil dispersion), 673 mg of N-(3-bromopropyl)phthalimide and 62.7 mg of sodium iodide were added under ice-cooling and the mixture was stirred at room temperature for 1 hour. Additional 83.6 mg of sodium hydride (60% oil dispersion) and 673 mg of N-(3-bromopropyl)phthalimide were added and the mixture was stirred at room temperature for 1.3 hours. Additional 83.6 mg of sodium hydride (60% oil suspension) and 673 mg of N-(3-bromopropyl)phthalimide were added and the mixture was stirred at room temperature for 3.5 hours. An aqueous solution of ammonium chloride was added to the reaction solution, the solvent was distilled off under reduced pressure and the residue was extracted once with chloroform. The chloroform layer was washed with an aqueous saturated solution of sodium chloride, and dried over anhydrous sodium sulfate, and the solvent was distilled off under reduced pressure. The residue was subjected to silica gel column chromatography (chloroform:methanol=80:1–60:1) to give 0.84 g (78%) of Compound 22.

NMR (90 MHz, $CDCl_3$) δ (ppm) 1.7–2.1 (2H, m), 1.91 (3H, s), 3.74 (2H, t, J=7.3), 3.86 (2H, t, J=6.7), 6.22 (2H, brs), 6.64 (1H, s), 7.21 (1H, t, J=10.4), 7.41 (2H, d, J=8.6), 7.6–7.9 (4H, m), 7.98 (2H, d, J=8.6)

MS (M/Z) 517 ($M^+$)

Molecular formula $C_{28}H_{21}F_2N_3O_5$=517

EXAMPLE 23

5-Amino-6,8-difluoro-2-[4-[(3-phthalimidopropyl)amino]phenyl]-4H-1-benzopyran-4-one (Compound 23)

0.83 g of Compound 22 was dissolved in 12 ml of dioxane, 8 ml of concentrated hydrochloric acid was added and the mixture was heated at reflux for 4 hours. The reaction solution was cooled on ice and adjusted to pH 8 by addition of a 10N aqueous solution of sodium hydroxide thereto, and the precipitated crystals were collected by filtration to give 605 mg (79%) of Compound 23.

NMR (90 NHz, DMSO-$d_6$) δ (ppm) 1.93 (2H, quint., J=6.7), 3.19 (2H, t, J=6.7), 3.71 (2H, t, J=6.8), 6.58 (1H, s), 6.68 (2H, d, J=8.8), 7.63 (1H, t, J=11.4), 7.73 (2H, d, J=8.8), 7.84 (4H, brs)

MS (M/Z) 475

Molecular formula $C_{26}H_{19}F_2N_3O_4$=475

EXAMPLE 24

5-Amino-2-[4-[(3-aminopropyl)amino]phenyl]-6,8-difluoro-4H-1-benzopyran-4-one (Compound 24)

600 mg of Compound 23 was dissolved in 75 ml of a mixed solvent of dimethylformamide and methanol (1:1), 0.613 ml of hydrazine monohydrate was added and the mixture was stirred at 50° to 60° C. for 1.5 hours. Additional 0.307 ml of hydrazine monohydrate was added and the mixture was stirred at 50° to 60° C. for 10 minutes. The reaction solution was concentrated under reduced pressure, the residue was subjected to silica gel column chromatography (chloroform:methanol:aqueous ammonia =9:1:1) to give Compound 24 which was dissolved in ethanol, a 5.5N hydrochloric acid-isopropylalcohol solution was added, and the precipitated crystals were collected by filtration to give 331 mg (69%) of Compound 24.

IR (KBr) ν ($cm^{-1}$) 3446, 3328, 1650, 1633, 1609, 1567, 1483, 1394, 1313, 1191, 1121, 986

NMR (270 Mhz, DMSO-$d_6$) δ (ppm) 1.90 (2H, quint., J=7.3), 2.91 (2H, m), 3.23 (2H, t, J=6.9), 6.62 (1H, s), 6.76 (2H, d, J=8.9), 7.66 (1H, t, J=11.1), 7.77 (2H, d, J=8.9), 8.12 (2H, brs)

MS (M/Z) 345 ($M^+$)

Molecular formula $C_{18}H_{17}F_2N_3O_2$=345

EXAMPLE 25

6,8-Difluoro-2-(3-fluoro-4-pivaloylaminophenyl)-5-pivaloylamino-4H-1-benzopyran-4-one (Compound 25)

A solution of 4.19 g of ethyl 3,5-difluoro-6-(N-ethoxycarbonyl-N-pivaloylamino)-2-methoxymethoxybenzoate obtained in Reference Example 3 and 1.98 g of 3'-fluoro-4'-pivaloylaminoacetophenone dissolved in 23 ml of dioxane was added dropwise to a suspension of 737 mg of sodium hydride (60% oil dispersion) in 10 ml of dioxane under heating at reflux and the mixture was heated at reflux for 2.3 hours. The reaction solution was cooled, water was added, and the aqueous layer was washed with n-hexane and extracted with ethyl acetate. The ethyl acetate layer was washed with an aqueous saturated solution of sodium chloride, dried over anhydrous sodium sulfate and subjected to silica gel column chromatography (chloroform:acetone= 40:1–30:1) to give 3.37 g (75%) of 1,3-diketone.

3.37 g of the resulting 1,3-diketone was dissolved in 80 ml of ethanol, 20 ml of concentrated hydrochloric acid was added and the mixture was stirred at room temperature for 6.6 hours. The reaction solution was cooled on ice, 100 ml of water was added and the precipitated crystals were collected by filtration to give 2.72 g (91%) of Compound 25.

NMR (90 MHz, $CDCl_3$) δ (ppm) 1.36 (9H, s), 1.38 (9H, s), 6.68 (1H, s), 7.35 (1H, t, J=9.8), 7.5–7.9 (2H, m), 8.60 (1H, t, J=8.4)

MS (M/Z) 474 ($M^+$)

Molecular formula $C_{25}H_{25}F_3N_2O_4$=474

EXAMPLE 26

5-Amino-2-(4-amino-3-fluorophenyl)-6,8-difluoro-4H-1-benzopyran-4-one (Compound 26)

3.90 g of Compound 25 was dissolved in 180 ml of dioxane, 180 ml of concentrated hydrochloric acid was added and the mixture was heated at reflux for 3 hours. The reaction solution was cooled on ice, and the precipitated crystals were collected by filtration and recrystallized from methanol/chloroform to give 1.31 g (52%) of Compound 26.

IR (KBr) ν ($cm^{-1}$) 3313, 1625, 1600, 1560, 1525, 4, 1390, 1308, 1120

NMR (270 MHz, DMSO-$d_6$) δ (ppm) 6.69 (1H, s), 6.88 (1H, t, J=8.7), 7.5–7.8 (3H, m)

MS (M/Z) 306 ($M^+$)

Molecular formula $C_{15}H_9F_3N_2O_2$=306

EXAMPLE 27

2-(4-Acetylamino-3-fluorophenyl)-5-amino-6,8-difluoro-4H-1-benzopyran-4-one (Compound 27)

1.66 g of Compound 26 was dissolved in 20 ml of pyridine, the solution was cooled on ice, 0.46 ml of acetic anhydride was added and the mixture was stirred at room temperature for 2.2 hours. Then, the reaction solution was added to 100 ml of ice water and the precipitated crystals were collected by filtration to give 1.82 g (96%) of Compound 27.

NMR (90 MHz, DMSO-$d_6$) δ (ppm) 2.15 (3H, s), 6.89 (1H, s), 7.03 (2H, brs), 7.5–8.0 (3H, m), 8.26 (1H, t, J=8.4), 9.99 (1H, brs)

MS (M/Z) 348 ($M^+$)

Molecular formula $C_{17}H_{11}F_3N_2O_3$=348

EXAMPLE 28

2-[4-[N-Acetyl-N-(3-phthalimidopropyl)amino]-3-fluorophenyl]-5-amino-6,8-difluoro-4H-1-benzopyran-4-one (Compound 28)

1.81 g of Compound 27 was dissolved in 60 ml of dimethylformamide, 208 mg of sodium hydride (60% oil dispersion), 1.67 g of N-(3-bromopropyl)phthalimide and 156 mg of sodium iodide were added and the mixture was stirred at room temperature for 2.5 hours. Additional 104 mg of sodium hydride (60% oil dispersion) and 697 mg of N-(3-bromopropyl)phthalimide were added and the mixture was stirred at room temperature for 1.8 hours. Additional 62.4 mg of sodium hydride (60% oil dispersion) and 418 mg of N-(3-bromopropyl)phthalimide were added and the mixture was stirred at room temperature for 2 hours. An aqueous solution of ammonium chloride was added to the reaction solution, the solvent was distilled off under reduced pressure and the residue was extracted once with chloroform. The chloroform layer was washed with an aqueous saturated solution of sodium chloride, and dried over anhydrous sodium sulfate, and the solvent was distilled off under reduced pressure. The residue was subjected to silica gel column chromatography (chloroform:methanol= 100:1–60:1) and recrystallized from chloroform/n-hexane to give 1.72 g (62%) of Compound 28.

NMR (90 MHz, CDCl$_3$) δ (ppm) 1.7–2.1 (2H, m), 1.90 (3H, s), 3.6–4.0 (4H, m), 6.23 (2H, brs), 6.63 (1H, s), 7.22 (1H, t, J=10.4), 7.49 (1H, t, J=7.41), 7.6–7.9 (6H, m)

MS (M/Z) 535 (M$^+$)

Molecular formula $C_{28}H_{20}F_3N_3O_5$=535

EXAMPLE 29

5-Amino-6,8-difluoro-2-[3-fluoro-4-[(3-phthalimidopropyl)amino]phenyl]-4H-1-benzopyran-4-one (Compound 29)

1.0 g of Compound 28 was dissolved in 12 ml of dioxane, 8 ml of concentrated hydrochloric acid was added and the mixture was heated at reflux for 4.3 hours. The reaction solution was cooled on ice and adjusted to pH 8 by addition of a 10N aqueous solution of sodium hydroxide thereto, and the precipitated crystals were collected by filtration to give 805 mg (87%) of Compound 29.

NMR (90 MHz, DMSO-d$_6$) δ (ppm) 1.94 (2H, quint., J=6.6), 3.1–3.4 (2H, m), 3.69 (2H, t, J=6.6), 6.33 (1H, m), 6.69 (1H, s), 6.84 (1H, t, J=8.8), 7.00 (2H, brs), 7.4–7.8 (3H, m), 7.84 (4H, s)

MS (M/Z) 493 (M$^+$)

Molecular formula $C_{26}H_{18}F_3N_3O_4$=493

EXAMPLE 30

5-Amino-2-[4-(3-aminopropylamino)-3-fluorophenyl]-6,8-difluoro-4H-1-benzopyran-4-one (Compound 30)

800 mg of Compound 29 was dissolved in 100 ml of a mixed solvent of dimethylformamide and methanol (1:1), 0.787 ml of hydrazine monohydrate was added and the mixture was stirred at 50° to 60° C. for 1 hour. The reaction solution was concentrated under reduced pressure, the residue was subjected to silica gel column chromatography (chloroform:methanol:aqueous ammonia=9:1:1) to give Compound 30 which was dissolved in ethanol, a 5.5N hydrochloric acid-isopropylalcohol solution was added, and the precipitated crystals were collected by filtration to give 321 mg (49%) of hydrochloride of Compound 30.

IR (KBr) ν (cm$^{-1}$) 1652, 1618, 1558, 1538, 1481, 1390, 1309, 1118, 987

NMR (270 MHz, DMSO-d$_6$) δ (ppm) 2.00 (2H, quint., J=7.1), 3.00 (2H, m), 3.4–3.6 (2H, m), 6.87 (1H, s), 7.07 (1H, t, J=8.9), 7.7–7.9 (3H, m)

MS (M/Z) 363 (M$^+$)

Molecular formula $C_{18}H_{16}F_3N_3O_2$=363

EXAMPLE 31

2-[4-[N-acetyl-N-(3-phthalimidopropyl)amino]-3-fluorophenyl]-6,8-difluoro-5-hexylamino-4H-1-benzopyran-4-one (Compound 31)

450 mg of Compound 28 was dissolved in 15 ml of dimethylformamide, 0.62 ml of 1-iodohexane and 34 mg of sodium hydride (60% oil dispersion) were added under ice-cooling and the mixture was stirred at room temperature for 2 hours. An aqueous solution of ammonium chloride was added, the reaction solution was concentrated under reduced pressure and the residue was extracted once with chloroform. The chloroform layer was washed with an aqueous saturated solution of sodium chloride, dried over anhydrous sodium sulfate and concentrated under reduced pressure. The residue was subjected to silica gel column chromatography (n-hexane:ethyl acetate=1:1–1:3) to give 184 mg (35%) of Compound 31.

NMR (90 MHz, CDCl$_3$) δ (ppm) 0.7–2.1 (11H, m), 1.90 (3H, s), 3.3–4.0 (6H, m), 6.59 (1H, s), 7.17 (1H, dd, J=13.4, 10.3), 7.48 (1H, t, J=7.9), 7.6–7.9 (6H, m), 8.73 (1H, brt)

MS (M/Z) 619 (M$^+$)

Molecular formula $C_{34}H_{32}F_3N_3O_5$=619

EXAMPLE 32

6,8-Difluoro-2-[3-fluoro-4-[(3-phthalimidopropyl)amino]phenyl]-5-hexylamino-4H-1-benzopyran-4-one (Compound 32)

200 mg of Compound 31 was dissolved in 4 ml of ethanol, 2 ml of concentrated hydrochloric acid was added and the mixture was heated at reflux for 4 hours. The reaction solution was cooled on ice and adjusted to pH 8 by addition of a 10N aqueous solution of sodium hydroxide thereto, and the precipitated crystals were collected by filtration and subjected to preparative thin layer chromatography (chloroform:acetone=20:1) to give 63 mg (34%) of Compound 32.

NMR (90 MHz, CDCl$_3$) δ (ppm) 0.8–1.8 (11H, m), 2.03 (2H, quint., J=6.4), 3.2–3.6 (4H, m), 3.84 (2H, t, J=6.4), 4.80 (1H, m), 6.42 (1H, s), 6.72 (1H, t, J=8.7), 7.10 (1H, dd, J=13.5, 10.4), 7.48 (1H, dd, J=10.4, 2.3), 7.6–8.0 (5H, m), 8.81 (1H, brt)

MS (M/Z) 577 (M$^+$)

Molecular formula $C_{32}H_{30}F_3N_3O_4$=577

EXAMPLE 33

2-[4-(3-Aminopropylamino)-3-fluorophenyl]-6,8-difluoro-5-hexylamino-4H-1-benzopyran-4-one (Compound 33)

60 mg of Compound 32 was dissolved in 30 ml of a mixed solvent of dimethylformamide and methanol, 0.050 ml of hydrazine monohydrate was added and the mixture was stirred at 60° to 70° C. for 4.3 hours. The reaction solution was concentrated under reduced pressure, and the residue was subjected to preparative thin layer chromatography (chloroform:methanol:aqueous ammonia=9:1:1) to give Compound 33 which was dissolved in chloroform. A 5.5N hydrochloric acid-isopropylalcohol solution was added, the solvent was distilled off under reduced pressure and the residue was treated with isopropyl ether to form the slurry from which 33.6 mg (67%) of hydrochloride of Compound 33 was obtained.

IR (KBr) ν (cm$^{-1}$) 2920, 1651, 1610, 1527, 1277, 982, 860

NMR (270 MHz, DMSO-d$_6$) δ (ppm) 0.86 (3H, t, J=6.7), 1.2–1.7 (10H, m), 1.8–2.0 (2H, m), 2.8–3.0 (2H, m), 3.3–3.5 (2H, m), 6.78 (1H, s), 6.90 (1H, t, J=8.7), 7.6–7.8 (3H, m)

MS (M/Z) 447 (M$^+$)

Molecular formula C$_{24}$H$_{28}$F$_3$N$_3$O$_2$=447

EXAMPLE 34

5-Amino-2-(4-amino-3,5-difluorophenyl)-6,8-difluoro-4H-1-benzopyran-4-one (Compound 34)

600 mg of sodium hydride (60% oil dispersion) was suspended in 20 ml a mixed solvent of dioxane-toluene (1:1), a solution of 2.18 g (5.5 mmol) of ethyl 3,5-difluoro-6-(N-pivaloylamino)-2-(2-tetrahydropyranyloxy)benzoate (Compound E) obtained in Reference Example 4 and 1.28 g (5.0 mmol) of 3',5'-difluoro-4'-pivaloylaminoacetophenone dissolved in 20 ml of the above mixed solvent was added dropwise and the mixture was heated at reflux for 2 hours. The reaction solution was cooled, water was added, and the aqueous layer was washed with n-hexane and extracted with ethyl acetate. The organic layer was washed with an aqueous saturated solution of sodium chloride, dried over anhydrous sodium sulfate and the solvent was distilled off under reduced pressure. The residue was purified by silica gel column chromatography (n-hexane:ethyl acetate=2:1–1:1) to give 1.07 g (36%) of 1,3-diketone.

1.06 g (1.78 mmol) of the resulting 1,3-diketone was dissolved in 9 ml of ethanol, 1 ml of concentrated hydrochloric acid was added, the mixture was stirred at room temperature for 5 hours, additional 1 ml of concentrated hydrochloric acid was added and the mixture was stirred at room temperature for 19 hours. Water was added to the reaction solution and the precipitated crystals were collected by filtration to give 858 mg (98%) of 6,8-difluoro-2-(3,5-difluoro-4-pivaloylaminophenyl)-5-pivaloylamino-4H-1-benzopyran-4-one.

NMR (90 MHz, CDCl$_3$) δ (ppm) 1.39 (18H, s), 6.62 (1H, s), 7.2–7.5 (3H, m), 7.75 (1H, brs), 10.4 (1H, brs)

MS (M/Z) 492 (M$^+$)

Molecular formula C$_{25}$H$_{24}$F$_4$N$_2$O$_4$=492

10 ml of dioxane and 5 ml of concentrated hydrochloric acid were added to the resulting 6,8-difluoro-2-(3,5-difluoro-4-pivaloylaminophenyl)-5-pivaloylamino-4H-1-benzopyran-4-one and the mixture was heated at reflux for 4 hours. Additional 5 ml of concentrated hydrochloric acid was added and the mixture was heated at reflux for 4 hours. The mixture was adjusted to pH 9 by addition of a 10N aqueous solution of sodium hydroxide thereto, the mixture was extracted with a mixed solvent of chloroform and methanol, the organic layer was washed with an aqueous saturated solution of sodium chloride and dried over anhydrous sodium sulfate, and the solvent was distilled off under reduced pressure. The residue was purified by silica gel column chromatography (chloroform:methanol=20:1) and recrystallized from chloroform/methanol to give 224 mg (41%) of Compound 34.

NMR (270 MHz, DMSO-d$_6$) δ (ppm) 6.17 (2H, brs), 6.80 (1H, s), 7.06 (2H, brs), 7.60 (2H, dd, J=7.7, 2.7), 7.71 (1H, t, J=11.1)

MS (M/Z) 324 (M$^+$)

Molecular formula C$_{15}$H$_8$F$_4$N$_2$O$_2$=324

EXAMPLE 35

5-Amino-2-(4-amino-3,6-dichlorophenyl)-6,8-difluoro-4H-1-benzopyran-4-one (Compound 35)

780 mg of sodium hydride (60% oil dispersion) was suspended in δ ml of a mixed solvent of dioxane and toluene (1:1), a solution of 2.97 g (6.5 mmol) of ethyl 3,5-difluoro-6-pivaloylamino-2-(2-tetrahydropyranyloxy)-4-trimethylsilylbenzoate (Compound F) obtained in Reference Example 5 and 1.71 g (6.0 mmol) of 3',5'-dichloro-4'-pivaloylaminoacetophenone dissolved in 18 ml of the above mixed solvent was added dropwise under heating at reflux and the mixture was heated at reflux for 40 minutes. The reaction solution was cooled, water was added and the mixture was extracted with ethyl acetate. The organic layer was washed with an aqueous saturated solution of sodium chloride and dried over anhydrous sodium sulfate and the solvent was distilled off under reduced pressure to give 3.85 g of 1,3-diketone.

This was subjected to the subsequent reaction without purification. That is, the above compound was dissolved in 40 ml of ethanol, 10 ml of concentrated hydrochloric acid was added and the mixture was stirred at room temperature for 18 hours. Water was added to the reaction solution and the precipitated crystals were collected by filtration to give 2.69 g of 2-(3,5-dichloro-4-pivaloylaminophenyl)-6,8-difluoro-5-pivaloylamino-7-trimethylsilyl-4H-1-benzopyran-4-one.

The above compound was dissolved in 50 ml of tetrahydrofuran, 1.7 ml of tetrabutylammonium fluoride (1M solution in tetrahydrofuran) was added under ice-cooling and the mixture was stirred at 0° C. for 20 minutes. Water was added thereto, the mixture was extracted with a mixed solvent of chloroform and methanol, and the organic layer was washed once with water and once with an aqueous saturated solution of sodium chloride and dried over anhydrous sodium sulfate. The solvent was distilled off under reduced pressure to give 2.61 g (three stages 84%) of 2-(3,5-dichloro-4-pivaloylaminophenyl)-6,8-difluoro-5-pivaloylamino-4H-1-benzopyran-4-one.

NMR (90 MHz, DMSO-d$_6$) δ (ppm) 1.28 (18H, s), 7.25 (1H, S), 8.02 (1H, t, J=10.3), 8.16 (2H, s), 9.51 (1H, brs), 10.0 (1H, brs)

MS (M/Z) 524/526 (M$^+$)

Molecular formula C$_{25}$H$_{24}$Cl$_2$F$_2$N$_2$O$_4$=525

10 ml of concentrated sulfuric acid was added to the resulting 1.07 g (2.04 mmol) of 2-(3,5-dichloro-4-pivaloylaminophenyl)-6,8-difluoro-5-pivaloylamino-4H-1-benzopyran-4-one and the mixture was stirred at 100° C. for 16 hours. The reaction solution was poured into ice water and the mixture was extracted with a mixed solvent of chloroform and methanol. The organic layer was washed with an aqueous saturated solution of sodium chloride and dried over anhydrous sodium chloride and the solvent was distilled off under reduced pressure. The residue was purified by silica gel column chromatography (chloroform:methanol=50:1–6:1) and triturated with chloroform to give 546 mg (75%) of Compound 35.

NMR (270 MHz, DMSO-d$_6$) δ (ppm) 6.38 (2H, brs), 6.83 (1H, s), 7.06 (2H, brs), 7.72 (1H, t, J=11.1), 7.87 (2H, s)

MS (M/Z) 356/358/360 (M$^+$)

Molecular formula C$_{15}$H$_8$Cl$_2$F$_2$N$_2$O$_2$=357

EXAMPLE 36

5-Amino-2-(4-amino-3,5-dibromophenyl)-6,8-difluoro-4H-1-benzopyran-4-one (Compound 36)

1.32 g of sodium hydride (60% oil dispersion) was suspended in 15 ml of dioxane, a solution of 5.03 g (11 mmol) of ethyl 3,5-difluoro-6-pivaloylamino-2-(2- tetrahydropyranyloxy)-4-trimethylsilylbenzoate (Compound F) obtained in Reference Example 5 and 2.93 g (10 mmol) of 4'-amino-3',5'-dibromoacetophenone dissolved in 35 ml of dioxane was added dropwise under heating at reflux and the mixture was heated at reflux for 1 hour. The reaction solution was cooled, water was added and the mixture was extracted with ethyl acetate. The organic layer was washed with an aqueous saturated solution of sodium chloride and dried over anhydrous sodium sulfate and the solvent was distilled off under reduced pressure to give 7.07 g of 1,3-diketone.

This was subjected to the subsequent reaction without purification. That is, the above compound was dissolved in 80 ml of ethanol, 20 ml of concentrated hydrochloric acid was added and the mixture was stirred at room temperature for 18 hours. Water was added to the reaction solution and the precipitated crystals were collected by filtration to give 2.42 g (two stages 46%) of 2-(4-amino-3,5-dibromophenyl)-6,8-difluoro-5-pivaloylamino-4H-1-benzopyran-4-one.

20 ml of concentrated sulfuric acid was added to the resulting 1.00 g (1.89 mmol) of 2-(4-amino-3,5-dibromophenyl)-6,8-difluoro-5-pivaloylamino-4H-1-benzopyran-4-one and the mixture was stirred at 100° C. for 1.3 hours. The reaction solution was adjusted to pH 9 by addition of ice and a 10N aqueous solution of sodium hydroxide thereto and the precipitated crystals were collected by filtration. The crystals were purified by silica gel column chromatography (chloroform:acetonitrile=40:1) and triturated with chloroform to give 378 mg (45%) of Compound 36.

NMR (270 MHz, DMSO-$d_6$) δ (ppm) 6.17 (2H, brs), 6.84 (1H, s), 7.06 (2H, brs), 7.72 (1H, t, J=11.1), 8.06 (2H, s)

MS (M/Z) 444/446/448 (M$^+$)

Molecular formula $C_{15}H_8Br_2F_2N_2O_2$=446

EXAMPLE 37

5-Amino-6,8-difluoro-2-(3-fluoro-4-methylaminophenyl)-4H-1-benzopyran-4-one (Compound 37)

500 mg (1.44 mmol) of Compound 27 obtained in Example 27 was dissolved in 30 ml of dimethylformamide under argon atmosphere and the solution was cooled on ice. 0.27 ml of iodomethane and 63 mg of sodium hydride (60% oil dispersion) were added, the mixture was stirred at the same temperature for 1 hour and the temperature was raised to room temperature to stir for additional 2 hours. Water was added to the reaction solution and the mixture was extracted twice with ethyl acetate. The organic layer was washed once with water and once with an aqueous saturated solution of sodium chloride and dried over anhydrous magnesium sulfate, the solvent was distilled off and the tan residue was purified by silica gel column chromatography (n-hexane:ethyl acetate=3:2) to give 2-[4-(N-acetyl-N-methylamino)-3-fluorophenyl]-5-amino-6,8-difluoro-4H-1-benzopyran-4-one.

NMR (90 MHz, CDCl$_3$) δ (ppm) 1.96 (3H, brs), 3.29 (3H, s), 6.23 (2H, brs), 6.63 (1H, s), 7.23 (1H, t, J=10.4), 7.40 (1H, t, J=7.9), 7.70 (1H, brs), 7.80 (1H, brs)

MS (M/Z) 362 (M$^+$)

Molecular formula $C_{18}H_{13}F_3N_2O_3$=362

500 mg (1.53 mmol) of the resulting 2-[4-(N-acetyl-N-methylamino)-3-fluorophenyl]-5-amino-6,8-difluoro-4H-1-benzopyran-4-one was dissolved in a mixed solvent of 10 ml of dioxane and 5 ml of concentrated hydrochloric acid and the solution was heated at reflux for 2.5 hours. The reaction solution was cooled, water was added, the mixture was made weak alkaline, and the precipitated crystals were collected by filtration and dried under reduced pressure. The resulting tan residue was purified twice by silica gel column chromatography (chloroform) to give 180 mg of Compound 37.

NMR (270 MHz, CDCl$_3$) 2.97 (3H, d, J=5.3), 4.45 (1H, brs), 6.19 (2H, brs), 6.48 (1H, s), 6.72 (1H, t, J=8.7), 7.16 (1H, t, J=10.6), 7.53 (1H, dd, J=12.7, 2), 7.63,(1H, dd, J=8.4, 1.8)

MS (M/Z) 320 (M$^+$)

Molecular formula $C_{16}H_{11}F_3N_2O_2$=320

EXAMPLE 38

5-Amino-6,8-difluoro-2-[4-(N,N-dimethylamino)-3-fluorophenyl]-4H-1-benzopyran-4-one (Compound 38)

3.36 g of sodium hydride (60% oil dispersion) was suspended in 50 ml of a mixed solvent of dioxane and toluene (1:1), a solution of 17.8 g (46 mmol) of ethyl 3,5-difluoro-6-pivaloylamino-2-(2-tetrahydropyranyloxy)benzoate obtained in Reference Example 4 and 7.61 g (42 mmol) .of 4'-(N,N-dimethylamino)-3'-fluoroacetophenone dissolved in 160 ml of the above mixed solvent was added dropwise under heating at reflux and the mixture was heated at reflux for 1.5 hours. The reaction solution was cooled, water was added, and the aqueous layer was washed with n-hexane and extracted with ethyl acetate. The organic layer was washed with an aqueous saturated solution of sodium chloride and dried over anhydrous sodium sulfate and the solvent was distilled off under reduced pressure to give 1,3-diketone, The resulting 1,3-diketone was dissolved in 160 ml of ethanol, 40 ml of concentrated hydrochloric acid was added and the mixture was stirred at room temperature for 2 hours and at 40° C. for 30 minutes. The reaction solution was cooled on ice and adjusted to pH 9 by addition of a 10N aqueous solution of sodium hydroxide thereto, and the precipitated crystals were collected by filtration to give 6.59 g (two stages 38%) of 6,8-difluoro-2-[4-(N,N-dimethylamino)-3-fluorophenyl]-5-pivaloylamino-4H-1-benzopyran-4-one.

NMR (90 MHz, CDCl$_3$) δ (ppm) 1.38 (9H, s), 3.04 (6H, d, J=1.5), 6.58 (1H, s), 6.86 (1H, t, J=9.0), 7.32 (1H, t, J=10.0), 7.4–7.7 (2H, m), 10.6 (1H, brs)

MS (M/Z) 418 (M$^+$)

Molecular formula $C_{22}H_{21}F_3N_2O_3$=418

4.00 g (9.57 mmol) of the resulting 6,8-difluoro-2-[4-(N, N-dimethylamino)-3-fluorophenyl]-5-pivaloylamino-4H-1-benzopyran-4-one was dissolved in 60 ml of dioxane, 40 ml of concentrated hydrochloric acid was added and the mixture was heated at reflux for δ hours. The reaction solution was cooled on ice and adjusted to pH 9 by addition of a 10N aqueous solution of sodium hydroxide thereto, and the mixture was extracted with chloroform. The organic layer was washed with an aqueous saturated solution of sodium chloride and dried over anhydrous sodium sulfate, and the solvent was distilled off under reduced pressure. The residue was purified by silica gel column chromatography (chloroform:acetone=30:1) and recrystallized from chloroform/n-hexane to give 2.52 g (79%) of Compound 38.

NMR (270 MHz, CDCl$_3$) δ (ppm) 3.05 (6H, d, J=1.5), 6.24 (2H, s), 6.51 (1H, s), 6.97 (1H, t, J=8.7), 7.18 (1H, t, J=10.6), 7.5–7.8 (2H, m)

MS (M/Z) 334 (M$^+$)

Molecular formula C$_{17}$H$_{13}$F$_3$N$_2$O$_2$=334

EXAMPLE 39

5-Amino-6,8-difluoro-2-[3-fluoro-4-(2-methoxyethylamino)phenyl]-4H-1-benzopyran-4-one (Compound 39)

1.20 g of sodium hydride (60% oil dispersion) was suspended in 30 ml of a mixed solvent of dioxane and toluene (1:1), a solution of 6.35 g (17 mmol) of ethyl 3,5-difluoro-6-pivaloylamino-2-(2-tetrahydropyranyloxy-)benzoate (Compound E) obtained in Reference Example 4 and 3.80 g (15 mmol) of 4'-[N-acetyl-N-(2-methoxyethyl)amino]-3'-fluoroacetophenone dissolved in 100 ml of the above mixed solvent was added dropwise under heating at reflux and the mixture was heated at reflux for 1.5 hours. The reaction solution was cooled, water was added, and the aqueous layer was washed with n-hexane and extracted with five times with ethyl acetate. The organic layer was washed with an aqueous saturated solution of sodium chloride and dried over anhydrous sodium sulfate and the solvent was distilled off under reduced pressure. The residue was purified by silica gel column chromatography (n-hexane:ethyl acetate=2:1–1:2) to give 4.12 g (45%) of 1,3-diketone.

4.11 g (6.94 mmol) of the resulting 1,3-diketone was dissolved in 16 ml of ethanol, 4.0 ml of concentrated hydrochloric acid was added and the mixture was stirred at 40° C. for 45 minutes. The reaction solution was cooled on ice, water was added and the mixture was extracted with chloroform. The organic layer was washed with an aqueous saturated solution of sodium chloride and dried over anhydrous sodium sulfate and the solvent was distilled off under reduced pressure. The residue was purified by silica gel column chromatography (chloroform:methanol=40:1–30:1) to give 3.32 g (98%) of 2-[4-[N-acetyl-N-(2-methoxyethyl)amino]-3-fluorophenyl]-6,8-difluoro-5-pivaloylamino-4H-1-benzopyran-4-one .

NMR (90 MHz, CDCl$_3$) δ (ppm) 1.39 (9H, s), 1.93 (3H, brs), 3.29 (3H, s), 3.5–4.1 (4H, m), 6.74 (1H, s), 7.39 (1H, t, J=10.0), 7.4–7.9 (3H, m), 10.4 (1H, brs)

MS (M/Z) 490 (M$^+$)

Molecular formula C$_{25}$H$_{25}$F$_3$N$_2$O$_5$=490

1.0 g (2.0 mmol) of the resulting 2-[4-[N-acetyl-N-(2-methoxyethyl)amino]-3-fluorophenyl]-6,8-difluoro-5-pivaloylamino-4H-1-benzopyran-4-one was dissolved in 10 ml of ethanol, 10 ml of concentrated hydrochloric acid was added and the mixture was heated at reflux for 4 hours. The reaction solution was cooled on ice and adjusted to pH 9 by addition of a 10N aqueous solution of sodium hydroxide thereto, and the mixture was extracted with a mixed solvent of chloroform and methanol. The organic layer was washed with an aqueous saturated solution of sodium chloride and dried over anhydrous sodium sulfate and the solvent was distilled off under reduced pressure. The residue was purified by silica gel column chromatography (chloroform:methanol=100:1–50:1) and recrystallized from n-hexane/ethyl acetate to give 278 mg (37%) of Compound 39.

NMR (270 MHz, DMSO-d$_6$) δ (ppm) 3.29 (3H, s), 3.38 (2H, q, J=5.4), 3.52 (2H, t, J=5.7), 6.31 (1H, brs), 6.72 (1H, s), 6.89 (1H, t, J=8.9), 7.04 (2H, brs), 7.6–7.8 (3H, m)

MS (M/Z) 364 (M$^+$)

Molecular formula C$_{18}$H$_{15}$F$_3$N$_2$O$_3$=364

EXAMPLE 40

5-Amino-2-[4-[2-(N',N'-dimethylamino)ethylamino]-3-fluorophenyl]-6,8-difluoro-4H-1-benzopyran-4-one (Compound 40)

1.30 g (3.74 mmol) of Compound 27 obtained in Example 27 was dissolved in 40 ml of dimethylformamide under argon atmosphere, 608 mg of sodium hydride (60% oil dispersion) and 1.09 g of 2-dimethylaminoethyl chloride hydrochloride were added under ice-cooling and the mixture was stirred at room temperature for 1 hour and at 50° to 60° C. for 30 minutes. The reaction solution was cooled on ice, water was added and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol:triethylamine=100:10:1) and recrystallized from ethyl acetate/isopropyl ether to give 493 mg (31%) of 2-[4-[N-acetyl-N-[2-(N',N'-dimethylamino)ethyl]amino]-3-fluorophenyl]-5-amino-6,8-difluoro-4H-1-benzopyran-4-one.

NMR (90 MHz, CDCl$_3$) δ (ppm) 1.90 (3H, brs), 2.19 (6H, s), 3.43 (2H, t, J=6.8), 3.80 (2H, m), 6.22 (2H, brs), 6.64 (1H, s), 7.22 (1H, t, J=10.4), 7.48 (1H, t, J=8.1), 7.7–7.9 (2H, m)

MS (M/Z) 419 (M$^+$)

Molecular formula C$_{21}$H$_{20}$F$_3$N$_3$O$_3$=419

485 mg (1.16 mmol) of the resulting 2-[4-[N-acetyl-N-[2-(N',N'-dimethylamino)ethyl]amino]-3-fluorophenyl]-5-amino-6,8-difluoro-4H-1-benzopyran-4-one was dissolved in 10 ml of dioxane, 5 ml of concentrated hydrochloric acid was added and the mixture was heated at reflux for 2.5 hours. The reaction solution was cooled on ice and adjusted to pH 9 by addition of a 10N aqueous solution of sodium hydroxide thereto, and the mixture was extracted with chloroform. The organic layer was washed with an aqueous saturated solution of sodium chloride and dried over anhydrous sodium sulfate and the solvent was distilled off under reduced pressure. The residue was purified by silica gel column chromatography (chloroform:methanol:aqueous ammonia=50:1:1) to give Compound 40 which was converted into hydrochloride according to the same manner as that in Example 16 to give 204 mg (42%).

NMR (270 MHz, DMSO-d$_6$) δ (ppm) 2.83 (6H, d, J=3.5), 3.2–3.4 (2H, m), 3.5–3.7 (2H, m), 6.63 (1H, brs), 6.78 (1H, s), 7.02 (1H, t, J=8.9), 7.05 (2H, brs), 7.6–7.8 (3H, m), 10.3 (1H, brs)

MS (M/Z) 377 (M$^+$)

Molecular formula C$_{19}$H$_{18}$F$_3$N$_3$O$_2$=377

EXAMPLE 41

5-Amino-6,8-difluoro-2-[3-fluoro-4-[2-(pyrrolidin-1-yl)ethylamino]phenyl]-4H-1-benzopyran-4-one (Compound 41)

1.00 g (2.87 mmol) of Compound 27 obtained in Example 27 was dissolved in 25 ml of dimethylformamide under argon atmosphere, 0.98 g of 1-(2-chloroethyl)pyrrolidine hydrochloride and 0.97 g of potassium tert-butoxide were added under ice-cooling and the mixture was stirred at 70° to 80° C. for 3 hours. Additional 0.49 g of 1-(2-chloroethyl)pyrrolidine hydrochloride and 0.32 g of potassium tert-butoxide were added and the mixture was stirred at the same temperature for 15 hours. The reaction solution was cooled on ice, water was added and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol=40:1-9:1) to give 0.37 g (29%) of 2-[4-[N-acetyl-N-[2-(N',N'-dimethylamino)ethyl]amino]-3-fluorophenyl]-5-amino-6,8-difluoro-4H-1-benzopyran-4-one.

NMR (90 MHz, CDCl$_3$) δ (ppm) 1.6–1.9 (4H, m), 1.91 (3H, s), 2.4–2.9 (6H, m), 3.7–4.1 (2H, m), 6.22 (2H, brs), 6.63 (1H, s), 7.22 (1H, dd, J=10.7, 10.4), 7.52 (1H, t, J=8.9), 7.5–7.8 (2H, m)

MS (M/Z) 445 (M$^+$)

Molecular formula C$_{23}$H$_{22}$F$_3$N$_3$O$_3$=445

0.37 g (0.83 mmol) of the resulting 2-[4-[N-acetyl-N-[2-(N',N'-dimethylamino)ethyl]amino]-3-fluorophenyl]-5-amino-6,8-difluoro-4H-1-benzopyran-4-one was dissolved in 20 ml of dioxane, 10 ml of concentrated hydrochloric acid was added and the mixture was heated at reflux for 2.5 hours. The reaction solution was cooled on ice and adjusted to pH 9 by addition of a 10N aqueous solution of sodium hydroxide thereto, and the mixture was extracted with chloroform. The organic layer was washed with an aqueous saturated solution of sodium chloride and dried over anhydrous sodium sulfate and the solvent was distilled off under reduced pressure. The residue was purified by silica gel column chromatography (chloroform:methanol=40:1-15:1) and recrystallized from ethyl acetate/n-hexane to give 137 mg (41%) of Compound 41. The resulting Compound 41 was converted into hydrochloride according to the same manner as that in Example 16.

NMR (270 MHz, CDCl$_3$) δ (ppm) 1.81 (4H, m), 2.57 (4H, t, J=6.4), 2.80 (2H, t, J=5.7), 3.30 (2H, q, J=5.7), 5.05 (1H, brs), 6.20 (2H, brs), 6.47 (1H, s), 6.72 (1H, t, J=8.6), 7.16 (1H, t, J=10.4), 7.53 (1H, dd, J=12.7, 2.0), 7.61 (1H, dd, J=8.6, 2.0) (free base)

MS (M/Z) 403 (M$^+$)

Molecular formula C$_{21}$H$_{20}$F$_3$N$_3$O$_2$=403

EXAMPLE 42

5-Amino-6,8-difluoro-2-[3-fluoro-4-(2-morpholinoethylamino)phenyl]-4H-1-benzopyran-4-one (Compound 42)

1.50 g (4.31 mmol) of Compound 27 obtained in Example 27 was dissolved in 30 ml of dimethylformamide under argon atmosphere, 517 mg of sodium hydride (60% oil dispersion) and 1.60 g of 1-(2-chloroethyl)morpholine hydrochloride were added under ice-cooling and the mixture was stirred at 50° to 60 ° C. for 1.5 hours. The reaction solution was cooled on ice, water was added and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol=30:1) to give 1.47 g (74%) of 2-[4-[N-acetyl-N-(2-morpholinoethyl)amino]-3-fluorophenyl]-5-amino-6,8-difluoro-4H-1-benzopyran-4-one.

NMR (90 MHz, CDCl$_3$) δ (ppm) 1.92 (3H, s), 2.3–2.6 (4H, m), 2.53 (2H, t, J=6.4), 3.60 (4H, t, J=4.6), 3.7–4.0 (2H, m), 6.22 (2H, brs), 6.64 (1H, s), 7.23 (1H, t, J=10.3), 7.50 (1H, t, J=7.9), 7.6–7.8 (2H, m)

MS (M/Z) 461 (M$^+$)

Molecular formula C$_{23}$H$_{22}$F$_3$N$_3$O$_4$=461

700 mg (1.52 mmol) of the resulting 2-[4-[N-acetyl-N-(2-morpholinoethyl)amino]-3-fluorophenyl]-5-amino-6,8-difluoro-4H-1-benzopyran-4-one was dissolved in 12 ml of dioxane, 8 ml of concentrated hydrochloric acid was added and the mixture was heated at reflux for 3.5 hours. The reaction solution was cooled on ice and adjusted to pH 9 by addition of a 10N aqueous solution of sodium hydroxide thereto, and the mixture was extracted with chloroform. The organic layer was washed with an aqueous saturated solution of sodium chloride and dried over anhydrous sodium sulfate and the solvent was distilled off under reduced pressure. The residue was purified by silica gel column chromatography (chloroform:methanol=20:1) and recrystallized from ethyl acetate to give Compound 42 which was converted into hydrochloride according to the same manner as that in Example 16 to give 315 mg (46%).

NMR (270 MHz, DMSO-d$_6$) δ (ppm) 3.0–4.1 (12H, m), 6.79 (1H, s), 7.04 (1H, t, J=8.7), 7.6–7.8 (3H, m), 11.1 (1H, brs)

MS (M/Z) 419 (M$^+$)

Molecular formula C$_{21}$H$_{20}$F$_3$N$_3$O$_3$=419

EXAMPLE 43

5-Amino-6,8-difluoro-2-[3-fluoro-4-(2-methylthioethylamino)phenyl]-4H-1-benzopyran-4-one (Compound 43)

1.00 g (2.87 mmol) of Compound 27 obtained in Example 27 was dissolved in 30 ml of dimethylformamide under argon atmosphere, 1.43 ml of chloroethyl methyl sulfide and 354 mg of potassium tert-butoxide were added under ice-cooling and the mixture was stirred at 50° to 60 ° C. for 1 hour. Additional 0.29 ml of chloroethyl methyl sulfide and 322 mg of potassium tert-butoxide were added and the mixture was stirred at the same temperature for 17 hours. The reaction solution was cooled on ice, water was added and the mixture was extracted with ethyl acetate. The organic layer was washed with an aqueous solution of sodium chloride and dried over anhydrous sodium sulfate and the solvent was distilled off under reduced pressure. The residue was purified by silica gel column chromatography (chloroform:methanol=30:1) to give 380 mg (32%) of 2-[4-[N-acetyl-N-(2-methylthioethyl)amino]-3-fluorophenyl]-5-amino-6,8-difluoro-4H-1-benzopyran-4-one.

NMR (90 MHz, CDCl$_3$) δ (ppm) 1.92 (3H, brs), 2.12 (3H, s), 2.67 (2H, brt, J=7.0), 3.91 (2H, brt, J=7.0), 6.22 (2H, brs), 6.64 (1H, s), 7.23 (1H, t, J=10.4), 7.47 (1H, t, J=8.0), 7.6–7.9 (2H, m)

MS (M/Z) 422 (M$^+$)

Molecular formula C$_{20}$H$_{17}$F$_3$N$_2$O$_3$S=422

380 mg(0.92 mmol) of the resulting 2-[4-[N-acetyl-N-(2-methylthioethyl)amino]-3-fluorophenyl]-5-amino-6,8-difluoro-4H-1-benzopyran-4-one was dissolved in 6 ml of dioxane, 4 ml of concentrated hydrochloric acid was added and the mixture was heated at reflux for 4 hours. The reaction solution was cooled on ice and adjusted to pH 9 by addition of a 10N aqueous solution of sodium hydroxide thereto, and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:acetone=20:1) and recrystallized from ethyl acetate/n-hexane to give 58 mg (16%) of Compound 43.

NMR (270 MHz, CDCl$_3$) δ (ppm) 2.16 (3H, s), 2.82 (2H, t, J=6.4), 3.47 (2H, t, J=6.4), 6.49 (1H, s), 6.76 (1H, t, J=8.4), 7.17 (1H, t, J=10.6), 7.55 (1H, dd, J=12.4, 2.0), 7.62 (1H, dd, J=8.4, 2.0)

Ms (M/z) 380 (M$^+$)

Molecular formula $C_{18}H_{15}F_3N_2O_2S$=380

EXAMPLE 44

5-Amino-6,8-difluoro-2-(4-ethoxycarbonylmethylamino-3-fluorophenyl)-4H-1-benzopyran-4-one (Compound 44)

3.48 g (10 mmol) of Compound 27 obtained in Example 27 was dissolved in 100 ml of dimethylformamide under argon atmosphere, 1.32 ml of ethyl bromoacetate and 1.23 g of potassium tert-butoxide were added under ice-cooling and the mixture was stirred at room temperature for 25 minutes. The reaction solution was cooled on ice, water was added and the mixture was extracted with ethyl acetate. The organic layer was washed with an aqueous saturated solution of sodium chloride and dried over anhydrous sodium sulfate and the solvent was distilled off under reduced pressure. The residue was triturated with ethyl acetate to give 3.20 g (57%) of 2-[4-(N-acetyl-N-ethoxycarbonylmethylamino)-3-fluorophenyl]-5-amino-6,8-difluoro-4H-1-benzopyran-4-one.

NMR (90 MHz, CDCl$_3$) δ (ppm) 1.28 (3H, t, J=7.3), 1.99 (3H, s), 4.20 (2H, q, J=7.3), 4.38 (2H, brs), 5.19 (2H, brs), 6.63 (1H, s), 7.22 (1H, t, J=10.4), 7.5–7.9 (3H, m)

MS (M/Z) 434 (M$^+$)

Molecular formula $C_{21}H_{17}F_3N_2O_5$=434

2.0 g (4.6 mmol) of the resulting 2-[4-(N-acetyl-N-ethoxycarbonylmethylamino)-3-fluorophenyl]-5-amino-6, 8-difluoro-4H-1-benzopyran-4-one was dissolved in 18 ml of ethanol, 12 ml of concentrated hydrochloric acid was added and the mixture was heated at reflux for 5 hours. The reaction solution was cooled on ice and adjusted to pH 9 by addition of a 10N aqueous solution of sodium hydroxide thereto, and the precipitated crystals were collected by filtration. The crystals were purified by silica gel column chromatography (chloroform:methanol=30:1) and recrystallized from ethyl acetate/n-hexane to give 821 mg (45%) of Compound 44.

NMR (270 MHz, CDCl$_3$) δ (ppm) 1.33 (3H, t, J=7.2), 4.01 (2H, s), 4.29 (2H, q, J=7.2), 6.51 (1H, s), 6.64 (1H, t, J=8.4), 7.18 (1H, t, J=10.6), 7.5–7.7 (2H, m)

MS (M/Z) 392 (M$^+$)

Molecular formula $C_{19}H_{15}F_3N_2O_4$=392

EXAMPLE 45

Sodium salt of 5-amino-2-(4-carboxymethylamino-3-fluorophenyl)-6,8-difluoro-4H-1-benzopyran-4-one (Compound 45)

30 ml ethanol and 4.3 ml of a 2N aqueous solution of sodium hydroxide were added to 560 mg (1.43 mmol) of Compound 44 obtained in Example 44 and the mixture was stirred at 50° C. for 10 minutes. The reaction solution was cooled to room temperature and the precipitated crystals were collected by filtration to give 533 mg (97%) of Compound 45.

NMR (270 MHz,DMSO-d$_6$) δ (ppm) 3.36 (2H, s), 5.90 (1H, brs), 6.68 (1H, t, J=8.9), 7.05 (2H, brs), 7.6–7.8 (3H, m)

FAB-MS (M/Z) 365 (M$^+$+1)

Molecular formula $C_{17}H_{11}F_3N_2O_4$=364

EXAMPLE 46

5-Amino-6,8-difluoro-2-[3-fluoro-4-(3-methoxypropylamino)phenyl]- 4H-1-benzopyran-4-one (Compound 46)

949 mg of 1-chloro-3-methoxypropane and 1.30 g of sodium iodide were dissolved in 20 ml of dimethylformamide under argon atmosphere and the mixture was stirred at 90° C. for 2 hours. The reaction solution was cooled on ice and 1.51 g (4.35mmol) of Compound 27 obtained in Example 27 and 89 mg of sodium hydride (60% oil dispersion) were added thereto. The mixture was stirred at room temperature for 1 hour, 943 mg of 1-chloro-3-methoxypropane and 191 mg of sodium hydride (60% oil dispersion) were added, the temperature was raised to 60° C. and the mixture was stirred for 2 days. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=100:1) to give 1.18 g (65%) of 2-[4-[N-acetyl-N-(3-methoxypropyl)amino]-3-fluorophenyl]-5-amino-6,8-difluoro-4H-1-benzopyran-4-one.

NMR (90 MHz, CDCl$_3$) δ (ppm) 1.6–2.1 (2H, m), 1.90 (3H, s), 3.27 (3H, s), 3.41 (2H, t, J=6.0), 3.81-(2H, t, J=7.4), 4.0–4.9 (2H, brs), 6.63 (1H, s), 7.22 (1H, t, J=10.4), 7.40 (1H, t, J=7.7), 7.69–7.80 (2H, m)

MS (M/Z) 420 (M$^+$)

Molecular formula $C_{21}H_{19}F_3N_2O_4$=420

501 mg (1.19 mmol) of the resulting 2-[4-[N-acetyl-N-(3-methoxypropyl)amino]-3-fluorophenyl]-5-amino-6,8-difluoro-4H-1-benzopyran-4-one was dissolved in 6 ml of dioxane, 6 ml of concentrated hydrochloric acid was added and the mixture was stirred for 3 hours under heating at reflux. The reaction solution was cooled on ice, water was added, the mixture was adjusted to pH 8, and the precipitated crystals were collected by filtration and purified by silica gel column chromatography (n-hexane:ethyl acetate=6:1) to give 279 mg (62%) of Compound 46.

NMR (270 MHz, CDCl$_3$) δ (ppm) 1.95 (2H, quint., J=6.1), 3.34 (2H, t, J=6.2), 3.38 (3H, s), 3.54 (2H, t, J=5.7), 4.80 (1H, brs), 6.19 (2H, brs), 6.47 (1H, s), 6.73 (1H, t, J=8.4), 7.16 (1H, t, J=10.4), 7.52 (1H, dd, J=12.9, 2.0), 7.60 (1H, dd, J=8.4, 2.0)

MS (M/Z) 378 (M$^+$)

Molecular formula $C_{19}H_{17}F_3N_2O_3$=378

EXAMPLE 47

5-Amino-6,8-difluoro-2-[4-[3-(N',N'-dimethylamino)propylamino]-3-fluorophenyl]-4H-1-benzopyran-4-one (Compound 47)

736 mg of sodium hydride (60% oil dispersion) was suspended in a mixed solvent of 10 ml of dioxane and 10 ml of toluene under argon atmosphere and the suspension was heated at reflux. 4.03 g (8.8 mmol) of Compound F obtained in Reference Example 5 and 2.46 g (8.8 mmol) of 4'-[N-acetyl-N-[3-(N',N'-dimethylamino)propyl]amino]-3'-fluoroacetophenone dissolved in a mixed solvent of 25 ml of dioxane and 25 ml of toluene were added dropwise thereto and the mixture was stirred for 1.5 hours. The reaction solution was cooled, water was added, the mixture was extracted with ethyl acetate, the organic layer was washed with an aqueous saturated solution of sodium chloride and dried over anhydrous sodium sulfate, and the solvent was distilled off under reduced pressure. The residue was purified by silica gel column chromatography (chloroform:methanol:aqueous ammonia=9:1:1) to give 3.40 g of the product as a mixture of two materials.

3.40 g of the resulting mixture was dissolved in 32 ml of ethanol, 8 ml of concentrated hydrochloric acid was added and the mixture was stirred at room temperature for 14 hours. Water and aqueous ammonia were added to the reaction solution and the mixture was extracted with a mixed solvent of chloroform and methanol (9:1). The organic layer was washed with an aqueous saturated solution of sodium chloride and dried over anhydrous sodium sulfate and the solvent was distilled off under reduced pressure. The residue was purified by silica gel column chromatography (chloroform:methanol:aqueous ammonia=40:1:1) to give 2.39 g of the product as a mixture of two materials.

1.07 g of the resulting mixture was dissolved in 8 ml of dioxane, 8 ml of concentrated hydrochloric acid was added and the mixture was stirred for 1 hour under heating at reflux. The reaction solution was cooled, water was added, the solution was made weak alkaline and the mixture was extracted twice with ethyl acetate. The organic layer was washed once with water and once with an aqueous saturated solution of sodium chloride and dried over anhydrous sodium sulfate and the solvent was distilled off under reduced pressure. The residue was purified by silica gel column chromatography (chloroform:methanol:aqueous ammonia=50:1:1) and recrystallized from ethyl acetate/n-hexane to give 358 mg of yellow crystals.

352 mg of the above crystals were dissolved in 20 ml of tetrahydrofuran, 1.5 ml of a tetrabutylammonium fluoride solution (1.0M) in tetrahydrofuran was added, the mixture was stirred at room temperature for 30 minutes, water was added and the mixture was extracted three times with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol:aqueous ammonia=50:1:1) to give 313 mg of Compound 47.

NMR (270 MHz, CDCl$_3$) δ (ppm) 1.83 (2H, quint., J=6.4), 2.27 (6H, s), 2.44 (2H, t, J=6.4), 3.31 (2H, brq., J=6.4), 5.71 (1H, brs), 6.20 (2H, brs), 6.47 (1H, s), 6.71 (1H, t, J=8.4), 7.16 (1H, t, J=10.6), 7.51 (1H, dd, J=12.6, 2.2), 7.60 (1H, dd, J=8.7, 1.7)

MS (M/Z) 391 (M$^+$)

Molecular formula $C_{20}H_{20}F_3N_3O_2$=391

EXAMPLE 48

5-Amino-6,8-difluoro-2-[3-fluoro-4-[3-(pyrrolidin-1-yl)propylamino]phenyl]-4H-1-benzopyran-4-one (Compound 48)

840 mg of sodium hydride (60% oil dispersion) was suspended in a mixed solvent of 10 ml of dioxane and 10 ml of toluene under argon atmosphere and the suspension was heated at reflux. A solution of 3.85 g (10 mmol) of Compound E obtained in Reference Example 4 and 3.06 g (10mmol) of 4'-[N-acetyl-N-[3-(pyrrolidin-1-yl)propyl]amino]-3'-fluoroacetophenone dissolved in a mixed solvent of 25 ml of dioxane and 25 ml of toluene was added dropwise thereto over 20 minutes and the mixture was stirred. After 2 hours, 80 mg of sodium hydride (60% oil dispersion) was added and the mixture was stirred for additional 30 minutes. The reaction solution was cooled on ice, water was added, and the mixture was washed with n-hexane and extracted with ethyl acetate. The organic layer was washed with an aqueous saturated solution of sodium chloride and dried over anhydrous magnesium sulfate and the solvent was distilled off under reduced pressure.

The resulting residue was dissolved in 50 ml of ethanol, 10 ml of concentrated hydrochloric acid was added and the mixture was stirred at room temperature for 7 hours and at 40° C. for 2 hours. The reaction solution was adjusted to pH 9 by addition of water thereto and the mixture was extracted with ethyl acetate. The organic layer was washed once with water and once with an aqueous saturated solution of sodium chloride, and dried over anhydrous magnesium sulfate. The solvent was distilled off under reduced pressure and the resulting residue was purified by silica gel column chromatography (chloroform:methanol:triethylamine=20:1:0.1) to give 2.42 g (45%) of 2-[4-[N-acetyl-N-[3-(pyrrolidin-1-yl)propyl]amino]-3-fluorophenyl]-6,8-difluoro-5-pivaloylamino-4H-1-benzopyran-4-one.

NMR (90 MHz, CDCl$_3$) δ (ppm) 1.40 (9H, s), 1.1–2.1 (9H, m), 2.4–2.8 (4H, m), 3.1–3.6 (2H, m), 3.77 (2H, t, J=7.0), 6.73 (1H, s), 7.30–7.53 (2H, m), 7.60–7.82 (2H, m,)

MS (M/Z) 543 (M$^+$)

Molecular formula $C_{29}H_{32}F_3N_3O_4$=543

1.00 g (1.84 mmol) of the resulting 2-[4-[N-acetyl-N-[3-(pyrrolidin-1-yl)propyl]amino]-3-fluorophenyl]-6,8-difluoro-5-pivaloylamino-4H-1-benzopyran-4-one was dissolved in 8 ml of dioxane, 8 ml of concentrated hydrochloric acid was added and the mixture was stirred for 1 hour under heating at reflux. The reaction solution was cooled and adjusted to pH 8 by addition of water thereto, and the mixture was extracted with ethyl acetate. The organic layer was washed with an aqueous saturated solution of sodium chloride and dried over anhydrous magnesium sulfate and the solvent was distilled off under reduced pressure. The residue was purified by silica gel column chromatography (chloroform:methanol:acetic acid=9:2:0.1) to give 738 mg (96%) of Compound 48.

NMR (270 MHz, CDCl$_3$) 67 (ppm) 1.82–1.93 (6H, m), 2.56 (4H, m), 2.67 (2H, t, J=6.3), 3.2–3.4 (2H, m), 6.19 (3H, brs), 6.46 (1H, s), 6.69 (1H, t, J=8.6), 7.15 (1H, t, J=10.6), 7.51 (1H, dd, J=12.5, 2.0), 7.59 (1H, dd, J=8.6, 2.3)

MS (M/Z) 417 (M$^+$)

Molecular formula $C_{22}H_{22}F_3N_3O_2$=417

EXAMPLE 49

5-Amino-6,8-difluoro-2-[3-fluoro-4-(3-methylthiopropylamino)phenyl]-4H-1-benzopyran-4-one (Compound 49)

840 mg of sodium hydride (60% oil dispersion) was suspended in a mixed solvent of 10 ml of dioxane and 10 ml of toluene under argon atmosphere and the suspension was heated at reflux. A solution of 3.85 g (10 mmol) of Compound E obtained in Reference Example 4 and 2.83 g (10mmol) of 4'-[N- acetyl-N-(3-methylthiopropyl)amino]-3'-fluoroacetophenone dissolved in a mixed solvent of 25 ml of dioxane and 25 ml of toluene was added dropwise and the mixture was stirred for 1 hour. The reaction solution was cooled on ice, water was added and the mixture was washed with n-hexane and extracted with ethyl acetate. The organic layer was washed with an aqueous saturated solution of sodium chloride and dried over anhydrous magnesium sulfate and the solvent was distilled off under reduced pressure.

The resulting residue was dissolved in 50 ml of ethanol, 10 ml of concentrated hydrochloric acid was added and the mixture was stirred at room temperature for 7 hours and at 40° C. for 2 hours. Water was added to the reaction solution and the mixture was extracted with ethyl acetate. The organic layer was washed once with water and once with an aqueous saturated solution of sodium chloride, and dried over anhydrous magnesium sulfate. The solvent was distilled off under reduced pressure and the resulting residue was purified by silica gel column chromatography (n-hexane:ethyl acetate=2:1) to give 2.51 g (48%) of 2-[4-[N-acetyl-N-(3-methylthiopropyl)amino]-3-fluorophenyl]-6,8-difluoro-5-pivaloylamino-4H-1-benzopyran-4-one.

NMR (90 MHz, CDCl$_3$) δ (ppm) 1.39 (9H, s), 1.7–2.1 (2H, m), 1.92 (3H, brs), 2.06 (3H, s), 2.52 (2H, t, J=7.5), 3.82 (2H, brt), 6.74 (1H, s), 7.28–7.52 (2H, m), 7.7–7.8 (2H, m), 10.4 (1H, brs)

Ms (M/z) 520 (M$^+$)

Molecular formula C$_{26}$H$_{27}$F$_3$N$_2$O$_4$S=520

1.00 g (1.92 mmol) of the resulting 2-[4-[N-acetyl-N-(3-methylthiopropyl)amino]-3-fluorophenyl]-6,8-difluoro-5-pivaloylamino-4H-1-benzopyran-4-one was dissolved in 8 ml of dioxane, 8 ml of concentrated hydrochloric acid was added and the mixture was stirred for 3 hours under heating at reflux. The reaction solution was cooled and adjusted to pH 8 by addition of water thereto, and the precipitated crystals were collected by filtration. The crystals were purified by silica gel column chromatography (n-hexane:ethyl acetate=2:1) and recrystallized twice from ethyl acetate/n-hexane to give 422 mg (56%) of Compound 49.

NMR (270 MHz, CDCl$_3$) δ (ppm) 1.98 (2H, quint., J=6.9), 2.14 (3H, s), 2.64 (2H, t, J=6.9), 3.36–3.43 (2H, m), 5.23 (1H, brs), 6.20 (2H, brs), 6.47 (1H, s), 6.77 (1H, t, J=8.4), 7.16 (1H, t, J=10.6), 7.53 (1H, dd, J=12.9, 2.2), 7.61 (1H, dd, J=7.9, 2.0)

MS (M/Z) 394 (M$^+$)

Molecular formula C$_{19}$H$_{17}$F$_3$N$_2$O$_2$S=394

EXAMPLE 50

5-Amino-6,8-difluoro-2-[3-fluoro-4-[3-(imidazol-1-yl)propylamino]phenyl]-4H-1-benzopyran-4-one (Compound 50)

1.02 g (2.92 mmol) of Compound 27 obtained in Example 27 was dissolved in 25 ml of dimethylformamide under argon atmosphere, 129 mg of sodium hydride (60% oil dispersion) and 2.9 ml of 1-bromo-3-chloropropane were added under ice-cooling and the mixture was stirred at room temperature for 1 hour. Water was added to the reaction solution and the mixture was extracted twice with ethyl acetate. The organic layer was washed once with water and once with an aqueous saturated solution of sodium chloride and dried over anhydrous sodium sulfate and the solvent was distilled off under reduced pressure. Recrystallization from ethyl acetate/acetonitrile afforded 434 mg (35%) of 2-[4-[N-acetyl-N-(3-chloropropyl)amino]-3-fluorophenyl]-5-amino-6,8-difluoro- 4H-1-benzopyran-4-one.

NMR (90 MHz, CDCl$_3$) δ (ppm) 1.91 (3H, brs), 2.04 (2H, quint., J=7.0), 3.57 (2H, t, J=6.5), 3.7–4.0 (2H, m), 6.22 (2H, brs), 6.64 (1H, s), 7.23 (1H, t, J=10.4), 7.40 (1H, t, J=7.9), 7.72–7.82 (2H, m)

MS (M/Z) 424 (M$^+$)

Molecular formula C$_{20}$H$_{16}$ClF$_3$N$_2$O$_3$=424

508 mg (1.20 mmol) of the resulting 2-[4-[N-acetyl-N-(3-chloropropyl)amino]-3-fluorophenyl]-5-amino-6,8-difluoro-4H-1-benzopyran-4-one was dissolved in 30 ml of dioxane, 30 ml of concentrated hydrochloric acid was added and the mixture was stirred for 3 hours under heating at reflux. The reaction solution was cooled on ice and adjusted to pH 8 by addition of water thereto, and the precipitated crystals were collected by filtration. The crystals were purified by silica gel column chromatography (n-hexane:ethyl acetate=4:1) to give 224 mg (49%) of 5-amino-2-[4-(3-chloropropylamino)-3-fluorophenyl]-6,8-difluoro-4H-1-benzopyran-4-one.

NMR (90 MHz, CDCl$_3$) δ (ppm) 2.13 (2H, quint., J=6.3), 3.47 (2H, q, J=6.4), 3.68 (2H, t, J=6.0), 4.45 (1H, m), 6.19 (2H, brs), 6.47 (1H, s), 6.78 (1H, t, J=8.7), 7.15 (1H, t, J=10.5), 7.45–7.67 (2H, m)

MS (M/Z) 382 (M$^+$)

Molecular formula C$_{18}$H$_{14}$ClF$_3$N$_2$O$_2$=382

190 mg (0.50 mmol) of the resulting 5-amino-2-[4-(3-chloropropylamino)-3-fluorophenyl]-6,8-difluoro-4H-1-benzopyran- 4-one was dissolved in 1.5 ml of dimethylformamide under argon atmosphere under ice-cooling, 17 ml of imidazole and 10 mg of sodium hydride (60% oil dispersion) were added and the mixture was stirred for 40 minutes. The temperature of the reaction was raised to room temperature, additional 10 mg of imidazole and 6.8 mg of sodium hydride (60% oil dispersion) were added and the mixture was stirred overnight. The reaction mixture was heated to 40° C., 10 mg of imidazole and 6.8 mg of sodium hydride (60% oil dispersion) were added and the mixture was stirred for 30 hours. Water was added to the reaction solution, the mixture was extracted with ethyl acetate, the organic layer was washed with an aqueous saturated solution of sodium chloride and dried over anhydrous sodium sulfate and the solvent was distilled off under reduced pressure. The residue was purified by preparative thin layer chromatography (chloroform:methanol=20:1) to give 18.3 mg (53%) of Compound 50.

NMR (270 MHz, DMSO-d$_6$) δ (ppm) 2.02 (2H, quint., J=6.9), 3.15 (2H, q, J=6.9), 4.07 (2H, t, J=6.9), 6.53 (1H, brs), 6.74 (1H, s), 6.79 (1H, t, J=8.9), 6.92 (1H, s), 7.06 (2H, brs), 7.22 (1H, s), 7.6–7.8 (4H, m)

MS (M/Z) 414 (M$^+$)

Molecular formula C$_{21}$H$_{17}$F$_3$N$_{O2}$=414

EXAMPLE 51

5-Amino-2-[4-(tert-butoxycarbonylamino)-3-fluorophenyl]-6,8-difluoro-4H-1-benzopyran-4-one (Compound 51)

3.03 g (8.70 mmol) of Compound 27 obtained in Example 27 was dissolved in 200 ml of dimethylformamide, 109 mg of dimethylaminopyridine and 3.0 ml of di-tert-butyl carbonate were added and the mixture was stirred at room temperature for 2 hours. Water was added to the reaction solution and the precipitated crystals were collected by filtration to give 3.44 g (88%) of 2-[4-[N-acetyl-N-(tert-butoxycarbonyl)amino]-3-fluorophenyl]-5-amino-6,8-difluoro-4H-1-benzopyran-4-one.

NMR (90 MHz, CDCl$_3$) δ (ppm) 1.41 (9H, s), 2.66 (3H, s), 6.20 (2H, brs), 6.63 (1H, s), 7.10–7.33 (2H, m), 7.65–7.76 (2H, m)

MS (M/Z) 448 (M$^+$)

Molecular formula C$_{22}$H$_{19}$F$_3$N$_2$O$_5$=448

3.43 g (7.65 mmol) of the resulting 2-[4-[N-acetyl-N-(tert-butoxycarbonyl)amino]-3-fluorophenyl]-5-amino-6,8-difluoro-4H-1-benzopyran-4-one was dissolved in 400 ml of acetonitrile, 2.2 ml of 2-(N,N-diethylamino)ethylamine was added and the mixture was stirred at room temperature for 4 hours. The precipitated crystals were dissolved in ethyl acetate, the solvent was distilled off under reduced pressure and the resulting residue was recrystallized from ethyl acetate to give 2.00 g (64%) of Compound 51.

NMR (90 MHz, CDCl$_3$) δ (ppm) 1.55 (9H, s), 6.20 (2H, brs), 6.56 (1H, s), 6.90 (1H, brs), 7.19 (1H, t, J=10.4), 7.56–7.71 (2H, m), 8.30 (1H, t, J=8.4)

MS (M/Z) 406 (M$^+$)

Molecular formula C$_{20}$H$_{17}$F$_3$N$_2$O$_4$=406

EXAMPLE 52

5-Amino-6,8-difluoro-2-[3-fluoro-4-[6-(imidazol-1-yl)hexylamino] phenyl]-4H-1-benzopyran-4-one (Compound 52)

5.00 g (14.4 mmol) of Compound 27 obtained in Example 27 was dissolved in 150 ml of dimethylformamide under argon atmosphere, 10.9 ml of 1,6-dibromohexane and 575 mg of sodium hydride (60% oil dispersion) were added under ice-cooling and the mixture was stirred at room temperature for 2 hours. Water was added to the reaction solution and the mixture was extracted with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:acetone=20:1) to give 6.11 g (83%) of 2-[4-[N-acetyl-N-(6-bromohexyl)amino]-3-fluorophenyl]-5-amino- 6,8-difluoro-4H-1-benzopyran-4-one.

NMR (90 MHz, CDCl$_3$) δ (ppm) 1.2–2.0 (8H, m), 1.90 (3H, s), 3.38 (2H, t, J=6.6), 3.6–3.9 (2H, m), 6.64 (1H, s), 7.23 (1H, t, J=10.4), 7.38 (1H, t, J=8.1), 7.6–7.9 (2H, m)

MS (M/Z) 510/512 (M$^+$)

Molecular formula C$_{23}$H$_{22}$BrF$_3$N$_2$O$_3$=511

6.10 g (11.9 mmol) of the resulting 2-[4-[N-acetyl-N-(6-bromohexyl)amino]-3-fluorophenyl]-5-amino-6,8-difluoro-4H-1-benzopyran-4-one was dissolved in 60 ml of dioxane, 40 ml of 47% aqueous HBr was added and the mixture was heated at reflux for 3 hours. The reaction solution was cooled on ice, water was added and the mixture was extracted with ethyl acetate. The organic layer was washed once with 5% aqueous sodium bicarbonate and once with an aqueous saturated solution of sodium chloride and dried over anhydrous sodium sulfate. The solvent was distilled off under reduced pressure, and the residue was purified by silica gel column chromatography (chloroform:methanol=100:1) to give 3.53 g (63%) of 5-amino-2-[4-(6-bromohexylamino)-3-fluorophenyl]-6,8-difluoro-4H-1-benzopyran-4-one.

NMR (90 MHz, CDCl$_3$) δ (ppm) 1.2–2.1 (8H, m), 3.24 (2H, brt, J=6.0), 3.42 (2H, t, J=6.5), 4.30 (1H, brs), 6.10 (2H, brs), 6.46 (1H, s), 6.72 (1H, t, J=8.7), 7.15 (1H, t, J=10.3), 7.4–7.7 (2H, m)

MS (M/Z) 468/470 (M$^+$)

Molecular formula C$_{21}$H$_{20}$BrF$_3$N$_2$O$_2$=469

3.53 g (7.53mmol) of the resulting 5-amino-2-[4-(6-bromohexylamino)-3-fluorophenyl]-6,8-difluoro-4H-1-benzopyran-4-one was dissolved in 100 ml of tetrahydrofuran under argon atmosphere, 5.12 g of imidazole and 3.01 g of sodium hydride (60% oil dispersion) were added and the mixture was heated at reflux for 2 hours. The reaction solution was cooled on ice, poured into aqueous ammonium chloride and extracted with ethyl acetate. The organic layer was washed with an aqueous saturated solution of sodium chloride and dried over anhydrous sodium sulfate. The solvent was distilled off under reduced pressure and the residue was purified by silica gel column chromatography (chloroform:methanol:triethylamine=90:10:1) to give Compound 52 which was converted into hydrochloride according to the same manner as that in Example 16 to give 3.13 g (84%).

NMR (270 MHz, DMSO-d$_6$) δ (ppm) 1.2–1.5 (4H, m), 1.58 (2H, quint., J=7.4), 1.82 (2H, quint., J=7.4), 3.17 (2H, t, J=6.9), 4.20 (2H, t, J=7.4), 6.72 (1H, s), 6.82 (1H, t, J=8.9), 7.6–7.8 (5H, m), 9.19 (1H, s)

MS (M/Z) 456 (M$^+$)

Molecular formula C$_{24}$H$_{23}$F$_3$N$_4$O$_2$=456

EXAMPLE 53

5-Amino-6,8-difluoro-2-[4-[6-(N',N'-dimethylamino)hexylamino]-3-fluorophenyl]-4H-1-benzopyran-4-one (Compound 53)

500 mg (1.07 mmol) of 5-amino-2-[4-(6-bromohexylamino)-3-fluorophenyl]-6,8-difluoro-4H-1-benzopyran-4-one obtained in Example 52 was dissolved in 15 ml of dimethylformamide, 1.47 g of potassium carbonate and 869 mg of dimethylamine hydrochloride were added and the mixture was stirred at room temperature for 16 hours. The reaction solution was poured into an aqueous ammonium chloride solution and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol:triethylamine=90:10:1) and recrystallized from chloroform/methanol/n-hexane to give Compound 53 which was converted into hydrochloride according to the same manner as that in Example 16 to give 117 mg (23%).

NMR (270 MHz, DMSO-d$_6$) δ (ppm) 1.3–1.5 (4H, m), 1.5–1.8 (4H, m), 2.73 (6H, s), 3.00 (2H, brt, J=8.2), 3.19 (2H, q, J=6.9), 6.42 (1H, brt), 6.72 (1H, s), 6.84 (1H, t, J=8.9), 7.05 (2H, brs), 7.6–7.8 (3H, m)

MS (M/Z) 433 (M$^+$)

Molecular formula C$_{23}$H$_{26}$F$_3$N$_3$O$_2$=433

EXAMPLE 54

5-Amino-6,8-difluoro-2-[3-fluoro-4-[6-(pyrrolidin-1-yl)hexylamino]phenyl]-4H-1-benzopyran-4-one (Compound 54)

500 mg (1.07 mmol) of 5-amino-2-[4-(6-bromohexylamino)-3-fluorophenyl]-6,8-difluoro-4H-1-benzopyran-4-one obtained in Example 52 was dissolved in 15 ml of tetrahydrofuran, 0.891 ml of pyrrolidine was added and the mixture was heated at reflux for 1.5 hours. Water was added to the reaction solution and the mixture was extracted with a mixed solvent of chloroform and methanol. The organic layer was washed with an aqueous saturated solution of sodium chloride and dried over anhydrous sodium sulfate and the solvent was distilled off under reduced pressure. The residue was purified by silica gel column chromatography (chloroform:methanol:triethylamine=90:10:1) and recrystallized from chloroform/n-hexane to give Compound 54 which was converted into hydrochloride according to the same manner as that in Example 16 to give 88 mg (17%).

NMR (270 MHz, CDCl$_3$) δ (ppm) 1.3–1.5 (4H, m), 1.59 (2H, quint., J=7.3), 1.69 (2H, quint., J=7.3), 1.82 (4H, quint., J=3.3), 2.50 (2H, t, J=7.8), 2.58 (4H, m), 3.23 (2H, q, J=6.9), 4.38 (1H, m), 6.20 (2H, brs), 6.47 (1H, s), 6.72 (1H, t, J=8.6), 7.16 (1H, t, J=10.4), 7.53 (1H, dd, J=12.9, 2.0), 7.60 (1H, dd, J=8.6, 2.0)

MS (M/Z) 459 (M⁺)

Molecular formula $C_{25}H_{28}F_3N_3O_2=459$

EXAMPLE 55

5-Amino-6,8-difluoro-2-[3-fluoro-4-(6-morpholinohexylamino)phenyl]-4H-1-benzopyran-4-one (Compound 55)

500 mg (1.07 mmol) of 5-amino-2-[4-(6-bromohexylamino)-3-fluorophenyl]-6,8-difluoro-4H-1-benzopyran-4-one obtained in Example 52 was dissolved in 15 ml of dimethylformamide, 0.93 ml of morpholine was added and the mixture was stirred at 50° to 60° C. for 1.5 hours. Water was added to the reaction solution and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol:triethylamine =200:10:1) and recrystallized from ethyl acetate/n-hexane to give Compound 55 which was converted into hydrochloride according to the same manner as that in Example 16 to give 349 mg (62%).

NMR (270 MHz, CDCl₃) δ (ppm) 1.3–1.5 (4H, m), 1.56 (2H, quint., J=7.1), 1.70 (2H, quint., J=7.0), 2.39 (2H, t, J=7.6), 2.50 (4H, brs), 3.23 (2H, q, J=6.6), 3.75 (4H, t, J=4.6), 4.37 (1H, m), 6.20 (2H, s), 6.47 (1H, s), 6.72 (1H, t, J=8.6), 7.16 (1H, t, J=10.6), 7.53 (1H, dd, J=12.9, 2.0), 7.60 (1H, dd, J=8.6, 2.0)

MS (M/Z) 475 (M⁺)

Molecular formula $C_{25}H_{28}F_3N_3O_3=475$

EXAMPLE 56

5-Amino-6,8-difluoro-2-[4-(5-(ethoxycarbonylpentylamino)-3-fluorophenyl]-4H-1-benzopyran-4-one (Compound 56)

1.00 g (2.87 mmol) of Compound 27 obtained in Example 27 was dissolved in 10 ml of dimethylformamide under argon atmosphere, 355 mg of potassium tert-butoxide and 1.02 ml of ethyl 6-bromohexanoate were added under ice-cooling and the mixture was stirred at room temperature for 4.5 hours. An aqueous ammonium chloride solution was added to the reaction solution and the mixture was extracted with ethyl acetate. The organic layer was washed with an aqueous saturated solution of sodium chloride, dried over anhydrous sodium sulfate and purified by silica gel column chromatography (chloroform:methanol=30:1) to give 1.26 g (85%) of 2-[4-[N-acetyl-N-(5-ethoxycarbonylpentyl)amino]-3-fluorophenyl]-5-amino-6,8-difluoro-4H-1-benzopyran-4-one.

NMR (90 MHz, CDCl₃) δ (ppm) 1.2–1.8 (6H, m), 1.24 (3H, t, J=7.0), 1.90 (3H, brs), 2.27 (2H, t, J=7.0), 3.71 (2H, t, J=6.8), 4.10 (2H, q, J=7.0), 6.22 (2H, brs), 6.64 (1H, s), 7.23 (1H, t, J=10.4), 7.37 (1H, t, J=8.1), 7.6–7.9 (2H, m)

MS (M/Z) 490 (M⁺)

Molecular formula $C_{25}H_{25}F_3N_2O_5=490$ 1.20 g (2.45mmol) of the resulting 2-[4-[N-acetyl-N-(5-ethoxycarbonylpentyl)amino]-3-fluorophenyl]-5-amino-6,8-difluoro-4H-1-benzopyran-4-one was dissolved in 10 ml of ethanol, 5 ml of concentrated hydrochloric acid was added and the mixture was heated at reflux for 2.5 hours. The reaction solution was cooled on ice, water was added and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:acetone=20:1) and recrystallized from ethyl acetate/n-hexane to give 386 mg (35%) of Compound 36.

NMR (270 MHz, CDCl₃) δ (ppm) 1.26 (3H, t, J=6.9), 1.4–1.8 (6H, m), 2.34 (2H, t, J=7.4), 3.24 (2H, q, J=6.9), 4.14 (2H, q, J=6.9), 4.38 (1H, m), 6.29 (2H, brs), 6.47 (1H, s), 7.16 (1H, t, J=10.4), 7.53 (1H, dd, J=12.9, 2.0), 7.60 (1H, dd, J=8.4, 2.0)

MS (M/Z) 448 (M⁺)

Molecular formula $C_{23}H_{23}F_3N_2O_4=448$

EXAMPLE 57

Sodium salt of 5-amino-2-[4-(5-carboxypentylamino)-3-fluorophenyl]-6,8-difluoro-4H-1-benzopyran-4-one (Compound 57)

367 mg (0.818 mmol) of Compound 56 obtained in Example 56 was dissolved in 10 ml of ethanol, 1.23 ml of a 2N aqueous solution of sodium hydroxide was added and the mixture was stirred at room temperature for 17 hours. The precipitated crystals were collected by filtration to give 261 mg (69%) of Compound 57.

NMR (270 MHz, DMSO-d₆) δ (ppm) 1.2–1.7 (6H, m), 1.90 (2H, t, J=7.4), 3.16 (2H, q, J=6.4), 6.43 (1H, m), 6.70 (1H, s), 6.81 (1H, t, J=8.4), 7.04 (2H, brs), 7.6–7.8 (3H, m)

FAB-MS (M/Z) 421 (M⁺+1)

Molecular formula $C_{21}H_{19}F_3N_2O_4=420$

EXAMPLE 58

6,8-Difluoro-2-[4-(N,N-dimethylamino)-3-fluorophenyl]-5-hexylamino-4H-1-benzopyran-4-one (Compound 58)

500 mg (1.50 mmol) of Compound 38 obtained in Example 38 was dissolved in 5 ml of dimethylformamide under argon atmosphere, 120 mg of sodium hydride (60% oil disperison) and 0.441 ml of 1-iodohexane were added under ice-cooling and the mixture was stirred at room temperature for 3 hours. An aqueous saturated solution of ammonium chloride was added to the reaction solution and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (n-hexane:ethyl acetate=6:1) and recrystallized from n-hexane/ethyl acetate to give Compound 58 which was converted into hydrochloride according to the same manner as that in Example 16 to give 494 mg (79%).

NMR (270 MHz, DMSO-d₆) δ (ppm) 0.86 (3H, t, J=6.7), 1.2–1.5 (6H, m), 1.54 (2H, quint., J=6.9), 2.96 (6H, d, J=1.5), 3.2–3.5 (2H, m), 6.81 (1H, s), 7.00 (1H, t, J=9.2), 7.6–7.8 (2H, m), 7.68 (1H, t, J=11.1), 8.82 (1H, brs)

Ms (M/z) 418 (M⁺)

Molecular formula $C_{23}H_{25}F_3N_2O_2=418$

EXAMPLE 59

5-(6-Bromohexylamino)-6,8-difluoro-2-[4-(N,N-dimethylamino)-3-fluorophenyl]-4H-1-benzopyran-4-one (Compound 59)

100 mg (1.50 mmol) of Compound 38 obtained in Example 38 was dissolved in 2 ml of dimethylformamide under argon atmosphere, 24 mg of sodium hydride (60% oil dispersion) and 2 ml of 1,6-dibromohexane were added under ice-cooling and the mixture was stirred at 0° C. for 2 hours. An aqueous saturated solution of ammonium chloride was added to the reaction solution and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (n-hexane:ethyl acetate=4:1) and recrystallized from n-hexane/ethyl acetate to give 92 mg (62%) of Compound 59.

NMR (270 MHz, CDCl$_3$) δ (ppm) 1.4–1.8 (8H, m), 3.01 (6H, d, J=1.7), 3.4–3.6 (2H, m), 3.41 (2H, t, J=6.8), 6.47 (1H, s), 6.86 (1H, t, J=8.9), 7.12 (1H, dd, J=13.4, 10.4), 7.4–7.6 (2H, m), 8.82 (1H, brs)

MS (M/Z) 496/498 (M$^+$)

Molecular formula C$_{23}$H$_{24}$BrF$_3$N$_2$O$_2$=497

EXAMPLE 60

6,8-Difluoro-2-[4-(N,N-dimethylamino)-3-fluorophenyl]-5-(6-hydroxyhexylamino)-4H-1-benzopyran-4-one (Compound 60)

1.0 g (2.99 mmol) of Compound 38 obtained in Example 38 was dissolved in 20 ml of dimethylformamide under argon atmosphere, 239 mg of sodium hydride (60% oil dispersion) and 1.87 g of tetrahydropyranyl ether of 6-iodo-1-hexanol were added under ice-cooling and the mixture was stirred at 0° C. for 1.3 hours. An aqueous saturated solution of ammonium chloride was added to the reaction solution and the mixture was extracted with ethyl acetate. The organic layer was washed with an aqueous saturated solution of sodium chloride and dried over anhydrous sodium sulfate and the solvent was distilled off under reduced pressure. 18 ml of ethanol and 2 ml of concentrated hydrochloric acid were added to the residue and the mixture was stirred at room temperature for 18 hours. The reaction solution was adjusted to pH 7 by addition of a 10N aqueous solution of sodium hydroxide thereto, and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol=40:1) and recrystallized from n-hexane/ethyl acetate to give 912 mg (70%) of Compound 60.

NMR (270 MHz, CDCl$_3$) δ (ppm) 1.3–1.8 (8H, m), 3.02 (6H, d, J=1.5), 3.45 (2H, m), 3.65 (2H, t, J=6.4), 6.48 (1H, s), 6.89 (1H, t, J=8.9), 7.13 (1H, dd, J=13.4, 9.9), 7.5–7.7 (2H, m), 8.82 (1H, brs)

MS (M/Z) 434 (M$^+$)

Molecular formula C$_{23}$H$_{25}$F$_3$N$_2$O$_3$=434

EXAMPLE 61

6,8-Difluoro-2-[4-(N,N-dimethylamino)-3-fluorophenyl]-5-(6-methoxyhexylamino)-4H-1-benzopyran-4-one (Compound 61)

500 mg (1.15 mmol) of Compound 60 obtained in Example 60 was dissolved in 20 ml of tetrahydrofuran under argon atmosphere, 92 mg of sodium hydride (60% oil dispersion) and 0.14 ml of iodomethane were added under ice-cooling and the mixture was stirred at room temperature for 1 hour. Thereafter, 0.22 ml of iodomethane was added and the mixture was heated at reflux for 3.5 hours. Additional 0.36 ml of iodomethane was added and the mixture was heated at reflux for 1 hour. The solvent was distilled off under reduced pressure, an aqueous saturated solution of ammonium chloride was added to the residue and the mixture was extracted with ethyl acetate. The organic layer was washed with an aqueous saturated solution of sodium chloride, dried over anhydrous sodium sulfate, and purified by silica gel column chromatography (chloroform:acetone=40:1), followed by recrystallization from n-hexane/ethyl acetate to give 300 mg (58%) of Compound 61.

NMR (270 MHz, CDCl$_3$) δ (ppm) 1.3–1.8 (8H, m), 3.01 (6H, d, J=1.5), 3.33 (3H, s), 3.37 (2H, t, J=6.7), 3.4–3.6 (2H, m), 6.47 (1H, s), 6.86 (1H, t, J=8.9), 7.12 (1H, dd, J=13.4, 10.4), 7.5–7.8 (2H, m), 8.82 (1H, brs)

MS (M/Z) 448 (M$^+$)

Molecular formula C$_{24}$H$_{27}$F$_3$N$_2$O$_3$=448

EXAMPLE 62

6,8-Difluoro-2-[4-(N,N-dimethylamino)-3-fluorophenyl]-5-[6-(N',N'-dimethylamino)hexylamino]-4H-1-benzopyran-4-one (Compound 62)

500 mg (0.01 mmol) of Compound 59 obtained in Example 59 was dissolved in 25 ml of dimethylformamide, 1.39 g of potassium carbonate and 820 mg of dimethylamine hydrochloride were added and the mixture was stirred at room temperature for 5.5 hours. 971 mg of potassium carbonate and 410 mg of dimethylamine hydrochloride were added and the mixture was stirred at room temperature for 16 hours. The reaction solution was poured into water, and the precipitated crystals were collected by filtration, purified by silica gel column chromatography (chloroform:methanol:triethylamine=90:10:1) and recrystallized from chloroform/ethyl acetate to give Compound 62 which was converted into hydrochloride according to the same manner as that in Example 16 to give 283 mg (53%).

NMR (270 MHz, CDCl$_3$) δ (ppm) 1.3–1.8 (8H, m), 2.21 (6H, s), 2.24 (2H, t, J=6.9), 3.01 (6H, d, J=1.3), 3.4–3.5 (2H, m), 6.46 (1H, s), 6.86 (1H, t, J=8.7), 7.12 (1H, dd, J=13.5, 10.2), 7.5–7.7 (2H, m), 8.81 (1H, brt)

MS (M/Z) 461 (M$^+$)

Molecular formula C$_{25}$H$_{30}$F$_3$N$_3$O$_2$=461

EXAMPLE 63

6,8-Difluoro-2-[4-(N,N-dimethylamino)-3-fluorophenyl]-5-[6-(pyrrolidin-1-yl)hexylamino]-4H-1-benzopyran-4-one (Compound 63)

500 mg (1.01 mmol) of Compound 59 obtained in Example 59 was dissolved in 5 ml of tetrahydrofuran, 0.17 ml of pyrrolidine was added and the mixture was heated at reflux for 5.5 hours. At 1 hour and 1.7 hours after the reaction was started, each 0.17 ml of pyrrolidine was added. At 3.5 hours and 4.5 hours, each 0.17 ml of pyrrolidine was added. At 3.5 hours and 4.5 hours, each 0.08 ml of pyrrolidine was added. Water was added to the reaction solution and the mixture was extracted with chloroform. The organic layer was washed with an aqueous saturated solution of sodium chloride and dried over anhydrous sodium sulfate and the solvent was distilled off under reduced pressure. The residue was purified by silica gel column chromatography (chloroform:methanol:triethylamine=90:10:1) and triturated with n-hexane to give Compound 63 which was converted into hydrochloride according to the same manner as that in Example 62 to give 465 mg (83%).

NMR (270 MHz, CDCl$_3$) δ (ppm) 1.3–2.0 (12H, m), 2.4–2.7 (6H, m), 3.01 (6H, d, J=1.5), 3.4–3.5 (2H, m), 6.47 (1H, s), 6.86 (1H, t, J=8.7), 7.12 (1H, dd, J=13.4, 9.9), 7.5–7.7 (2H, m), 8.81 (1H, brt)

MS (M/Z) 487 (M$^+$)

Molecular formula C$_{27}$H$_{32}$F$_3$N$_3$O$_2$=487

EXAMPLE 64

6,8-Difluoro-2-[4-(N,N-dimethylamino)-3-fluorophenyl]-5-[6-(imidazol-1-yl)hexylamino]-4H-1-benzopyran-4-one (Compound 64)

500 mg (1.01 mmol) of Compound 59 obtained in Example 59 was dissolved in 10 ml of tetrahydrofuran, 137 mg imidazole and 80 mg of sodium hydride (60% oil dispersion) were added and the mixture was heated at reflux for 2.3 hours. At 1.5 hours after the reaction was started, 40 mg of sodium hydride (60% oil disperison) was added. An aqueous solution of ammonium chloride was added to the reaction solution and the mixture was extracted with chloroform. The organic layer was washed with an aqueous saturated solution of sodium chloride and dried over anhydrous sodium sulfate and the solvent was distilled off under reduced pressure. The residue was purified by silica gel column chromatography (chloroform:methanol:triethylamine=200:10:1) and triturated with n-hexane to give Compound 64 which was converted into hydrochloride according to the same manner as that in Example 16 to give 447 mg (73%).

NMR (270 MHz, DMSO-$d_6$) δ (ppm) 1.2–1.5 (4H, m), 1.5–1.7 (2H, m), 1.7–1.9 (2H, m), 2.98 (6H, d, J=1.5), 3.3–3.5 (2H, m), 4.19 (2H, t, J=7.2), 6.80 (1H, s), 7.01 (1H, t, J=9.2), 7.6–7.8 (5H, m), 9.15 (1H, s)

MS (M/Z) 484 ($M^+$)

Molecular formula $C_{26}H_{27}F_3N_4O_2$=484

EXAMPLE 65

5-(6-Aminohexylamino)-6,8-difluoro-2-[4-(N,N-dimethylamino)-3-fluorophenyl]-4H-1-benzopyran-4-one (Compound 65)

500 mg (1.01 mmol) of Compound 59 obtained in Example 59 was dissolved in 10 ml of tetrahydrofuran under argon atmosphere, 372 mg potassium phthalimide was added under ice-cooling and the mixture was stirred at room temperature for 45 minutes and at 60° to 70° C. for 1.5 hours. 10 ml of dimethylformamide was added and the mixture was stirred at 70° to 80° C. for 2 hours. Water was added to the reaction solution and the mixture was extracted with ethyl acetate. The organic layer was washed with an aqueous saturated solution of sodium chloride and dried over anhydrous sodium sulfate and the solvent was distilled off under reduced pressure.

The above product was dissolved in a mixed solvent of 10 ml of methanol and 10 ml of dimethylformamide, 0.59 ml of hydrazine monohydrate was added and the mixture was stirred at 60° to 70° C. for 1.7 hours. The solvent was distilled off under reduced pressure and the residue was purified by silica gel column chromatography (chloroform-chloroform:methanol:ammonia=90:5:5) to give Compound 65 which was converted into hydrochloride according to the same manner as that in Example 16 to give 275 mg (two stages 54%).

NMR (270 MHz, DMSO-$d_6$) δ (ppm) 1.3–1.7 (8H, m), 2.7–2.9 (2H, m), 2.98 (6H, d, J=1.6), 3.3–3.5 (2H, m), 6.82 (1H, s), 7.01 (1H, t, J=9.1), 7.6–7.8 (2H, m), 7.71 (1H, dd, J=13.9, 10.9), 7.88 (1H, brs)

MS (M/Z) 433 ($M^+$)

Molecular formula $C_{23}H_{26}F_3N_3O_2$=433

EXAMPLE 66

2-(4-Amino-3-fluorophenyl)-6,8-difluoro-5-pentylamino-4H-1-benzopyran-4-one (Compound 66)

5.00 g (16.3 mmol) of Compound 26 obtained in Example 26 was dissolved in 50 ml of pyridine, 2.2 ml of pivaloyl chloride was added under ice-cooling and the mixture was stirred at room temperature for 1.5 hours. Water was added to the reaction solution and the precipitated crystals were collected by filtration to give 6.35 g (100%) of 5-amino-6,8-difluoro-2-(3-fluoro-4-pivaloylaminophenyl)-4H-1-benzopyran-4-one.

NMR (90 MHz, CDCl$_3$) δ (ppm) 1.36 (9H, s), 6.19 (2H, brs), 6.58 (1H, s), 7.20 (1H, dd, J=10.8, 10.3), 7.5–7.9 (3H, m), 8.59 (1H, t, J=8.6)

MS (M/Z) 390 ($M^+$)

Molecular formula $C_{20}H_{17}F_3N_2O_3$=390

505 mg (1.29 mmol) of the resulting 5-amino-6,8-difluoro-2-(3-fluoro-4-pivaloylaminophenyl)-4H-1-benzopyran-4-one was dissolved in 15 ml of dimethylformamide under argon atmosphere, 155 mg of sodium hydride (60% oil dispersion) and 0.35 ml of 1-iodopentane were added and the mixture was stirred at the same temperature for 30 minutes. 0.17 ml of 1-iodopentane was added and the mixture was stirred for additional 2 hours. An aqueous saturated solution of ammonium chloride was added to the reaction solution and the mixture was extracted twice with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform) to give 333 mg (56%) of 6,8-difluoro-2-(3-fluoro-4-pivaloylaminophenyl)-5-pentylamino-4H-1-benzopyran-4-one.

NMR (90 MHz, CDCl$_3$) δ (ppm) 0.8–1.0 (3H, m), 1.36 (9H, s), 1.2–1.9 (6H, m) 3.38–3.49 (2H, m), 6.66 (1H, s), 7.29 (1H, t, J=10.1), 7.5–7.9 (3H, m), 8.52 (1H, t, J=8.6)

MS (M/Z) 460 ($M^+$)

Molecular formula $C_{25}H_{27}F_3N_2O_3$=460

6 ml of dioxane and 6 ml of concentrated hydrochloric acid were added to 390 mg (0.85 mmol) of the resulting 6,8-difluoro-2-(3-fluoro-4-pivaloylaminophenyl)-5-pentylamino-4H-1-benzopyran-4-one and the mixture was heated at reflux for 1 hour. The reaction solution was cooled on ice, water was added, and the mixture was made neutral. The mixture was extracted twice with ethyl acetate, the organic layer was washed with an aqueous saturated solution of sodium chloride and dried over anhydrous sodium sulfate, and the solvent was distilled off under reduced pressure. The residue was purified by silica gel column chromatography (n-hexane:ethyl acetate=5:1) to give 292 mg (92%) of Compound 66.

NMR (270 MHz, CDCl$_3$) δ (ppm) 0.91 (3H, t, J=7.2), 1.3–1.5 (4H, m), 1.6–1.8 (2H, m), 3.41–3.48 (2H, m), 6.47 (1H, s), 6.84 (1H, t, J=8.7), 7.15 (1H, dd, J=12.9, 9.9), 7.50 (1H, dd, J=7.9, 2.0), 7.54 (1H, dd, J=13.4, 2.0)

MS (M/Z) 376 ($M^+$)

Molecular formula $C_{20}H_{19}F_3N_2O_2$=376

EXAMPLE 67

2-(4-Amino-3-fluorophenyl)-6,8-difluoro-5-hexylamino-4H-1-benzopyran-4-one (Compound 67)

505 mg (1.29 mmol) of 5-amino-6,8-difluoro-2-(3-fluoro-4-pivaloylaminophenyl)-4H-1-benzopyran-4-one was dissolved in 15 ml of dimethylformamide under argon atmosphere, 156 mg of sodium hydride (60% oil dispersion) and 0.38 ml of 1-iodohexane were added under ice-cooling and the mixture was stirred at the same temperature for 30 minutes. 0.19 ml of 1-iodohexane was added and the mixture was stirred for additional 2 hours. An aqueous saturated solution of ammonium chloride was added to the reaction solution and the mixture was extracted twice with ethyl acetate. The organic layer was washed with an aqueous saturated solution of sodium chloride and dried over anhydrous sodium sulfate and the solvent was distilled off under reduced pressure. The residue was purified by silica gel column chromatography (n-hexane:ethyl acetate=5:1) to give 487 mg (79%) of 6,8-difluoro-2-(3-fluoro-4-pivaloylaminophenyl)-5-hexylamino-4H-1-benzopyran-4-one.

NMR (90 MHz, CDCl$_3$) δ (ppm) 0.8–1.0 (3H, m), 1.36 (9H, s), 1.2–1.9 (8H, m), 3.38–3.49 (2H, m), 6.66 (1H, s), 7.29 (1H, t, J=10.1), 7.5–7.9 (2H, m), 8.52 (1H, t, J=8.6)

MS (M/Z) 474 (M$^+$)

Molecular formula C$_{26}$H$_{29}$F$_3$N$_2$O$_3$=474

6 ml of dioxane and 6 ml of concentrated hydrochloric acid were added to 470 mg (0.99 mmol) of the resulting 6,8-difluoro-2-(3-fluoro-4-pivaloylaminophenyl)-5-hexylamino-4H-1-benzopyran-4-one and the mixture was heated at reflux for 1 hour. The reaction solution was cooled on ice, water was added, and the solution was made neutral. The mixture was extracted twice with ethyl acetate, the organic layer was washed with an aqueous saturated solution of sodium chloride and dried over anhydrous sodium sulfate, and the solvent was distilled off under reduced pressure. The residue was purified by silica gel column chromatography (n-hexane:ethyl acetate=4:1) to give 377 mg (87%) of Compound 67.

NMR (270 MHz, CDCl$_3$) δ (ppm) 0.89 (3H, t, J=6.7), 1.2–1.6 (6H, m), 1.66 (2H, quint., J=7.2), 3.41–3.48 (2H, m), 6.47 (1H, s), 6.84 (1H, t, J=8.7), 7.15 (1H, dd, J=13.1, 10.1), 7.50 (1H, dd, J=7.9, 2.0), 7.54 (1H, dd, J=13.9, 2.0)

MS (M/Z) 390 (M$^+$)

Molecular formula C$_{21}$H$_{21}$F$_3$N$_2$O$_2$=390

EXAMPLE 68

2-(4-Amino-3-fluorophenyl)-6,8-difluoro-5-heptylamino-4H-1-benzopyran-4-one (Compound 68)

505 mg (1.29 mmol) of 5-amino-6,8-difluoro-2-(3-fluoro-4-pivaloylaminophenyl)-4H-1-benzopyran-4-one obtained in Example 66 was dissolved in 15 ml of dimethylformamide under argon atmosphere, 156 mg of sodium hydride (60% oil dispersion) and 0.42 ml of 1-iodoheptane were added under ice-cooling and the mixture was stirred for 2 hours. An aqueous saturated solution of sodium chloride was added to the reaction solution and the mixture was extracted twice with ethyl acetate. The organic layer was washed with an aqueous saturated solution of sodium chloride and dried over anhydrous sodium sulfate, and the solvent was distilled off under reduced pressure. The residue was purified by silica gel column chromatography (n-hexane:ethyl acetate=5:1) to give 460 mg (73%) of 6,8-difluoro-2-(3-fluoro-4-pivaloylaminophenyl)-5-heptylamino-4H-1-benzopyran-4-one.

NMR (90 MHz, CDCl$_3$) δ (ppm) 0.8–1.9 (13H, m), 1.36 (9H, s), 3.40–3.60 (2H, m), 6.57 (1H, s), 7.17 (1H, dd, J=13.1, 10.2), 7.58–7.75 (3H, m), 8.59 (1H, t, J=8.6)

Ms (M/z) 488 (M$^+$)

Molecular formula C$_{27}$H$_{31}$F$_3$N$_2$O$_3$=488

6 ml of dioxane and 6 ml of concentrated hydrochloric acid were added to 460 mg (0.94 mmol) of the resulting 6,8-difluoro-2-(3-fluoro-4-pivaloylaminophenyl)-5-heptylamino-4H-1-benzopyran-4-one and the mixture was heated at reflux for 1.5 hours. The reaction solution was cooled on ice, water was added, and the precipitated crystals were collected by filtration and purified by silica gel column chromatography (n-hexane:ethyl acetate=6:1) to give 358 mg (94%) of Compound 68.

NMR (270 MHz, CDCl$_3$) δ (ppm) 0.88 (3H, t, J=6.9), 1.2–1.5 (8H, m), 1.5–1.7 (2H, m), 3.39–3.48 (2H, m), 4.17 (2H, brs), 6.45 (1H, s), 6.83 (1H, t, J=8.7), 7.12 (1H, dd, J=13.4, 10.4), 7.50–7.58 (2H, m), 8.81 (1H, brs)

MS (M/Z) 404 (M$^+$)

Molecular formula C$_{22}$H$_{23}$F$_3$N$_2$O$_2$=404

EXAMPLE 69

2-(4-Amino-3-fluorophenyl)-5-(5-chlorohexylamino)-6,8-difluoro-4H-1-benzopyran-4-one (Compound 69)

512 mg (1.31 mmol) of 5-amino-6,8-difluoro-2-(3-fluoro-4-pivaloylaminophenyl)-4H-1-benzopyran-4-one obtained in Example 66 was dissolved in 15 ml of dimethylformamide under argon atmosphere, 160 mg of sodium hydride (60% oil disperison) and 0.35 ml of 6-bromo-1-hexene were added under ice-cooling and the mixture was stirred at room temperature for 2 hours. An aqueous saturated solution of ammonium chloride was added to the reaction solution and the mixture was extracted three times with ethyl acetate. The organic layer was washed with an aqueous saturated solution of sodium chloride and dried over anhydrous sodium sulfate, and the solvent was distilled off under reduced pressure. The residue was purified by silica gel column chromatography (n-hexane:ethyl acetate=6:1) to give 409 mg (66%) of 6,8-difluoro-2-(3-fluoro-4-pivaloylaminophenyl)-5-(5-hexenylamino)-4H-1-benzopyran-4-one.

NMR (90 MHz, CDCl$_3$) δ (ppm) 1.36 (9H, s), 1.3–2.3 (6H, m), 3.3–3.6 (2H, m), 4.85–5.11 (2H, m), 5.6–6.0 (1H, m), 6.64 (1H, s), 7.26 (1H, t, J=11.1), 7.5–7.9 (3H, m), 8.62 (1H, t, J=8.6)

MS (M/Z) 472 (M$^+$)

Molecular formula C$_{26}$H$_{27}$F$_3$N$_2$O$_3$=472

6 ml of dioxane and 6 ml of concentrated hydrochloric acid were added to 440 mg (0.93 mmol) of the resulting 6,8-difluoro-2-(3-fluoro-4-pivaloylaminophenyl)-5-(5-hexenylamino)-4H-1-benzopyran-4-one and the mixture was heated at reflux for 1.5 hours. The reaction solution was cooled on ice, and the precipitated crystals were collected by filtration, purified by silica gel column chromatography (n-hexane:ethyl acetate=8:1) and recrystallized from n-hexane/ethyl acetate and subsequently n-hexane/chloroform to give 291 mg (74%) of Compound 69.

NMR (270 MHz, CDCl$_3$) δ (ppm) 1.51 (3H, d, J=6.4), 1.4–1.8 (6H, m), 3.42–3.50 (2H, m), 4.04 (1H, sextet., J=6.4), 4.18 (2H, brs), 6.46 (1H, s), 6.84 (1H, t, J=8.7), 7.13 (1H, dd, J=13.4, 10.4), 7.50–7.58 (2H, m), 8.83 (1H, brs)

MS (M/Z) 424 (M$^+$)

Molecular formula C$_{21}$H$_{20}$ClF$_3$N$_2$O$_2$=424

EXAMPLE 70

2-(4-Amino-3-fluorophenyl)-6,8-difluoro-5-isopentylamino-4H-1-benzopyran-4-one (Compound 70)

510 mg (1.32 mmol) of 5-amino-6,8-difluoro-2-(3-fluoro-4-pivaloylaminophenyl)-4H-1-benzopyran-4-one obtained in Example 66 was dissolved in 15 ml of dimethylformamide under argon atmosphere, 160 mg of sodium hydride (60% oil dispersion) and 0.35 ml of isoamyl bromide were added under ice-cooling and the mixture was stirred at room temperature for 1.5 hours. 0.16 ml of isoamyl bromide was added and the mixture was stirred for additional 1 hour. An aqueous saturated solution of ammonium chloride was added to the reaction solution and the mixture was extracted twice with ethyl acetate. The organic layer was washed with an aqueous saturated solution of sodium chloride and dried over anhydrous sodium sulfate and the solvent was distilled off under reduced pressure. The residue was purified by silica gel column chromatography (n-hexane:ethyl acetate= 5:1) to give 310 mg (51%) of 6,8-difluoro-2-(3-fluoro-4-pivaloylaminophenyl)-5-isopentylamino-4H-1-benzopyran-4-one.

NMR (90 MHz, CDCl$_3$) δ (ppm) 0.94 (6H, d, J=5.9), 1.36 (9H, s), 1.2–2.1 (3H, m), 3.38–3.53 (2H, m), 6.54 (1H, s), 7.15 (1H, dd, J=13.3, 10.2), 7.5–7.8 (3H, m), 8.57 (1H, t, J=8.6)

MS (M/Z) 460 (M$^+$)

Molecular formula $C_{25}H_{27}F_3N_2O_3$ 6 ml of dioxane and 6 ml of concentrated hydrochloric acid were added to 283 mg (0.61 mmol) of the resulting 6,8-difluoro-2-(3-fluoro-4-pivaloylaminophenyl)-5-isopentylamino-4H-1-benzopyran-4-one and the mixture was heated at reflux for 1 hour. The reaction solution was cooled on ice, water was added, the solution was made neutral, and the precipitated crystals were collected by filtration and purified by silica gel column chromatography (n-hexane:ethyl acetate=4:1-3:1) to give 207 mg (89%) of Compound 70.

NMR (270 MHz, CDCl$_3$) δ (ppm) 0.94 (6H, d, J=6.4), 1.53 (2H, td, J=7.4, 6.9), 1.72 (1H, m), 3.46 (2H, m), 4.17 (2H, brs), 6.45 (1H, s), 6.83 (1H, t, J=8.9), 7.12 (1H, dd, J=13.4, 10.4), 7.50–7.58 (2H, m), 8.77 (1H, brs)

MS (M/Z) 376 (M$^+$)

Molecular formula $C_{20}H_{19}F_3N_2O_2=376$

EXAMPLE 71

2-(4-Amino-3-fluorophenyl)-6,8-difluoro-5-(4-methylpentylamino)-4H-1-benzopyran-4-one (Compound 71)

515 mg (1.32 mmol) of 5-amino-6,8-difluoro-2-(3-fluoro-4-pivaloylaminophenyl)-4H-1l-benzopyran-4-one obtained in Example 66 was dissolved in 15 ml of dimethylformamide under argon atmosphere, 160 mg of sodium hydride (60% oil dispersion) and 0.38 ml of 1-bromo-4-methylpentane were added under ice-cooling and the mixture was stirred at room temperature for 2 hours. An aqueous saturated solution of ammonium chloride was added to the reaction solution and the mixture was extracted twice with ethyl acetate. The organic layer was washed with an aqueous saturated solution of sodium chloride and dried over anhydrous sodium sulfate and the solvent was distilled off under reduced pressure. The residue was purified by silica gel chromatography (n-hexane:ethyl acetate=6:1) to give 334 mg (53%) of 6,8-difluoro-2-(3-fluoro-4-pivaloylaminophenyl)-5-(4-methylpentylamino)-4H-1-benzopyran-4-one.

NMR (90 MHz, CDCl$_3$) δ (ppm) 0.90 (6H, d, J=6.2), 1.2–1.7 (5H, m), 1.34 (9H, s), 3.38–3.49 (2H, m), 6.54 (1H, s), 7.14 (1H, dd, J=14.4, 9.8), 7.5–7.8 (3H, m), 8.57 (1H, t, J=8.4), 8.8 (1H, brs)

MS (M/Z) 474 (M$^+$)

Molecular formula $C_{26}H_{29}F_3N_2O_3=474$ 6 ml of dioxane and 6 ml of concentrated hydrochloric acid were added to 321 mg (0.68 mmol) of the resulting 6,8-difluoro-2-(3-fluoro-4-pivaloylaminophenyl)-5-(4-methylpentylamino)-4H-1-benzopyran-4-one and the mixture was heated ar reflux for 1 hour. The reaction solution was cooled on ice, water was added, the solution was made neutral, and the precipitated crystals were collected by filtration and purified by silica gel column chromatography (n-hexane:ethyl acetate=5:1) to give 230 mg (87%) of Compound 71.

NMR (270 MHz, CDCl$_3$) δ (ppm) 0.90 (6H, d, J=6.9), 1.24–1.32 (2H, m), 1.55–1.66 (3H, m), 3.41–3.47 (2H, m), 4.17 (2H, brs), 6.46 (1H, s), 6.84 (1H, t, J=8.7), 7.12 (1H, dd, J=13.4, 10.4), 7.32–7.58 (2H, m), 8.80 (1H, brs)

MS (M/Z) 390 (M$^+$)

Molecular formula $C_{21}H_{21}F_3N_2O_2=390$

EXAMPLE 72

2-(4-Amino-3-fluorophenyl)-5-(3-aminopropylamino)-6,8-difluoro-4H-1-benzopyran-4-one (Compound 72)

814 mg (2.09 mmol) of 5-amino-6,8-difluoro-2-(3-fluoro-4-pivaloylaminophenyl)-4H-1-benzopyran-4-one obtained in Example 66 was dissolved in 15 ml of dimethylformamide under argon atmosphere, 256 mg of sodium hydride (60% oil dispersion) and 0.42 ml of 1-bromo-3-chloropropane were added under ice-cooling and the mixture was stirred at room temperature for 3 hours. Water was added to the reaction solution and the mixture was extracted twice with ethyl acetate. The organic layer was washed twice with an aqueous saturated solution of sodium chloride and dried over anhydrous sodium sulfate and the solvent was distilled off under reduced pressure. The residue was purified by silica gel column chromatography (n-hexane:ethyl acetate=6:1) to give 193 mg (20%) of 5-(3-chloropropylamino)-6,8-difluoro-2-(3-fluoro-4-pivaloylaminophenyl)-4H-1-benzopyran-4-one.

NMR (90 MHz, CDCl$_3$) δ (ppm) 1.36 (9H, s), 2.09 (2H, quint., J=6.3), 3.5–3.8 (2H, m), 3.65 (2H, t, J=6.4), 6.56 (1H, s), 7.17 (1H, dd, J=14.0, 10.3), 7.5–7.9 (3H, m), 8.58 (1H, t, J=8.2), 8.24 (1H, brs)

MS (M/Z) 466 (M$^+$)

Molecular formula $C_{23}H_{22}ClF_3N_2O_3=466$ 177 mg (0.38 mmol) of the resulting 5-(3-chloropropylamino)-6,8-difluoro-2-(3-fluoro-4-pivaloylaminophenyl)-4H-1-benzopyran-4-one was dissolved in 10 ml of dimethylformamide under argon atmosphere, 124 mg of sodium azide was added and the mixture was stirred at 70° C. for 18 hours. Water was added to the reaction solution, and the precipitated crystals were collected by filtration and purified by silica gel column chromatography (n-hexane:ethyl acetate=4:1) to give 179 mg (100%) of 5-(3-azidopropylamino)-6,8-difluoro-2-(3-fluoro-4-pivaloylaminophenyl)-4H-1-benzopyran-4-one.

NMR (90 MHz, CDCl$_3$) δ (ppm) 1.36 (9H, s), 1.91 (2H, quint., J=6.6), 3.4–3.7 (2H, m), 3.43 (2H, t, J=6.7), 6.56 (1H, s), 7.14 (1H, dd, J=13.4, 10.4), 7.5–7.9 (3H, m), 8.59 (1H, t, J=9.0), 8.80 (1H, brs)

MS (M/Z) 473 (M$^+$)

Molecular formula $C_{23}H_{22}F_3N_5O_3=473$ 161 mg (0.34 mmol) of the resulting 5-(3-azidopropylamino)-6,8-difluoro-2-(3-fluoro-4-pivaloylaminophenyl)-4H-1-benzopyran-4-one was dissolved in a mixed solvent of 10 ml of dioxane and 10 ml of concentrated hydrochloric acid and the mixture was heated at reflux for 1 hour. The reaction solution was cooled on ice, water was added and the mixture was extracted twice with ethyl acetate. The organic layer was washed with an aqueous saturated solution of sodium chloride and dried over anhydrous sodium sulfate and the solvent was distilled off under reduced pressure to give 142 mg of crude product of 2-(4-amino-3-fluorophenyl)-5-(3-azidopropylamino)-6,8-difluoro-4H-1-benzopyran-4-one.

NMR (90 MHz, CDCl$_3$) δ (ppm) 1.90 (2H, quint., J=6.7), 3.43 (2H, t, J=7.0), 3.5–3.8 (2H, m), 4.17 (2H, brs), 6.46 (1H, s), 6.83 (1H, t, J=8.4), 7.14 (1H, dd, J=13.4, 10.1), 7.4–7.7 (2H, m), 8.80 (1H, brs)

FAB-MS (M/Z) 390 (M$^+$+1)

Molecular formula C$_{18}$H$_{14}$F$_3$N$_5$O$_2$=389

114 mg (0.29 mmol) of the resulting crude product of 2-(4-amino-3-fluorophenyl)-5-(3-azidopropylamino)-6,8-difluoro-4H-1-benzopyran-4-one was dissolved in 5 ml of tetrahydrofuran, 117 mg of triphenylphosphine was added, the mixture was stirred at room temperature for 1 hour, 5 ml of water was added and the mixture was stirred for 2 hours. The mixture was extracted twice with ethyl acetate, and the organic layer was washed with an aqueous saturated solution of sodium chloride and dried over anhydrous sodium sulfate. The solvent was distilled off under reduced pressure and the residue was purified by preparative thin layer chromatography (chloroform:methanol:aqueous ammonia=9:1:1) to give 82 mg (77%) of Compound 72.

NMR (270 MHz, DMSO-d$_6$) δ (ppm) 1.62 (2H, quint., J=6.4), 2.62 (2H, t, J=6.9), 3.3–3.5 (2H, m), 6.11 (2H, brs), 6.71 (1H, s), 6.87 (1H, t, J=8.9), 7.5–7.8 (3H, m), 8.82 (1H, m)

MS (M/Z) 363 (M$^+$)

Molecular formula C$_{18}$H$_{16}$F$_3$N$_3$O$_2$=363

EXAMPLE 73

5-(4-Aminobutylamino)-2-(4-amino-3-fluorophenyl)-6,8-difluoro-4H-1-benzopyran-4-one (Compound 73)

1.01 g (2.59 mmol) of 5-amino-6,8-difluoro-2-(3-fluoro-4-pivaloylaminophenyl)-4H-1-benzopyran-4-one obtained in Example 66 was dissolved in 20 ml of dimethylformamide under argon atmosphere, 228 mg of sodium hydride (60% oil dispersion) and 1.5 ml of 1-bromo-4-chlorobutane were added under ice-cooling and the mixture was stirred at room temperature for 3 hours. 228 mg of sodium hydride (60% oil dispersion) and 1.5 ml of 1-bromo-4-chlorobutane were further added and the mixture was stirred for additional 1 hour. Water was added to the reaction solution and the mixture was extracted three times with ethyl acetate. The organic layer was washed twice with an aqueous saturated solution of sodium chloride and dried over anhydrous sodium sulfate and the solvent was distilled off under reduced pressure. The residue was purified by silica gel column chromatography (n-hexane:ethyl acetate=6:1) to give 396 mg (32%) of 5-(4-chlorobutylamino)-6,8-difluoro-2-(3-fluoro-4-pivaloylaminophenyl)-4H-1-benzopyran-4-one.

NMR (90 MHz, CDCl$_3$) δ (ppm) 1.35 (9H, s), 1.7–2.1 (4H, m), 3.4–3.7 (2H, m), 3.57 (2H, t, J=6.3), 6.55 (1H, s), 7.16 (1H, dd, J=13.3, 10.2), 7.5–7.9 (3H, m), 8.58 (1H, t, J=8.4), 8.80 (1H, brs)

FAB-MS (M/Z) 481 (M$^+$+1)

Molecular formula C$_{24}$H$_{24}$ClF$_3$N$_2$O$_3$=480

516 mg (1.07 mmol) of the resulting 5-(4-chlorobutylamino)-6,8-difluoro-2-(3-fluoro-4-pivaloylaminophenyl)-4H-1-benzopyran-4-one was dissolved in 30 ml of dimethylformamide under argon atmosphere, 350 mg of sodium azide was added and the mixture was stirred at 70° C. for 17 hours. Water was added to the reaction solution and the precipitated crystals were collected by filtration.

457 mg (0.94 mmol) of the above product was dissolved in a mixed solvent of 40 ml of dioxane and 20 ml of concentrated hydrochloric acid and the mixture was heated at reflux for 7 hours. The reaction solution was cooled on ice and the precipitated crystals were collected by filtration.

303 mg (0.76 mmol) of the above product was dissolved in 20 ml of tetrahydrofuran, 297 mg of triphenylphosphine was added under ice-cooling, the mixture was stirred at room temperature for 1 hour, 20 ml of water was added and the mixture was stirred for 6 hours. The mixture was extracted twice with ethyl acetate, and the organic layer was washed with an aqueous saturated solution of sodium chloride and dried over anhydrous sodium sulfate. The solvent was distilled off under reduced pressure and the residue was purified by column chromatography (chloroform:methanol:aqueous ammonia=9:1:1) to give 184 mg (65%) of Compound 73.

NMR (270 MHz, DMSO-d$_6$) δ (ppm) 1.5–1.8 (4H, m), 2.7–2.9 (2H, m), 3.3–3.5 (2H, m), 6.72 (1H, s), 6.88 (1H, t, J=8.9), 7.5–7.8 (3H, m)

MS (M/Z) 377 (M$^+$)

Molecular formula C$_{19}$H$_{18}$F$_3$N$_3$O$_2$=377

EXAMPLE 74

6,8-Difluoro-2-(4-ethoxycarbonylmethylamino-3-fluorophenyl)-5-hexylamino-4H-1-benzopyran-4-one (Compound 74)

1.20 g (2.76 mmol) of 2-[4-(N-acetyl-N-ethoxycarbonylmethylamino)-3-fluorophenyl]-5-amino-6,8-difluoro-4H-1-benzopyran-4-one obtained in Example 44 was dissolved in 20 ml of dimethylformamide under argon atmosphere, 111 mg of sodium hydride (60% oil dispersion) and 0.82 ml of 1-iodohexane were added under ice-cooling and the mixture was stirred at room temperature for 1.7 hours. 33 mg of sodium hydride was added and the mixture was stirred for additional 40 minutes. A 10% aqueous solution of citric acid was added to the reaction solution and the mixture was extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:acetonitrile=10:1) to give 433 mg (28%) of 2-[4-(N-acetyl-N-ethoxycarbonylmethylamino)-3-fluorophenyl]-6,8-difluoro-5-hexylamino-4H-1-benzopyran-4-one.

NMR (90 MHz, CDCl$_3$) δ (ppm) 0.8–1.0 (3H, m), 1.1–1.9 (8H, m), 1.28 (3H, t, J=7.0), 1.99 (3H, s), 3.3–3.6 (2H, m), 4.20 (2H, q, J=7.0), 4.37 (2H, brs), 6.63 (1H, s), 7.23 (1H, dd, J=13.2, 10.2), 7.5–7.9 (3H, m)

Ms (M/Z) 518 (M$^+$)

Molecular formula C$_{27}$H$_{29}$F$_3$N$_2$O$_5$=518

422 mg (0.815 mmol) of the resulting 2-[4-(N-acetyl-N-ethoxycarbonylmethylamino)-3-fluorophenyl]-6,8-difluoro-5-hexylamino-4H-1-benzopyran-4-one was dissolved in 9 ml of ethanol, 6 ml of concentrated hydrochloric acid was added and the mixture was stirred at reflux for 2 hours. The reaction solution was cooled on ice, water was added and the mixture was extracted with ethyl acetate. The organic layer was washed with an aqueous saturated solution of sodium chloride and dried over anhydrous sodium sulfate, and the solvent was distilled off under reduced pressure. The residue was purified by silica gel column chromatography (chloroform:acetone=40:1) and recrystallized from ethyl acetate/n-hexane to give 162 mg of Compound 74.

NMR (270 MHz, DMSO-$d_6$) δ (ppm) 0.89 (3H, t, J=6.7), 1.2–1.5 (6H, m), 1.33 (3H, t, J=6.9), 1.66 (2H, quint, J=7.4), 3.45 (2H, td, J=7.2, 3.5), 4.01 (2H, s), 4.29 (2H, q, J=6.9), 6.48 (1H, s), 6.64 (1H, t, J=8.4), 7.16 (1H, dd, J=12.9, 9.9), 7.5–7.7 (2H, m)

MS (M/Z) 476 (M$^+$)

Molecular formula $C_{25}H_{27}F_3N_2O_4$=476

EXAMPLE 75

2-(4-Carboxymethylamino-3-fluorophenyl)-6,8-difluoro-5-hexylamino-4H-1-benzopyran-4-one (Compound 75)

143 mg (0.276 mmol) of Compound 74 obtained in Example 74 was dissolved in 12 ml of dioxane, 8 ml of concentrated hydrochloric acid was added and the mixture was heated ar reflux for 10 minutes. The reaction solution was cooled on ice, water was added and the mixture was extracted with ethyl acetate. The organic layer was washed twice with water and once with an aqueous saturated solution of sodium chloride and dried over anhydrous sodium sulfate, and the solvent was distilled off under reduced pressure. The residue was recrystallized from ethyl acetate/n-hexane to give 95 mg (77%) of Compound 75.

NMR (270 MHz, DMSO-$d_6$) δ (ppm) 0.89 (3H, t, J=6.7), 1.2–1.5 (6H, m), 1.61 (2H, quint., J=6.9), 3.42 (2H, td, J=6.9, 4.5), 3.98 (2H, s), 6.47 (1H, s), 6.68 (1H, t, J=8.7), 7.20 (1H, dd, J=13.4, 10.4), 7.54 (1H, dd, J=12.6, 2.0), 7.60 (1H, dd, J=8.4, 2.0)

FAB-MS (M/Z) 449 (M$^+$+1)

Molecular formula $C_{23}H_{23}F_3N_2O_4$=448

EXAMPLE 76

6,8-Difluoro-2-(3-fluoro-4-methylaminophenyl)-5-(4-pentenylamino)-4H-1-benzopyran-4-one (Compound 76)

1.99 g (4.73 mmol) of Compound 51 obtained in Example 51 was dissolved in 80 ml of dimethylformamide under argon atmosphere, 212 mg. of sodium hydride (60% oil disperison) and 0.60 ml of iodomethane were added and the mixture was stirred at room temperature for 1 hour. An aqueous saturated solution of ammonium chloride was added to the reaction solution, the precipitated crystals were collected by filtration and dissolved in ethanol, and the solvent was distilled off under reduced pressure. The residue was purified by silica gel column chromatography (chloroform) to give 2.09 g of 5-amino-2-[4-[N-(tert-butoxycarbonyl)-N-methylamino]-3-fluorophenyl]-6,8-difluoro-4H-1-benzopyran-4-one.

NMR (90 MHz, CDCl$_3$) δ (ppm) 1.44 (9H, S), 3.25 (3H, d, J=0.7), 6.20 (2H, brs), 6.60 (1H, s), 7.21 (1H, t, J=10.6), 7.38 (1H, t, J=7.9), 7.58–7.72 (2H, m)

MS (M/Z) 420 (M$^+$)

Molecular formula $C_{21}H_{19}F_3N_2O_4$=420

852 mg (2.03mmol) of the resulting 5-amino-2-[4-[N-(tert-butoxycarbonyl)-N-methylamino]-3-fluorophenyl]-6,8-difluoro-4H-1-benzopyran-4-one was dissolved in 30 ml of dimethylformamide under argon atmosphere, 165 mg of sodium hydride (60% oil dispersion) and 0.48 ml of 5-bromo-1-pentene were added under ice-cooling and the mixture was stirred at room temperature for 2 hours. 85 mg of sodium hydride (60% oil dispersion) and 0.24 ml of 5-bromo-1-pentene were added and the mixture was stirred for additional 1 hour. An aqueous saturated solution of ammonium chloride was added to the reaction solution and the mixture was extracted twice with ethyl acetate. The organic layer was washed with an aqueous saturated solution of sodium chloride and dried over anhydrous sodium sulfate, and the solvent was distilled off under reduced pressure. The residue was purified by silica gel column chromatography (n-hexane:ethyl acetate=7:1) to give 239 mg (24%) of 2-[4-[N-(tert-butoxycarbonyl)-N-methylamino]-3-fluorophenyl]-6,8-difluoro-5-(4-pentenylamino)-4H-benzopyran-4-one.

NMR (90 MHz, CDCl$_3$) δ (ppm) 1.44 (9H, s), 1.5–1.9 (2H, m), 2.0–2.4 (2H, m), 3.24 (3H, d, J=0.7), 3.49 (2H, m), 4.93–5.13 (2H, m), 5.6–6.0 (1H, m), 6.58 (1H, s), 7.16 (1H, dd, J=13.3, 10.2), 7.46 (1H, t, J=7.7), 7.59–7.71 (2H, m), 8.80 (1H, brs)

FAB-MS (M/Z) 489 (M$^+$+1)

Molecular formula $C_{26}H_{27}F_3N_2O_4$=488

212 mg (0.434mmol) of the resulting 2-[4-[N-(tert-butoxycarbonyl)-N-methylamino]-3-fluorophenyl]-6,8-difluoro-5-(4-pentenylamino)-4H-benzopyran-4-one was dissolved in 5 ml of tetrahydrofuran, 5 ml of trifluoroacetic acid was added under ice-cooling and the mixture was stirred at room temperature for 17 hours. The solvent was distilled off under reduced pressure, water was added and the .mixture was extracted with ethyl acetate. The organic layer was washed once with an aqueous saturated solution of sodium bicarbonate and once with an aqueous saturated solution of sodium chloride and dried over anhydrous sodium sulfate, and the solvent was distilled off under reduced pressure. The residue was purified by silica gel column chromatography (chloroform:n-hexane=3:2) to give 143 mg (81%) of Compound 76.

NMR (270 MHz, CDCl$_3$) δ (ppm) 1.73 (2H, m), 2.17 (2H, m), 2.97 (3H, d, J=5.4), 3.41–3.56 (2H, m), 4.45 (1H, brs), 4.97–5.10 (2H, m), 5.82 (1H, ddt, J=17.1, 10.1, 6.7), 6.45 (1H, s), 6.72 (1H, t, J=8.7), 7.11 (1H, dd, J=13.4, 10.4), 7.52 (1H, dd, J=12.4, 2.0), 7.62 (1H, dd, J=8.7, 2.0), 8.85 (1H, brs)

Ms (M/Z) 388 (M$^+$)

Molecular formula $C_{21}H_{19}F_3N_2O_2$=388

EXAMPLE 77

6,8-Difluoro-2-(3-fluoro-4-methylaminophenyl)-5-(5-hexenylamino)-4H-1-benzopyran-4-one (Compound 77)

828 mg (1.97 mmol) of 5-amino-2-[4-[N-(tert-butoxycarbonyl)-N-methylamino]-3-fluorophenyl]-6,8-difluoro-4H-1-benzopyran-4-one obtained in Example 76 was dissolved in 40 ml of dimethylformamide under argon atmosphere, 160 mg of sodium hydride (60% oil dispersion) and 0.53 ml of 6-bromo-1-hexene were added under ice-cooling and the mixture was stirred at room temperature for 2 hours. Additional 80 mg of sodium hydride (60% oil dispersion) and 0.27 ml of 6-bromo-1-hexene were added and the mixture was stirred for additional 1.5 hours. Art aqueous saturated solution of ammonium chloride was added to the reaction solution and the mixture was extracted three times with ethyl acetate. The organic layer was washed with an aqueous saturated solution of sodium chloride and dried over anhydrous sodium sulfate, and the solvent was distilled off under reduced pressure. The residue was purified by silica gel column chromatography (n-hexane:ethyl acetate=8:1) to give 315 mg (32%) of 2-[4-[N-(tert-butoxycarbonyl)-N-methylamino]-3-fluorophenyl]-6,8-difluoro-5-(5-hexenylamino)-4H-1-benzopyran-4-one.

NMR (270 MHz, CDCl$_3$) δ (ppm) 1.44 (9H, s), 1.40–1.71 (4H, m), 2.10 (2H, bq, J=7.1), 3.25 (3H, s), 3.48 (2H, m), 4.93–5.06 (2H, m), 5.81 (1H, ddt, J=17.2, 10.2, 6.6), 6.56 (1H, s), 7.16 (1H, dd, J=13.5.10.2), 7.38 (1H, brt, J=8.1), 7.62–7.68 (2H, m), 8.80 (1H, brs)

MS (M/Z) 502 (M$^+$)

Molecular formula C$_{27}$H$_{29}$F$_3$N$_2$O$_4$=502

295 mg (0.605 mmol) of the resulting 2-[4-[N-(tert-butoxycarbonyl)-N-methylamino]-3-fluorophenyl]-6,8-difluoro-5-(5-hexenylamino)-4H-1-benzopyran-4-one was dissolved in 6 ml of tetrahydrofuran, 5 ml of trifluoroacetic acid was added under ice-cooling and the mixture was stirred at room temperature for 12 hours. The solvent was distilled off under reduced pressure, water was added and the mixture was extracted with ethyl acetate. The organic layer was washed once with an aqueous saturated solution of sodium bicarbonate and once with an aqueous saturated solution of sodium chloride and dried over anhydrous sodium sulfate, and the solvent was distilled off under reduced pressure. The residue was purified by silica gel column chromatography (Chloroform:n-hexane=3:2) to give 226 mg (96%) of Compound 77.

NMR (270 MHz, CDCl$_3$) δ (ppm) 1.42–1.70 (6H, m), 2.10 (2H, q, J=6.9), 2.97 (3H, d, J=5.4), 3.40–3.49 (2H, m), 4.45 (1H, brs), 4.92–5.05 (2H, m), 5.81 (1H, ddt, J=17.1, 10.1, 6.7), 6.44 (1H, s), 6.72 (1H, t, J=8.7), 7.11 (1H, dd, J=13.4, 10.4), 7.52 (1H, dd, J=12.4, 2.0), 7.62 (1H, dd, J=8.7, 2.0), 8.83 (1H, brs)

MS (M/Z) 402 (M$^+$)

Molecular formula C$_{22}$H$_{21}$F$_3$N$_2$O$_2$=402

EXAMPLE 78

6,8-Difluoro-2-(3-fluoro-4-methylaminophenyl)-5-(3-methoxypropylamino)-4H-1-benzopyran-4-one (Compound 78)

1.03 g (2.64 mmol) of 5-amino-6,8-difluoro-2-(3-fluoro-4-pivaloylaminophenyl)-4H-1-benzopyran-4-one obtained in Example 66 was dissolved in 20 ml of dimethylformamide, 310 mg of sodium hydride (60% oil dispersion) and 1.04 g of 3-(tetrahydropyran-2-yloxy)-1-iodopropane were added under ice-cooling and the mixture was stirred for 2 hours. Water was added to the reaction solution and the mixture was extracted twice with ethyl acetate. The organic layer was washed once with water and once with an aqueous saturated solution of sodium chloride and dried over anhydrous magnesium sulfate, and the solvent was distilled off under reduced pressure. The residue was purified by silica gel column chromatography (n-hexane:ethyl acetate=5:1) to give 1.11 g of a mixture of the desired 6,8-difluoro-2-(3-fluoro-4-pivaloylaminophenyl)-5-[3-(tetrahydropyran-2-yloxy)-propylamino]-4H-1-benzopyran-4-one and the raw material.

The above mixture was dissolved in a mixed solvent of 20 ml of methanol and 10 ml of tetrahydrofuran, 79 mg of p-toluenesulfonic acid was added and the mixture was stirred at room temperature for 24 hours. Water was added to the reaction solution, the precipitated crystals were collected by filtration and purified by silica gel column chromatography (n-hexane:ethyl acetate=3:1) to give 502 mg (two stages 42%) of 6,8-difluoro-2-(3-fluoro-4-pivaloylaminophenyl)-5-(3-hydroxypropylamino)-4H-1-benzopyran-4-one.

NMR (90 MHz, CDCl$_3$) δ (ppm) 1.36 (9H, s), 1.90 (2H, quint., J=6.3), 3.4–3.8 (2H, m), 3.80 (2H, t, J=6.2), 6.55 (1H, s), 7.15 (1H, dd, J=13.4, 10.3), 7.57–7.81 (3H, m), 8.58 (1H, t, J=8.2), 8.80 (1H, brs)

FAB-MS (M/Z) 449 (M$^+$+1)

Molecular formula C$_{23}$H$_{23}$F$_3$N$_2$O$_4$=448

483 mg (1.08 mmol) of the resulting 6,8-difluoro-2-(3-fluoro-4-pivaloylaminophenyl)-5-(3-hydroxypropylamino)-4H-1-benzopyran-4-one was dissolved in 10 ml of dimethylformamide under argon atmosphere, 0.34 ml of iodomethane and 140 mg of sodium hydride (60% oil dispersion) were added under ice-cooling and the mixture was stirred at room temperature for 2 hours. Water was added to the reaction solution and the mixture was extracted twice with ethyl acetate. The organic layer was washed twice with an aqueous saturated solution of sodium chloride and dried over anhydrous sodium sulfate and the solvent was distilled off under reduced pressure. The residue was purified by silica gel column chromatography (n-hexane:ethyl acetate=8:1) to give 284 mg (55%) of 6,8-difluoro-2-[3-fluoro-4-(N-methyl-N-pivaloylamino)phenyl]-5-(3-methoxypropylamino)-4H-1-benzopyran-4-one.

NMR (90 MHz, CDCl$_3$) δ (ppm) 1.12 (9H, s), 1.90 (2H, m), 3.23 (3H, s), 3.35 (3H, s), 3.4–3.8 (2H, m), 3.50 (2H, t, J=6.2), 6.61 (1H, s), 7.18 (1H, dd, J=13.4, 10.3), 7.41 (1H, t, J=8.0), 7.64–7.76 (3H, m), 8.80 (1H, brs)

MS (M/Z) 476 (M$^+$)

Molecular formula C$_{25}$H$_{27}$F$_3$N$_2$O$_4$=476

10 ml of dioxane and 10 ml of concentrated hydrochloric acid were added to 270 mg (0.567 mmol) of the resulting 6,8-difluoro-2-[3-fluoro-4-(N-methyl-N-pivaloylamino)phenyl]-5-(3-methoxypropylamino)-4H-1-benzopyran-4-one and the mixture was heated at reflux for 30 minutes. The reaction solution was cooled on ice, water was added, the solution was made neutral, and the precipitated crystals were collected by filtration and purified by silica gel column chromatography (n-hexane:ethyl acetate=3:1) to give 190 mg (85%) of Compound 78.

NMR (270 MHz, CDCl$_3$) δ (ppm) 1.89 (2H, quint., J=6.3), 2.97 (3H, d, J=5.4), 3.35 (3H, s), 3.50 (2H, t, J=6.2), 3.54 (2H, m), 4.45 (1H, brs), 6.45 (1H, s), 6.72 (1H, t, J=8.7), 7.12 (1H, dd, J=13.4, 10.4), 7.52 (1H) dd, J=12.9, 2.0), 7.62 (1H, dd, J=8.4, 2.0)

MS (M/Z) 392 (M$^+$)

Molecular formula C$_{20}$H$_{19}$F$_3$N$_2$O$_3$=392

EXAMPLE 79

2-[4-(3-aminopropylamino)-3-fluorophenyl]-6,8-difluoro-5-pentylamino-4H-1-benzopyran-4-one (Compound 79)

810 mg (1.91 mmol) of 2-[4-[N-acetyl-N-(3-chloropropyl)amino]-3-fluorophenyl]-5-amino-6,8-difluoro-4H-1-benzopyran-4-one obtained in Example 50 was dissolved in 40 ml of dimethylformamide under argon atmosphere, 622 mg of sodium azide was added at room temperature and the mixture was stirred at 70° C. for 4 hours. Water was added to the reaction solution, the mixture was extracted twice with ethyl acetate, the organic layer was washed once with water and once with an aqueous saturated solution of sodium chloride and dried over anhydrous sodium sulfate, and the solvent was distilled off under reduced pressure to give 870 mg of 2-[4-[N-acetyl-N-(3-azidopropyl)amino]-3-fluorophenyl]-5-amino-6,8-difluoro-4H-1-benzopyran-4-one.

NMR (90 MHz, CDCl$_3$) δ (ppm) 1.82 (2H, m), 1.91 (3H, s), 3.37 (2H, t, J=6.7), 3.8 (2H, m), 6.22 (2H, brs), 6.64 (1H, s), 7.23 (1H, t, J=10.4), 7.40 (1H, t, J=8.0), 7.72–7.84 (2H, m)

MS (M/Z) 431 (M⁺)

Molecular formula $C_{20}H_{16}F_3N_5O_3=431$ 751 mg (1.74 mmol) of the resulting 2-[-4-[N-acetyl-N-(3-azidopropyl)amino]-3-fluorophenyl]-5-amino-6,8-difluoro-4H-1-benzopyran-4-one was dissolved in 25 ml of dimethylformamide under argon atmosphere, 141 mg of sodium hydride (60% oil dispersion) and 0.45 ml of 1-iodopentane were added under ice-cooling and the mixture was stirred at room temperature for 1 hour. Water was added to the reaction solution, the mixture was extracted twice with ethyl acetate, a 10% aqueous solution of citric acid was added to the aqueous layer and the mixture was further extracted with ethyl acetate. The organic layer was washed once with an aqueous saturated solution of sodium chloride and dried over anhydrous sodium sulfate, and the solvent was distilled off under reduced pressure. The residue was purified by silica gel column chromatography (n-hexane:ethyl acetate=3:1) to give 659 mg (75%) of 2-[4-[N-acetyl-N-(3-azidopropyl)amino]-3-fluorophenyl]-6,8-difluoro-4-pentylamino-4H-1-benzopyran-4-one.

NMR (90 MHz, CDCl₃) δ (ppm) 0.8–1.0 (3H, m), 1.2–2.0 (8H, m), 1.90 (3H, s), 3.36 (2H, t, J=6.8), 3.3–3.6 (2H, m), 3.6–4.0 (2H, m), 6.60 (1H, s), 7.17 (1H, dd, J=13.3, 10.2), 7.39 (1H, t, J=7.7), 7.70–7.81 (2H, m)

Ms (M/z) 501 (M⁺)

Molecular formula $C_{25}H_{26}F_3N_5O_3=501$ 51 mg (0.10 mmol) of the resulting 2-[4-[N-acetyl-N-(3-azidopropyl)amino]-3-fluorophenyl]-6,8-difluoro-5-pentylamino-4H-1-benzopyran-4-one was dissolved in a mixed solvent of 1.5 ml of dioxane and 1.5 ml of concentrated hydrochloric acid and the mixture was heated at reflux for 3 hours. The reaction solution was cooled, water was added, the solution was made weak alkaline and the mixture was extracted twice with ethyl acetate. The organic layer was washed once with water and once with an aqueous saturated solution of sodium chloride and dried over anhydrous sodium sulfate, and the solvent was distilled off under reduced pressure. The residue was purified by preparative thin layer chromatography (chloroform) to give 26 mg (56%) of 2-[4-(3-azidopropylamino)-3-fluorophenyl]-6,8-difluoro-5-pentylamino-4H-1-benzopyran-4-one.

NMR (90 MHz, CDCl₃) δ (ppm) 0.8–1.0 (3H, m), 1.2–1.8 (6H, m), 1.94 (2H, quint., J=6.6), 3.41 (2H, t, J=6.2), 3.48 (2H, t, J=6.6), 4.45 (1H, brs), 6.44 (1H, s), 6.75 (1H, t, J=8.7), 7.11 (1H, dd, J=13.4, 10.3), 7.45–7.67 (2H, m), 8.80 (1H, brs)

MS (M/Z) 459 (M⁺)

Molecular formula $C_{23}H_{24}F_3N_5O_2=459$ 330 mg (0.72 mmol) of the resulting 2-[4-(3-azidopropylamino)-3-fluorophenyl]-6,8-difluoro-5-pentylamino-4H-1-benzopyran-4-one was dissolved in 20 ml of tetrahydrofuran, 284 mg of triphenylphosphine was added under ice-cooling, the mixture was warmed to room temperature, 10 ml of water was added and the mixture was stirred overnight. The solvent was distilled off under reduced pressure and extracted with ethyl acetate. The organic layer was washed with an aqueous saturated solution of sodium chloride and dried over anhydrous sodium sulfate and the solvent was distilled off under reduced pressure. The residue was purified by silica gel column chromatography (chloroform:methanol=50:1-chloroform:methanol:aqueous ammonia= 50:1:1) to give 278 mg (89%) of Compound 79.

NMR (270 MHz, CDCl₃) δ (ppm) 0.91 (3H, t, J=6.9), 1.25–1.75 (6H, m), 1.83 (2H, quint., J=6.4), 2.91 (2H, t, J=6.4), 3.30–3.37 (2H, m), 3.39–3.48 (2H, m), 5.10 (1H, brs), 6.43 (1H, s), 6.73 (1H, t, J=8.4), 7.11 (1H, dd, J=13.4, 10.4), 7.51 (1H, dd, J=12.4, 2.0), 7.59 (1H, dd, J=8.4, 1.5), 8.82 (1H, brs)

MS (M/Z) 433 (M⁺)

Molecular formula $C_{23}H_{26}F_3N_3O_2=433$

EXAMPLE 80

5-Amino-2-(4-amino-3-fluorophenyl)-6,8-difluoro-7-methyl-4H-1-benzopyran-4-one (Compound 80)

(1) 70.0 mL (500 mmol) of diisopropylamine was dissolved in 140 mL of tetrahydrofuran under argon atmosphere and 288 mL of a 1.6M solution of 460 mmol of n-butyl lithium in n-hexane was added dropwise while keeping an internal temperature at −10° to0° C. The reaction solution was cooled to −60° C. or below (internal temperature) and a solution of 77.0 g (200 mmol) of compound E obtained in Reference Example 4 in 600 mL of tetrahydrofuran was added dropwise. The mixture was stirred at the same temperature for 2 hours to lithiate 4-position. 19 mL (0.30 mol) of iodomethane was added thereto and the mixture was further stirred for 30 minutes. Water was added to the reaction solution, the temperature of the solution was raised to room temperature and the solution was extracted once with ethyl acetate. The organic layer was washed once with an aqueous saturated solution of sodium chloride and dried over anhydrous sodium sulfate. The solvent was distilled off under reduced pressure and the residue was triturated with n-hexane to give 75.9 g of ethyl 3,5-difluoro-4-methyl-6-pivaloylamino-2-(2-tetrahydropyranyloxy)benzoate (yield: 95%).

NMR (90 MHz, CDCl₃) δ (ppm) 1.19 (s, 9H), 1.37 (t, 3H, J=7.0 Hz), 1.4–2.0 (m,6H), 2.23 (t,3H,J=2.2 Hz), 3.4–4.2 (m, 2H), 4.34 (q, 2H, J=7.0 Hz), 5.28 (brs, 1H), 7.69 (brs, 1H)

FAB-MS (M/Z) 400 (M⁺+H)

Molecular formula $C_{20}H_{27}F_2NO_5=399$ (2) 430 mg (10.8 mmol) of sodium hydride (60% oil dispersion) was suspended in a mixed solvent of 2 mL of toluene and 2 mL of 1,4-dioxane under argon atmosphere, a solution obtained by dissolving 1.51 g (3.78 mmol) of the above ethyl 3,5-difluoro-4-methyl-6-pivaloylamino-2-(2-tetrahydropyranyloxy)benzoate and 750 mg (3.15 mmol) of compound G obtained in Reference Example 6 in a mixed solvent of 10 mL of toluene and 10 mL of 1,4-dioxane was added thereto dropwise while heating at reflux and the mixture was further stirred for 50 minutes. The reaction solution was cooled on ice, water was added and the mixture was extracted once with ethyl acetate. The organic layer was washed once with an aqueous saturated solution of sodium chloride, dried over anhydrous sodium sulfate and the solvent was distilled off under reduced pressure. The residue was dissolved in 40 mL of ethanol, 10 mL of concentrated sulfuric acid was added thereto and the mixture was stirred at room temperature for 12 hours. Water was added to the reaction solution and the precipitated crystals were collected by filtration to give 834 mg of 6,8-difluoro-2-(3-fluoro-4-pivaloylaminophenyl)-7-methyl-5-pivaloylamino-4H-1-benzopyran-4-one (yield: 54%).

NMR (90 MHz, CDCl₃) δ (ppm) 1.36 (s, 9H), 1.38 (s, 9H), 2.41 (t, 3H, J=2.2 Hz), 6.64 (s, 1H), 7.5–7.9 (m, 3H), 8.59 (t, 1H, J=8.4 Hz), 10.5 (brs, 1H)

EIMS (M/Z) 488 (M⁺)

Molecular formula $C_{26}H_{27}F_3N_2O_4=488$ (3) 50 mL of 1,4-dioxane and 25 mL of concentrated hydrochloric acid were added to 800 mg (1.64 mmol) of the above 6,8-difluoro-2-(3-fluoro-4-pivaloylaminophenyl)-7-methyl-5-pivaloylamino-4H-1-benzopyran-4-one and the mixture was stirred under heating at reflux for 2 hours. The reaction solution was poured into ice water, and the solution was made basic and extracted once with chloroform. The organic layer was washed once with an aqueous saturated solution of sodium chloride and dried over anhydrous sodium sulfate. The solvent was distilled off under reduced pressure, and the residue was purified by silica gel column chromatography (chloroform:methanol=40:1) and recrystallized from ethyl acetate/n-hexane to give 183 mg of Compound 80 (yield: 35%).

NMR (270 MHz, CDCl$_3$) δ (ppm) 2.33 (t, 3H, J=2.0 Hz), 4.17 (brs, 2H), 6.12 (brs, 2H), 6.45 (s, 1H), 6.84 (t, 1H, J=8.4 Hz), 7.5–7.6 (m, 2H)

EIMS (M/Z) 320 (M$^+$)

Molecular formula $C_{16}H_{11}F_3N_2O_2$=320

EXAMPLE 81

5-Amino-2-(4-amino-3-fluorophenyl)-7-ethyl-6,8-difluoro-4H-1-benzopyran-4-one (Compound 81)

(1) Substantially the same manner as that in Example 80 (1) was repeated except that 2.40 mL (30.0 mmol) of iodoethane was used in place of iodomethane and the resulting compound was purified by silica gel column chromatography (n-hexane:ethyl acetate=3:1), to give 2.78 g of ethyl 4-ethyl-3,5-difluoro-6-pivaloylamino-2-(2-tetrahydropyranyloxy)benzoate (yield: 67%).

NMR (90 MHz, CDCl$_3$) δ (ppm) 1.20 (t, 3H, J=7.7 Hz), 1.29 (s, 18H), 1.37 (t, 3H, J=7.0 Hz), 1.4–2.0 (m, 6H), 2.72 (q, 2H, J=7.7 Hz), 3.4–4.2 (m, 2H), 4.34 (q, 2H, J=7.0 Hz), 5.28 (brs, 1H), 7,67 (brs, 1H)

FAB-MS (M/Z) 414 (M$^+$+H)

Molecular formula $C_{21}H_{29}F_2NO_5$=413

(2) Substantially the same manner as that in Example (2) was repeated except that 2.00 g of the above ethyl 4-ethyl-3,5-difluoro-6-pivaloylamino-2-(2-tetrahydropyranyloxy)benzoate and 960 mg (4.04 mmol) of compound G obtained in Reference Example 6 were used, to give 84 mg of 7-ethyl-6,8-difluoro-2-(3-fluoro-4-pivaloylaminophenyl)-5-pivaloylamino-4H-1-benzopyran-4-one (yield: 41%).

NMR (90 MHz, CDCl$_3$) δ (ppm) 1.35 (t, 3H, J=7.5 Hz), 1.36 (s, 9H), 1.38 (s, 9H), 2.7–3.1 (m, 2H), 6.65 (s, 1H), 7,5–7.9 (m, 3H), 8.59 (t, 1H, 8.4 Hz), 10.5 (brs, 1H)

EIMS (M/Z) 502 (M$^+$)

Molecular formula $C_{27}H_{29}F_3N_2O_4$=502

(3) Substantially the same manner as that in Example (3) was repeated except that 800 mg (1.59 mmol) of the above 7-ethyl-6,8-difluoro-2-(3-fluoro-4-pivaloylaminophenyl)--pivaloylamino-4H-1-benzopyran-4-one was used, to give 235 mg of Compound 81 (yield: 44%).

NMR (270 MHz, DMSO-d$_6$) δ (ppm) 1.21 (t, 3H, J=7.6 Hz), 2.74 (q, 2H, J=7.6 Hz), 6.08 (brs, 2H), 6.66 (s, 1H), 6.87 (t, H, J=8.8 Hz), 6.99 (brs, 2H), 7.59 (dd, 1H, J=8.6, 2.0 Hz), 7.65 (dd, 1H, J=13.0, 2.0 Hz)

EIMS (M/Z) 334 (M$^+$)

Molecular formula $C_{17}H_{13}F_3N_2O_2$=334

EXAMPLE 82

5-Amino-2-(4-amino-3-fluorophenyl)-7-(1-butyl)-6,8-difluoro-4H-1-benzopyran-4-one (Compound 82)

(1) Substantially the same manner as that in Example (1) was repeated except that 3.41 mL (30.0 mmol) of 1-iodobutane was used in place of iodomethane and the resulting compound was purified by silica gel column chromatography (n-hexane:ethyl acetate=4:1), to give 1.30 g of ethyl 4-(1-butyl)-3,5-difluoro-6-pivaloylamino-2-(2-tetrahydropyranyloxy)benzoate (yield: 29%).

NMR (90 MHz, CDCl$_3$) δ (ppm) 0.92 (t, 3H, J=5.9 Hz), 1.29 (s, 9H), 1.37 (t, 3H, J=7.0 Hz), 1.4–2.0 (m, 10H), 2.69 (brt, 2H), 3.4–4.2 (m, 2H), 4.34 (q, 2H, J=7.0 Hz), 5,27 (brs, 1H), 7.67 (brs, 1H)

FAB -MS (Negative) (M/Z) 440 (M$^+$–H)

Molecular formula $C_{23}H_{33}F_2NO_5$=441

(2) Substantially the same manner as that in Example 1 (2) was repeated except that 1.30 g (2.95 mmol) of the above ethyl 4-(1-butyl)-3,5-difluoro-6-pivaloylamino-2-(2-tetrahydropyranyloxy)benzoate and 585 mg (2.46 mmol) of compound G obtained in Reference Example 6 were used, to give 470 mg of 7-(1-butyl)-6,8-difluoro-2-(3-fluoro-4-pivaloylaminophenyl)-5-pivaloylamino-4H-1-benzopyran-4-one (yield: 36%).

NMR (90 MHz, DMSO-d$_6$) δ (ppm) 0.96 (t, 3H, J=6.3 Hz), 1.2–1.9 (m, 7H), 1.36 (s, 9H), 1.39 (s, 9H), 2.7–3.0 (m, 2H), 6.64 (S, 1H), 7.5–7.9 (m, 3H), 8.59 (t, 1H, J=8.4 Hz), 10.5 (brs, 1H)

EIMS (M/Z) 530 (M$^+$)

Molecular formula $C_{29}H_{33}F_3N_2O_4$=530

(3) Substantially the same manner as that in Example 80 (3) was repeated except that 450 mg (0.849 mmol) of the above 7-(1-butyl)-6,8-difluoro-2-(3-fluoro-4-pivaloylaminophenyl)-5-pivaloylamino-4H-1-benzopyran-4-one was used, to give 144 mg of Compound 82 (yield: 47%).

NMR (270 MHz, CDCl$_3$) δ (ppm) 0.95 (t, 3H, J=7.4 Hz), 1.40 (sextet, 2H, J=7.4 Hz), 1.63 (quint., 2H, J=7.4 Hz), 2.79 (t, 2H, J=7.4 Hz), 4.16 (brs, 2H), 6.12 (brs, 2H), 6.46 (s, H), 6.84 (t, 1H, J=8.7 Hz), 7.5–7.6 (m, 2H)

EIMS (M/Z) 362 (M$^+$)

Molecular formula $C_{19}H_{17}F_3N_2O_2$=362

EXAMPLE 83

5-Amino-2-(4-amino-3-fluorophenyl)-6,8-difluoro-7-(1-hexyl)-4H-1-benzopyran-4-one (Compound 83)

(1) Substantially the same manner as that in Example 80 (1) was repeated except that 4.43 mL (30.0 mmol) of 1-iodohexane was used in place of iodomethane and the resulting compound was purified by silica gel column chromatography (n-hexane:ethyl acetate=4:1), to give 3.32 g of ethyl 3,5-difluoro-4-(1-hexyl)-6-pivaloylamino-2-(2-tetrahydropyranyloxy)benzoate (yield: 71%).

NMR (90 MHz, CDCl$_3$) δ (ppm) 0.7–1.0 (m, 3H), 1.29 (s, H), 1.37 (t, 3H, J=7.0 Hz), 1.4–2.0 (m, 14H), 2.5–2.9 (m, 2H), 3.4–4.2 (m, 2H), 4.34 (q, 2H, J=7.0 Hz), 5.26 (brs, 1H), 7.67 (brs, 1H)

FAB-MS (Negative) (M/Z) 468 (M$^+$-H)

Molecular formula $C_{25}H_{37}F_2NO_5$=469

(2) Substantially the same manner as that in Example 80 (2) was repeated except that 3.31 g (7.06 mmol) of the above ethyl 3,5-difluoro-4-(1-hexyl)-6-pivaloylamino-2-(2-tetrahydropyranyloxy)benzoate and 1.40 g (5.88 mmol) of a compound G obtained in Reference Example 6 were used, to give 1.41 g of 6,8-difluoro-2-(3-fluoro-4-pivaloylaminophenyl)-7-(1-hexyl)-5-pivaloylamino-4H-1-benzopyran-4-one (yield:43%).

NMR (90 MHz, CDCl$_3$) δ (ppm) 0.8–1.0 (m, 3H), 1.1–1.8 (m, 8H), 1.36 (s, 9H), 1.38 (s, 9H), 2.7–3.0 (m, 2H), 6.64 (s, H), 7.5–7.9 (m, 3H), 8.59 (t, 1H, 8.4 Hz), 10.5.(brs, 1H)

EIMS (M/Z) 558 (M⁺)

Molecular formula $C_{31}H_{37}F_3N_2O_4=558$ (3) Substantially the same manner as that in Example 80 (3) was repeated except that 35 g (2.42 mmol) of the above 6,8-difluoro-2-(3-fluoro-4-pivaloylaminophenyl)-7-(1-hexyl)-5-pivaloylamino-4H-1-benzopyran-4-one was used, to give 499 mg of Compound 83 (yield: 53%).

NMR (270 MHz, CDCl₃) δ (ppm) 0.89 (t, 3H, J=6.9 Hz), 1.2–1.5 (m, 6H), 1.64 (quint., 2H, J=7.4 Hz), 2.78 (t, 2H, J=7.4 Hz), 4.16 (brs, 2H), 6.16 (brs, 2H), 6.46 (s, 1H), 6.84 (t, 1H, J=8.9 Hz), 7.5–7.6 (m, 2H)

EIMS (M/Z) 390 (M⁺)

Molecular formula $C_{21}H_{21}F_3N_2O_2=390$

EXAMPLE 84

5-Amino-2-(4-amino-3-fluorophenyl)-7-bromo-6,8-difluoro-4H-1-benzopyran-4-one (Compound 85)

(1) Substantially the same manner as that in Example 80 (1) was repeated except that 2.59 mL (30.0 mmol) of 1,2-dibromoethane was used in place of iodomethane and the resulting compound was purified by silica gel column chromatography (n-hexane:ethyl acetate=4:1), to give 2.26 g of ethyl 4-bromo-3,5-difluoro-6-pivaloylamino-2-(2-tetrahydropyranyloxy) benzoate (yield: 49%).

NMR (90 MHz, CDCl₃) δ (ppm) 1.29 (s, 9H), 1.38 (t, H, J=7.0 Hz), 1.4–2.0 (m, 6H), 3.4–4.2 (m, 2H), 4.35 (q, 2H, J=7.0 Hz), 5.32 (brs, 1H), 7.65 (brs, 1H)

FAB-MS (Negative) (M/Z) 462,464 (M⁺-H)

Molecular formula $C_{19}H_{2479}BrF_2NO_5=463$ (2) Substantially the same manner as that in Example 80 (2) was repeated except that 2.05 g (4.42 mmol) of the above ethyl 4-bromo-3,5-difluoro-6-pivaloylamino-2-(2-tetrahydropyranyloxy)benzoate and 956 mg (4.02 mmol) of a compound G obtained in Reference Example 6 were used, to give 1.27 g of 7-bromo-6,8-difluoro-2-(3-fluoro-4-pivaloylaminophenyl)-5-pivaloylamino-4H-1-benzopyran-4-one (yield: 57%).

NMR (90 MHz, CDCl₃) δ (ppm) 1.37 (s, 9H), 1.38 (s, H), 6.68 (s, 1H), 7.5–8.0 (m, 3H), 8.60 (t, 1H, J=8.4 Hz), 10.6 (brs, 1H)

FAB-MS (M/Z) 553, 555 (M⁺+H)

Molecular formula $C_{25}H_{2479}BrF_3N_2O_4=552$ (3) Substantially the same manner as that in Example 80 (3) was repeated except that 500 mg (0.938 mmol) of the above 7-bromo-6,8-difluoro-2-(3-fluoro-4-pivaloylaminophenyl)- -pivaloylamino-4H-1-benzopyran-4-one was used, to give 138 mg of Compound 85 (yield: 38%).

NMR (270 MHz, DMSO-d₆) δ (ppm) 6.13 (brs, 2H), 6.72 (s, 1H), 6.87 (t, 1H, J=8.9 Hz), 7.27 (brs, 2H), 7.59 (dd, 1H, J=8.4, 1.5 Hz), 7.66 (dd, 1H, J=12.7, 1.5 Hz)

EIMS (M/Z) 386,384 (M⁺)

Molecular formula $C_{15}H_{879}BrF_3N_2O_2=384$

EXAMPLE 85

5-Amino-2-(4-amino-3-fluorophenyl)-6,8-difluoro-7-methylthio-4H-1-benzopyran-4-one (Compound 89)

(1) Substantially the same manner as that in Example 80 (1) was repeated except that 1.80 mL (20.0 mmol) of dimethyl disulfide was used in place of iodomethane, to give 3.82 g of ethyl 3,5-difluoro-4-methylthio-6-pivaloylamino-2-(2-tetrahydropyranyloxy)benzoate (yield: 89%).

NMR (90 MHz, CDCl₃) δ (ppm) 1.29 (s, 9H), 1.37 (t, H, J=7.0 Hz), 1.4–2.0 (m, 6H), 3.4–4.2 (m, 2H), 4.34 (q, 2H, J=7.0 Hz), 5.28 (brs, 1H), 7.63 (brs, 1H)

FAB-MS (Negative) (M/Z) 430 (M⁺-H)

Molecular formula $C_{20}H_{27}NO_5S=431$ (2) Substantially the same manner as that in Example (2) was repeated except that 3.56 g (8.26 mmol) of the above ethyl 3,5-difluoro-4-methylthio-6-pivaloylamino-2-(2-tetrahydropyranyloxy)benzoate and 1.63 g (6.88 mmol) of compound G obtained in Reference Example 6 were used, to give 2.07 g of 6,8-difluoro-2-(3-fluoro-4-pivaloylaminophenyl)-7-methylthio-5-pivaloylamino-4H-1-benzopyran-4-one (yield: 58%).

NMR (90 MHz, CDCl₃) δ (ppm) 1.36 (s, 9H), 1.38 (s, H), 2.66 (t, 3H, J=1.3 Hz), 6.65 (s, 1H), 7.5–7.9 (m, 2H), 8.60 (t, 1H, J=8.4 Hz)

EIMS (M/Z) 520 (M⁺)

Molecular formula $C_{26}H_{27}F_3N_2O_4S=520$ (3) 511 mg (0.983 mmol) of the above 6,8-difluoro-2-(3-fluoro-4-pivaloylaminophenyl)-7-methylthio-5-pivaloylamino-H-1-benzopyran-4-one was dissolved in 20 mL of concentrated sulfuric acid and the solution was stirred at 50° C. for 10 minutes. The reaction solution was poured into ice water, the solution was made neutral and the precipitated crystals were collected by filtration. The crystals were purified by silica gel column chromatography (chloroform) and recrystallized from ethyl acetate/n-hexane to give 309 mg of Compound 89 (yield:

NMR (270 MHz, DMSO-d₆) δ (ppm) 2.59 (s, 3H), 6.11 (brs, 2H), 6.69 (s, 1H), 6.86 (t, 1H, J=8.7 Hz), 7.10 (brs, 2H), 7.59 (dd, 1H, J=8.4, 2.0 Hz), 7.66 (dd, 1H, J=12.9, 2.0 Hz)

EIMS (M/Z) 352 (M⁺)

Molecular formula $C_{16}H_{11}F_3N_2O_2S=352$

EXAMPLE 86

5-Amino-2-(4-amino-3-fluorophenyl)-6,8-difluoro-7-hydroxy-4H-1-benzopyran-4-one (Compound 86)

(1) 7.00 mL (50.0 mmol) of diisopropylamine was dissolved in 14 mL of tetrahydrofuran under argon atmosphere and 30 mL of a 1.6M solution of 48 mmol of n-butyl lithium in n-hexane was added thereto dropwise while keeping an internal temperature at −10° to 0° C. The reaction solution was cooled to −60° C. or below (internal temperature) and a solution of 7.70 g (20.0 mmol) of compound E obtained in Reference Example 4 in 60 mL of tetrahydrofuran was added dropwise. The mixture was stirred at the same temperature for 2 hours to lithiate 4-position. 2.7 mL (24 mmol) of trimethoxyborane was added and the temperature of the mixture was raised to 0° C. for 20 minutes. 4.0 mL of acetic acid and 8.0 mL of 30% hydrogen peroxide were added to the reaction solution and the mixture was stirred at room temperature for 20 hours. An aqueous solution of sodium hydrogensulfite was added to the reaction solution, the temperature of the mixture was raised to room temperature and the mixture was washed once with ethyl acetate. The aqueous layer was made acidic by addition of 2N hydrochloric acid and extracted once with ethyl acetate. The organic layer was washed once with water and once with an aqueous saturated solution of sodium chloride and dried over anhydrous sodium sulfate. The solvent was distilled off under reduced pressure and the residue was triturated with n-hexane to give 4.33 g of ethyl 3,5-difluoro-4-hydroxy-6-pivaloylamino-2-(2-tetrahydropyranyloxy)benzoate (yield: 54%).

NMR (90 MHz, CDCl$_3$) δ (ppm) 1.30 (s, 9H), 1.37 (t, 3H, J=7.0 Hz), 1.4–2.0 (m, 6H), 3.4–4.2 (m, 2H), 4.34 (q, 2H, J=7.0 Hz), 5.28 (brs, 1H), 8.15 (brs, 1H)

FAB-MS (Negative) (M/Z) 400 (M$^+$-H)

Molecular formula C$_{19}$H$_{25}$F$_2$NO$_6$=401

(2) 4.23 g (10.5 mmol) of the above ethyl 3,5-difluoro-4-hydroxy-6-pivaloylamino-2-(2-tetrahydropyranyloxy)benzoate was dissolved in 50 mL of dichloromethane, 2.4 mL (13.7 mmol) of diisopropylethylamine and 0.96 mL (12.6 mmol) of chloromethyl methyl ether were added under ice-cooling and the mixture was stirred at the same temperature for 30 minutes. Water was added to the reaction solution and the mixture was extracted once with chloroform. The organic layer was washed once with an aqueous saturated solution of sodium chloride and dried over anhydrous sodium sulfate. The solvent was distilled off under reduced pressure and the residue was triturated with n-hexane to give 4.33 g of ethyl 3,5-difluoro-4-methoxymethoxy-6-pivaloylamino-2-(2-tetrahydropyranyloxy)benzoate (yield: 93%).

NMR (90 MHz, CDCl$_3$) δ (ppm) 1.29 (s, 9H), 1.37 (t, 3H, J=7.0 Hz), 1.4–2.0 (m, 6H), 3.57 (s, 3H), 4.34 (q, 2H, J=7.0 Hz), 5.21 (s, 2H), 5.28 (brs, 1H), 7,80 (brs, 1H)

FAB-MS (Negative) (M/Z) 444 (M$^+$-H)

Molecular formula C$_{21}$H$_{29}$F$_2$NO$_7$=445

(3) Substantially the same manner as that in Example 80 (2) was repeated except that 3.98 g (8.94 mol) of the above ethyl 3,5-difluoro-4-methoxymethoxy-6-pivaloylamino-2-(2-tetrahydropyranyloxy)benzoate and 2.17 g (9.17 mmol) of a compound G obtained in Reference Example 6 were used, to give 1.15 g of 6,8-difluoro-2-(3-fluoro-4-pivaloylaminophenyl)-7-hydroxy-5-pivaloylamino-4H-1-benzopyran-4-one (yield: 26%).

NMR (90 MHz, CDCl$_3$) δ (ppm) 1.36 (s, 9H), 1.37 (s, 9H), 6.59 (s, 1H), 7.5–7.9 (m, 3H), 8.53 (t, 1H, J=8.4 Hz), 10.6 (brs, 1H), 10.9 (brs, 1H)

EIMS (M/Z) 490 (M$^+$)

Molecular formula C$_{25}$H$_{25}$F$_3$N$_2$O$_5$=490

(4) Substantially to the same manner as that in Example 85 (3) was repeated except that 409 mg (0.834 mmol) of the above 6,8-difluoro-2-(3-fluoro-4-pivaloylaminophenyl)-7-hydroxy-5-pivaloylamino-4H-1-benzopyran-4-one was used, and the resulting compound was purified by silica gel column chromatography (chloroform:methanol=200: 1–9:1) and recrystallized from methanol/isopropyl ether, to give 139 mg of Compound 86 (yield: 52%).

NMR (270 MHz, DMSO-d$_6$) δ (ppm) 6.02 (brs, 2H), 6.57 (s, 1H), 6.87 (t, 1H, J=8.7 Hz), 6,97 (brs, 2H), 7.56 (dd, 1H, J=8.4, 2.0 Hz), 7.62 (dd, 1H, J=12.9, 2.0 Hz), 11.3 (brs, 1H)

EIMS (M/Z) 322 (M$^+$)

Molecular formula C$_{15}$H$_9$F$_3$N$_2$O$_3$=322

EXAMPLE 87

5-Amino-2-(4-amino-3-chlorophenyl)-6,8-difluoro-7-methyl-4H-1-benzopyran-4-one (Compound 103)

(1) Substantially the same manner as that in Example 80 (2) was repeated except that 14.6 g (36.7 mmol) of ethyl 3,5-difluoro-4-methyl-6-pivaloylamino-2-(2-tetrahydropyranyloxy)benzoate obtained in Example 80 (1) and 7.73 g (30.6 mmol) of a compound H obtained in Reference Example 7 were used, to give 8.41 g of 2-(3-chloro-4-pivaloylaminophenyl)-6,8-difluoro-7-methyl-5-pivaloylamino-4H-1-benzopyran-4-one (yield: 55%).

NMR (90 MHz, CDCl$_3$) δ (ppm) 1.38 (s, 18H), 2.41 (t, 3H, J=2.2 Hz), 6.64 (s, 1H), 7.82 (dd, 1H, J=9.0, 2.0 Hz), 7.95 (d, 1H, J=2.0 Hz), 8.22 (brs, 1H), 8.66 (d, 1H, J=9.0 Hz)

EIMS (M/Z) 504 (M$^+$)

Molecular formula C$_{26}$H$_{27}$$^{35}$ClF$_2$N$_2$O$_4$=504

(2) 8.29 g (16.5 mmol) of the above 2-(3-chloro-4-pivaloylaminophenyl)-6,8-difluoro-7-methyl-5-pivaloylamino-4H-1-benzopyran-4-one was dissolved in 60 mL of concentrated sulfuric acid and the solution was stirred at 50° C. for 10 minutes. The reaction solution was poured into ice water and the precipitated crystals were collected by filtration. The crystals were triturated with a 1N aqueous solution of sodium hydroxide and collected by filtration again. The crystals were recrystallized twice from ethyl acetate/n-hexane to give 2.42 g of Compound 103 (yield: 44%).

NMR (270 MHz, DMSO-d$_6$) δ (ppm) 2.27 (t, 3H, J=1.7 Hz), 6.24 (brs, 2H), 6.66 (s, 1H), 6.89 (d, 1H, J=8.4 Hz), 6.97 (brs, 2H), 7.69 (dd, 1H, J=8.9, 2.0 Hz), 7.83 (d, 1H, J=2.0 Hz)

EIMS (M/Z) 336 (M$^+$)

Molecular formula C$_{16}$H$_{11}$$^{35}$ClF$_2$N$_2$O$_2$=336

EXAMPLE 88

5-Amino-2-(4-amino-3,5-dichlorophenyl)-6,8-difluoro-7-methyl-4H-1-benzopyran-4-one (Compound 104)

(1) Substantially the same manner as that in Example 80 t (2) was repeated except that 4.66 g (11.7 mmol) of ethyl 3,5-difluoro-4-methyl-6-pivaloylamino-2-(2-tetrahydropyranyloxy)benzoate obtained in Example 80 (1) and 2.88 g (9.72 mmol) of compound K obtained in Reference Example 9 were used, and the resulting compound was recrystallized from chloroform/n-hexane, to give 3.73 g of 2-(3,5-dichloro-4-pivaloylaminophenyl)-6,8-difluoro-7-methyl-5-pivaloylamino-4H-1-benzopyran-4-one (yield: 71%).

NMR (90 MHz, CDCl$_3$) δ (ppm) 1.40 (s, 18H), 2.42 (t, 3H, J=2.2 Hz), 6.63 (s, 1H), 7.78 (s, 3H), 10.3 (brs, 1H)

EIMS (M/Z) 538 (M$^+$)

Molecular formula C$_{26}$H$_{26}$$^{35}$Cl$_2$F$_2$N$_2$O$_4$=538

(2) Substantially the same manner as that in Example 87 (2) was repeated except that 1.52 g (2.83 mmol) of the above 2-(3,5-dichloro-4-pivaloylaminophenyl)-6,8-difluoro-7-methyl-5-pivaloylamino-4H-1-benzopyran-4-one was used, and the resulting compound was recrystallized three times from acetic acid, to give 657 mg of Compound 104 (yield 63%).

NMR (270 MHz, DMSO-d$_6$) t (ppm) 2.27 (t, 3H, J=2.0 Hz), 6.36 (brs, 2H), 6.78 (s, 1H), 6.98 (brs, 2H), 7.86 (s, 2H)

EIMS (M/Z) 370 (M$^+$)

Molecular formula C$_{16}$H$_{10}$$^{35}$Cl$_2$F$_2$N$_2$O$_2$=370

EXAMPLE 89

5-Amino-2-(4-amino-3-ethylphenyl)-6,8-difluoro-7-methyl-4H-1-benzopyran-4-one (Compound 105)

(1) Substantially the same manner as that in Example 80 (2) was repeated except that 6.90 g (17.3 mmol) of ethyl 3,5-difluoro-4-methyl-6-pivaloylamino-2-(2-tetrahydropyranyloxy)benzoate obtained in Example 80 (1) and 2.84 g (11.5 mmol) of compound J obtained in Reference Example were used, and the resulting compound was recrystallized from ethyl acetate/n-hexane, to give 1.15 g of 2-(3-ethyl-4-pivaloylaminophenyl)-6,8-difluoro-7-methyl-5-pivaloylamino-4H-1-benzopyran-4-one (yield: 20%).

NMR (90 MHz, CDCl$_3$) δ (ppm) 1.33 (t, 3H, J=7.7 Hz), 1.37 (s, 9H), 1.38 (s, 9H), 2.40 (t, 3H, J=2.2 Hz), 2.67 (q, 2H, J=7.7 Hz), 6.67 (s, 1H), 7.56 (brs, 1H), 7.6–7.9 (m, 2H), 8.24 (d, 1H, J=9.0 Hz)

EIMS (M/Z) 498 (M$^+$)

Molecular formula C$_{28}$H$_{32}$F$_2$N$_2$O$_4$=498

(2) Substantially the same manner as that in Example 87 (2) was repeated except that 1.10 g (2.21 mmol) of the above 2-(3-ethyl-4-pivaloylaminophenyl)-6,8-difluoro-7-methyl-5-pivaloylamino-4H-1-benzopyran-4-one was used, and the resulting compound was recrystallized from ethyl acetate/n-hexane, to give 488 mg of Compound 105 (yield: 67%).

NMR (270 MHz, DMSO-d$_6$) δ (ppm) 1.18 (t, 3H, J=7.4 Hz), 2.27 (brs, 3H), 2.4–2.6 (m, 2H), 5.83 (brs, 2H), 6.56 (s, 1H), 6.70 (d, 1H, J=9.4 Hz), 6.96 (brs, 2H), 7.5–7.6 (m, 2H)

EIMS (M/Z) 330 (M$^+$)

Molecular formula C$_{18}$H$_{16}$F$_2$N$_2$O$_2$=330

EXAMPLE 90

5,7-Diamino-2-(4-amino-3,5-dichlorophenyl)-6,8-difluoro-4H-1-benzopyran-4-one (Compound 106)

(1) Substantially the same manner as that in Example 80 (1) was repeated except that 7.88 g (40.0 mmol) of p-toluenesulfonyl azide was used in place of iodomethane and the resulting compound was purified by silica gel column chromatography (n-hexane:ethyl acetate=6:1-3:1), to give 7.14 g of ethyl 4-azido-3,5-difluoro-6-pivaloylamino-2-(2-tetrahydropyranyloxy)benzoate (yield: 84%).

NMR (90 MHz, CDCl$_3$) δ (ppm) 1.29 (s, 9H), 1.37 (t, 3H, J=7.0 Hz), 1.4–2.0 (m, 6H), 3.4–4.2 (m, 2H), 4.34 (q, 2H, J=7.0 Hz), 5.28 (brs, 1H), 7.81 (brs, 1H)

FAB-MS (M/Z) 427 (M$^+$+H)

Molecular formula C$_{19}$H$_{24}$F$_2$NO$_5$=426

(2) 4.64 g (10.9 mmol) of the above ethyl 4-azido-3,5-difluoro-6-pivaloylamino-2-(2-tetrahydropyranyloxy)benzoate was dissolved in 100 mL of methanol, 2.90 g (76.7 mmol) of sodium borohydride was added in several portions under ice-cooling, 10 mL of water was further added and the mixture was stirred at room temperature for 4.5 hours. The solvent was distilled off under reduced pressure, water was added and the mixture was extracted once with ethyl acetate. The organic layer was washed with an aqueous saturated solution of sodium chloride and dried over anhydrous sodium sulfate. The solvent was distilled off under reduced pressure and the residue was purified by silica gel column chromatography (chloroform:methanol=100:1) to give 4.09 g of ethyl 4-amino-3,5-difluoro-6-pivaloylamino-2-(2-tetrahydropyranyloxy)benzoate (yield: 94%).

NMR (90 MHz, CDCl$_3$) δ (ppm) 1.29 (s, 9H), 1.36 (t, 3H, J=7.0 Hz), 1.4–2.0 (m, 6H), 3.4–4.2 (m, 2H), 4.06 (brs, 2H), 4.32 (q, 2H, J=7.0 Hz), 5.24 (brs, 1H), 8.27 (brs, 1H)

FAB-MS (M/Z) 401 (m$^+$+H)

Molecular formula C$_{19}$H$_{26}$F$_2$N$_2$O$_5$=400

(3) 809 mg (2.02 mmol) of the above ethyl 4-amino-3,5-difluoro-6-pivaloylamino-2-(2-tetrahydropyranyloxy)benzoate was dissolved in 20 mL of dimethylformamide under argon atmosphere, 240 mg (6.00 mmol) of sodium hydride and 1.4 mL (6.0 mmol) of di-tert-butyl dicarbonate were added under ice-cooling and the mixture was stirred at the same temperature for 6 hours. Water was added to the reaction solution and the mixture was extracted once with ethyl acetate. The organic layer was washed with an aqueous saturated solution of sodium chloride and dried over anhydrous sodium sulfate. The solvent was distilled off under reduced pressure and the residue was purified by silica gel column chromatography (n-hexane:ethyl acetate=4:1) to give 740 mg of ethyl 4-tert-butoxycarbonylamino-3,5-difluoro-6-pivaloylamino-2-(2-tetrahydropyranyloxy)benzoate (yield: 73%).

NMR (90 MHz, CDCl$_3$) δ (ppm) 1.29 (s, 9H), 1.39 (t, 3H, J=7.3 Hz), 1.43 (s, 9H), 1.4–2.0 (m, 6H), 3.4–4.2 (m, 2H), 4.34 (q, 2H, J=7.3 Hz), 5.31 (brs, 1H), 7.53 (brs, 1H)

(4) Substantially the same manner as that in Example 80 (2) was repeated except that 3.64 g (7.28 mmol) of the above ethyl 4-tert-butoxycarbonylamino-3,5-difluoro-6-pivaloylamino-2-(2-tetrahydropyranyloxy)benzoate and 1.75 g (6.08 mmol) of a compound K obtained in Reference Example 9 were used, and the resulting compound was purified by silica gel column chromatography (chloroform:methanol=100:1), to give 400 mg of 7-amino-2-(3,5-dichloro-4-pivaloylaminophenyl)-6,8-difluoro-4H-1-benzopyran-4-one (yield: 12%) .

NMR (90 MHz, CDCl$_3$) δ (ppm) 1.38 (s, 9H), 1.40 (s, 9H), 4.57 (brs, 2H), 6.56 (s, 1H), 7.81 (s, 2H)

FAB-HS (M/Z) 540 (M$^+$+H)

Molecular formula C$_{25}$H$_{25}$$^{35}$Cl$_2$F$_2$N$_2$O$_4$=539

(5) Substantially the same manner as that in Example 87 (2) was repeated except that 400 mg (0.741 mmol) of the above 7-amino-2-(3,5-dichloro-4-pivaloylaminophenyl)-6,8-difluoro-4H-1-benzopyran-4-one was used, and the resulting compound was triturated with isopropyl ether, to give 202 mg of Compound 106 (yield: 73%).

NMR (270 MHz, DMSO-d$_6$) δ (ppm) 6.24 (brs, 2H), 6.28 (brs, 2H), 6.68 (s, 1H), 6.84 (brs, 2H), 7.83 (s, 2H)

EIMS (M/Z) 371 (M$^+$)

Molecular formula C$_{15}$H$_9$$^{35}$Cl$_2$F$_2$N$_3$O$_2$=371

EXAMPLE 91

5-Amino-2-(4-amino-3-fluorophenyl)-7-chloro-6,8-difluoro-4H-1-benzopyran-4-one (Compound 84)

(1) 1.54 mL (11.0 mmol) of diisopropylamine was dissolved in 10 mL of tetrahydrofuran under argon atmosphere and 6.3 mL of a 1.6 M solution of 10 mmol of n-butyl lithium in n-hexane was added dropwise while keeping an internal temperature at −10 to 0° C. The reaction solution was cooled to −60° C. or below (internal temperature) and a solution of 1.19 g (2.50 mmol) of compound L obtained in Reference Example 10 dissolved in a mixed solvent of 50 mL of tetrahydrofuran and 10 mL of hexamethylphosphoric triamide was added dropwise. The mixture was stirred at the same temperature for 2 hours to lithiate 7-position. 802 mg (6.00 mol) of N-chlorosuccinimide was added and the mixture was stirred for additional 10 minutes. Water was added to the reaction solution, the temperature of the mixture was raised to room temperature and the mixture was extracted once with ethyl acetate. The organic layer was washed once with an aqueous saturated solution of sodium chloride and dried over anhydrous sodium sulfate. The solvent was distilled off under reduced pressure and the residue was purified by silica gel column chromatography (chloroform:acetone=60:1) to give 384 mg of 7-chloro-6,8-difluoro-2-(3-fluoro-4-pivaloylaminophenyl)-5-pivaloylamino-4H-1-benzopyran-4-one (yield: 30%).

NMR (90 MHz, CDCl$_3$) δ(ppm) 1.36 (s, 9H), 1.38 (s, 9H), 6.67 (s, 1H), 7.5–7.9 (m, 3H), 8.61 (dd, 1H, J=9.2, 8.4 Hz), 10.5 (brs, 1H)

FAB-MS (M/Z) 509 (M$^+$+H)

Molecular formula $C_{25}H_{24}{}^{35}ClF_3N_2O_4=508$ (2) Substantially the same manner as that in Example 87 (2) was repeated except that 343 mg (0.675 mmol) of 7-chloro-6,8-difluoro-2-(3-fluoro-4-pivaloylaminophenyl)-5-pivaloylamino-4H-1-benzopyran-4-one was used, and the resulting compound was triturated with isopropyl ether, to give 168 mg of Compound 84 (yield: 73%).

NMR (270 MHz, DMSO-$d_6$) δ (ppm) 6.11 (brs, 2H), 6.71 (s, 1H), 6.87 (t, 1H, J=8.9 Hz), 7.30 (brs, 2H), 7.59 (dd, 1H, J=8.9, 2.0 Hz), 7.65 (dd, 1H, J=12.9, 2.0 Hz)

EIMS (M/Z) 340 (M$^+$)

Molecular formula $C_{15}H_8{}^{35}ClF_3N_2O_2=340$

EXAMPLE 92

5-Amino-2-(4-amino-3-fluorophenyl)-7-ethoxycarbonyl-6,8-difluoro-4H-1-benzopyran-4-one (Compound 92)

(1) Substantially the same manner as that in Example 91 (1) was repeated except that 0.29 mL (5.0 mmol) of ethyl chloroformate was used in place of N-chlorosuccinimide and the resulting compound was purified by silica gel column chromatography (chloroform:ethyl acetate=40:1), to give 900 mg of 7-ethoxycarbonyl-6,8-difluoro-2-(3-fluoro-4-pivaloylaminophenyl)-5-pivaloylamino-4H-1-benzopyran-4-one (yield: 66%).

NMR (90 MHz, CDCl$_3$) δ (ppm) 1.36 (s, 9H), 1.38 (s, 9H), 1.43 (t, 3H, J=7.0 Hz), 4.49 (q, 2H, J=7.0 Hz), 6.69 (s, 1H), 7.5–7.9 (m, 3H), 8.60 (t, 1H, J=8.5 Hz), 10.4 (brs, 1H)

EIMS (M/Z) 546 (M$^+$)

Molecular formula $C_{28}H_{29}F_3N_2O_4=546$ (2) 740 mg (1.36 mol) of the above 7-ethoxycarbonyl-6,8-difluoro-2-(3-fluoro-4-pivaloylaminophenyl)-5-pivaloylamino-4H-1-benzopyran-4-one was subjected to the depivaloylation with concentrated sulfuric acid substantially in the same manner as that in Example 87 (2). The resulting solution was adjusted to pH 7 and extracted once with ethyl acetate. The organic layer was washed once with an aqueous saturated solution of sodium chloride and dried over anhydrous sodium sulfate. The solvent was distilled off under reduced pressure, and the residue was purified by silica gel column chromatography (chloroform) and recrystallized from ethyl acetate/n-hexane to give 259 mg of Compound 92 (yield: 50%).

NMR (270 MHz, DMSO-$d_6$) δ (ppm) 1.34 (t, 3H, J=7.2 Hz), 4.43 (q, 2H, J=7.2 Hz), 6.15 (brs, 2H), 6.67 (s, 1H), 6.87 (t, 1H, J=8.9 Hz), 7.26 (brs, 2H), 7.61 (dd, 1H, J=8.4, 2.0 Hz), 7.67 (dd, 1H, J=12.9, 2.0 Hz)

EIMS (M/Z) 378 (M$^+$)

Molecular formula $C_{18}H_{13}F_3N_2O_4=378$

EXAMPLE 93

5-Amino-2-(4-amino-3-fluorophenyl)-7-azido-6,8-difluoro-4H-1-benzopyran-4-one (Compound 94)

(1) Substantially the same manner as that in Example 91 (1) was repeated except that 1.78 g (9.00 mmol) of p-toluenesulfonyl azide was used in place of N-chlorosuccinimide and the precipitated crystals were collected by filtration after water was added to the reaction solution and the temperature was raised to room temperature, to give 3.11 g of 7-azido-6,8-difluoro-2-(3-fluoro-4-pivaloylaminophenyl)-5-pivaloylamino-4H-1-benzopyran-4-one (yield: 81%).

NMR (90 MHz, DMSO-$d_6$) δ (ppm) 1.26 (s, 9H), 1.29 (s, 9H), 7.08 (s, 1H), 7.7–8.0 (m, 3H), 9.19 (brs, 1H), 10.2 (brs, 1H)

FAB-MS (Negative) (M/Z) 514 (M$^+$–H)

Molecular formula $C_{25}H_{24}F_3N_5O_4=515$ (2) Substantially the same manner as that in Example 92 (2) was repeated except that 320 mg (0.621 mol) of the above 7-azido-6,8-difluoro-2-(3-fluoro-4-pivaloylaminophenyl)-5-pivaloylamino-4H-1-benzopyran-4-one was used, and the resulting compound was purified by preparative thin layer chromatography (chloroform:methanol= 20:1), to give 180 mg of Compound 94 (yield: 84%).

NMR (270 MHz, DMSO-$d_6$) δ (ppm) 6.12 (brs, 2H), 6.67 (s, 1H), 6.85 (t, 1H, J=8.7 Hz), 7.22 (brs, 2H), 7.57 (dd, 1H, J=8.4, 2.0 Hz), 7.64 (dd, 1H, J=12.9, 2.0 Hz)

EIMS (M/Z) 347 (M$^+$)

Molecular formula $C_{15}H_8F_3N_5O_2=347$

EXAMPLE 94

5-Amino-2-(4-amino-3-fluorophenyl)-6,8-difluoro-7-(1-hydroxyethyl)-4H-1-benzopyran-4-one (Compound 99)

(1) Substantially the same manner as that in Example 91 (1) was repeated except that 1 mL (large excess) of acetaldehyde was introduced in a gaseous condition in place of N-chlorosuccinimide and the resulting compound was purified by silica gel column chromatography (chloroform:acetonitrile=30:1–9:1), to give 730 mg of 6,8-difluoro-2-(3-fluoro-4-pivaloylaminophenyl)-7-(1-hydroxyethyl)-5-pivaloylamino-4H-1-benzopyran-4-one (yield: 70%).

NMR (90 MHz, CDCl$_3$) δ (ppm) 1.37 (s, 9H), 1.38 (s, 9H), 1.72 (d, 3H, J=6.8 Hz), 2.5–2.8 (m, 1H), 5.2–5.5 (m, 1H), 6.64 (s, 1H), 7.5–7.9 (m, 3H), 8.57 (t, 1H, J=8.5 Hz), 10.4 (brs, 1H)

FAB-MS (M/Z) 519 (M$^+$+H)

Molecular formula $C_{27}H_{29}F_3N_2O_5=518$ (2) Substantially the same manner as that in Example 92 (2) was repeated except that 320 mg (0.621 mol) of the above 6,8-difluoro-2-(3-fluoro-4-pivaloylaminophenyl)-7-(1-hydroxyethyl)-5-pivaloylamino-4H-1-benzopyran-4-one was used, and the resulting compound was purified by preparative thin layer chromatography (chloroform:methanol=20:1), to give 8.0 mg of Compound 99 (yield: 6.1%).

NMR (270 MHz, DMSO-$d_6$) δ (ppm) 1.51 (d, 3H, J=6.9 Hz), 5.1–5.3 (m, 1H), 5.55 (d, 1H, J=4.5 Hz), 6.09 (brs, 2H), 6.68 (s, 1H), 6.87 (t, 1H, J=8.9 Hz), 6.99 (brs, 2H), 7.60 (dd, 1H, J=8.4, 2.0 Hz), 7.66 (dd, 1H, J=12.9, 2.0 Hz)

FAB-MS (M/Z) 351 (M$^+$+H)

Molecular formula $C_{17}H_{13}F_3N_2O_3=350$

EXAMPLE 95

5-Amino-2-(4-amino-3-fluorophenyl)-6,8-difluoro-7-methoxy-4H-1-benzopyran-4-one (Compound 87)

(1) 348 mg (0.710 mmol) of 6,8-difluoro-2-(3-fluoro-4-pivaloylaminophenyl)-7-hydroxy-5-pivaloylamino-4H-1-benzopyran-4-one obtained in Example 86 (3) was dissolved in 35 mL of acetone, 166 mg (1.20 mmol) of potassium carbonate and 0.45 mL (7.1 mmol) of iodomethane were added and the mixture was heated at reflux for 40 minutes. The reaction solution was filtered, the filtrate was concentrated, water was added to the residue and the mixture was extracted once with ethyl acetate. The organic layer was washed twice with a 1N aqueous solution of sodium hydroxide, once with water and once with an aqueous saturated solution of sodium chloride and dried over anhydrous sodium sulfate. The solvent was distilled off under reduced pressure and the residue was purified by silica gel column chromatography (chloroform) to give 280 mg of 6,8-difluoro-2-(3-fluoro-4-pivaloylaminophenyl)-7-methoxy-5-pivaloylamino-4H-1-benzopyran-4-one (yield: 78%).

NMR (90 MHz, CDCl$_3$) δ (ppm) 1.36 (s, 9H), 1.38 (s, 9H), 4.22 (t, 3H, 1,8 Hz), 6.61 (s, 1H), 7.5–7.9 (m, 3H), 8.58 (dd, 1H, J=8.6, 7.3 Hz), 10.6 (brs, 1H)

EIMS (M/Z) 504 (M$^+$)

Molecular formula C$_{26}$H$_{27}$F$_3$N$_2$O$_5$=504

(2) Substantially the same manner as that in Example 87 (2) was repeated except that 260 mg (0.516 mmol) of the above 6,8-difluoro-2-(3-fluoro-4-pivaloylaminophenyl)-7-methoxy-5-pivaloylamino-4H-1-benzopyran-4-one was used, and the resulting crystals were purified by silica gel column chromatography (chloroform:acetone=80:1), to give 126 mg of Compound 87 (yield: 73%).

NMR (270 MHz, DMSO-d$_6$) δ (ppm) 4.09 (t, 3H, J=1.5 Hz), 6.07 (brs, 2H), 6.64 (s, 1H), 6.87 (t, 1H, J=8.9 Hz), 7.22 (brs, 2H), 7.57 (dd, 1H, J=8.4, 2.0 Hz), 7.64 (dd, 1H, J=12.9, 2.0 Hz)

EIMS (M/Z) 336 (M$^+$)

Molecular formula C$_{16}$H$_{11}$F$_3$N$_2$O$_3$=336

EXAMPLE 96

5-Amino-2-(4-amino-3-fluorophenyl)-7-(2-dimethylaminoethoxy)-6,8-difluoro-4H-1-benzopyran-4-one (Compound 88)

(1) 490 mg (1.00mmol) of 6,8-difluoro-2-(3-fluoro-4-pivaloylaminophenyl)-7-hydroxy-5-pivaloylamino-4H-1-benzopyran-4-one obtained in Example 86 (3) was dissolved in 40 mL of dimethylformamide, 3.60 mg (26.0 mmol) of potassium carbonate and 2.88 g (20.0 mmol) of 2-dimethylaminoethyl chloride hydrochloride were added and the mixture was stirred at 50° C. for 12 hours. The reaction solution was filtered, the filtrate was concentrated, water was added to the residue and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=30:1) to give 230 mg of 7-(2-dimethylaminoethoxy)-6,8-difluoro-2-(3-fluoro-4-pivaloylaminophenyl)-5-pivaloylamino-4H-1-benzopyran-4-one (yield: 41%).

NMR (90 MHz, CDCl$_3$) δ (ppm) 1.36 (s, 9H), 1.38 (s, 9H), 2.36 (s, 6H), 2.79 (t, 2H, J=5.5 Hz), 4.48 (t, 2H, J=5.5 Hz), 6.62 (s, 1H), 7.5–7.9 (m, 3H), 8.58 (dd, 1H, J=8.6, 7.3 Hz), 10.6 (brs, 1H)

EIMS (M/Z) 561 (M$^+$)

Molecular formula C$_{29}$H$_{34}$F$_3$N$_3$O$_5$=561

(2) Substantially the same manner as that in Example (2) was repeated except that 250 mg (0.446 mmol) of the above 7-(2-dimethylaminoethoxy)-6,8-difluoro-2-(3-fluoro-4-pivaloylaminophenyl)-5-pivaloylamino-4H-1-benzopyran-4-one was used, and the resulting crystals were purified by silica gel column chromatography (chloroform:methanol=30:1), to give 170 mg of Compound 88 (yield: 97%). This compound was dissolved in 10 mL of 2-propanol, 0.5 mL of a 1N hydrochloric acid/2-propanol solution was added dropwise and 5 mL of isopropyl ether was further added. The precipitated crystals were collected by filtration to give a hydrochloride of Compound 88.

NMR (270 MHz, DMSO-d$_6$) δ (ppm) 2.89 (s, 6H), 3.56 (t, 2H, J=5.0HZ), 4.67 (t, 2H, J=5.0 Hz), 6.08 (brs, 2H), 6.67 (s, 1H), 6.87 (t, 1H, 8.9 Hz), 7.17 (brs, 2H), 7.5–7.7 (m, 2H), 10.6 (brs, 1H) (hydrochloride)

EIMS (M/Z) 393 (M$^+$)

Molecular formula C$_{19}$H$_{18}$F$_3$N$_3$O$_3$=393

EXAMPLE 97

5-Amino-2-(4-amino-3-fluorophenyl)-6,8-difluoro-7-methylsulfinyl-4H-1-benzopyran-4-one (Compound 90)

(1) 204 mg (0.392mmol) of 6,8-difluoro-2-(3-fluoro-4-pivaloylaminophenyl)-7-methylthio-5-pivaloyiamino-4H-1-benzopyran-4-one obtained in Example 85 (2) was dissolved in 5 mL of dichloromethane, 86 mg (0.39 mmol) of m-chloroperbenzoic acid was added under ice-cooling and the mixture was stirred at the same temperature for 2 hours. An aqueous solution of sodium hydrogensulfite was added to the reaction solution and the mixture was extracted once with chloroform. The organic layer was washed once with an aqueous solution of sodium bicarbonate, once with water and once with an aqueous saturated solution of sodium chloride and dried over anhydrous sodium sulfate. The solvent was distilled off under reduced pressure and the residue was purified by silica gel column chromatography (chloroform:methanol=100:1) to give 200 mg of 6,8-difluoro-2-(3-fluoro-4-pivaloylaminophenyl)-7-methylsulfinyl-5-pivaloylamino-4H-1-benzopyran-4-one (yield: 95%).

NMR (90 MHz, CDCl$_3$) δ (ppm) 1.36 (s, 9H), 1.38 (s, 9H), 3.23 (s, 3H), 6.71 (s, 1H), 7.5–7.9 (m, 3H), 8.60 (t, 1H, J=8.4 Hz)

EIMS (M/Z) 536 (M$^+$)

Molecular formula C$_{26}$H$_{27}$F$_3$N$_2$O$_5$S=536

(2) Substantially the same manner as that in Example 87 (2) was repeated except that 170 mg (0.317 mmol) of the above 6,8-difluoro-2-(3-fluoro-4-pivaloylaminophenyl)-7-methylsulfinyl-5-pivaloylamino-4H-1-benzopyran-4-one was used, and the resulting crystals were triturated with ethyl acetate, to give 104 mg of Compound 90 (yield: 89%).

NMR (270 MHz, DMSO-d$_6$) δ (ppm) 3.19 (s, 3H), 6.16 (brs, 2H), 6.76 (s, 1H), 6.87 (t, 1H, J=8.7 Hz), 7.31 (brs, 2H), 7.62 (dd, 1H, J=8.4, 2.0 Hz), 7.68 (dd, 1H, J=12.9, 2.0 Hz)

FAB-MS (M/Z) 369 (M$^+$+H)

Molecular formula C$_{16}$H$_{11}$F$_3$N$_2$O$_3$S=368

EXAMPLE 98

5-Amino-2-(4-amino-3-fluorophenyl)-6,8-difluoro-7-methylsulfonyl-4H-1-benzopyran-4-one (Compound 91)

(1) 203 mg (0.391mmol) of 6,8-difluoro-2-(3-fluoro-4-pivaloylaminophenyl)-7-methylthio-5-pivaloylamino-4H-1-benzopyran-4-one obtained in Example 85 (2) was dissolved in 5 mL of dichloromethane, 850 mg (3.91 mmol) of m-chloroperbenzoic acid was added under ice-cooling and the mixture was stirred at room temperature for 3 hours. An aqueous solution of sodium hydrogensulfite was added to the reaction solution and the mixture was extracted once with chloroform. The organic layer was washed once with an aqueous solution of sodium bicarbonate, once with water and once with an aqueous saturated solution of sodium chloride and dried over anhydrous sodium sulfate. The solvent was distilled off under reduced pressure and the residue was purified by silica gel column chromatography (chloroform:ethyl acetate=40:1) to give 204 mg of 6,8-difluoro-2-(3-fluoro-4-pivaloylaminophenyl)-7-methylsulfonyl-5-pivaloylamino-4H-1-benzopyran-4-one (yield: 94%).

NMR (90 MHz, CDCl$_3$) δ (ppm) 1.36 (s, 9H), 1.38 (s, 9H), 3.43 (s, 3H), 6.74 (s, 1H), 7.5–7.9 (m, 3H), 8.64 (t, 1H, J=8.4 Hz)

EIMS (M/Z) 552 (M$^+$)

Molecular formula C$_{26}$H$_{27}$F$_3$N$_2$O$_6$S=552

(2) Substantially the same manner as that in Example 87 (2) was repeated except that 176 mg (0.319 mmol) of the above 6,8-difluoro-2-(3-fluoro-4-pivaloylaminophenyl)-7-methylsulfonyl-5-pivaloylamino-4H-1-benzopyran-4-one was used, and the resulting crystals were triturated with ethyl acetate, to give 78 mg of Compound 91 (yield: 64%).

NMR (270 MHz, DMSO-d$_6$) δ (ppm) 3.50 (s, 3H), 6.19 (brs, 2H), 6.80 (s, 1H), 6.84 (t, 1H, J=9.4 Hz), 7.39 (brs, 2H), 7.62 (dd, 1H, J=8.4, 2.0 Hz), 7.70 (dd, 1H, J=12.9, 2.0 Hz)

FAB-MS (M/Z) 385 (M$^+$+H)

Molecular formula C$_{16}$H$_{11}$F$_3$N$_2$O$_4$=384

EXAMPLE 99

5-Amino-2-(4-amino-3-fluorophenyl)-7-carboxy-6,8-difluoro-4H-1-benzopyran-4-one (Compound 93)

121 mg (0.320 mmol) of Compound 92 obtained in Example 92 (2) was suspended in a mixed solvent of 10 mL of ethanol and 5 mL of methanol, 0.4 mL of a 5N aqueous solution of sodium hydroxide was added and the mixture was stirred at 50° C. for 2.5 hours. The reaction solution was cooled on ice, the solution was adjusted to pH 4 and the precipitated crystals were collected by filtration to give 101 mg of Compound 93 (yield: 90%).

NMR (270 MHz, DMSO-d$_6$) δ (ppm) 6.14 (brs, 2H), 6.74 (s, 1H), 6.87 (t, 1H, J=8.9 Hz), 7.20 (brs, 2H), 7.60 (dd, 1H, J=8.4, 2.0 Hz), 7.67 (dd, 1H, J=13.4, 2.0 Hz)

FAB-MS (M/Z) 351 (M$^+$+H)

Molecular formula C$_{16}$H$_9$F$_3$N$_2$O$_4$=350

EXAMPLE 100

5,7-Diamino-2-(4-amino-3-fluorophenyl)-6,8-difluoro-4H-1-benzopyran-4-one (Compound 95)

(1) 3.50 g (6.80 mmol) of 7-azido-6,8-difluoro-2-(3-fluoro-4-pivaloylaminophenyl)-5-pivaloylamino-4H-1-benzopyran-4-one obtained in Example 93 (1) was suspended in 120 mL of tetrahydrofuran, 1.96 g (7.48 mmol) of triphenylphosphine was added and the mixture was stirred at room temperature for 2 hours. To this was added 50 mL of 1N hydrochloric acid and the mixture was further stirred for 10 hours. The mixture was adjusted to pH 9 by addition of a 10N aqueous solution of sodium hydroxide thereto, and the precipitated crystals were collected by filtration and purified by silica gel column chromatography (chloroform-chloroform:methanol=40:1) to give 2.83 g of 7-amino-6,8-difluoro-2-(3-fluoro-4-pivaloylaminophenyl)-5-pivaloylamino-4H-1-benzopyran-4-one (yield: 85%).

NMR (90 MHz, DMSO-d$_6$) δ (ppm) 1.27 (s, 18H), 6.58 (brs, 2H), 6.87 (s, 1H), 7.7–8.0 (m, 3H), 9.18 (brs, 1H), 10.4 (brs, 1H)

EIMS (M/Z) 489 (M$^+$)

Molecular formula C$_{25}$H$_{26}$F$_3$N$_3$O$_4$=489

(2) Substantially the same manner as that in Example 85 (3) was repeated except that 404 mg (0.826 mmol) of the above 7-amino-6,8-difluoro-2-(3-fluoro-4-pivaloylaminophenyl)-5-pivaloylamino-4H-1-benzopyran-4-one was used, and the resulting compound was purified by silica gel column chromatography (chloroform:methanol=100:1) and recrystallized from ethyl acetate/n-hexane, to give 183 mg of Compound 95 (yield: 69%).

NMR (270 MHz, DMSO-d$_6$) δ (ppm) 5.99 (brs, 2H), 6.20 (brs, 2H), 6.48 (s, 1H), 6.82 (brs, 2H), 6.85 (t, 1H, J=8.4 Hz), 7.54 (dd, 1H, J=8.4, 2.0 Hz), 7.60 (dd, 1H, J=12.9, 2.0 Hz)

FAB-MS (M/Z) 322 (M$^+$+H)

Molecular formula C$_{15}$H$_{10}$F$_3$N$_3$O$_2$=321

EXAMPLE 101

5-Amino-2-(4-amino-3-fluorophenyl)-7-dimethylamino-6,8-difluoro-4H-1-benzopyran-4-one (Compound 96)

(1) 510 mg (1.04 mmol) of 7-amino-6,8-difluoro-2-(3-fluoro-4-pivaloylaminophenyl)-5-pivaloylamino-4H-1-benzopyran-4-one obtained in Example 100 (1) was dissolved in 15 mL of dimethylformamide under argon atmosphere, 212 mg (5.30 mmol) of sodium hydride (60% oil suspension) and 0.17 mL (2.6 mmol) of iodomethane were added under ice-cooling and the mixture was stirred at the same temperature for 2 hours. Water was added to the reaction solution and the mixture was extracted twice with chloroform. The organic layer was washed once with water and once with an aqueous saturated solution of sodium chloride and dried over anhydrous sodium sulfate. The solvent was distilled off under reduced pressure and the residue was purified by silica gel column chromatography (chloroform:acetone=100:1) to give 290 mg of 7-dimethylamino-6,8-difluoro-2-(3-fluoro-4-pivaloylaminophenyl)-5-pivaloylamino-4H-1-benzopyran-4-one (yield: 54%).

NMR (90 MHz, CDCl$_3$) δ (ppm) 1.36 (s, 9H), 1.38 (s, 9H), 3.12 (t, 3H, J=2.6 Hz), 6.56 (s, 1H), 6.4–6.8 (m, 2H), 6.88 (brd, 1H), 8.47 (t, 1H, J=8.4 Hz), 10.6 (brs, 1H)

EIMS (M/Z) 517 (M$^+$)

Molecular formula C$_{27}$H$_{30}$F$_3$N$_3$O$_4$=517

(2) Substantially the same manner as that in Example 85 (3) was repeated except that 290 mg (0.561 mmol) of the above 7-dimethylamino-6,8-difluoro-2-(3-fluoro-4-pivaloylaminophenyl)-5-pivaloylamino-4H-1-benzopyran-4-one was used, and the resulting compound was purified by silica gel column chromatography (chloroform:acetone=70:1) and recrystallized from ethyl acetate/n-hexane, to give 66 mg of Compound 96 (yield: 34%).

NMR (270 MHz, DMSO-d$_6$) δ (ppm) 3.00 (t, 6H, J=2.5 Hz), 6.00 (brs, 2H), 6.56 (s, 1H), 6.86 (t, 1H, J=8.4 Hz), 6.89 (brs, 2H), 7.56 (dd, 1H, J=8.4, 2.0 Hz), 7.61 (dd, 1H, J=12.9, 2.0 Hz)

EIMS (M/Z) 349 (H$^+$)

Molecular formula C$_{17}$H$_{14}$F$_3$N$_3$O$_2$=349

EXAMPLE 102

5-Amino-2-(4-amino-3-fluorophenyl)-7-(3-dimethylaminopropylamino)-6,8-difluoro-4H-1-benzopyran-4-one (Compound 97)

(1) 1.17 g (2.39 mmol) of 7-amino-6,8-difluoro-2-(3-fluoro-4-pivaloylaminophenyl)-5-pivaloylamino-4H-1-benzopyran-4-one obtained in Example 100 (1) was dissolved in 40 mL of pyridine, 2.3 mL (24 mmol) of acetic anhydride and 30 mg (0.24 mmol) of N,N-dimethylaminopyridine were added and the mixture was stirred at 50° C. for 18 hours. The reaction solution was poured into ice water and the precipitated crystals were collected by filtration.

The above crystals were dissolved in 15 mL of dimethylformamide, 0.94 g of potassium carbonate and 2.2 mL of 1-chloro-3-iodopropane were added and the mixture was stirred at 50° C. for 9 hours. Water was added to the reaction solution and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform) to give 1.16 g of 7-[N-acetyl-N-(3-chloropropyl)amino]-6,8-difluoro-2-(3-fluoro-4-pivaloylaminophenyl)-5-pivaloylamino-4H-1-benzopyran-4-one (yield: 80%).

NMR (270 MHz, CDCl$_3$) δ (ppm) 1.37 (s, 9H), 1.39 (s, 9H), 2.0–2.2 (m, 2H), 2.03 (s, 3H), 3.60 (t, 2H, J=6.7 Hz), 3.8–4.0 (m, 2H), 6.73 (s, 1H), 7.6–7.8 (m, 2H), 7.74 (brd, 1H, J=3.0 Hz), 8.65 (t, 1H, J=8.4 Hz), 10.7 (brs, 1H)

EIMS (M/Z) 607 (M$^+$)

Molecular formula C$_{30}$H$_{33}$$^{35}$ClF$_3$N$_3$O$_5$=607

(2) 932 mg (1.54 mmol) of the above 7-[N-acetyl-N-(3-chloropropyl)amino]-6,8-difluoro-2-(3-fluoro-4-pivaloylaminophenyl)-5-pivaloylamino-4H-1-benzopyran-4-one was dissolved in 10 mL of dimethylformamide under argon atmosphere, 320 mg (7.68 mmol) of sodium iodide, 1.25 g (15.4 mmol) of dimethylamine hydrochloride and 2.12 g (15.4 mmol) of potassium carbonate were added and the mixture was stirred at 70° C. for 23 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform-chloroform:methanol:aqueous ammonia= 40:1:1) to give 603 mg of 7-[N-acetyl-N-(3-dimethylaminopropyl)amino]-6,8-difluoro-2-(3-fluoro-4-pivaloylaminophenyl)-5-pivaloylamino-4H-1-benzopyran-4-one (yield: 64%).

NMR (90 MHz, CDCl$_3$) δ (ppm) 1.36 (s, 9H), 1.38 (s, 9H), 1.6–2.5 (m, 4H), 2.01 (s, 3H), 2.20 (s, 6H), 6.71 (s, 1H), 7.5–7.9 (m, 3H), 8.63 (t, 1H, J=8.4 Hz), 10.6 (brs, 1H)

FAB-MS (M/Z) 617 (M$^+$+H)

Molecular formula C$_{32}$H$_{39}$F$_3$N$_4$O$_5$=616

(3) 549 mg (0.890 mmol) of the above 7-[N-acetyl-N-(3-dimethylaminopropyl)amino]-6,8-difluoro-2-(3-fluoro-4-pivaloylaminophenyl)-5-pivaloylamino-4H-1-benzopyran-4-one was dissolved in 15 mL of concentrated sulfuric acid and the solution was stirred at 50° C. for 10 minutes. The reaction solution was poured into ice water, the mixture was adjusted to pH 8 and extracted once with ethyl acetate. The organic layer was washed once with water and once with an aqueous saturated solution of sodiumchloride and dried over anhydrous sodium sulfate. The solvent was distilled off under reduced pressure and the residue was purified by silica gel column chromatography (chloroform:methanol:aqueous ammonia=20:1:1) to give 297 mg of Compound 97 (yield: 82%). This compound was converted into hydrochloride according to the same manner as that in Example 96 (2).

NMR (270 MHz, CDCl$_3$) δ (ppm) 1.80 (quint., 2H, J=6.4 Hz), 2.27 (s, 6H), 2.44 (t, 2H, J=6.4 Hz), 3.62 (m, 2H), 4.17 (brs, 2H), 5.74 (brs, 1H), 6.07 (brs, 2H), 6.37 (s, 1H), 6.82 (t, 1H, J=8.4 Hz), 7.4–7.6 (m, 2H) (free base)

EIMS (M/Z) 406 (M$^+$)

Molecular formula C$_{20}$H$_{21}$F$_3$N$_4$O$_2$=406

EXAMPLE 103

5-Amino-2-(4-amino-3-fluorophenyl)-6,8-difluoro-7-(4-methylpiperazin-1-yl)-4H-1-benzopyran-4-one (Compound 98)

(1) 580 mg (1.05 mmol) of 7-bromo-6,8-difluoro-2-(3-fluoro-4-pivaloylaminophenyl)-5-pivaloylamino-4H-1-benzopyran-4-one obtained in Example 84 (2) was dissolved in 6 mL of dimethyl sulfoxide, 1.2 mL (10.5 mmol) of N-methylpiperazine was added and the mixture was stirred at 100° C. for 7 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=20:1) to give 350 mg of 6,8-difluoro-2-(3-fluoro-4-pivaloylaminophenyl)-7-(4-methylpiperazin-1-yl)-5-pivaloylamino-4H-1-benzopyran-4-one (yield: 58%).

NMR (90 MHz, CDCl$_3$) δ (ppm) 1.36 (s, 9H), 1.38 (s, 9H), 2.38 (s, 3H), 2.5–2.7 (m, 4H), 3.4–3.6 (m, 4H), 6.58 (s, 1H), 7.5–7.9 (m, 3H), 8.58 (t, 1H, J=8.8 Hz), 10.6 (brs, 1H)

EIMS (M/Z) 572 (M$^+$)

Molecular formula C$_{30}$H$_{35}$F$_3$N$_4$O$_4$=572

(2) 340 mg (0.594 mmol) of the above 6,8-difluoro-2-(3-fluoro-4-pivaloylaminophenyl)-7-(4-methylpiperazin-1-yl)-5-pivaloylamino-4H-1-benzopyran-4-one was dissolved in 20 mL of 1,4-dioxane, 10 mL of concentrated hydrochloric acid was added and the mixture was heated at reflux for 2.5 hours. The reaction solution was cooled on ice, adjusted to pH 10 and extracted twice with chloroform (containing a small amount of methanol). The organic layer was washed once with an aqueous saturated solution of sodium chloride and dried over anhydrous sodium sulfate. The solvent was distilled off under reduced pressure and the residue was purified by silica gel column chromatography (chloroform:methanol=12:1) to give 117 mg of Compound 98 (yield: 49%).

NMR (270 MHz, DMSO-d$_6$) δ (ppm) 2.23 (s, 3H), 2.4–2.5 (m, 4H), 3.2–3.4 (m, 4H), 6.05 (brs, 2H), 6.59 (s, 1H), 6.86 (t, 1H, J=8.9 Hz), 6.92 (brs, 2H), 7.5–7.7 (m, 2H)

EIMS (M/Z) 404 (M$^+$)

Molecular formula C$_{20}$H$_{19}$F$_3$N$_4$O$_2$=404

EXAMPLE 104

5-Amino-2-(4-amino-3-fluorophenyl)-6,8-difluoro-7-vinyl-4H-1-benzopyran-4-one (Compound 100)

Substantially the same manner as that in Example 92 (2) was repeated except that 205 mg (0.396 mmol) of 6,8-difluoro-2-(3-fluoro-4-pivaloylaminophenyl)-7-(1-hydroxyethyl)-5-pivaloylamino-4H-1-benzopyran-4-one obtained in Example 94 (1) was used, and the resulting compound was purified by preparative thin layer chromatography (chloroform:methanol=20:1), to give 18 mg of Compound 100 (yield: 14%).

NMR (270 MHz, CDCl$_3$) δ (ppm) 4.17 (brs, 2H), 5.77 (dd, 1H, J=11.9, 1.0 Hz), 6.17 (brs, 2H), 6.22 (d, 1H, J=17.8 Hz), 6.47 (s, 1H), 6.81 (dd, 1H, J=17.8, 11.9 Hz), 6.84 (t, 1H, J=8.7 Hz), 7.5–7.7 (m, 2H)

EIMS (M/Z) 332 (M$^+$)

Molecular formula C$_{17}$H$_{11}$F$_3$N$_2$O$_2$=332

EXAMPLE 105

7-Acetyl-5-amino-2-(4-amino-3-fluorophenyl)-6,8-difluoro-4H-1-benzopyran-4-one (Compound 101)

(1) 206 mg (0.398 mmol) of 6,8-difluoro-2-(3-fluoro-4-pivaloylaminophenyl)-7-(1-hydroxyethyl)-5-pivaloylamino-4H-1-benzopyran-4-one obtained in Example 94 (1) was suspended in 20 mL of toluene, 348 mg (3.98 mmol) of manganese dioxide was added and the mixture was heated at reflux for 2 hours. The reaction solution was filtered, the solvent was distilled off under reduced pressure and the residue was purified by silica gel column chromatography (chloroform:acetonitrile=50:1) to give 179 mg of 7-acetyl-6,8-difluoro-2-(3-fluoro-4-pivaloylaminophenyl)-5-pivaloylamino-4H-1-benzopyran-4-one (yield: 87%).

NMR (90 MHz, $CDCl_3$) δ (ppm) 1.36 (s, 9H), 1.38 (s, 9H), 2.69 (brs, 3H), 6.70 (s, 1H), 7.5–7.9 (m, 3H), 8.62 (dd, 1H, J=8.7, 8.1 Hz), 10.5 (brs, 1H)

FAB-MS (M/Z) 517 ($M^++H$)

Molecular formula $C_{27}H_{27}F_3N_2O_5$=516

(2) Substantially the same manner as that in Example 85 (3) was repeated except that 158 mg (0.305 mmol) of the above 7-acetyl-6,8-difluoro-2-(3-fluoro-4-pivaloylaminophenyl)-5-pivaloylamino-4H-1-benzopyran-4-one was used, and the resulting compound was purified by silica gel column chromatography (chloroform:methanol=40:1) and triturated with isopropyl ether, to give 73 mg of Compound 101 (yield: 69%).

NMR (270 MHz, DMSO-$d_6$) δ (ppm) 2.63 (s, 3H), 6.14 (brs, 2H), 6.74 (s, 1H), 6.87 (t, 1H, J=8.7 Hz), 7.24 (brs, 2H), 7.60 (dd, 1H, J=8.9, 2.0 Hz), 7.67 (dd, 1H, J=12.9, 2.0 Hz)

EIMS (M/Z) 348 ($M^+$)

Molecular formula $C_{17}H_{11}F_3N_2O_3$=348

EXAMPLE 106

2-(4-Amino-3-fluorophenyl)-7-dimethylamino-6,8-difluoro-5-methylamino-4H-1-benzopyran-4-one (Compound 102)

(1) 1.47 g (3.00 mmol) of 7-amino-6,8-difluoro-2-(3-fluoro-4-pivaloylaminophenyl)-5-pivaloylamino-4H-1-benzopyran-4-one obtained in Example 100 (1) was dissolved in 40 mL of dimethylformamide under argon atmosphere, 600 mg (15.0 mmol) of sodium hydride (60% oil dispersion) and 0.41 mL (6.6 mmol) of iodomethane were added under ice-cooling and the mixture was stirred at the same temperature for 2 hours. Water was added to the reaction solution and the mixture was extracted twice with chloroform. The organic layer was washed once with water and once with an aqueous saturated solution of sodium chloride and dried over anhydrous sodium sulfate. The solvent was distilled off under reduced pressure and the residue was purified by silica gel column chromatography (chloroform:acetone=30:1) to give 790 mg of 7-dimethylamino- 6,8-difluoro-2-(3-fluoro-4-pivaloylaminophenyl)-5-(N-methyl-N-pivaloylamino)-4H-1-benzopyran-4-one (yield: 50%).

(2) Substantially the same manner as that in Example 85 (3) was repeated except that 605 mg (1.14 mmol) of the above 7-dimethylamino-6,8-difluoro-2-(3-fluoro-4-pivaloylaminophenyl)-5-(N-methyl-N-pivaloylamino)-4H-1-benzopyran-4-one was used, and the resulting compound was purified by silica gel column chromatography (chloroform) and recrystallized from ethyl acetate/n-hexane, to give 306 mg of Compound 102 (yield: 74%).

NMR (270 MHz, $CDCl_3$) δ (ppm) 3.05 (t, 6H, J=2.5 Hz), 3.09 (dd, 3H, J=6.2, 5.9 Hz), 4.12 (brs, 2H), 6.38 (s, 1H), 6.82 (t, 1H, J=8.7 Hz), 7.4–7.6 (m, 2H)

EIMS (M/Z) 363 ($M^+$)

Molecular formula $C_{18}H_{16}F_3N_3O_2$=363

EXAMPLE 107

2-(4-Amino-3-fluorophenyl)-6,8-difluoro-5-(1-hexylamino)-7-methyl-4H-1-benzopyran-4-one (Compound 107)

(1) 1.21 g (3.77 mmol) of Compound 80 obtained in Example 80 (3) was dissolved in 10 mL of pyridine, 0.46 mL (3.77 mmol) of pivaloyl chloride was added under ice-cooling and the mixture was stirred at the same temperature for 1 hour. The reaction solution was poured into ice water and the precipitated crystals were collected by filtration to give 1.48 g of 5-amino-6,8-difluoro-2-(3-fluoro-4-pivaloylaminophenyl)-7-methyl-4H-1-benzopyran-4-one (yield: 97%).

NMR (90 MHz, $CDCl_3$) δ (ppm) 1.36 (s, 9H), 2.34 (t, 3H, J=2.1 Hz), 4.21 (brs, 2H), 6.55 (s, 1H), 7.5–7.9 (m, 3H), 8.57 (t, 1H, J=8.6 Hz)

EIMS (M/Z) 404 ($M^+$)

Molecular formula $C_{21}H_{19}F_3N_2O_3$=404

(2) 653 mg (1.62 mmol) of the above 5-amino-6,8-difluoro-2-(3-fluoro-4-pivaloylaminophenyl)-7-methyl-4H-1-benzopyran-4-one was dissolved ion 20 mL of dimethylformamide under argon atmosphere, 200 mg (5.00 mmol) of sodium hydride (60% oil dispersion) and 0.48 mL (3.2 mmol) of 1-iodohexane were added under ice-cooling and the mixture was stirred at room temperature for 20 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by medium pressure liquid chromatography to give 422 mg of 6,8-difluoro-2-(3-fluoro-4-pivaloylaminophenyl)-5-(1-hexylamino)-7-methyl-4H-1-benzopyran-4-one (yield: 54%).

NMR (90 MHz, $CDCl_3$) δ (ppm) 0.8–1.0 (m, 3H), 1.1–1.9 (m, 8H), 1.36 (s, 9H), 2.31 (t, 3H, J=2.2 Hz), 3.48 (m, 2H), 6.52 (s, 1H), 7.5–7.9 (m, 3H), 8.57 (t, 1H, J=8.6 Hz), 8.66 (brs, 1H)

EIMS (M/Z) 488 ($M^+$)

Molecular formula $C_{27}H_{31}F_3N_2O_3$=488

(3) Substantially the same manner as that in Example 85 (3) was repeated except that 405 mg (0.830 mmol) of the above 6,8-difluoro-2-(3-fluoro-4-pivaloylaminophenyl)-5-(1-hexylamino )-7-methyl-4H-1-benzopyran-4-one was used, and the resulting compound was purified by silica gel column chromatography (chloroform), to give 270 mg of Compound 107 (yield: 81%).

NMR (270 MHz, $CDCl_3$) δ (ppm) 0.89 (t, 3H, J=7.2 Hz), 1.2–1.5 (m, 6H), 1.5–1.7 (m, 2H), 2.30 (t, 3H, J=2.5 Hz), 3.4–3.5 (m, 2H), 4.15 (brs, 2H), 6.42 (s, 1H), 6.83 (t, 1H, J=8.9 Hz), 7.3–7.5 (m, 2H), 8.70 (brs, 1H)

EIMS (M/Z) 404 ($M^+$)

Molecular formula $C_{22}H_{23}F_3N_2O_2$=404

EXAMPLE 108

2-(4-Amino-3-fluorophenyl)-6,8-difluoro-5-(1-heptylamino)-7-methyl-4H-1-benzopyran-4-one (Compound 108)

(1) Substantially the same manner as that in Example 107 (2) was repeated except that 650 mg (1.61 mmol) of 5-amino-6,8-difluoro-2-(3-fluoro-4-pivaloylaminophenyl)-

7-methyl-4H-1-benzopyran-4-one obtained in Example 107 (1) and 0.53 mL (3.22 mol) of 1-iodoheptane were used, to give 369 mg of 6,8-difluoro-2-(3-fluoro-4-pivaloylaminophenyl)-5-(1-heptylamino)-7-methyl-4H-1-benzopyran-4-one (yield: 46%).

NMR (90 MHz, CDCl$_3$) δ (ppm) 0.7–1.8 (m, 13H), 1.36 (s, 9H), 2.31 (t, 3H, J=2.2 Hz), 6.51 (s, 1H), 7.4–7.8 (m, 3H), 8.57 (t, 1H, J=8.6 Hz), 8.64 (brs, 1H)

EIMS (M/Z) 502 (M$^+$)

Molecular formula C$_{28}$H$_{33}$F$_3$N$_2$O$_3$=502

(2) Substantially the same manner as that in Example 85 (3) was repeated except that 351 mg (0.699 mmol) of the above 6,8-difluoro-2-(3-fluoro-4-pivaloylaminophenyl)-5-(1-heptylamino)-7-methyl-4H-1-benzopyran-4-one was used, and the resulting compound was purified by silica gel column chromatography (chloroform), to give 250 mg of Compound 108 (yield: 86%).

NMR (270 MHz, CDCl$_3$) δ (ppm) 0.88 (t, 3H, J=6.9 Hz), 1.2–1.5 (m, 8H), 1.5–1.7 (m, 2H), 2.30 (t, 3H, J=2.5 Hz), 3.4–3.5 (m, 2H), 4.15 (brs, 2H), 6.42 (s, 1H), 6.83 (t, 1H, J=8.7 Hz), 7.4–7.6 (m, 2H), 8.69 (brs, 1H)

EIMS (M/Z) 418 (M$^+$)

Molecular formula C$_{23}$H$_{25}$F$_3$N$_2$O$_2$=418

EXAMPLE 109

6,8-Difluoro-2-[3-fluoro-4-(1-propylamino)phenyl]-7-methyl-5-(1-pentylamino)-4H-1-benzopyran-4-one (Compound 109)

(1) 2.68 g (8.38 mmol) of Compound 1 obtained in Example 80 (3) was dissolved in 30 mL of pyridine, 0.88 mL (9.2 mmol) of acetic anhydride was added under ice-cooling and the mixture was stirred at 50° C. for 18 hours. The reaction solution was poured into ice water and the precipitated crystals were collected by filtration to give 3.03 g of 2-(4-acetylamino-3-fluorophenyl)-5-amino-6,8-difluoro-7-methyl-4H- 1-benzopyran-4-one (yield: 100%).

NMR (90 MHz, DMSO-d$_6$) δ (ppm) 2.15 (s, 3H), 2.28 (t, 3H, J=2.2 Hz), 6.86 (s, 1H), 6.95 (brs, 2H), 7.6–8.0 (m, 2H), 8.25 (t, 1H, J=8.8 Hz), 9.98 (brs, 1H)

EIMS (M/Z) 362 (M$^+$)

Molecular formula C$_{18}$H$_{13}$F$_3$N$_2$O$_3$=362

(2) 506 mg (1.40 mmol) of the above 2-(4-acetylamino-3-fluorophenyl)-5-amino-6,8-difluoro-7-methyl-4H-1-benzopyran-4-one was dissolved in 30 mL of dimethylformamide under argon atmosphere, 60 mg (1.5 mmol) of sodium hydride (60% oil dispersion) and 0.28 mL (2.8 mmol) of 1-iodopropane were added thereto under ice-cooling and the mixture was stirred at room temperature for 6 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform) to give 315 mg of 2-[4-[N-acetyl-N-(1-propyl)amino]-3-fluorophenyl]-5-amino-6,8-difluoro-7-methyl-4H-1-benzopyran-4-one (yield: 56%).

NMR (90 MHz, CDCl$_3$) δ (ppm) 0.90 (t, 3H, J=7.3 Hz), 1.50 (quint., 2H, J=7.5 Hz), 1.90 (s, 3H), 2.35 (t, 3H, J=2.2 Hz), 3.68 (t, 3H, J=7.5 Hz), 6.11 (brs, 2H), 6.61 (s, 1H), 7.37 (t, 1H, J=8.4 Hz), 7.6–7.8 (m, 2H)

EIMS (M/Z) 404 (M$^+$)

Molecular formula C$_{21}$H$_{19}$F$_3$N$_2$O$_3$=404

(3) 299 mg (0.740mmol) of the above 2-[4-[N-acetyl-N-(1-propyl)amino]-3-fluorophenyl]-5-amino-6,8-difluoro-7-methyl-4H-1-benzopyran-4-one was dissolved in 10 mL of dimethylformamide under argon atmosphere, 60 mg (1.5 mmol) of sodium hydride (60% oil dispersion) and 0.98 mL (7.4 mmol) of 1-iodopentane were added under ice-cooling and the mixture was stirred at room temperature for 6 hours. Water was added to the reaction solution and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform) to give 91.2 mg of 2-[4-[N-acetyl-N-(1-propyl)amino]-3-fluorophenyl]-6,8-difluoro-7-methyl-5-(1-pentylamino)-4H-1-benzopyran-4-one (yield: 26%).

NMR (90 MHz, CDCl$_3$) δ (ppm) 0.7–2.0 (m, 14H), 1.90 (s, 3H), 2.33 (t, 3H, J=2.2 Hz), 3.3–3.8 (m, 4H), 6.58 (s, 1H), 7.34 (t, 1H, J=8.4 Hz), 7.6–7.8 (m, 2H)

EIMS (M/Z) 474 (M$^+$)

Molecular formula C$_{26}$H$_{29}$F$_3$N$_2$O$_3$=474

(4) Substantially the same manner as that in Example 92 (2) was repeated except that 77 mg (0.16 mmol) of the above 2-[4-[N-acetyl-N-(1-propyl)amino]-3-fluorophenyl]-6,8-difluoro- 7-methyl-5-(1-pentylamino)-4H-1-benzopyran-4-one was used, and the resulting compound was purified by silica gel column chromatography (n-hexane:ethyl acetate= 5:1) and recrystallized from n-hexane, to give 36 mg of Compound 109 (yield: 51%).

NMR (270 MHz, CDCl$_3$) δ (ppm) 0.91 (t, 3H, J=6.9 Hz), 1.04 (t, 3H, 7.4 Hz), 1.2–1.8 (m, 8H), 2.30 (t, 3H, J=2.5 Hz), 3.20 (t, 2H, J=7.2 Hz), 3.4–3.5 (m, 2H), 4.40 (brs, 1H), 6.42 (s, 1H), 6.73 (t, 1H, J=8.7 Hz), 7.53 (dd, 1H, J=12.9, 2.0 Hz), 7.59 (dd, 1H, J=8.9, 2.0 Hz), 8.81 (brs, 1H)

FAB-MS (M/Z) 433 (M$^+$+H)

Molecular formula C$_{24}$H$_{27}$F$_3$N$_2$O$_2$=432

EXAMPLE 110

2-[4-(1-Butylamino)-3-fluorophenyl]-6,8-difluoro-7-methyl-5-(1-pentylamino)-4H-1-benzopyran-4-one (Compound 110)

(1) Substantially the same manner as that in Example 109 (2) was repeated except that 0.33 mL (2.85 mmol) of 1-iodobutane was used in place of 1-iodopropane, to give 334 mg of 2-[4-[N-acetyl-N-(1-butyl)amino]-3-fluorophenyl]-5-amino-6,8-difluoro-7-methyl-4H-1-benzopyran-4-one (yield: 56%).

NMR (90 MHz, CDCl$_3$) δ (ppm) 0.8–1.0 (m, 3H), 1.1–1.7 (m, 4H), 1.90 (s, 3H), 2.35 (t, 3H, J=2.2 Hz), 3.6–3.9 (m, 2H), 6.15 (brs, 2H), 6.61 (s, 1H), 7.37 (t, 1H, J=8.4 Hz), 7.6–7.8 (m, 2H)

EIMS (M/Z) 418 (M$^+$)

Molecular formula C$_{22}$H$_{21}$F$_3$N$_2$O$_3$=418

(2) Substantially the same manner as that in Example 109 (3) was repeated except that 319 mg (0.762 mmol) of the above 2-[4-[N-acetyl-N-(1-butyl)amino]-3-fluorophenyl]-5-amino-6,8-difluoro-7-methyl-4H-1-benzopyran-4-one was used, to give 105 mg of 2-[4-[N-acetyl-N-(1-butyl)amino]-3-fluorophenyl]-6,8-difluoro-7-methyl-5-(1-pentylamino)-4H-1-benzopyran-4-one (yield: 28%).

NMR (90 MHz, CDCl$_3$) δ (ppm) 0.8–2.0 (m, 16H), 1.89 (s, 3H), 2.32 (t, 3H, J=2.2 Hz), 3.3–3.8 (m, 4H), 6.58 (s, 1H), 7.36 (t, 1H, J=8.4 Hz), 7.6–7.8 (m, 2H), 8.67 (brs, 1H)

EIMS (M/Z) 488 (M⁺)

Molecular formula $C_{27}H_{31}F_3N_2O_3=488$ (3) Substantially the same manner as that in Example 92 (2) was repeated except that 92 mg (0.19 mmol) of the above 2-[4-[N-acetyl-N-(1-butyl)amino]-3-fluorophenyl]-6,8-difluoro-7-methyl-5-(1-pentylamino)-4H-1-benzopyran-4-one was used, and the resulting compound was purified by silica gel column chromatography (n-hexane/ethyl acetate=5:1) and recrystallized from n-hexane, to give 50 mg of Compound 110 (yield: 59%).

NMR (270 MHz, CDCl₃) δ (ppm) 0.91 (t, 3H, J=6.9 Hz), 0.98 (t, 3H, J=7.4 Hz), 1.2–1.8 (m, 10H), 2.30 (t, 3H, J=2.2 Hz), 3.23 (t, 2H, J=7.4 Hz), 3.4–3.5 (m, 2H), 4.30 (brs, 1H), 6.42 (s, 1H), 6.72 (t, 1H, J=8.7 Hz), 7.52 (dd, 1H, J=12.9, 2.0 Hz), 7.59 (dd, 1H, J=8.4, 2.0 Hz), 8.79 (brs, 1H)

FAB-MS (M/Z) 447 (M⁺+H)

Molecular formula $C_{25}H_{29}F_3N_2O_2=446$

EXAMPLE 111

6,8-Difluoro-2-[3-fluoro-4-(1-pentylamino)phenyl]-7-methyl-5-(1-pentylamino)-4H-1-benzopyran-4-one (Compound 111)

(1) 510 mg (1.41 mmol) of 2-(4-acetylamino-3-fluorophenyl)-5-amino-6,8-difluoro-7-methyl-4H-1-benzopyran-4-one obtained in Example 109 (1) was dissolved in 30 mL of dimethylformamide under argon atmosphere, 58 mg (1.5 mmol) of sodium hydride (60% oil dispersion) and 0.37 mL (2.8 mmol) of 1-iodopentane were added under ice-cooling and the mixture was stirred at room temperature for 4 hours. The reaction solution was cooled on ice, 117 mg (2.93 mmol) of sodium hydride (60% oil dispersion) and 0.37 mL (2.8 mmol) of 1-iodopentane were added and the mixture was stirred at room temperature for 50 minutes. An aqueous solution of ammonium chloride was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform) to give 153 mg of 2-[4-[N-acetyl-N-(1-pentyl)amino]-3-fluorophenyl]-6,8-difluoro-7-methyl-5-(1-pentylamino)-4H-1-benzopyran-4-one (yield: 22%).

NMR (90 MHz, CDCl₃) δ (ppm) 0.7–2.0 (m, 18H), 1.89 (s, 3H), 2.32 (t, 3H, J=2.2 Hz), 3.3–3.8 (m, 4H), 6.58 (s, 1H), 7.36 (t, 1H, J=7.7 Hz), 7.6–7.9 (m, 2H), 8.68 (brs, 1H)

EIMS (M/Z) 502 (M⁺)

Molecular formula $C_{28}H_{33}F_3N_2O_3=502$ (2) Substantially the same manner as that in Example 92 (2) was repeated except that 122 mg (0.243 mmol) of the above 2-[4-[N-acetyl-N-(1-pentyl)amino]-3-fluorophenyl]-6,8-difluoro-7-methyl-5-(1-pentylamino)-4H-1-benzopyran-4-one was used, and the resulting compound was purified by silica gel column chromatography (n-hexane/ethyl acetate) and recrystallized from n-hexane, to give 70 mg of Compound 111 (yield: 63%).

NMR (270 MHz, CDCl₃) δ (ppm) 0.91 (t, 3H, J=6.9 Hz), 0.94 (t, 3H, J=6.9 Hz), 1.2–1.8 (m, 12H), 2.30 (t, 3H, J=2.5 Hz), 3.22 (t, 3H, J=6.9 Hz), 3.4–3.5 (m, 2H), 4.35 (brs, 1H), 6.42 (s, 1H), 6.72 (t, 1H, J=8.7 Hz), 7.52 (dd, 1H, J=12.9, 2.0 Hz), 7.59 (dd, 1H, J=8.4, 2.0 Hz), 8.82 (brs, 1H)

FAB-MS (M/Z) 461 (M⁺+H)

Molecular formula $C_{26}H_{31}F_3N_2O_2=460$

EXAMPLE 112

5-Amino-2-(4-amino-3-fluorophenyl)-7-ethynyl-6,8-difluoro-4H-1-benzopyran-4-one (Compound 112)

(1) 30 mg (0.054mmol) of 7-bromo-6,8-difluoro-2-(3-fluoro-4-pivaloylaminophenyl)-5-pivaloylamino-4H-1-benzopyran-4-one obtained in Example 84 (2) was dissolved in a mixed solvent of 0.5 mL of dimethylformamide and 0.5 mL of triethylamine, 1 mg (0.004 mmol) of palladium (II) acetate, 2 mg (0.008 mmol) of triphenylphosphine and 38 μL (0.27 mmol) of trimethylsilylacetylene were added and the mixture was stirred at 50° C. for 2 hours. The reaction solution was cooled to room temperature, water was added thereto and the mixture was extracted once with ethyl acetate. The organic layer was washed twice with 2N hydrochloric acid, once with water and once with an aqueous saturated solution of sodium chloride and dried over anhydrous sodium sulfate. The solvent was distilled off under reduced pressure and the residue was purified by preparative thin layer chromatography (chloroform:acetonitrile=19:1) to give 12 mg of 6,8-difluoro-2-(3-fluoro-4-pivaloylaminophenyl)-5-pivaloylamino-7-(2-trimethylsilylethynyl)-4H-1-benzopyran-4-one (yield: 39%).

NMR (90 MHz, CDCl₃) δ (ppm) 0.30 (s, 9H), 1.36 (s, 9H), 1.38 (s, 9H), 6.66 (s, 1H), 7.4–7.9 (m, 3H), 8.60 (t, 1H, J=8.1 Hz)

FAB-MS (M/Z) 571 (M⁺+H)

Molecular formula $C_{30}H_{33}F_3N_2O_4Si=570$ (2) 3 mL of concentrated sulfuric acid was added to 37 mg (0.065 mmol) of the above 6,8-difluoro-2-(3-fluoro-4-pivaloylaminophenyl)-5-pivaloylamino-7-(2-trimethylsilylethynyl)-4H-1-benzopyran-4-one and the mixture was stirred at 50° C. for 10 minutes. The reaction solution was poured into ice water and the mixture was extracted once with ethyl acetate. The organic layer was washed once with 1N aqueous solution of sodium hydroxide, once with water and once with an aqueous saturated solution of sodium chloride and dried over anhydrous sulfate. The solvent was distilled off under reduced pressure and the residue was purified by preparative thin layer chromatography (chloroform:acetonitrile=9:1) to give 15 mg of Compound 112 (yield: 70%).

NMR (270 MHz, DMSO-d₆) δ (ppm) 5.04 (s, 1H), 6.14 (brs, 2H), 6.73 (s, 1H), 6.87 (t, 1H, J=8.9 Hz), 7.19 (brs, 2H), 7.60 (dd, 1H, J=8.4, 2.0 Hz), 7.67 (dd, 1H, J=12.9, 2.0 Hz)

EIMS (M/Z) 330 (M⁺)

Molecular formula $C_{17}H_9F_3N_2O_2=330$

EXAMPLE 113

5-Amino-2-(4-amino-3-fluorophenyl)-6,7,8-trifluoro-4H-1-benzopyran-4-one (Compound 113)

(1) 10 mL of thionyl chloride was added to 962 mg (4.88 mmol) of compound N obtained in Reference Example 12 under argon atmosphere and the mixture was heated at reflux for 1 hour. Thionyl chloride was distilled off under reduced pressure, 15 mL of dichloromethane, a solution of 1.17 g (4.06 mmol) of compound M obtained in Reference Example 11 in 20 mL of dichloromethane and 0.42 mL of triethylamine were added thereto and the mixture was stirred at room temperature for 2 hours. Water was added to the reaction solution, the organic layer was washed once with an aqueous saturated solution of sodium chloride and dried over anhydrous sodium sulfate. The solvent was distilled off under reduced pressure and the residue was purified by silica gel column chromatography (n-hexane:ethyl acetate=4:1-

1:1) to give 1.21 g of 2-acetyl-4,5,6-trifluoro-3-pivaloylaminophenyl-4 acetylamino-3-fluorobenzoate (yield: 76%).

NMR (90 MHz, CDCl$_3$) δ(ppm) 1.29 (s, 9H), 2.28 (s, 3H), 2.46 (s, 3H), 7.5–8.1 (m, 4H), 8.61 (dd, 1H, J=8.8, 7.5 Hz)

(2) 0.83 mL (5.9 mmol) of diisopropylamine was dissolved in 10 mL of tetrahydrofuran under argon atmosphere, 3.5 mL of a 1.6 M solution of n-butyl lithium in n-hexane was added dropwise under ice-cooling and the solution was cooled to −78 °C. To this solution was added a solution of 838 mg (1.79 mmol) of the above 2-acetyl-4,5,6-trifluoro-3-pivaloylaminophenyl 4-acetylamino-3-fluorobenzoate in 20 mL of tetrahydrofuran was added dropwise and the mixture was stirred for 2 hours while the temperature of the mixture was gradually raised to 0° C. An aqueous solution of ammonium chloride was added to the reaction solution, the mixture was extracted twice with ethyl acetate, the organic layer was washed once with an aqueous saturated solution of sodium chloride and dried over anhydrous sodium sulfate. The solvent was distilled off under reduced pressure, the residue was dissolved in 24 mL of ethanol, 6 mL of concentrated hydrochloric acid was added and the mixture was stirred at room temperature for 4 hours. Water was added to the reaction solution and the precipitated crystals were collected by filtration to give 330 mg of 2-(4-acetylamino-3-fluorophenyl)-6,7,8-trifluoro-5-pivaloylamino-4H-1-benzopyran-4-one (yield: 77%).

NMR (90 MHz, DMSO-d$_6$) δ (ppm) 1.29 (s, 9H), 2.16 (s, 3H), 7.09 (s, 1H), 7.7–8.0 (m, 2H), 8.29 (t, 1H, J=8.4 Hz), 10.0 (brs, 1H), 10.4 (brs, 1H)

EIMS (M/Z) 450 (M$^+$)

Molecular formula $C_{22}H_{18}F_4N_2O_4$=450

(3) Substantially the same manner as that in Example 85 (3) was repeated except that 366 mg (0.812 mmol) of the above 2-(4-acetylamino-3-fluorophenyl)-6,7,8-trifluoro-5-pivaloylamino-4H-1-benzopyran-4-one was used, and the resulting compound was purified by silica gel column chromatography (chloroform:ethyl acetate=20:1–10:1) and recrystallized from ethyl acetate/n-hexane, to give 200 mg of Compound 113 (yield: 76%).

NMR (270 MHz, DMSO-d$_6$) δ (ppm) 6.11 (brs, 2H), 6.69 (s, 1H), 6.86 (t, 1H, J=8.9 Hz), 7.40 (brs, 2H), 7.57 (dd, 1H, J=8.4, 2.4 Hz), 7.64 (dd, 1H, J=12.9, 2.0 Hz)

EIMS (M/Z) 324 (M$^+$)

Molecular formula $C_{15}H_8F_4N_2O_2$=324

EXAMPLE 114

2-(4-Amino-3-fluorophenyl)-6,8-difluoro-7-methyl-5-(3-methylbutylamino)-4H-1-benzopyran-4-one (Compound 114)

(1) 1.03 g (2.54mmol) of 5-amino-6,8-difluoro-2-(3-fluoro-4-pivaloylaminophenyl)-7-methyl-4H-1-benzopyran-4-one obtained in Example 107 (1) was dissolved in 20 mL of dimethylformamide under argon atmosphere, 308 mg (7.62 mmol) of sodium hydride (60% oil dispersion) and 0.77 mL (6.4 mmol) of 1-bromo-3-methylbutane were added and the mixture was stirred at room temperature for 4 hours. Water was added to the reaction solution, the mixture was extracted once with ethyl acetate, the organic layer was washed once with an aqueous saturated solution of sodium chloride and dried over anhydrous sodium sulfate. The solvent was distilled off under reduced pressure and the residue was purified by silica gel column chromatography (chloroform:n-hexane=3:1) to give 708 mg of 6,8-difluoro-2-(3-fluoro-4-pivaloylaminophenyl)-7-methyl-5-(3-methylbutylamino)-4H-1-benzopyran-4-one (yield: 59%).

NMR (90 MHz, CDCl$_3$) δ (ppm) 0.94 (d, 6H, J=6.2 Hz), 1.35 (s, 9H), 1.4–1.8 (m, 2H), 2.31 (t, 3H, J=2.4 Hz), 3.3–3.7 (m, 2H), 6.51 (s, 1H), 7.5–7.8 (m, 3H), 8.56 (t, 1H, J=8.6 Hz), 8.5–8.7 (m, 1H)

EIMS (M/Z) 474 (M$^+$)

Molecular formula $C_{26}H_{29}F_3N_2O_3$=474

(2) Substantially the same manner as that in Example 85 (3) was repeated except that 692 mg (1.46 mmol) of the above 6,8-difluoro-2-(3-fluoro-4-pivaloylaminophenyl)-7-methyl-5-(3-methylbutylamino)-4H-1-benzopyran-4-one was used, and the resulting compound was purified by silica gel column chromatography (chloroform) and recrystallized from 2-propanol, to give 371 mg of Compound 114 (yield: 65%).

NMR (270 MHz, CDCl$_3$) δ (ppm) 0.94 (d, 6H, J=6.4 Hz), 53 (q, 2H, J=6.9 Hz), 1.6–1.8 (m, 2H), 2.30 (t, 3H, J=2.2 Hz), 3.4–3.5 (m, 2H), 4.16 (brs, 2H), 6.42 (s, 1H), 6.83 (t, 1H, J=8.6 Hz), 7.4–7.6 (m, 2H), 8.6–8.7 (m, 1H)

EIMS (M/Z) 390 (M$^+$)

Molecular formula $C_{21}H_{21}F_3N_2O_2$=390

EXAMPLE 115

2-(4-Amino-3-fluorophenyl)-6,8-difluoro-7-methyl-5-(4-methylpentylamino)-4H-1-benzopyran-4-one (Compound 115)

(1) Substantially the same manner as that in Example 114 (1) was repeated except that 1.02 g (2.54 mmol) of 5-amino-6,8-difluoro-2-(3-fluoro-4-pivaloylaminophenyl)-7-methyl-4H-1-benzopyran-4-one obtained in Example 107 (1), 306 mg (7.65 mmol) of sodium hydride (60% oil dispersion) and 0.90 mL (6.3 mmol) of 1-bromo-4-methylpentane were used under argon atmosphere, to give 718 mg of 6,8-difluoro-2-(3-fluoro-4-pivaloylaminophenyl)-7-methyl-5-(4-methylpentylamino)-4H-1-benzopyran-4-one (yield: 58%).

NMR (90 MHz, CDCl$_3$) δ (ppm) 0.90 (d, 6H, J=6.2 Hz), 1.3–1.9 (m, 4H), 1.36 (s, 9H), 2.31 (t, 3H, J=2.4 Hz), 3.3–3.6 (m, 2H), 6.51 (s, 1H), 7.5–7.9 (m, 3H), 8.5–8.8 (m, 1H), 8.56 (t, 1H, J=8.5 Hz)

MS (M/Z) 488 (M$^+$)

Molecular formula $C_{27}H_{31}F_3N_2O_3$=488

(2) Substantially to the same manner as that in Example 85 (3) was repeated except that 685 mg (1.40 mmol) of the above 6,8-difluoro-2-(3-fluoro-4-pivaloylaminophenyl)-7-methyl-5-(4-methylpentylamino)-4H-1-benzopyran-4-one was used, and the resulting compound was purified by silica gel column chromatography (chloroform) and recrystallized from 2-propanol, to give 271 mg of Compound 115 (yield: 48%).

NMR (270 MHz, CDCl$_3$) δ (ppm) 0.89 (d, 6H, J=6.4 Hz), 1.2–1.4 (m, 2H), 1.5–1.7 (m, 3H), 2.30 (t, 3H, J=2.5 Hz), 3.3–3.5 (m, 2H), 4.16 (brs, 2H), 6.43 (s, 1H), 6.83 (t, 1H, J=8.7 Hz), 7.4–7.6 (m, 2H), 8.7–8.8 (m, 1H)

MS (M/Z) 404 (M$^+$)

Molecular formula $C_{22}H_{23}F_3N_2O_2$=404

EXAMPLE 116

2-(4-Amino-3-fluorophenyl)-5-(3-dimethylaminopropylamino)-6,8-difluoro-7-methyl-4H-1-benzopyran-4-one (Compound 116)

(1) 10.1 g (25.0 mmol) of 5-amino-6,8-difluoro-2-(3-fluoro-4-pivaloylaminophenyl)-7-methyl-4H-1-benzopyran-4-one obtained in Example 107 (1) was dissolved in 150 mL of dimethylformamide under argon atmosphere, a solution of 20.2 g (74.8 mmol) of 2-(3-iodopropyloxy)-3,4,5,6-tetrahydropyran in 10 mL of dimethylformamide and 2.00 g (50.0 mmol) of sodium hydride (60% oil dispersion) were added under ice-cooling and the mixture was stirred at room temperature for 7.3 hours. The reaction solution was cooled on ice, water was added, the solvent was distilled off under reduced pressure, water was further added and the mixture was extracted once with ethyl acetate. The organic layer was washed once with water and once with an aqueous saturated solution of sodium chloride, dried over anhydrous sodium sulfate and the solvent was distilled off under reduced pressure. The residue was dissolved in 250 mL of ethanol, 500 mg (2.16 mmol) of dl-camphorsulfonic acid was added and the mixture was stirred at 50° C. for 7 hours. The solvent was distilled off under reduced pressure, water was added to the residue, the mixture was extracted twice with chloroform, the organic layer was washed once with an aqueous saturated solution of sodium chloride and dried over anhydrous sodium sulfate. The solvent was distilled off under reduced pressure and the residue was purified by silica gel column chromatography (chloroform:ethyl acetate=2:1) to give 3.00 g of 6,8-difluoro-2-(3-fluoro-4-pivaloylaminophenyl)-5-(3-hydroxyproyplamino)-7-methyl-4H-1-benzopyran-4-one (yield: 30%).

NMR (90 MHz, CDCl$_3$) δ (ppm) 1.36 (s, 9H), 1.92 (quint., 2H, J=6.8 Hz), 2.32 (t, 3H, J=2.4 Hz), 3.59 (td, 2H, J=6.8, 3.6 Hz), 3.81 (t, 2H, J=6.8 Hz), 6.53 (s, 1H), 7.5–7.8 (m, 3H), 8.57 (t, 1H, J=8.4 Hz)

FAB-MS (M/Z) 463 (M$^+$+H)

Molecular formula $C_{24}H_{25}F_3N_2O_4$=462

(2) 3.96 g (8.57 mmol) of the above 6,8-difluoro-2-(3-fluoro-4-pivaloylaminophenyl)-5-(3-hydroxypropylamino)-7-methyl-4H-1-benzopyran-4-one was dissolved in 100 mL of pyridine under ice-cooling, 1.3 mL (17 mmol) of methanesulfonyl chloride was added and the mixture was stirred at the same temperature for 1 hour. Water was added to the reaction solution and the precipitated crystals were collected by filtration to give 4.62 g of 6,8-difluoro-2-(3-fluoro-4-pivaloylaminophenyl)-5-(3-methanesulfonyloxypropylamino)-7-methyl-4H-1-benzopyran-4-one (yield: 100%).

NMR (90 MHz, CDCl$_3$) δ (ppm) 1.36 (s, 9H), 2.09 (quint., 2H, J=6.3 Hz), 2.33 (t, 3H, J=2.3 Hz), 3.04 (s, 3H), 3.3–3.7 (m, 2H), 4.37 (t, 2H, J=6.0 Hz), 6.54 (s, 1H), 7.5–7.8 (m, 3H), 8.58 (t, 1H, J=8.4 Hz)

EIMS (M/Z) 540 (M$^+$)

Molecular formula $C_{25}H_{27}F_3N_2O_6S$=540

(3) 1.02 g (1.89 mmol) of the above 6,8-difluoro-2-(3-fluoro-4-pivaloylaminophenyl)-5-(3-methanesulfonyloxypropylamino)-7-methyl-4H-1-benzopyran-4-one was dissolved in 30 mL of dimethylformamide, 1.54 g (18.9 mmol) of dimethylamine hydrochloride and 2.60 g (18.9 mmol) of potassium carbonate were added and the mixture was stirred at 50° C. for 24 hours. Water was added to the reaction solution and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol:=100:1-9:1) to give 660 mg of 6,8-difluoro-5-(3-dimethylaminopropylamino)-2-(3-fluoro-4-pivaloylaminophenyl)-7-methyl-4H-1-benzopyran-4-one (yield: 71%).

NMR (90 MHz, CDCl$_3$) δ (ppm) 1.35 (s, 9H), 1.7–1.9 (m, 2H), 2.29 (s, 9H), 2.3–2.6 (m, 2H), 3.4–3.7 (m, 2H), 6.52 (s, 1H), 7.5–7.7 (m, 3H), 8.57 (t, 1H, J=8.4 Hz), 8.6–8.7 (m, 1H)

EIMS (M/Z) 489 (M$^+$)

Molecular formula $C_{26}H_{30}F_3N_3O_3$=489

(4) Substantially the same manner as that in Example 85 (3) was repeated except that 624 mg (1.28 mmol) of the above 6,8-difluoro-5-(3-dimethylaminopropylamino)-2-(3-fluoro-4-pivaloylaminophenyl)-7-methyl-4H-1-benzopyran-4-one was used, and the resulting compound was purified by silica gel column chromatography (chloroform:methanol=9:1-chloroform:methanol:aqueous ammonia=20:1:1) and recrystallized from ethanol/n-hexane, to give 472 mg of Compound 116 (yield: 91%).

NMR (270 MHZ, CDCl$_3$) δ (ppm) 1.82 (quint., 2H, J=7.3 Hz), 2.27 (s, 6H), 2.29 (t, 3H, J=2.3 Hz), 2.42 (t, 2H, J=7.4 Hz), 3.4–3.6 (m, 2H), 4.18 (brs, 2H), 6.42 (s, 1H), 6.83 (t, 1H, J=8.7 Hz), 7.4–7.7 (m, 2 H), 8.7–8.8 (m, 1H)

EIMS (M/Z) 405 (M$^+$)

Molecular formula $C_{21}H_{22}F_3N_3O_2$=405

EXAMPLE 117

2-(4-Amino-3-fluorophenyl)-5-(3-diethylaminopropylamino)-6,8-difluoro-7-methyl-4H-1-benzopyran-4-one (Compound 117)

(1) 1.02 g (1.89 mmol) of 6,8-difluoro-2-(3-fluoro-4-pivaloylaminophenyl)-5-(3-methanesulfonyloxypropylamino)-7-methyl-4H-1-benzopyran-4-one obtained in Example 116 (2) was dissolved in 30 mL of dimethylformamide, 2.0 mL (18.9 mmol) of diethylamine was added and the mixture was stirred at 80° C. for 15 hours. Water and a 1N aqueous solution of sodium hydroxide were added to the reaction solution and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=100:1-9:1) to give 860 mg of 5-(3-diethylaminopropylamino)-6,8-difluoro-2-(3-fluoro-4-pivaloylaminophenyl)-7-methyl-4H-1-benzopyran-4-one (yield: 88%).

NMR (90 MHz, CDCl$_3$) δ (ppm) 1.06 (t, 6H, J=7.3 Hz), 1.35 (s, 9H), 1.7–1.9 (m, 2H), 2.31 (t, 3H, J=2.4 Hz), 2.5–2.8 (m, 2H), 2.60 (q, 4H, J=7.3 Hz), 3.3–3.7 (m, 2H), 6.52 (s, 1H), 7.5–7.7 (m, 3H), 8.57 (t, 1H, 8.4 Hz), 8.6–8.7 (m, 1H)

EIMS (M/Z) 517 (M$^+$)

Molecular formula $C_{28}H_{34}F_3N_3O_3$=517

(2) Substantially the same manner as that in Example 85 (3) was repeated except that 820 mg (1.59 mmol) of the above 5-(3-diethylaminopropylamino)-6,8-difluoro-2-(3-fluoro-4-pivaloylaminophenyl)-7-methyl-4H-1-benzopyran-4-one was used, and the resulting compound was purified by silica gel column chromatography (chloroform:methanol=9:1-chloroform:methanol:aqueous ammonia=20:1:1) and recrystallized from ethanol/n-hexane, to give 584 mg of Compound 117 (yield: 85%).

NMR (270 MHz, CDCl$_3$) δ (ppm) 1.05 (t, 6H, J=7.2 Hz), 1.81 (quint., 2H, J=7.4 Hz), 2.55 (q, 4H, J=7.2 Hz), 2.57 (t, 2H, J=7.4 Hz), 3.4–3.6 (m, 2H), 4.17 (brs, 2H), 6.42 (s, 1H), 6.83 (t, 1H, J=8.7 Hz), 7.4–7.6 (m, 2H), 8.7–8.8 (m, 1H)

EIMS (M/Z) 433 (M$^+$)

Molecular formula $C_{23}H_{26}F_3N_3O_2$=433

EXAMPLE 118

5-Amino-2-(4-amino-3-fluorophenyl)-6,8-difluoro-7-hydroxymethyl-4H-1-benzopyran-4-one (Compound 118)

(1) Substantially the same manner as that in Example 80 (1) was repeated except that 385 mg (1.00 mmol) of compound E obtained in Reference Example 4 was used and 0.39 mL (5.0 mmol) of dimethylformamide was used in place of iodomethane, to give 402 mg of ethyl 3,5-difluoro-4-formyl-6-pivaloylamino-2-(2-tetrahydropyranyloxy) benzoate (yield: 97%).

NMR (90 MHz, CDCl$_3$) δ (ppm) 1.29 (s, 9H), 1.39 (t, 3H, J=7.0 Hz), 1.4–2.0 (m, 6H), 3.4–4.1 (m, 2H), 4.37 (q, 2H, J=7.0 Hz), 5.3–5.4 (m, 1H), 7.52 (brs, 1H), 10.32 (s, 1H)

FAB-MS (M/Z) 414 (M$^+$+H)

Molecular formula $C_{20}H_{25}F_2NO_6$=413

(2) 22.3 g (54.0 mmol) of the above ethyl 3,5-difluoro-4-formyl-6-pivaloylamino-2-(2-tetrahydropyranyloxy)benzoate was dissolved in 260 mL of methanol, 1.02 g (27.0 mmol) of sodium borohydride was added under ice-cooling and the mixture was stirred at the same temperature for 1 hour. Water was added to the reaction solution, the solvent was distilled off to about 50 mL under reduced pressure, water was further added and the mixture was extracted twice with ethyl acetate. The organic layer was washed once with an aqueous saturated solution of sodium chloride, dried over anhydrous sodium sulfate and the solvent was distilled off under reduced pressure to give 22.0 g of ethyl 3,5-difluoro-4-hydroxymethyl-6-pivaloylamino-2-(2-tetrahydropyranyloxy) benzoate (yield: 98%).

NMR (90 MHz, CDCl$_3$) δ(ppm) 1.29 (s, 9H), 1.38 (t, 3H, J=7.3 Hz), 1.4–2.0 (m, 6H), 3.4–4.1 (m, 2H), 4.35 (q, 2H, J=7.3 Hz), 4.7–4.8 (brs, 2H), 5.2–5.4 (m, 1H), 7.68 (brd, 1H)

FAB-MS (M/Z) 416 (M$^+$+H)

Molecular formula $C_{20}H_{27}F_2NO_6$=415

(3) 213 mg (0.50 mmol) of the above ethyl 3,5-difluoro-4-hydroxymethyl-6-pivaloylamino-2-(2-tetrahydropyranyloxy)benzoate was dissolved in 5 mL of dichloromethane, 68 mg (1.0 mmol) of imidazole and 302 mg (2.00 mmol) of tert-butyldimethylsilyl chloride were added and the mixture was heated at reflux for 30 minutes. The reaction solution was cooled on ice, water was added and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (n-hexane:ethyl acetate=4:1) to give 256 mg of ethyl 4-tert-butyldimethylsilyloxymethyl-3,5-difluoro-6-pivaloylamino-2-(2-tetrahydropyranyloxy)benzoate (yield: 98%).

NMR (90 MHz, CDCl$_3$) δ (ppm) 0.03 (s, 6H), 0.83 (s, 9H), 1.23 (s, 9H), 1.32 (t, 3H, J=7.0 Hz), 1.4–2.0 (m, 6H), 3.4–4.1 (m, 2H), 4.28 (q, 2H, J=7.0 Hz), 4.70 (t, 2H, J=1.7 Hz), 5.2–5.3 (m, 1H), 7.52 (brs, 1H)

FAB-MS (M/Z) 525 (M$^+$+H)

Molecular formula $C_{26}H_{41}F_2NO_6Si$=525

(4) Substantially the same manner as that in Example 80 (2) was repeated except that 29.0 g (55.2 mmol) of the above ethyl 4-tert-butyldimethylsilyloxymethyl-3,5-difluoro-6-pivaloylamino-2-(2-tetrahydropyranyloxy) benzoate and 11.4 g (48.2mmol) of compound G obtained in Reference Example 6 were used, to give 9.69 g of 6,8-difluoro-2-(3-fluoro-4-pivaloylaminophenyl)-7-hydroxymethyl-5-pivaloylamino-4H-1-benzopyran-4-one (yield: 40%).

NMR (90 MHz, DMSO-d$_6$) δ (ppm) 1.27 (s, 9H), 1.29 (s, 9H), 4.6–4.7 (m, 2H), 5.56 (t, 1H, J=5.7 Hz), 7.07 (s, 1H), 7.7–8.0 (m, 3H), 9.20 (brs, 1H), 10.0 (brs, 1H)

EIMS (M/Z) 504 (M$^+$)

Molecular formula $C_{26}H_{27}F_3N_2O_5$=504

(5) 40 mL of ethanol and 20 mL of concentrated hydrochloric acid were added to 903 mg (1.79 mmol) of the above 6,8-difluoro-2-(3-fluoro-4-pivaloylaminophenyl)-7-hydroxymethyl-5-pivaloylamino-4H-1-benzopyran-4-one and the mixture was heated at reflux for 6.5 hours. The reaction solution was cooled on ice and adjusted to pH 7 to 8 by addition of a 10N aqueous solution of sodium hydroxide thereto, and the precipitated crystals were collected by filtration. The crystals were purified by silica gel column chromatography (chloroform:methanol=40:1-9:1) and triturated with ethyl acetate to give 364 mg of Compound 118 (yield: 60%).

NMR (270 MHz, DMSO-d$_6$) δ (ppm) 4.5–4.6 (m, 2H), 5.44 (t, 1H, J=4.9 Hz), 6.11 (brs, 2H), 6.69 (s, 1H), 6.87 (t, 1H, J=8.4 Hz), 7.03 (brs, 2H), 7.5–7.7 (m, 2H)

EIMS (M/Z) 336 (M$^+$)

Molecular formula $C_{16}H_{11}F_3N_2O_3$=336

EXAMPLE 119

5-Amino-2-(4-amino-3-fluorophenyl)-6,8-difluoro-7-hydroxysulfonyloxymethyl-4H-1-benzopyran-4-one (Compound 119)

10 mL of concentrated sulfuric acid was added to 1.00 g (1.98 mmol) of 6,8-difluoro-2-(3-fluoro-4-pivaloylaminophenyl)-7-hydroxymethyl-5-pivaloylamino-4H-1-benzopyran-4-one obtained in Example 118 (4) and the mixture was stirred at 50° C. for 20 minutes. The reaction solution was cooled on ice, ice water was added and the precipitated crystals were collected by filtration. The crystals were purified by silica gel column chromatography (chloroform:methanol=9:1-chloroform:methanol:aqueous ammonia=40:10:1) and triturated with ethanol to give 293 mg of Compound 119 (yield: 36%).

NMR (270 MHz, DMSO-d$_6$) δ (ppm) 4.91 (s, 2H), 6.12 (brs, 2H), 6.70 (s, 1H), 6.88 (t, 1H, J=8.9 Hz), 7.06 (brs, 2H), 7.61 (dd, 1H, J=8.6, 2.0 Hz), 7.67 (dd, 1H, J=12.9, 1.7 Hz)

FAB-MS (M/Z) 417 (M$^+$+H)

Molecular formula $C_{16}H_{11}F_3N_2O_6S$=416

EXAMPLE 120

5-Amino-2-(4-amino-3-fluorophenyl)-7-aminomethyl-6,8-difluoro-4H-1-benzopyran-4-one (Compound 120)

(1) 3.30 g (6.55 mmol) of 6,8-difluoro-2-(3-fluoro-4-pivaloylaminophenyl)-7-hydroxymethyl-5-pivaloylamino-4H-1-benzopyran-4-one obtained in Example 118 (4) was dissolved in 70 mL of dimethylformamide, 4.6 mL of triethylamine and 1.0 mL of methanesulfonyl chloride were added under ice-cooling and the mixture was stirred at room temperature for 10 minutes. Water was added to the reaction solution and the mixture was extracted twice with ethyl acetate. The organic layer was washed once with water and once with an aqueous saturated solution of sodium chloride, and dried over anhydrous sodium sulfate, and the solvent was distilled off under reduced pressure to give 3.57 g of 6,8-difluoro-2-(3-fluoro-4-pivaloylaminophenyl)-7-methanesulfonyloxymethyl-5-pivaloylamino-4H-1-benzopyran-4-one (yield: 94%).

NMR (90 MHz, CDCl$_3$) δ (ppm) 1.36 (9H, s), 1.38 (9H, s), 3.10 (s, 3H), 5.48 (brs, 2H), 6.69 (s, 1H), 7.5–7.9 (m, 3H), 8.61 (t, 1H, J=8.4 Hz), 10.4 (brs, 1H)

FAB-MS (M/Z) 583 (M$^+$+H)

Molecular formula C$_{27}$H$_{29}$F$_3$N$_2$O$_7$S=582

(2) 400 mg (0.687 mmol) of the above 6,8-difluoro-2-(3-fluoro-4-pivaloylaminophenyl)-7-methanesulfonyloxymethyl-5-pivaloylamino-4H-1-benzopyran-4-one was dissolved in 50 mL of an about 6N solution of ammonia in methanol and the solution was stirred at room temperature for 9 hours. Water was added to the reaction solution and the mixture was extracted twice with chloroform. The organic layer was washed once with water and once with an aqueous saturated solution of sodium chloride and dried over sodium sulfate. The solvent was distilled off under reduced pressure and the residue was purified by silica gel column chromatography (chloroform:methanol=30:1) to give 142 mg of 7-aminomethyl-6,8-difluoro-2-(3-fluoro-4-pivaloylaminophenyl)-5-pivaloylamino-4H-1-benzopyran-4-one (yield: 41%).

NMR (90 MHz, CDCl$_3$) δ (ppm) 1.37 (s, 9H), 1.38 (s, 9H), 4.1–4.2 (m, 2H), 6.60 (s, 1H), 7.5–7.9 (m, 3H), 8.60 (t, 1H, J=8.8 Hz), 10.5 (brs, 1H)

FAB-MS (M/Z) 504 (M$^+$+H)

Molecular formula C$_{26}$H$_{28}$F$_3$N$_3$O$_4$=503

(3) Substantially the same manner as that in Example 92 (2) was repeated except that 2.99 g (5.94 mmol) of the above 7-aminomethyl-6,8-difluoro-2-(3-fluoro-4-pivaloylaminophenyl)-5-pivaloylamino-4H-1-benzopyran-4-one was used, and the resulting compound was purified by silica gel column chromatography (chloroform:methanol=20:1-chloroform:methanol:aqueous ammonia=9:1:1) and triturated with chloroform, to give 1.59 g of Compound 120 (yield: 80%).

NMR (270 MHz, DMSO-D$_6$) δ (ppm) 3.80 (s, 2H), 6.08 (brs, 2H), 6.67 (s, 1H), 6.87 (t, 1H, J=8.9 Hz), 7.00 (brs, 2H), 7.59 (dd, 1H, J=8.4, 2.0 Hz), 7.66 (dd, 1H, J=12.9, 2.0 Hz)

FAB-MS (M/Z) 336 (M$^+$+H)

Molecular formula C$_{16}$H$_{12}$F$_3$N$_3$O$_2$=335

EXAMPLE 121

Hydrochloride of 5-amino-2-(4-amino-3-fluorophenyl)-7-dimethylaminomethyl-6,8-difluoro-4H-1-benzopyran-4-one (Compound 121)

(1) 800 mg (1.37 mmol) of 6,8-difluoro-2-(3-fluoro-4-pivaloylaminophenyl)-7-methanesulfonyloxymethyl-5-pivaloylamino-4H-1-benzopyran-4-one obtained in Example 120 (1) was dissolved in 10 mL of dimethylformamide, 558 mg (6.85 mmol) of dimethylamine hydrochloride and 945 mg (6.85 mmol) of potassium carbonate were added and the mixture was stirred at room temperature for 45 minutes. Water was added to the reaction solution and the mixture was extracted once with ethyl acetate. The organic layer was washed once with water and once with an aqueous saturated solution of sodium chloride, and dried over anhydrous sodium sulfate, and the solvent was distilled off under reduced pressure to give 727 mg of 7-dimethylaminomethyl-6,8-difluoro-2-(3-fluoro-4-pivaloylaminophenyl)-5-pivaloylamino-4H-1-benzopyran-4-one (yield: 100%).

NMR (90 MHz, CDCl$_3$) δ (ppm) 1.36 (s, 9H), 1.38 (s, 9H), 2.36 (s, 6H), 3.81 (brs, 2H), 6.67 (s, 1H), 7.5–7.8 (m, 3H), 8.59 (t, 1H, J=8.4 Hz), 10.4 (brs, 1H)

FAB-MS (M/Z) 532 (M$^+$+H)

Molecular formula C$_{28}$H$_{32}$F$_3$N$_3$O$_4$=531

(2) Substantially the same manner as that in Example 85 (3) was repeated except that 715 mg (1.35 mmol) of the above 7-dimethylaminomethyl-6,8-difluoro-2-(3-fluoro-4-pivaloylaminophenyl)-5-pivaloylamino-4H-1-benzopyran-4-one was used, and the resulting compound was purified by silica gel column chromatography (chloroform:methanol=30:1-9:1) and recrystallized from ethanol/methanol, to give 360 mg of Compound 121 (yield: 73%). This compound was dissolved in 60 mL of ethanol, 2 mL of a 1N hydrochloric acid/2-propanol solution was added dropwise and 60 mL of isopropyl ether was further added. The precipitated crystals were collected by filtration to give a hydrochloride of Compound 121.

NMR (270 MHz, DMSO-d$_6$) δ (ppm) 2.84 (s, 6H), 4.47 (brs, 2H), 6.16 (brs, 2H), 6.76 (s, 1H), 6.88 (t, 1H, J=8.9 Hz), 7.25 (brs, 2H), 7.61 (dd, 1H, J=8.6, 2.0 Hz), 7.67 (dd, 1H, J=12.9, 2.0 Hz), 10.7 (brs, 1H)

FAB-MS (M/Z) 364 (M$^+$+H)

Molecular formula C$_{18}$H$_{16}$F$_3$N$_3$O$_2$=363

EXAMPLE 122

5-Amino-2-(4-amino-3-fluorophenyl)-6,8-difluoro-7-methoxymethyl-4H-1-benzopyran-4-one (Compound 122)

(1) 800 mg (1.37 mmol) of 6,8-difluoro-2-(3-fluoro-4-pivaloylaminophenyl)-7-methanesulfonyloxymethyl-5-pivaloylamino-4H-1-benzopyran-4-one obtained in Example 120 (1) was dissolved in 200 mL of methanol and the solution was heated at reflux for 24 hours. The solvent was distilled off under reduced pressure, the residue was dissolved in chloroform, washed once with an aqueous saturated solution of sodium chloride and dried over anhydrous sodium sulfate. The solvent was distilled off under reduced pressure and the residue was purified by silica gel column chromatography (chloroform:acetonitrile=20:1) to give 610 mg of 6,8-difluoro-2-(3-fluoro-4-pivaloylaminophenyl)-7-methoxymethyl-5-pivaloylamino-4H-1-benzopyran-4-one (yield: 86%).

NMR (90 MHz, CDCl$_3$) δ (ppm) 1.36 (s, 9H), 1.38 (s, 9H), 3.44 (s, 3H), 4.72 (t, 2H, J=1.8 Hz), 6.67 (s, 1H), 7.6–7.9 (m, 3H), 8.60 (t, 1H, J=8.6 Hz), 10.4 (brs, 1H)

FAB-MS (M/Z) 519 (M$^+$+H)

Molecular formula C$_{27}$H$_{29}$F$_3$N$_2$O$_5$=518

(2) Substantially the same manner as that in Example 92 (2) was repeated except that 610 mg (1.18 mmol) of the above 6,8-difluoro-2-(3-fluoro-4-pivaloylaminophenyl)-7-methoxymethyl-5-pivaloylamino-4H-1-benzopyran-4-one was used, and the resulting compound was purified by silica gel column chromatography (chloroform: acetonitrile=9:1) and recrystallized from ethyl acetate, to give 267 mg of Compound 122 (yield: 65%).

NMR (270 MHz, DMSO-d$_6$) δ (ppm) 3.31 (s, 3H), 4.57 (brs, 2H), 6.10 (brs, 2H), 6.69 (s, 1H), 6.87 (t, 1H, J=8.9 Hz), 7.06 (brs, 1H), 7.5–7.7 (m, 2H)

EIMS (M/Z) 350 (M$^+$)

Molecular formula C$_{17}$H$_{13}$F$_3$N$_2$O$_3$=350

EXAMPLE 123

7-Acetoxymethyl-5-amino-2-(4-amino-3-fluorophenyl)-6,8-difluoro-4H-1-benzopyran-4-one (Compound 123)

6.02 g (11.9 mmol) of 6,8-difluoro-2-(3-fluoro-4-pivaloylaminophenyl)-7-hydroxymethyl-5-pivaloylamino-4H-1-benzopyran-4-one obtained in Example 118 (4) was dissolved in a mixed solvent of 160 mL of acetic acid and 40 mL of concentrated sulfuric acid and the solution was stirred at 100° C. for 35 minutes. The reaction solution was cooled on ice, poured into ice water and the mixture was extracted twice with ethyl acetate. The organic layer was washed twice with a 1N aqueous solution of sodium hydroxide, once with water and once with an aqueous saturated solution of sodium chloride and dried over anhydrous sodium sulfate. The solvent was distilled off under reduced pressure, the residue was purified by silica gel column chromatography (chloroform:methanol=100:1) and recrystallized from chloroform/methanol/n=hexane to give 2.43 g of Compound 123 (yield: 54%).

NMR (270 MHz, CDCl$_3$) δ (ppm) 2.11 (s, 3H), 5.29 (t, 2H, J=1.5 Hz), 6.49 (s, 1H), 6.84 (t, 1H, J=8.7 Hz), 7.5–7.6 (m, 2H)

FAB-MS (M/Z) 379 (M$^+$+H)

Molecular formula $C_{18}H_{13}F_3N_2O_4$=378

EXAMPLE 124

5-Amino-2-(4-amino-3-fluorophenyl)-6,8-difluoro-7-(1-propanoyloxymethyl)-4H-1-benzopyran-4-one (Compound 124)

Substantially the same manner as that in Example 123 was repeated except that 1.06 g (2.10 mmol) of 6,8-difluoro-2-(3-fluoro-4-pivaloylaminophenyl)-7-hydroxymethyl-5-pivaloylamino-4H-1-benzopyran-4-one obtained in Example 118 (4), 32 mL of propionic acid and 8 mL of concentrated sulfuric acid were used, and the resulting compound was purified by silica gel column chromatography (chloroform:acetonitrile=20:1) and high performance liquid chromatography, to give 261 mg of Compound 124 (yield: 32%).

NMR (270 MHz, DMSO-d$_6$) δ (ppm) 1.04 (t, 3H, J=7.6 Hz), 2.36 (q, 2H, J=7.6 Hz), 5.24 (brs, 2H), 6.10 (brs, 2H), 6.70 (s, 1H), 6.87 (t, 1H, J=8.6 Hz), 7.10 (brs, 2H), 7.59 (dd, 1H, J=8.6, 2.0 Hz), 7.65 (dd, 1H, J=12.9, 2.0 Hz)

EIMS (M/Z) 392 (M$^+$)

Molecular formula $C_{19}H_{15}F_3N_2O_4$=392

EXAMPLE 125

5-Amino-2-(4-amino-3-fluorophenyl)-6,8-difluoro-7-(1-hexanoyloxymethyl)-4H-1-benzopyran-4-one (Compound 125)

Substantially the same manner as that in Example 123 was repeated except that 1.06 g (2.10 mmol) of 6,8-difluoro-2-(3-fluoro-4-pivaloylaminophenyl)-7-hydroxymethyl-5-pivaloylamino-4H-1-benzopyran-4-one obtained in Example 118 (4), 24 mL of hexanoic acid and 6 mL of concentrated sulfuric acid were used, and the resulting compound was purified by silica gel column chromatography (chloroform:acetonitrile=30:1–20:1) and recrystallized from ethyl acetate/n-hexane, to give 489 mg of Compound 125 (yield: 55%).

NMR (270 MHz, CDCl$_3$) δ (ppm) 0.88 (t, 3H, J=6.4 Hz), 1.2–1.3 (m, 4H), 1.64 (quint., 2H, J=7.4Hz), 2.35 (t, 2H, J=7.4Hz), 5.29 (s, 2H), 6.49 (s, 1H), 6.84 (t, 1H, J=8.9 Hz), 7.5–7.6 (m, 2H)

EIMS (M/Z) 434 (M$^+$)

Molecular formula $C_{22}H_{21}F_3N_2O_4$=434

EXAMPLE 126

2-[4-(3-Aminopropylamino)-3-fluorophenyl]-5-butylamino-6,8-difluoro-4H-1-benzopyran-4-one (Compound 126)

(1) 1.01 g (2.35 mmol) of 2-[4-[N-acetyl-N-(3-azidopropyl) amino]-3-fluorophenyl]-5-amino-6,8-difluoro-4H-1-benzopyran- 4-one obtained in Example 79 was dissolved in 30 mL of dimethylformamide under argon atmosphere, 1.34 mL (11.8 mmol) of 1-iodobutane and 190 mg (4.75 mmol) of sodium hydride (60% oil dispersion) were added and the mixture was stirred at room temperature for 45 minutes. An aqueous solution of ammonium chloride was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (n-hexane:ethyl acetate=2:1) to give 726 mg of 2-[4-[N-acetyl-N-(3-azidopropyl)amino]-3-fluorophenyl]-5-butylamino-6,8-difluoro-4H-1-benzopyran-4-one (yield: 63%).

NMR (90 MHz, CDCl$_3$) δ (ppm) 0.96 (t, 3H, J=6.2 Hz), 1.3–2.0 (m, 6H), 1.90 (brs, 3H), 3.36 (t, 2H, J=6.6 Hz), 3.3–4.0 (m, 4H), 6.60 (s, 1H), 7.17 (dd, 1H, J=13.4, 10.1 Hz), 7.3–7.5 (m, 1H), 7.6–7.9 (m, 2H), 8.76 (m, 1H)

MS (M/Z) 487 (M$^+$)

Molecular formula $C_{24}H_{24}F_3N_5O_3$=487

(2) 693 mg (1.42 mmol) of the above 2-[4-[N-acetyl-N-(3-azidopropyl)amino]-3-fluorophenyl]-5-butylamino-6,8-difluoro-4H-1-benzopyran-4-one was dissolved in 20 mL of dioxane, 10 mL of concentrated hydrochloric acid was added and the mixture was heated at reflux for 3 hours. The reaction solution was cooled on ice and adjusted to pH 7 by addition of a 10N aqueous solution of sodium hydroxide thereto, and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (n-hexane:ethyl acetate=4:1) to give 470 mg of 2-[4-(3-azidoproylamino)-3-fluorophenyl]-5-butylamino-6,8-difluoro-4H-1-benzopyran-4-one (yield: 74%).

NMR (90 MHz, CDCl$_3$) δ (ppm) 0.9–1.1 (m, 3H), 1.2–1.9 (m, 4H), 1.94 (quint., 2H, J=6.5 Hz), 3.2–3.6 (m, 6H), 6.43 (s, 1H), 6.74 (t, 1H, J=9.0 Hz), 7.11 (dd, 1H, J=13.4, 10.3 Hz), 7.4–7.7 (m, 2H), 8.80 (m, 1H)

MS (M/Z) 445 (M$^+$)

Molecular formula $C_{22}H_{22}F_3N_5O_2$=445

(3) 438 mg (0.984 mmol) of the above 2-[4-(3-azidopropylamino)-3-fluorophenyl]-5-butylamino-6,8-difluoro-4H-1-benzopyran-4-one was dissolved in 25 mL of tetrahydrofuran, 389 mg (1.48mmol) of triphenylphosphine was added under ice-cooling and the mixture was stirred at room temperature for 1 hour. 25 mL of water was added thereto and the mixture was further stirred for 5.5 hours. The mixture was extracted twice with ethyl acetate, and the organic layer was washed once with an aqueous saturated solution of sodium chloride and dried over anhydrous sodium sulfate. The solvent was distilled off under reduced pressure and the residue was purified by silica gel column chromatography (chloroform:methanol:aqueous ammonia= 9:1:1) to give 380 mg of Compound 126 (yield: 92%), which was converted to hydrochloride according to the conventional method.

NMR (270 MHz, DMSO-d$_6$) δ (ppm) 0.91 (t, 3H, J=7.4 Hz), 1.37 (sextet, 2H, J=7.4 Hz), 1.53 (quint., 2H, J=7.4 Hz), 1.88 (quint., 2H, J=6.9 Hz), 2.8–3.0 (m, 2H), 3.2–3.6 (m, 4H), 6.75 (s, 1H), 6.90 (t, 1H, H=8.7 Hz), 7.6–7.8 (m, 2H)

MS (M/Z) 419 (M$^+$)

Molecular formula C$_{22}$H$_{24}$F$_3$N$_3$O$_2$=419

EXAMPLE 127

2-[4-(3-dimethylaminopropylamino)-3-fluorophenyl]-6,8-difluoro-5-pentylamino-4H-1-benzopyran-4-one (Compound 127)

(1) 6.31 g (14.9 mmol) of 2-[4-[N-acetyl-N-(3-chloropropyl) amino]-3-fluorophenyl]-5-amino-6,8-difluoro-4H-1-benzopyran-4-one obtained in Example 50 was dissolved in 240 mL of methyl ethyl ketone, 6.09 g (149 mmol) of sodium iodide was added and the mixture was heated at reflux for 4 hours. The reaction solution was cooled to room temperature and filtered. The solvent was distilled off under reduced pressure and the residue was purified by silica gel column chromatography (chloroform-chloroform:methanol=50:1) to give 7.17 g of 2-[4-[N-acetyl-N-(3-iodopropyl)amino]-3-fluorophenyl]-5-amino-6,8-difluoro-4H-1-benzopyran-4-one (yield: 93%).

NMR (90 MHz, CDCl$_3$) δ (ppm) 1.91 (brs, 3H), 2.09 (quint., 2H, J=7.0 Hz), 3.17 (t, 2H, J=7.0 Hz), 3.7–4.0 (m, 2H), 6.64 (s, 1H), 7.23 (t, 1H, J=10.5 Hz), 7.39 (t, 1H, J=8.1 Hz), 7.6–7.9 (m, 2H)

FAB-MS (M/Z) 517 (M$^+$+H)

Molecular formula C$_{20}$H$_{16}$F$_3$IN$_2$O$_3$=516

(2) 7.16 g (13.9 mmol) of the above 2-[4-[N-acetyl-N-(3-iodopropyl)amino]-3-fluorophenyl]-5-amino-6,8-difluoro-4H-1-benzopyran-4-one was dissolved in 150 mL of dimethylformamide under argon atmosphere, 5.68 g (69.5 mmol) of dimethylamine hydrochloride and 9.61 g (69.5 mmol) of potassium carbonate were added and the mixture was stirred at room temperature for 14 hours. Water was added to the reaction solution and the mixture was extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=20:1–6:1-chloroform:methanol:aqueous ammonia=9:1:1) to give 4.13 g of 2-[4-[N-acetyl-N-(3-dimethylaminopropyl)amino]-3-fluorophenyl]-5-amino-6,8-difluoro-4H-1-benzopyran-4-one (yield: 69%).

NMR (90 MHz, CDCl$_3$) δ (ppm) 1.6–2.0 (m, 2H), 1.91 (brs, 3H), 2.1–2.5 (m, 2H), 2.25 (s, 6H), 3.76 (t, 2H, J=7.0 Hz), 6.22 (brs, 2H), 6.64 (s, 1H), 7.23 (t, 1H, J=10.3 Hz), 7.41 (t, 1H, J=8.1 Hz), 7.6–7.9 (m, 2H)

MS (M/Z) 433 (M$^+$)

Molecular formula C$_{22}$H$_{22}$F$_3$N$_3$O$_3$=433

(3) 1.01 g (2.33 mmol) of the above 2-[4-[N-acetyl-N-(3-dimethylaminopropyl)amino]-3-fluorophenyl]-5-amino-6,8-difluoro-4H-1-benzopyran-4-one was dissolved in 20 mL of dimethylformamide under argon atmosphere, 190 mg (4.75 mmol) of sodium hydride (60% oil dispersion) and 0.61 mL (4.7 mmol) of 1-iodopentane were added under ice-cooling and the mixture was stirred at room temperature for 50 minutes. Water was added to the reaction solution and the mixture was extracted twice with ethyl acetate. The organic layer was washed once with an aqueous saturated solution of sodium chloride and dried over anhydrous sodium sulfate. The solvent was distilled off under reduced pressure and the residue was purified by silica gel column chromatography (chloroform:methanol=20:1–9:1) to give 759 mg of 2-[4-[N-acetyl-N-(3-dimethylaminopropyl)amino]-3-fluorophenyl]-6,8-difluoro-5-pentylamino-4H-1-benzopyran-4-one (yield: 65%).

NMR (90 MHz, CDCl$_3$) δ (ppm) 0.9–1.1 (m, 3H), 1.3–2.0 (m, 8H), 1.90 (brs, 3H), 2.20 (s, 6H), 2.2–2.5 (m, 2H), 3.3–3.7 (m, 2H), 3.68 (t, 2H, J=7.5 Hz), 6.60 (s, 1H), 7.16 (dd, 1H, J=13.4, 10.3 Hz), 7.39 (t, 1H, J=7.9 Hz), 7.6–7.9 (m, 2H), 8.7–8.9 (m, 1H)

FAB-MS (M/Z) 504 (M$^+$+H)

Molecular formula C$_{27}$H$_{32}$F$_3$N$_3$O$_3$=503

(4) 10 mL of concentrated sulfuric acid was added to 725 mg (1.44 mmol) of the above 2-[4-[N-acetyl-N-(3-dimethylaminopropyl)amino]-3-fluorophenyl]-6,8-difluoro-5-pentylamino-4H-1-benzopyran-4-one and the mixture was stirred at 80° C. for 20 minutes. The reaction solution was poured into ice water, the mixture was adjusted to pH 7 by addition of a 10N aqueous solution of sodium hydroxide thereto, and the precipitated crystals were collected by filtration. The crystals were purified by silica gel column chromatography (chloroform:methanol=20:1–9:1) and recrystallized from ethyl acetate/n-hexane to give 473 mg of Compound 127 (yield: 71%), which was converted to hydrochloride according to the conventional method.

NMR (270 MHz, DMSO-d$_6$) δ (ppm) 0.87 (t, 3H, J=6.9 Hz), 1.2–1.4 (m, 4H), 1.5–1.6, (m, 2H), 1.9–2.1 (m, 2H), 2.74 (s, 6H), 3.1–3.2 (m, 2H), 3.3–3.4 (m, 2H), 6.5–6.6 (m, 1H), 6.77 (s, 1H), 6.91 (t, 1H, J=8.9 Hz), 7.6–7.8 (m, 3H), 8.8–8.9 (m, 1H), 10.3 (brs, 1H)

FAB-MS (M/Z) 462 (M$^+$+H)

Molecular formula C$_{25}$H$_{30}$F$_3$N$_3$O$_2$=461

EXAMPLE 128

2-[4-(3-Dimethylaminopropylamino)-3-fluorophenyl]-6,8-difluoro-5-(4-methylpentylamino)-4H-1-benzopyran-4-one (Compound 128)

(1) 1.01 g (2.33 mmol) of 2-[4-[N-acetyl-N-(3-dimethylaminopropyl) amino]-3-fluorophenyl]-5-amino-6,8-difluoro-4H-1-benzopyran-4-one obtained in Example 127 (2) was dissolved in 20 mL of dimethylformamide under argon atmosphere, 190 mg (4.75 mmol) of sodium hydride (60% oil dispersion) and 0.66 mL (4.7 mmol) of 1-bromo-4-methylpentane were added under ice-cooling and the mixture was stirred at room temperature for 1 hour. Water was added to the reaction solution and mixture was extracted twice with ethyl acetate. The organic layer was washed once with an aqueous saturated solution of sodium chloride and dried over anhydrous sodium sulfate. The solvent was distilled off under reduced pressure and the residue was purified by silica gel column chromatography (chloroform:methanol=20:1–9:1) to give 595 mg of 2-[4-[N-acetyl-N-(3-dimethylaminopropyl)amino]-3-fluorophenyl]-6,8-difluoro-5-(4-methylpentylamino)-4H-1-benzopyran-4-one (yield: 49%).

NMR (90 MHz, CDCl$_3$) δ (ppm) 0.90 (d, 6H, J=6.2 Hz), 1.2–2.0 (m, 7H), 1.91 (brs, 3H), 2.22 (s, 6H), 2.36 (t, 2H, J=7.3 Hz), 3.3–3.6 (m, 2H), 3.76 (t, 2H, J=7.3 Hz), 6.60 (s, 1H), 7.17 (dd, 1H, J=13.4, 10.3 Hz), 7.40 (t, 1H, J=8.2 Hz), 7.6–7.8 (m, 2H), 8.6–8.9 (m, 1H)

FAB-MS (M/Z) 518 (M$^+$+H)

Molecular formula C$_{28}$H$_{34}$F$_3$N$_3$O$_3$=517

(2) Substantially the same manner as that in Example 127 (4) was repeated except that 575 mg (1.11 mmol) of the above 2-[4-[N-acetyl-N-(3-dimethylaminopropyl)amino]-3-fluorophenyl]-6,8-difluoro-5-(4-methylpentylamino)-4H-1-benzopyran-4-one was used, to give 347 mg of Compound 128 (yield: 66%).

NMR (270 MHz, CDCl$_3$) δ (ppm) 0.89 (d, 6H, J=6.9 Hz), 1.2–1.4 (m, 2H), 1.5–1.9 (m, 5H), 1.85 (quint., 2H, J=6.4 Hz), 2.29 (s, 6H), 2.47 (t, 2H, J=6.4 Hz), 3.3–3.4 (m, 2H), 3.4–3.5 (m, 2H), 5.6–5.7 (m, 1H), 6.43 (s, 1H), 6.71 (t, 1H, J=8.4 Hz), 7.11 (dd, 1H, J=13.4, 10.3 Hz), 7.50 (dd, 1H, J=12.9, 2.0 Hz), 7.59 (dd, 1H, J=8.4, 2.0 Hz), 8.8–8.9 (m, 1H)

FAB-MS (M/Z) 476 (M$^+$+H)

Molecular formula C$_{26}$H$_{32}$F$_3$N$_3$O$_2$=475

EXAMPLE 129

2-(4-Amino-3-fluorophenyl)-6,8-difluoro-5-[3-(imidazol-1-yl)propylamino]-4H-1-benzopyran-4-one (Compound 129)

6.02 g (15.4 mmol) of 5-amino-6,8-difluoro-2-(3-fluoro-4-pivaloylaminophenyl)-4H-1-benzopyran-4-one obtained in Example 66 was dissolved in 120 mL of dimethylformamide under argon atmosphere, 8.34 g (30.8 mmol) of 2-(3-iodopropyloxy)tetrahydropyran and 1.86 g (46.5 mmol) of sodium hydride (60% oil dispersion) were added under ice-cooling and the mixture was stirred at room temperature for 1.2 hours. Water was added to the reaction solution and the mixture was extracted twice with ethyl acetate. The organic layer was washed once with water and once with an aqueous saturated solution of sodium chloride and dried over anhydrous sodium sulfate, and the solvent was distilled off under reduced pressure. The residue was dissolved in 150 mL of ethanol, 720 mg (3.10 mmol) of dl-camphorsulfonic acid and 10 mL of water were added and the mixture was stirred at 50° C. for 2 hours. The solvent was distilled off under reduced pressure, the residue was dissolved in chloroform, and the solution was washed once with an aqueous saturated solution of sodium chloride and dried over anhydrous sodium sulfate. The solvent was distilled off under reduced pressure and the residue was purified by silica gel column chromatography (chloroform:acetonitrile=4:1–3:1) to give 4.85 g of 6,8-difluoro-2-(3-fluoro-4-pivaloylaminophenyl)-5-(3-hydroxypropylamino)-4H-1-benzopyran-4-one (yield: 70%).

NMR (90 MHz, CDCl$_3$) δ (ppm) 1.36 (s, 9H), 1.92 (quint., 2H, J=6.6 Hz), 3.4–3.7 (m, 2H), 3.81 (t, 2H, J=6.2 Hz), 6.56 (s, 1H), 7.16 (dd, 1H, J=13.8, 10.3 Hz), 7.5–7.8 (m, 3H), 8.58 (t, 1H, J=8.6 Hz)

MS (M/Z) 448 (M$^+$)

Molecular formula C$_{23}$H$_{23}$F$_3$N$_2$O$_4$=448

(2) 2.98 g (6.65 mmol) of the above 6,8-difluoro-2-(3-fluoro-4-pivaloylaminophenyl)-5-(3-hydroxypropylamino)-4H-1-benzopyran-4-one was dissolved in 100 mL of pyridine, 1.1 mL (14 mmol) of methanesulfonyl chloride was added under ice-cooling and the mixture was stirred for 50 minutes. Water was added to the reaction solution and the precipitated crystals were collected by filtration to give 3.46 g of 6,8-difluoro-2-(3-fluoro-4-pivaloylaminophenyl)-5-(3-methanesulfonyloxypropylamino)-4H-1-benzopyran-4-one (yield: 99%).

NMR (90 MHz, CDCl$_3$) δ (ppm) 1.36 (s, 9H), 2.08 (quint., 2H, J=6.2 Hz), 3.04 (s, 3H), 3.5–3.7 (m, 2H), 4.36 (t, 2H, J=6.0 Hz), 6.57 (s, 1H), 7.17 (dd, 1H, J=13.4, 10.1 Hz), 7.5–7.8 (m, 3H), 8.58 (t, 1H, J=8.4 Hz)

FAB-MS (M/Z) 527 (M$^+$+H)

Molecular formula C$_{24}$H$_{25}$F$_3$N$_2$O$_6$S=526

(3) 719 mg (1.37 mmol) of the above 6,8-difluoro-2-(3-fluoro-4-pivaloylaminophenyl)-5-(3-methanesulfonyloxypropylamino)-4H-1-benzopyran-4-one was dissolved in 30 mL of dimethylformamide under argon atmosphere, 932 mg (13.7 mmol) of imidazole and 657 mg (16.4 mmol) of sodium hydride (60% oil dispersion) were added and the mixture was stirred for 4.5 hours. Water was added to the reaction solution and the mixture was extracted once with ethyl acetate. The organic layer was washed with an aqueous saturated solution of sodium chloride and dried over anhydrous sodium sulfate. The solvent was distilled off under reduced pressure and the residue was purified by silica gel column chromatography (chloroform:methanol=100:1) to give 600 mg of 6,8-difluoro-2-(3-fluoro-4-pivaloylaminophenyl)-5-[3-(imidazol-1-yl)propylamino]-4H-1-benzopyran-4-one (yield: 88%).

NMR (90 MHz, CDCl$_3$) δ (ppm) 1.36 (s, 9H), 2.11 (quint., 2H, J=6.4 Hz), 3.3–3.6 (m, 2H), 4.11 (t, 2H, J=6.8 Hz), 6.59 (s, 1H), 6.95 (s, 1H), 7.08 (s, 1H), 7.17 (dd, 1H, J=13.4, 10.3 Hz), 7.54 (s, 1H), 7.6–7.8 (m, 3H), 8.59 3H, J=8.4 Hz), 8.8–9.0 (m, 1H)

MS (M/Z) 498 (M$^+$)

Molecular formula C$_{26}$H$_{25}$F$_3$N$_4$O$_3$=498

(4) Substantially the same manner as that in Example 127 (4) was repeated except that 600 mg (1.21 mmol) of the above 6,8-difluoro-2-(3-fluoro-4-pivaloylaminophenyl)-5-[3-(imidazol-1-yl)propylamino]-4H-1-benzopyran-4-one was used, treatment with 20 mL of concentrated sulfuric acid was carried out and the resulting compound was recrystallized from methanol, to give 341 mg of Compound 129 (yield: 68%).

NMR (270 MHz, DMSO-d$_6$) 1.99 (quint., 2H, J=6.9 Hz), 3.3–3.4 (m, 2H), 4.04 (t, 2H, J=6.9 Hz), 6.13 (brs, 2H), 6.76 (s, 1H), 6.88 (t, 1H, J=8.7 Hz), 7.17 (s, 1H), 7.5–7.8 (m, 2H), 7.60 (s, 1H), 7.72 (dd, 1H, J=13.9, 10.4 Hz), 8.8–8.9 (m, 1H)

MS (M/Z) 414 (M$^+$)

Molecular formula C$_{21}$H$_{17}$F$_3$N$_4$O$_2$=414

EXAMPLE 130

2-(4-Amino-3-fluorophenyl)-5-(3-dimethylaminopropylamino)-6,8-difluoro-4H-1-benzopyran-4-one (Compound 130)

(1) 709 mg (1.35mmol) of 6,8-difluoro-2-(3-fluoro-4-pivaloylaminophenyl)-5-(3-methanesulfonyloxypropylamino)-4H-1-benzopyran- 4-one obtained in Example 129 (2) was dissolved in 30 mL of dimethylformamide under argon atmosphere, 1.10 g (13.5 mmol) of dimethylamine hydrochloride and 1.86 g (13.5 mmol) of potassium carbonate were added and the mixture was stirred at 50° C. for 39 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=100:1) to give 444 mg of 5-(3-dimethylaminopropylamino)-6,8-difluoro-2-(3-fluoro-4-pivaloylaminophenyl)-4H-1-benzopyran-4-one (yield: 69%).

NMR (90 MHz, CDCl$_3$) δ (ppm) 1.36 (s, 9H), 1.81 (quint., 2H, J=7.5 Hz), 2.26 (s, 6H), 2.42 (t, 2H, J=7.1 Hz), 3.4–3.7 (m, 2H), 6.55 (s, 1H), 7.14 (dd, 1H, J=13.4, 10.3 Hz), 7.5–7.8 (m, 3H), 8.57 (t, 1H, J=8.4 Hz), 8.7–8.9 (m, 1H)

MS (M/Z) 475 (M$^+$)

Molecular formula $C_{25}H_{28}F_3N_3O_3$=475

(2) Substantially the same manner as that in Example 127 (4) was repeated except that 444 mg (0.935 mmol) of the above 5-(3-dimethylaminopropylamino)-6,8-difluoro-2-(3-fluoro-4-pivaloylaminophenyl)-4H-1-benzopyran-4-one was used, and the resulting compound was recrystallized from ethanol/n-hexane, to give 321 mg of Compound 130 (yield: 88%).

NMR (270 MHz, DMSO-d$_6$) δ (ppm) 1.65 (quint., 2H, J=6.9 Hz), 2.11 (s, 6H), 2.26 (t, 2H, J=7.2 Hz), 3.3–3.5 (m, 2H), 6.12 (brs, 2H), 6.72 (s, 1H), 6.86 (t, 1H, 8.9 Hz), 7.5–7.8 (m, 3H), 8.8–8.9 (m, 1H)

MS (M/Z) 391 (M$^+$)

Molecular formula $C_{20}H_{20}F_3N_3O_2$=391

EXAMPLE 131

2-(4-Amino-3-fluorophenyl)-5-(3-diethylaminopropylamino)-6,8-difluoro-4H-1-benzopyran-4-one (Compound 131)

(1) 3.50 g (6.65 mmol) of 6,8-difluoro-2-(3-fluoro-4-pivaloylaminophenyl)-5-(3-methanesulfonyloxypropylamino)-4H-1-benzopyran-4-one obtained in Example 129 (2) was dissolved in 100 mL of dimethylformamide under argon atmosphere, 6.88 mL (66.5 mmol) of diethylamine and 9.18 g (66.5 mmol) of potassium carbonate were added and the mixture was stirred at 50° C. for 7 hours. Then, 6.88 mL (66.5 mmol) of diethylamine and 9.18 g (66.5 mmol) of potassium carbonate were further added and the mixture was stirred at 50° C. for 16 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=100:1–9:1) to give 1.68 g of 5-(3-diethylaminopropylamino)-6,8-difluoro-2-(3-fluoro-4-pivaloylaminophenyl)- 4H-1-benzopyran-4-one (yield: 50%).

NMR (90 MHz, CDCl$_3$) δ (ppm) 1.10 (t, 6H, J=7.0 Hz), 1.35 (s, 9H), 1.7–2.1 (m, 2H), 2.65 (q, 4H, J=7.0 Hz), 2.70 (t, H, J=7.0 Hz), 3.4–3.7 (m, 2H), 6.55 (s, 1H), 7.15 (dd, 1H, J=13.4, 10.3 Hz), 7.5–7.8 (m, 3H), 8.57 (t, 1H, J=8.1 Hz), 8.6–8.9 (m,

MS (M/Z) 503 (M$^+$)

Molecular formula $C_{27}H_{32}F_3N_3O_3$=503

(2) Substantially the same manner as that in Example 127 (4) was repeated except that 1.68 g (3.33 mmol) of the above5-(3-diethylaminopropylamino)-6,8-difluoro-2-(3-fluoro-4-pivaloylaminophenyl)-4H-1-benzopyran-4-one was used, treatment with 20 mL of concentrated sulfuric acid was carried out and the resulting compound was recrystallized from ethanol/n-hexane, to give 943 mg of Compound 131 (yield: 68%).

NMR (270 MHz, CDCl$_3$) δ (ppm) 1.04 (t, 6H, J=7.2 Hz), 1.80 (quint., 2H, J=7.2 Hz), 2.56 (q, 4H, J=7.2 Hz), 2.57 (t, H, J=7.2 Hz), 3.4–3.6 (m, 2H), 4.18 (brs, 2H), 6.46 (s, 1H), 6.83 (t, 1H, J=8.9 Hz), 7.13 (dd, 1H, J=13.4, 10.4 Hz), 7.5–7.6 (m, 2H), 8.8–8.9 (m, 1H)

MS (M/Z) 419 (M$^+$)

Molecular formula $C_{22}H_{24}F_3N_3O_2$=419

EXAMPLE 132

2-(4-Amino-3-fluorophenyl)-6,8-difluoro-5-[3-(pyrrolidin-1-yl)propylamino]-4H-1-benzopyran-4-one (Compound 132)

(1) 709 mg (1.35 mmol) of 6,8-difluoro-2-(3-fluoro-4-pivaloylaminophenyl)-5-(3-methanesulfonyloxypropylamino)-4H-1-benzopyran-4-one obtained in Example 129 (2) was dissolved in 30 mL of dimethylformamide under argon atmosphere, 1.14 mL (13.5 mmol) of pyrrolidine and 1.86 g (13.5 mmol) of potassium carbonate were added and the mixture was stirred at 50° C. for 8 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=100:9:1) to give 431 mg of 6,8-difluoro-2-(3-fluoro-4-pivaloylaminophenyl)-5-[3-(pyrrolidin-1-yl)propylamino]-4H-1-benzopyran-4-one (yield: 64%).

NMR (90 MHz, CDCl$_3$) δ (ppm) 1.36 (s, 9H), 1.6–2.1 (m, 6H), 2.5–2.8 (m, 6H), 3.4–3.7 (m, 2H), 6.55 (s, 1H), 7.14 (dd, 1H, J=13.2, 10.3 Hz), 7.5–7.8 (m, 3H), 8.57 (t, 1H, J=8.4 Hz), 8.6–8.9 (m, 1H)

MS (M/Z) 501 (M$^+$)

Molecular formula $C_{27}H_{30}F_3N_3O_3$=501

(2) Substantially the same manner as that in Example 127 (4) was repeated except that 402 mg (0.802 mmol) of the above 6,8-difluoro-2-(3-fluoro-4-pivaloylaminophenyl)-5-[3-(pyrrolidin-1-yl)propylamino]-4H-1-benzopyran-4-one was used, and the resulting compound was recrystallized from ethanol/n-hexane, to give 213 mg of Compound 132 (yield: 64%).

NMR (270 MHz, CDCl$_3$) δ (ppm) 1.7–2.0 (m, 6H), 2.5–2.6 (m, 6H), 3.4–3.6 (m, 2H), 4.18 (brs, 2H), 6.45 (s, 1H), 6.83 (t, 1H, J=8.7 Hz), 7.12 (dd, 1H, J=13.4, 10.4 Hz), 7.4–7.6 (m, 2H), 8.8–8.9 (m, 1H)

MS (M/Z) 417 (M$^+$)

Molecular formula $C_{22}H_{22}F_3N_3O_2$=419

EXAMPLE 133

2-(4-Amino-3-fluorophenyl)-6,8-difluoro-5-[3-(4-methylpiperazin-1-yl)propylamino]-4H-1-benzopyran-4-one (Compound 133)

(1) 612 mg (1.16mmol) of 6,8-difluoro-2-(3-fluoro-4-pivaloylaminophenyl)-5-(3-methanesulfonyloxypropylamino)-4H-1-benzopyran-4-one obtained in Example 129 (2) was dissolved in 30 mL of dimethylformamide under argon atmosphere, 1.30 mL (11.6 mmol) of 1-methylpiperazine was added and the mixture was stirred at 50° C. for 6.6 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol= 100:1–10:1) to give 493 mg of 6,8-difluoro-2-(3-fluoro-4-pivaloylaminophenyl)-5-[3-(4-methylpiperazin-1-yl)propylamino]-4H-1-benzopyran-4-one (yield: 80%).

NMR (90 MHz, CDCl$_3$) δ (ppm) 1.36 (s, 9H), 1.7–2.1 (m, H), 2.29 (s, 3H), 2.3–2.6 (m, 10H), 3.3–3.6 (m, 2H), 6.54 (s, 1H), 7.14 (dd, 1H, J=13.6, 10.3 Hz), 7.5–7.8 (m, 3H), 8.57 (t, 1H, J=8.1 Hz), 8.6–8.9 (m, 1H)

FAB-MS (M/Z) 531 (M$^{+\!+\!H}$)

Molecular formula $C_{28}H_{33}F_3N_4O_3$=530

(2) Substantially the same manner as that in Example 127 (4) was repeated except that 463 mg (0.874 mmol) of the above 6,8-difluoro-2-(3-fluoro-4-pivaloylaminophenyl)-5-[3-(4-methylpiperazin- 1-yl)propylamino]-4H-1-benzopyran-4-one was used, and the resulting compound was recrystallized from ethyl acetate/n-hexane, to give 322 mg of Compound 133 (yield: 83%).

NMR (270 MHz, CDCl$_3$) δ (ppm) 1.81 (quint., 2H, J=6.9 Hz), 2.32 (s, 3H), 2.4–2.6 (m, 8H), 2.47 (t, 2H, J=6.9 Hz), 3.4–3.6 (m, 2H), 4.18 (brs, 2H), 6.44 (s, 1H), 6.83 (t, 1H, J=8.7 Hz), 7.12 (dd, 1H, J=13.6, 10.1 Hz), 7.4–7.6 (m, 2H), 8.8–8.9 (m, 1H)

FAB-MS (M/Z) 447 (M$^+$+H)

Molecular formula $C_{23}H_{25}F_3N_4O_2$=446

EXAMPLE 134

2-(4-Amino-3-fluorophenyl)-6,8-difluoro-5-(3-morpholinopropylamino)-4H-1-benzopyran-4-one (Compound 134)

(1) 607 mg (1.16 mmol) of 6,8-difluoro-2-(3-fluoro-4-pivaloylaminophenyl)-5-(3-methanesulfonyloxypropylamino)-4H-1-benzopyran-4-one obtained in Example 129 (2) was dissolved in 30 mL of dimethylformamide under argon atmosphere, 1.00 mL (11.6 mmol) of morpholine was added and the mixture was stirred at 50° C. for 22 hours. Water was added to the reaction solution and the mixture was extracted twice with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:methanol=100:1) to give 523 mg of 6,8-difluoro-2-(3-fluoro-4-pivaloylaminophenyl)-5-(3-morpholinopropylamino)-4H-1-benzopyran-4-one (yield: 88%).

NMR (90 MHz, CDCl$_3$) δ (ppm) 1.35 (s, 9H), 1.7–2.0 (m, 2H), 2.3–2.6 (m, 2H), 3.3–3.8 (m, 4H), 6.55 (s, 1H), 7.14 (dd, 1H, J=13.6, 10.3 Hz), 7.5–7.8 (m, 3H), 8.58 (t, 1H, J=8.4 Hz), 8.6–8.9 (m, 1H)

MS (M/z) 517 (M$^+$)

Molecular formula $C_{27}H_{30}F_3N_3O_4$=517

(2) Substantially the same manner as that in Example 127 (4) was repeated except that 457 mg (0.883 mmol) of the above 6,8-difluoro-2-(3-fluoro-4-pivaloylaminophenyl)-5-(3-morpholinopropylamino)-4H-1-benzopyran-4-one was used, and the resulting compound was recrystallized from ethyl acetate/n-hexane, to give 334 mg of Compound 134 (yield: 87%).]

NMR (270 MHz, CDCl$_3$) δ (pm) 1.8–2.0 (m, 2H), 2.51 (brs, 6H), 3.4–3.6 (m, 2H), 3.75 (brs, 4H), 4.18 (brs, 2H), 6.45 (s, 1H), 6.83 (t, 1H, J=8.9 Hz), 7.13 (dd, 1H, J=13.4, 9.9 Hz), 7.4–7.6 (m, 2H), 8.8–8,9 (m, 1H)

FAB-MS (M/Z) 434 (M$^+$+H)

Molecular formula $C_{22}H_{22}F_3N_3O_3$=433

EXAMPLE 135

2-(4-Amino-3-fluorophenyl)-6,8-difluoro-5-(4-dimethylaminobutylamino)-4H-1-benzopyran-4-one (Compound 135)

(1) 1.52 g (3.90 mmol) of 5-amino-6,8-difluoro-2-(3-fluoro-4-pivaloylaminophenyl)-4H-1-benzopyran-4-one obtained in Example 66 was dissolved in 30 mL of dimethylformamide under argon atmosphere, 2.25 mL (19.5 mmol) of 1-bromo-4-chlorobutane and 470 mg (11.8 mmol) of sodium hydride (60% oil dispersion) were added under ice-cooling and the mixture was stirred at room temperature for 1.3 hours. The reaction solution was cooled on ice, water was added and the mixture was extracted three times with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:ethyl acetate=100:1) to give 1.06 g of 5-(4-chlorobutylamino)-6,8-difluoro-2-(3-fluoro-4-pivaloylaminophenyl)-4H-1-benzopyran-4-one (yield: 57%).

NMR (90 MHz, CDCl$_3$) δ (ppm) 1.36 (s, 9H), 1.7–2.0 (m, 4H), 3.4–3.7 (m, 4H), 6.56 (s, 1H), 7.16 (dd, 1H, J=13.4, 10.3 Hz), 7.5–7.8 (m, 3H), 8.58 (t, 1H, J=8.4 Hz)

FAB-MS (M/Z) 481 (M$^+$+H)

Molecular formula $C_{24}H_{24}ClF_3N_2O_3$=480

(2) 489 mg (1.02 mmol) of the above 5-(4-chlorobutylamino)-6,8-difluoro-2-(3-fluoro-4-pivaloylaminophenyl)-4H-1-benzopyran-4-one was dissolved in 20 mL of dimethylformamide under argon atmosphere, 332 mg (5.10 mmol) of sodium azide was added and the mixture was stirred at 70° C. for 10 hours. Water was added to the reaction solution and the precipitated crystals were collected by filtration to give 332 mg of 5-(4-azidobutylamino)-6,8-difluoro-2-(3-fluoro-4-pivaloylaminophenyl)-4H-1-benzopyran-4-one (yield: 67%).

IR (KBr) ν (cm$^{-1}$) 2092

NMR (90 MHz, CDCl$_3$) δ (ppm) 1.36 (s, 9H), 1.5–1.8 (m, 4H), 3.2–3.6 (m, 4H), 6.55 (s, 1H), 7.15 (dd, 1H, J=13.4, 10.3 Hz), 7.5–7.8 (m, 3H), 8.58 (t, 1H, J=8.4 Hz), 8.6–8.9 (m, 1H)

MS (M/Z) 487 (M$^+$)

Molecular formula $C_{24}H_{24}F_3N_5O_3$=487

(3) 332 mg (0.682 mmol) of the above 5-(4-azidobutylamino)-6, 8-difluoro-2-(3-fluoro-4-pivaloylaminophenyl)-4H-1-benzopyran-4-one was dissolved in 20 mL of tetrahydrofuran, 272 mg (1.02 mmol) of triphenylphosphine and 20 mL of water were added and the mixture was stirred at room temperature for 22 hours. Ethyl acetate was added to the reaction solution, and the organic layer was separated, washed with an aqueous saturated solution of sodium chloride and dried over anhydrous sodium sulfate. The solvent was distilled off under reduced pressure and the residue was purified by silica gel column chromatography (chloroform:methanol=20:1-chloroform:methanol:aqueous ammonia=9:1:1) to give 260 mg of 5-(4-aminobutylamino)-6,8-difluoro-2-(3-fluoro-4-pivaloylaminophenyl)-4H-1-benzopyran-4-one (yield: 83%).

NMR (90 MHz, CDCl$_3$) δ (ppm) 1.35 (s, 9H), 1.6–2.2 (m, 6H), 3.1–3.7 (m, 4H), 6.53 (s, 1H), 7.14 (dd, 1H, J=13.4, 10.3 Hz), 7.5–7.8 (m, 3H), 8.57 (t, 1H, J=8.4 Hz), 8.6–8.9 (m, 1H)

MS (M/Z) 461 (M$^+$)

Molecular formula $C_{24}H_{26}F_3N_3O_3$=461

(4) 190 mg (0.412 mmol) of the above 5-(4-aminobutylamino)-6,8-difluoro-2-(3-fluoro-4-pivaloylaminophenyl)-4H-1-benzopyran-4-one was dissolved in 10 mL of methanol, 0.23 mL (8.2 mmol) of a 37% aqueous solution of formaldehyde, 259 mg (4.12 mmol) of sodium cyanoborohydride and a solution of 0.24 mL (4.1 mmol) of acetic acid in 0.48 mL of methanol were added and the mixture was stirred at room temperature for 24 hours. Ethyl acetate was added to the reaction solution, and the organic layer was separated, washed twice with a 1N aqueous solution of sodium hydroxide and twice with an aqueous saturated solution of sodium chloride, and dried over anhydrous sodium sulfate. The solvent was distilled off under reduced pressure and the residue was purified by high performance liquid chromatography (column: YMC SH-365-15 S-15, acetonitrile: a 0.1M aqueous solution of ammonium acetate= 7:3, 40 mL/min.) to give 116 mg of 5-(4-dimethylaminobutylamino)-6,8-difluoro-2-(3-fluoro-4-pivaloylaminophenyl)-4H-1-benzopyran-4-one (yield: 57%).

NMR (90 MHz, CDCl$_3$) δ (ppm) 1.36 (s, 9H), 1.5–1.8 (m, 4H), 2.1–2.3 (m, 2H), 2.23 (s, 6H), 3.3–3.6 (m, 2H), 6.54 (s, 1H), 7.14 (dd, 1H, J=13.4, 10.3 Hz), 7.5–7.8 (m, 3H), 8.57 (t, 1H, J=8.4 Hz), 8.6–8.9 (m, 1H)

MS (M/Z) 489 (M$^+$)

Molecular formula $C_{26}H_{30}F_3N_3O_3$=489

(5) Substantially the same manner as that in Example 127 (4) was repeated except that 116 mg (0.237 mmol) of the above 5-(4-dimethylaminobutylamino)-6,8-difluoro-2-(3-fluoro-4-pivaloylaminophenyl)-4H-1-benzopyran-4-one was used, and the resulting compound was purified by preparative thin layer chromatography (chloroform:methanol:aqueous ammonia=9:1:1), to give 86.1 mg of Compound 135 (yield: 90%).

NMR (270 MHz, CDCl$_3$) δ (ppm) 1.5–1.9 (m, 4H), 2.25 (s, 6H), 2.33 (t, 2H, J=6.9 Hz), 3.4–3.6 (m, 2H), 4.17 (brs, 2H), 6.44 (s, 1H), 6.83 (t, 1H, J=8.9 Hz), 7.12 (dd, 1H, J=13.4, 10.4 Hz), 7.5–7.6 (m, 2H), 8.8–8.9 (m, 1H)

Ms (M/z) 405 (M$^+$)

Molecular formula $C_{21}H_{22}F_3N_3O_2$=405

EXAMPLE 136

2-(4-Amino-3-fluorophenyl)-6,8-difluoro-5-(5-methylhexylamino)-4H-1-benzopyran-4-one (Compound 136)

(1) 853 mg (2.19mmol) of 5-amino-6,8-difluoro-2-(3-fluoro-4-pivaloylaminophenyl)-4H-1-1-benzopyran-4-one obtained in Example 66 was dissolved in 20 mL of dimethylformamide under argon atmosphere, 788 mg (4.38 mmol) of 1-bromo-5-methylhexane and 266 mg (6.65mmol) of sodium hydride (60% oil dispersion) were added under ice-cooling and the mixture was stirred at room temperature for 5.5 hours. The reaction solution was cooled on ice, water was added and the mixture was extracted with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform: n-hexane=3:1) to give 762 mg of 6,8-difluoro-2-(3-fluoro-4-pivaloylaminophenyl)-5-(5-methylhexylamino)-4H-1-benzopyran-4-one (yield: 71%).

NMR (90 MHz, CDCl$_3$) δ (ppm) 0.87 (d, 6H, J=5.9 Hz), 1.1–1.8 (m, 7H), 1.36 (s, 9H), 3.3–3.6 (m, 2H), 6.58 (s, 1H), 7.14 (dd, 1H, J=13.4, 10.3 Hz), 7.5–7.8 (m, 3H), 8.59 (t, 1H, J=8.4 Hz)

MS (M/Z) 488 (M$^+$)

Molecular formula $C_{27}H_{31}F_3N_2O_2$=488

(2) Substantially the same manner as that in Example 127 (4) was repeated except that 743 mg (1.52 mmol) of the above 6,8-difluoro-2-(3-fluoro-4-pivaloylaminophenyl)-5-(5-methylhexylamino)-4H-1-benzopyran-4-one was used, and the resulting compound was recrystallized from 2-propanol, to give 177 mg of Compound 136 (yield: 29%).

NMR (270 MHz, CDCl$_3$) δ (ppm) 0.87 (d, 6H, J=6.4 Hz), 1.1–1.7 (m, 7H), 3.4–3.5 (m, 2H), 6.46 (s, 1H), 6.83 (t, 1H, J=8.7 Hz), 7.13 (dd, 1H, J=13.4, 10.4 Hz), 7.4–7.6 (m, 2H)

MS (M/Z) 404 (M$^+$)

Molecular formula $C_{22}H_{23}F_3N_2O_2$=404

EXAMPLE 137

2-(4-Amino-3-fluorophenyl)-6,8-difluoro-5-(4-methyl-3-pentenylamino)-4H-1-benzopyran-4-one (Compound 137)

(1) 2.41 g (5.94 mmol) of Compound 51 obtained in Example 51 was dissolved in 60 mL of dimethylformamide under argon atmosphere, 237 mg (5.94 mmol) of sodium hydride (60% oil dispersion) and 0.47 mL (6.24mmol) of chloromethyl methyl ether were added under ice-cooling and the mixture was stirred at room temperature for 40 minutes. The reaction solution was cooled on ice, water was added and the mixture was extracted with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:acetonitrile=30:1) to give 2.47 g of 5-amino-2-[4-[N-(tert-butoxycarbonyl)-N-methoxymethylamino]-3-fluorophenyl]- 6,8-difluoro-4H-1-benzopyran-4-one (yield: 92%).

NMR (90 MHz, CDCl$_3$) δ (ppm) 1.45 (s, 9H), 3.44 (s, 3H), 5.00 (s, 2H), 6.61 (s, 1H), 7.20 (dd, 1H, J=10.8, 0.1 Hz), 7.45 (t, 1H, J=7.5 Hz), 7.5–7.7 (m, 2H)

FAB-MS (M/Z) 451 (M$^+$+H)

Molecular formula $C_{22}H_{21}F_3N_2O_5$=450

(2) 2.70 g (6.00 mmol) of the above 5-amino-2-[4-[N-(tert-butoxycarbonyl)-N-methoxymethylamino]-3-fluorophenyl]-6,8-difluoro-4H-1-benzopyran-4-one was dissolved in 60 mL of dimethylformamide under argon atmosphere, 480 mg (12.0 mmol) of sodium hydride (60% oil dispersion) and 4.0 mL (30 mmol) of 5-bromo-2-methyl-2-pentene were added under ice-cooling and the mixture was stirred at room temperature for 18 hours. The reaction solution was cooled on ice, water was added and the mixture was extracted twice with ethyl acetate. The organic layer was washed twice with water and once with an aqueous saturated solution of sodium chloride and dried over anhydrous sodium sulfate. The solvent was distilled off under reduced pressure and the residue was purified by silica gel column chromatography (chloroform:acetonitrile=30:1) to give 1.21 g of 2-[4-[N-(tert-butoxycarbonyl)-N-methoxymethylamino]-3-fluorophenyl]-6,8-difluoro-5-(4-methyl-3-pentenylamino)-4H-1-benzopyran-4-one (yield: 38%).

NMR (90 MHz, CDCl$_3$) δ (ppm) 1.44 (s, 9H), 1.63 (s, 3H), 1.71 (s, 3H), 2.1–2.4 (m, 2H), 3.3–3.6 (m, 2H), 3.44 (s, 3H), 5.00 (s, 2H), 5.0–5.3 (m, 1H), 6.58 (s, 1H), 7.15 (dd, 1H, J=13.4, 10.3 Hz), 7.45 (t, 1H, J=7.5 Hz), 7.5–7.7 (m, 2H)

FAB-MS (M/Z) 533 (M$^+$+H)

Molecular formula $C_{28}H_{31}F_3N_2O_5$=532

(3) 1.03 g (1.94 mmol) of the above 2-[4-[N-(tert-butoxycarbonyl)-N-methoxymethylamino]-3-fluorophenyl]-6,8-difluoro-5-(4-methyl-3-pentenylamino)-4H-1-benzopyran-4-one was dissolved in 80 mL of ethanol, 20 mL of 50% sulfuric acid was added and the mixture was stirred at room temperature for 18 hours. Water was added to the reaction solution and the mixture was extracted twice with ethyl acetate. The organic layer was washed once with an aqueous saturated solution of sodium bicarbonate, once with water and once with an aqueous saturated solution of sodium chloride and dried over anhydrous sodium sulfate. The solvent was distilled off under reduced pressure and the residue was purified by silica gel column chromatography (n-hexane:ethyl acetate=5:2–2:1) to give 520 mg of Compound 137 (yield: 69%).

NMR (270 MHz, CDCl$_3$) δ (ppm) 1.63 (s, 3H), 1.71 (s, 3H), 2.33 (q, 2H, J=7.3 Hz), 3.45 (td, 2H, J=6.9, 4.0 Hz), 4.25 (brs, 2H), 6.46 (s, 1H), 6.84 (t, 1H, J=8.9 Hz), 7.14 (dd, 1H, J=13.2, 10.2 Hz), 7.4–7.6 (m, 2H), 8.90 (brs, 1H)

Ms (M/Z) 388 (M$^+$)

Molecular formula $C_{21}H_{19}F_3N_2O_2$=388

EXAMPLE 138

2-(4-Amino-3-fluorophenyl)-6,8-difluoro-5-(4-hydroxy-4-methylpentylamino)-4H-1-benzopyran-4-one (Compound 138)

16 mg (0.041 mmol) of Compound 137 obtained in Example 137 was dissolved in 3 mL of ethanol, 3 mL of 50% sulfuric acid was added and the mixture was stirred at 100° C. for 1 hour. The reaction solution was cooled on ice, water was added and the mixture was extracted twice with ethyl acetate. The organic layer was washed once with an aqueous saturated solution of sodium bicarbonate, once with water and once with an aqueous saturated solution of sodium chloride and dried over anhydrous sodium sulfate. The solvent was distilled off under reduced pressure to give 14 mg of Compound 138 (yield: 84%).

NMR (270 MHz, DMSO-d$_6$) δ (ppm) 1.07 (s, 6H), 1.4–1.7 (m, 4H), 3.3–3.4 (m, 2H), 4.13 (s, 1H), 6.09 (brs, 2H), 6.71 (s, 1H), 6.87 (t, 1H, J=8.9 Hz), 7.5–7.8 (m, 3H), 8.8–8.9 (m, 1H)

FAB-MS (M/Z) 407 (M$^+$+H)

Molecular formula $C_{21}H_{21}F_3N_2O_3$=406

EXAMPLE 139

2-(4-Amino-3-fluorophenyl)-5-(5-dimethylaminopentylamino)-6,8-difluoro-4H-1-benzopyran-4-one (Compound 139)

(1) 2.05 g (5.26mmol) of 5-amino-6,8-difluoro-2-(3-fluoro-4-pivaloylaminophenyl)-4H-1-benzopyran-4-one obtained in Example 66 was dissolved in 50 mL of dimethylformamide under argon atmosphere, 3.6 mL (26.3 mmol) of 1,5-dibromopentane and 631 mg (15.8 mmol) of sodium hydride (60% oil dispersion) were added and the mixture was stirred at room temperature for 1.2 hours. The reaction solution was cooled on ice, water was added and the mixture was extracted with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (chloroform:ethyl acetate=60:1) to give 1.68 g of 5-(5-bromopentylamino)-6,8-difluoro-2-(3-fluoro-4-pivaloylaminophenyl)-4H-1-benzopyran-4-one (yield: 59%).

NMR (90 MHz, CDCl$_3$) δ (ppm) 1.36 (s, 9H), 1.4–2.1 (m, 6H), 3.3–3.6 (m, 2H), 3.41 (t, 2H, J=6.6 Hz), 6.57 (s, 1H), 7.17 (dd, 1H, J=13.2, 10.1 Hz), 7.5–7.8 (m, 3H), 8.58 (t, 1H, J=8.4 Hz)

FAB-MS (M/Z) 539, 541 (M$^+$+H)

Molecular formula $C_{25}H_{26}{}^{79}BrF_3N_3O_3$=538

(2) Substantially the same manner as that in Example 130 (1) was repeated except that 1.47 g (2.73 mmol) of the above 5-(5-bromopentylamino)-6,8-difluoro-2-(3-fluoro-4-pivaloylaminophenyl)-4H-1-benzopyran-4-one was reacted with 2.22 g (27.3 mmol) of dimethylamine hydrochloride and 3.77 g (27.3 mmol) of potassium carbonate and the resulting compound was purified by silica gel column chromatography (chloroform:methanol=9:1), to give 1.02 g. of 5-(5-dimethylaminopentylamino)-6,8-difluoro-2-(3-fluoro-4-pivaloylaminophenyl)-4H-1-benzopyran-4-one (yield: 74%).

NMR (90 MHz, CDCl$_3$) 1.35 (s, 9H), 1.4–1.7 (m, 6H), 2.2–2.5 (m, 2H), 2.28 (s, 6H), 3.3–3.5 (m, 2H), 6.54 (s, 1H), 7.14 (dd, 1H, J=13.4, 10.3 Hz), 7.5–7.8 (m, 3H), 8.57 (t, 1H, J=8.4 Hz), 8.6–8.8 (m, 1H)

FAB-MS (M/Z) 504 (M$^+$+H)

Molecular formula $C_{27}H_{32}F_3N_3O_3$=503

(3) Substantially the same manner as that in Example 127 (4) was repeated except that 909 mg (1.81 mmol) of the above 5-(5-dimethylaminopentylamino)-6,8-difluoro-2-(3-fluoro-4-pivaloylaminophenyl)-4H-1-benzopyran-4-one was used, treatment with 15 mL of concentrated sulfuric acid was carried out and the resulting compound was recrystallized from ethyl acetate/n-hexane, to give 638 mg of Compound 139 (yield: 84%).

NMR (270 MHz, CDCl$_3$) δ (ppm) 1.3–1.7 (m, 6H), 2.26 (s, 6H), 2.32 (t, 2H, J=7.5 Hz), 3.4–3.5 (m, 2H), 4.18 (brs, 2H), 6.44 (s,1H), 6.83 (t, 1H, J=8.9 Hz), 7.12 (dd, 1H, J=13.4, 10.4 Hz), 7.5–7.6 (m, 2H), 8.8–8.9 (m, 1H)

FAB-MS (M/Z) 420 (M$^+$+H)

Molecular formula $C_{22}H_{24}F_3N_3O_2$=419

EXAMPLE 140

2-(4-Amino-3-fluorophenyl)-5-carboxymethylamino-6,8-difluoro-4H-1-benzopyran-4-one (Compound 140)

(1) 1.02 g (2.62mmol) of 5-amino-6,8-difluoro-2-(3-fluoro-4-pivaloylaminophenyl)-4H-1-benzopyran-4-one obtained in Example 66 was dissolved in 30 mL of dimethylformamide under argon atmosphere, 5.8 mL (52.3 mmol) of ethyl bromoacetate and 1.80 g (13.1 mmol) of potassium carbonate were added and the mixture was stirred at 100° C. for 21 hours. The reaction solution was cooled on ice, an aqueous saturated solution of ammonium chloride was added and the precipitated crystals were collected by filtration. The mother liquor was extracted with ethyl acetate, and the organic layer was washed with water and with an aqueous saturated solution of sodium chloride and dried over anhydrous sodium sulfate. The solvent was distilled off under reduced pressure, the residue was added to the above crystals and the mixture was purified by silica gel column chromatography (chloroform:acetonitrile=25:1) to give 824 mg of 5-ethoxycarbonylmethylamino-6,8-difluoro-2-(3-fluoro-4-pivaloylaminophenyl)-4H-1-benzopyran-4-one (yield: 66%).

NMR (90 MHz, CDCl$_3$) δ (ppm) 1.27 (t, 3H, J=7.3 Hz), 1.36 (s, 9H), 4.21 (d, 2H, J=5.3 Hz), 4.23 (q, 2H, J=7.1 Hz), 6.60 (s, 1H), 7.15 (dd, 1H, J=13.4, 10.1 Hz), 7.5–7.8 (m, 3H), 8.58 (t, 1H, J=8.4 Hz)

MS (M/Z) 476 (M$^+$)

Molecular formula $C_{24}H_{23}F_3N_2O_5$=476

(2) Substantially the same manner as that in Example 127 (4) was repeated except that 776 mg (1.63 mmol) of the above 5-ethoxycarbonylmethylamino-6,8-difluoro-2-(3- fluoro-4-pivaloylaminophenyl)-4H-1-benzopyran-4-one was used, and the resulting compound was recrystallized from ethyl acetate, to give 390 mg of 2-(4-amino-3-fluorophenyl)-5-ethoxycarbonylmethylamino-6,8-difluoro-4H-1-benzopyran-4-one (yield: 61%).

NMR (90 MHz, CDCl$_3$) 1.27 (t, 3H, J=7.0 Hz), 4.19 (d, 2H, J=5.3 Hz), 4.20 (q, 2H, J=7.0 Hz), 6.48 (s, 1H), 6.89 (t, 1H, J=8.8 Hz), 7.15 (dd, 1H, J=13.3, 10.2 Hz), 7.4–7.6 (m, 2H)

FAB-MS (M/Z) 393 (M$^+$+H)

Molecular formula C$_{19}$H$_{15}$F$_3$N$_2$O$_4$=392

(3) 305 mg (0.779 mmol) of the above 2-(4-amino-3-fluorophenyl)-5-ethoxycarbonylmethylamino-6,8-difluoro-4H-1-benzopyran-4-one was dissolved in 20 mL of ethanol, a 2N aqueous solution of sodium hydroxide was added and the mixture was stirred at 50° C. for 40 minutes. The reaction solution was cooled on ice and the crystals were collected by filtration. The crystals were suspended in water, the suspension was adjusted to pH 2 by addition of hydrochloric acid thereto, and the crystals were collected by filtration again and purified by silica gel column chromatography (chloroform:methanol:acetic acid=90:10:1) to give 148 mg of Compound 140 (yield: 52%).

NMR (270 MHz, DMSO-d$_6$) δ (ppm) 4.07 (t, 2H, J=5.2 Hz), 6.10 (brs, 2H), 6.71 (s, 1H), 7.87 (t, 1H, J=8.9 Hz), 7.5–7.8 (m, 3H), 9.1–9.2 (m, 1H)

FAB-MS (M/Z) 365 (M$^+$+H)

Molecular formula C$_{17}$H$_{11}$F$_3$N$_2$O$_4$=364

EXAMPLE 141

2-(4-Amino-3-fluorophenyl)-5-(3-carboxypropylamino)-6,8-difluoro-4H-1-benzopyran-4-one (Compound 141)

(1) 1.03 g (2.64 mmol) of 5-amino-6,8-difluoro-2-(3-fluoro-4-pivaloylaminophenyl)-4H-1-benzopyran-4-one obtained in Example 66 was dissolved in 30 mL of dimethylformamide under argon atmosphere, 11.5 mL (79.2 mmol) of ethyl 4-bromobutyrate, 1.83 g (13.3 mmol) of potassium carbonate and 3.96 g (26.4 mmol) of sodium iodide were added and the mixture was stirred at 100° C. for 48 hours. The reaction solution was cooled on ice, an aqueous saturated solution of ammonium chloride was added and the mixture was extracted with ethyl acetate. The organic layer was washed once with water and once with an aqueous saturated solution of sodium chloride and dried over anhydrous sodium sulfate. The solvent was distilled off under reduced pressure, and the residue was purified by silica gel column chromatography (chloroform:acetonitrile=25:1) and recrystallized from ethyl acetate/n-hexane to give 720 mg of 5-(3-ethoxycarbonylpropylamino)-6,8-difluoro-2-(3-fluoro-4-pivaloylaminophenyl)-4H-1-benzopyran-4-one (yield: 54%).

NMR (90 MHz, CDCl$_3$) 1.25 (t, 3H, J=7.0 Hz), 1.36 (s, 9H), 1.8–2.1 (m, 2H), 2.43 (t, 2H, J=7.5 Hz), 3.3–3.6 (m, 2H), 4.05 (q, 2H, J=7.0 Hz), 6.57 (s, 1H), 7.14 (dd, 1H, J=13.4, 10.3 Hz), 7.5–7.8 (m, 3H), 8.58 (t, 1H, J=8.4 Hz)

Ms (M/Z) 504 (M$^+$)

Molecular formula C$_{26}$H$_{27}$F$_3$N$_2$O$_5$=504

(2) Substantially the same manner as that in Example 127 (4) was repeated except that 695 mg (1.38 mmol) of the above 5-(3-ethoxycarbonylpropylamino)-6,8-difluoro-2-(3-fluoro-4-pivaloylaminophenyl)-4H-1-benzopyran-4-one was used, and the resulting compound was recrystallized from ethyl acetate, to give 366 mg of 2-(4-amino-3-fluorophenyl)-5-(3-ethoxycarbonylpropylamino)-6,8-difluoro-4H-1-benzopyran-4-one (yield: 63%).

NMR (90 MHz, CDCl$_3$) δ (ppm) 1.25 (t, 3H, J=7.0 Hz), 1.8–2.1 (m, 2H), 2.42 (t, 2H, J=7.0 Hz), 3.3–3.6 (m, 2H), 4.12 (q, 2H, J=7.0 Hz), 6.45 (s, 1H), 6.86 (t, 1H, J=8.6 Hz), 7.13 (dd, 2H, J=13.4, 10.3 Hz), 7.4–7.6 (m, 2H)

FAB-MS (M/Z) 421 (M$^+$+H)

Molecular formula C$_{21}$H$_{19}$F$_3$N$_2$O$_4$=420

(3) 303 mg (0.722mmol) of the above 2-(4-amino-3-fluorophenyl)-5-(3-ethoxycarbonylpropylamino)-6,8-difluoro-4H-1-benzopyran-4-one was dissolved in 20 mL of ethanol, 1.5 mL of a 2N aqueous solution of sodium hydroxide was added and the mixture was stirred at 50° C. for 5 hours. The reaction solution was cooled on ice and adjusted to pH 7 by addition of hydrochloric acid thereto, and the mixture was extracted with ethyl acetate. The organic layer was washed with an aqueous saturated solution of sodium chloride and dried over anhydrous sodium sulfate. The solvent was distilled off under reduced pressure and the residue was purified by silica gel column chromatography (chloroform:methanol:acetic acid=20:1:0.1) to give 115 mg of Compound 141 (yield: 41%).

NMR (270 MHz, DMSO-d$_6$) δ (ppm) 1.77 (quint., 2H, J=7.4 Hz), 2.30 (t, 2H, J=7.4 Hz), 3.3–3.4 (m, 2H), 6.12 (brs, 2H), 6.73 (s, 1H), 6.87 (t, 1H, J=8.9 Hz), 7.60 (dd, 1H, J=8.4, 2.0 Hz), 7.67 (dd, 1H, J=12.9, 2.0 Hz), 7.72 (dd, 1H, J=13.6, 11.1Hz), 8.8–8.9 (m, 1H)

FAB-MS (M/Z) 393 (M$^+$+H)

Molecular formula C$_{19}$H$_{15}$F$_3$N$_2$O$_4$=392

EXAMPLE 142

5-Amino-2-(4-amino-3-fluorophenyl)-6,8-difluoro-7-(4-methylpiperazinylmethyl)-4H-1-benzopyran-4-one (Compound 142)

(1) Substantially the same manner as that in Example 121 (1) was repeated except that 4-methylpiperazine was used instead of dimethylamine hydrochloride, to give 6,8-difluoro-2-(3-fluoro-4-pivaloylaminophenyl)-7-(4-methylpiperazinylmethyl)-5-pivaloylamino-4H-1-benzopyran-4-one (yield: 97%).

NMR (90 MHz, CDCl$_3$) δ (ppm) 1.36 (s, 9H), 1.38 (s, 9H), 2.36 (s, 3H), 2.3–2.7 (m, 8H), 3.86 (brs, 2H), 6.66 (s, 1H), 7.5–7.9 (m, 3H), 8.59 (t, 1H, J=8.4 Hz), 10.5 (s, 1H)

FAB-MS (M/Z) 587 (M$^+$+H)

Molecular formula C$_{31}$H$_{37}$F$_3$N$_4$O$_4$=586

(2) Substantially the same manner as that in Example 85 (3) was repeated except that the above 6,8-difluoro-2-(3-fluoro- 4-pivaloylaminophenyl)-7-(4-methylpiperazinylmethyl)-5-pivaloylamino-4H-1-benzopyran-4-one was used, to give Compound 142 (yield: 100%).

NMR (270 MHz, CDCl$_3$) δ (ppm) 2.28 (s, 3H), 2.4–2.7 (m, 8H), 3.81 (t, 2H, J=8.4 Hz), 4.18 (brs, 2H), 6.17 (brs, 2H), 6.47 (s, 1H), 6.83 (t, 1H, J=8.4 Hz), 7.5–7.6 (m, 2H)

FAB-MS (M/Z) 419 (M$^+$+H)

Molecular formula C$_{21}$H$_{21}$F$_3$N$_4$O$_2$=418

EXAMPLE 143

5-Amino-2-(4-amino-3-fluorophenyl)-6,8-difluoro-7-morpholinomethyl-4H-1-benzopyran-4-one (Compound 143)

(1) Substantially the same manner as that in Example 121 (1) was repeated except that morpholine was used instead of dimethylamine hydrochloride, to give 6,8-difluoro-2-(3- fluoro-4-pivaloylaminophenyl)-7-morpholinomethyl-5-pivaloylamino-4H-1-benzopyran-4-one (yield: 96%).

NMR (90 MHz, CDCl$_3$) δ (ppm) 1.36 (s, 9H), 1.38 (s, 9H), 2.5–2.7 (m, 4H), 3.6–3.8 (m, 4H), 3.89 (brs, 2H), 6.67 (s, 1H), 7.5–7.8 (m, 3H), 8.61 (t, 1H, J=8.4 Hz), 10.5 (s, 1H)

FAB-MS (M/Z) 574 (M$^+$+H)

Molecular formula C$_{30}$H$_{34}$F$_3$N$_3$O$_5$=573

(2) Substantially the same manner as that in Example 85 (3) was repeated except that the above 6,8-difluoro-2-(3-fluoro-4-pivaloylaminophenyl)-7-molpholinomethyl- 5-pivaloylamino-4H-1-benzopyran-4-one was used, to give Compound 143 (yield: 95%).

NMR (270 MHz, CDCl$_3$) δ (ppm) 2.61 (brs, 4H), 3.74 (brs, 4H), 3.83 (brs, 2H), 4.18 (brs, 2H), 6.21 (brs, 2H), 6.49 (s, 1H), 6.84 (t, 1H, J=8.4 Hz), 7.5–7.7 (m, 2H)

FAB-MS (M/Z) 406 (M$^+$+H)

Molecular formula C$_{20}$H$_{18}$F$_3$N$_3$O$_3$=405

EXAMPLE 144

5-Amino-2-(4-amino-3-fluorophenyl)-6,8-difluoro-7-propylaminomethyl-4H-1-benzopyran-4-one (Compound 144)

(1) Substantially the same manner as that in Example 121 (1) was repeated except that propylamine was used instead of dimethylamine hydrochloride, to give 6,8-difluoro-2-(3-fluoro-4-pivaloylaminophenyl)-5-pivaloylamino-7-propylaminomethyl-4H-1-benzopyran-4-one (yield: 88%).

NMR (90 MHz, CDCl$_3$) δ (ppm) 0.92 (t, 3H, J=7.0 Hz), 1.36 (s, 9H), 1.38 (s, 9H), 1.53 (sextet, 2H, J=7.0 Hz), 2.62 (t, 2H, J=7.0 Hz), 4.10 (s, 2H), 6.66 (s, 1H), 7.5–7.9 (m, 3H), 8.61 (t, 1H, J=8.4 Hz), 10.5 (s, 1H)

FAB-MS (M/Z) 546 (M$^+$+H)

Molecular formula C$_{29}$H$_{34}$F$_3$N$_3$O$_4$=545

(2) Substantially the same manner as that in Example 85 (3) was repeated except that the above 6,8-difluoro-2-(3-fluoro-4-pivaloylaminophenyl)-5-pivaloylamino-7-propylaminomethyl-4H-1-benzopyran-4-one was used, to give Compound 144 (yield: 93%).

NMR (270 MHz, CDCl$_3$) δ (ppm) 0.92 (t, 3H, J=7.0 Hz), 1.51 (sextet, 2H, J=7.0 Hz), 2.59 (t, 2H, J=7.0 Hz), 4.01 (s, 2H), 4.18 (brs, 2H), 6.18 (brs, 2H), 6.48 (s, 1H), 6.84 (t, 1H, J=8.4 Hz), 7.5–7.6 (m, 3H)

FAB-MS (M/Z) 378 (M$^+$+H)

Molecular formula C$_{19}$H$_{18}$F$_3$N$_3$O$_2$=377

EXAMPLE 145

5-Amino-2-(4-amino-3-fluorophenyl)-6,8-difluoro-7-hexylaminomethyl-4H-1-benzopyran-4-one (Compound 145)

(1) Substantially the same manner as that in Example 121 (1) was repeated except that hexylamine was used instead of dimethylamine hydrochloride, to give 6,8-difluoro-2-(3-fluoro- 4-pivaloylaminophenyl)-7-hexylaminomethyl-5-pivaloylamino-4H-1-benzopyran-4-one (yield: 91%).

NMR (90 MHz, CDCl$_3$) δ (ppm) 0.87 (t, 3H, J=7.0 Hz), 1.2–1.4 (m, 6H), 1.36 (s, 9H), 1.38 (s, 9H), 2.64 (t, 2H, J=6.7 Hz), 4.10 (s, 2H), 6.66 (s, 1H), 7.5–7.9 (m, 3H), 8.61 (t, 1H, J=8.4 Hz), 10.5 (s, 1H)

FAB-MS (M/Z) 588 (M$^+$+H)

Molecular formula C$_{32}$H$_{40}$F$_3$N$_3$O$_4$=587

(2) Substantially the same manner as that in Example 85 (3) was repeated except that the above 6,8-difluoro-2-(3-fluoro-4-pivaloylaminophenyl)-7-hexylaminomethyl-5-pivaloylamino-4H-1-benzopyran-4-one was used, to give Compound 145 (yield: 74%).

NMR (270 MHz, CDCl$_3$) δ (ppm) 0.87 (t, 3H, J=6.9 Hz), 1.2–1.4 (m, 6H), 1.4–1.6 (m, 2H), 2.60 (t, 2H, J=6.9 Hz), 4.10 (s, 2H), 6.18 (brs, 2H), 6.48 (s, 1H), 6.84 (t, 1H, J=8.7 Hz), 7.5–7.6 (m, 2H)

FAB-MS (M/Z) 378 (M$^+$+H)

Molecular formula C$_{19}$H$_{18}$F$_3$N$_3$O$_2$=377

EXAMPLE 146

5-Amino-2-(4-amino-3-fluorophenyl)-7-(2-dimethylaminoethylaminomethyl)-6,8-difluoro-4H-1-benzopyran-4-one (Compound 146)

(1) Substantially the same manner as that in Example 121 (1) was repeated except that N,N-dimethylethylenediamine was used instead of dimethylamine hydrochloride, to give 7-(2-dimethylaminoethylaminomethyl)-6,8-difluoro-2-(3-fluoro-4-pivaloylaminophenyl)-5-pivaloylamino-4H-1-benzopyran-4-one (yield: 78%).

NMR (90 MHz, CDCl$_3$) δ (ppm) 1.36 (s, 9-H), 1.38 (s, 9H), 2.22 (s, 6H), 2.47 (q, 2H, J=5.3 Hz), 2.68 (t, 2H, J=5.9 Hz), 4.10 (brs, 2H), 6.66 (s, 1H), 7.5–7.8 (m, 3H), 8.60 (t, 1H, J=8.4 Hz), 10.5 (s, 1H)

FAB-MS (M/Z) 575 (M$^+$+H)

Molecular formula C$_{30}$H$_{37}$F$_3$N$_4$O$_4$=574

(2) Substantially the same manner as that in Example 85 (3) was repeated except that the above 7(2-dimethylaminoethylaminomethyl)-6,8-difluoro-2-(3-fluoro-4-pivaloylaminophenyl)-5-pivaloylamino-4H-1-benzopyran-4-one was used, to give Compound 146 (yield: 83%).

NMR (270 MHz, CDCl$_3$) δ (ppm) 2.21 (s, 6H), 2.44 (t, 2H, J=6.2 Hz), 2.72 (t, 2H, J=6.2 Hz), 4.02 (s, 2H), 4.20 (s, 2H), 6.18 (brs, 2H), 6.48 (s, 1H), 6.84 (t, 1H, J=8.7 Hz), 7.5–7.6 (m, 2H)

FAB-MS (M/Z) 406 (M$^+$+H)

Molecular formula C$_{20}$H$_{21}$F$_3$N$_4$O$_2$=405

EXAMPLE 147

5-Amino-2-(4-amino-3-fluorophenyl)-6,8-difluoro-7-(2-hydroxyethylaminomethyl)-4H-1-benzopyran-4-one (Compound 147)

(1) Substantially the same manner as that in Example 121 (1) was repeated except that ethanolamine was used instead of dimethylamine hydrochloride, to give 6,8-difluoro-2-(3-fluoro-4-pivaloylaminophenyl)-7-(2-hydroxyethylaminomethyl)-5-pivaloylamino-4H-1-benzopyran-4-one (yield: 78%).

NMR (270 MHz, CDCl$_3$) δ (ppm) 1.37 (s, 9H), 1.38 (s, 9H), 2.82 (t, 2H, J=4.9 Hz), 3.67 (t, 2H, J=4.9 Hz), 4.13 (s, 2H), 6.67 (s, 1H), 7.6–7.8 (m, 2H), 7.84 (d, 1H, J=3.9 Hz), 8.60 (t, 1H, J=8.4 Hz), 10.5 (s, 1H)

EI-MS (M/Z) 547 (M$^+$)

Molecular formula C$_{28}$H$_{32}$F$_3$N$_3$O$_5$=547

(2) Substantially the same manner as that in Example 85 (3) was repeated except that the above 6,8-difluoro-2-( 3-fluoro-4-pivaloylaminophenyl)-7-(2-hydroxyethylaminomethyl)-5-pivaloylamino-4H-1-benzopyran-4-one was used, to give Compound 147 (yield: 78%).

NMR (270 MHz, DMSO-d$_6$) δ (ppm) 2.57 (t, 2H, J=5.4 Hz), 3.45 (q, 2H, J=5.4 Hz), 3.86 (s, 2H), 4.46 (t, 1H, J=4.9 Hz), 6.08 (s, 2H), 6.68 (s, 1H), 6.86 (t, 1H, J=8.4 Hz), 7.01 (brs, 2H), 7.5–7.7 (m, 2H)

FAB-MS (M/Z) 380 (M$^+$+H)

Molecular formula C$_{18}$H$_{16}$F$_3$N$_3$O$_3$=379

EXAMPLE 148

5-Amino-2-(4-amino-3-fluorophenyl)-7-{bis(2-hydroxyethyl)aminomethyl}-6,8-difluoro-4H-1-benzopyran-4-one (Compound 148)

(1) Substantially the same manner as that in EXAMPLE 121 (1) was repeated except that diethanolamine was used instead of dimethylamine hydrochloride, to give 7-{bis(2-hydroxyethyl)aminomethyl}-6,8-difluoro-2-(3-fluoro-4-pivaloylaminophenyl)-5-pivaloylamino-4H-1-benzopyran-4-one (yield: 78%).

NMR (270 MHz, CDCl$_3$) δ (ppm) 1.37 (s, 18H), 2.79 (t, 4H, J=4.9 Hz), 3.67 (t, 2H, J=4.9 Hz), 4.01 (s, 2H), 6.68 (s, 1H), 7.6–7.8 (m, 2H), 7.83 (d, 1H, J=3.9 Hz), 8.61 (t, 1H, J=8.4 Hz), 10.5 (s, 1H)

FAB-MS (M/Z) 592 (M$^+$)

Molecular formula C$_{30}$H$_{36}$F$_3$N$_3$O$_6$=591

(2) Substantially the same manner as that in EXAMPLE 85 (3) was repeated except that the above 7-{bis(2-hydroxyethyl)aminomethyl}-6,8-difluoro-2-(3-fluoro-4-pivaloylaminophenyl)-5-pivaloylamino-4H-1-benzopyran- 4-one was used, to give Compound 148 (yield: 60%).

NMR (270 MHz, DMSO-d$_6$) δ (ppm) 2.58 (t, 4H, J=5.9 Hz), 3.47 (q, 4H, J=5.9 Hz), 3.82 (brs, 2H), 4.35 (t, 2H, J=5.4 Hz), 6.09 (brs, 2H), 6.68 (s, 1H), 6.86 (t, 1H, J=8.4 Hz), 7.01 (brs, 2H), 7.5–7.7 (m, 2H)

FAB-MS (M/Z) 424 (M$^+$+H)

Molecular formula C$_{20}$H$_{20}$F$_3$N$_3$O$_4$=423

EXAMPLE 149

5-Amino-2-(4-amino-3-fluorophenyl)-7-(1,3-dihydroxy-2-propylaminomethyl)-6,8-difluoro-4H-1-benzopyran-4-one (Compound 149)

(1) Substantially the same manner as that in EXAMPLE 121 (1) was repeated except that 2-amino-1,3-propanediol was used instead of dimethylamine hydrochloride, to give 7-(1,3-dihydroxy-2-propylaminomethyl)-6,8-difluoro-2-(3-fluoro-4-pivaloylaminophenyl)-5-pivaloylamino-4H-1-benzopyran-4-one. This compound was used for the next step without purification.

NMR (270 MHz, CDCl$_3$) δ (ppm) 1.36 (s, 9H), 1.37 (s, H), 2.75 (quint., 1H, J=4.9 Hz), 3.51 (dd, 2H, J=11.4, 4.9 Hz), 3.63 (dd, 2H, J=11.4, 4.9 Hz), 4.18 (s, 2H), 6.738 (s, 1H), 7.6–7.7 (m, 2H), 7.83 (d, 1H, J=3.5 Hz), 8.60 (t, 1H, J=8.4 Hz), 10.5 (s, 1H)

FAB-MS (M/Z) 578 (M$^+$)

Molecular formula C$_{29}$H$_{34}$F$_3$N$_3$O$_6$=577

(2) Substantially the same manner as that in EXAMPLE 85 (3) was repeated except that the above 7-(1,3-dihydroxy-2-propylaminomethyl)-6,8-difluoro-2-(3-fluoro-4-pivaloylaminophenyl)-5-pivaloylamino-4H-1-benzopyran-4-one was used, to give Compound 149 (yield: 34%).

NMR (270 MHz, DMSO-d$_6$) δ (ppm) 2.5–2.6 (m, 1H), 3.3–3.5 (m, 4H), 3.93 (brs, 2H), 4.47 (brs, 2H), 6.09 (brs, 2H), 6.68 (s, 1H), 6.87 (t, 1H, J=8.9 Hz), 7.01 (brs, 2H), 7.60 (dd, 1H, J=8.4, 2.0 Hz), 7.66 (dd, 1H, J=12.9, 2.0 Hz)

FAB-MS (M/Z) 410 (M$^+$+H)

Molecular formula C$_{19}$H$_{18}$F$_3$N$_3$O$_4$=409

EXAMPLE 150

5-Amino-2-(4-amino-3-fluorophenyl)-6,8-difluoro-7-propyloxymethyl-4H-1-benzopyran-4-one (Compound 150)

(1) 582 mg (1.00 mmol) of 6,8-difluoro-2-(3-fluoro-4-pivaloylaminophenyl)-7-methanesulfonyloxymethyl-5-pivaloylamino-4H-1-benzopyran-4-one obtained in EXAMPLE 120 (1) was dissolved in 100 mL of propanol, and the solution was stirred at 100° C. for 2 hours. The solvent was distilled off under reduced pressure to give the crude product of 6,8-difluoro-2-(3-fluoro-4-pivaloylaminophenyl)-5-pivaloylamino-7-propyloxymethyl-4H-1-benzopyran-4-one. This compound was used for the next step without further purification.

NMR (90 MHz, CDCl$_3$) δ (ppm) 0.92 (t, 3H, J=6.8 Hz), 1.36 (s, 9H), 1.38 (s, 9H), 1.4–1.7 (m, 2H), 3.51 (t, 2H, J=6.6 Hz), 4.75 (brs, 2H), 6.67 (s, 1H), 7.5–7.8 (m, 3H), 8.61 (t, 1H, J=8.4 Hz), 10.5 (s, 1H)

EI-MS (M/Z) 546 (M$^+$)

Molecular formula C$_{29}$H$_{33}$F$_3$N$_2$O$_5$=546

(2) The above 6,8-difluoro-2-(3-fluoro-4-pivaloylaminophenyl)-5-pivaloylamino-7-propyloxymethyl-4H-1-benzopyran-4-one was dissolved in 30 mL of a 50% aqueous solution of sulfuric acid, and the solution was stirred at 100° C. for 15 minutes. Then, the mixture was poured into ice-water and neutralized. The precipitate was collected and purified by silica gel column chromatography (chloroform:methanol=100:1) followed by recrystallization from ethyl acetate/n-hexane, to give 286 mg of Compound 150 (yield: 76%).

NMR (270 MHz, CDCl$_3$) δ (ppm) 0.93 (t, 3H, J=7.4 Hz), 1.63 (sextet, 2H, J=6.9 Hz), 3.50 (t, 2H, J=6.9 Hz), 4.69 (t, 2H, J=2.0 Hz), 6.48 (s, 1H), 6.84 (t, 1H, J=8.9 HZ), 7.5–7.6 (m, 2H)

FAB-MS (M/Z) 379 (M$^+$+H)

Molecular formula C$_{19}$H$_{17}$F$_3$N$_2$O$_3$=378

EXAMPLE 151

5-Amino-2-(4-amino-3-fluorophenyl)-6,8-difluoro-7-hexyloxymethyl-4H-1-benzopyran-4-one (Compound 151)

(1) Substantially the same manner as that in EXAMPLE 150 (1) was repeated except that hexanol was used instead of propanol, to give 6,8-difluoro-2-(3-fluoro-4-pivaloylaminophenyl)-7-hexyloxymethyl-5-pivaloylamino-4H-1-benzopyran- 4-one. This compound was used for the next step without purification.

NMR (90 MHz, CDCl$_3$) δ (ppm) 0.7–1.0 (m, 3H), 1.1–1.7 (m, 8H), 1.36 (s, 9H), 1.38 (s, 9H), 3.54 (t, 2H, J=6.5 Hz), 4.74 (brs, 2H), 6.67 (s, 1H), 7.5–7.8 (m, 3H), 8.61 (t, 1H, J=8.4 Hz), 10.5 (s, 1H)

EI-MS (M/Z) 588 (M$^+$)

Molecular formula C$_{32}$H$_{39}$F$_3$N$_2$O$_5$=588

(2) Substantially the same manner as that in EXAMPLE 150 (2) was repeated except that the above 6,8-difluoro-2-(3-fluoro-4-pivaloylaminophenyl)-7-hexyloxymethyl-5-pivaloylamino-4H-1-benzopyran-4-one was used, to give Compound 151 (yield: 79%).

NMR (270 MHz, CDCl$_3$) δ (ppm) 0.88 (t, 3H, J=6.9 Hz), 1.2–1.4 (m, 6H), 1.60 (quint., 2H, J=6.9 Hz), 3.52 (t, 2H, J=6.9 Hz), 4.68 (t, 2H, J=2.0 Hz), 6.48 (s, 1H), 6.84 (t, 1H, J=8.9 Hz), 7.5–7.6 (m, 2H)

FAB-MS (M/Z) 421 (M$^+$+H)

Molecular formula $C_{22}H_{23}F_3N_2O_3$=420

EXAMPLE 152

5-Amino-2-(4-amino-3-fluorophenyl)-6,8-difluoro-7-(4-methylpentyloxymethyl)-4H-1-benzopyran-4-one (Compound 152)

(1) Substantially the same manner as that in EXAMPLE 150 (1) was repeated except that 4-methylpentanol was used instead of propanol, to give 6,8-difluoro-2-(3-fluoro-4-pivaloylaminophenyl)-7-(4-methylpentyloxymethyl)- 5-pivaloylamino-4H-1-benzopyran-4-one. This compound was used for the next step without purification.

NMR (270 MHz, CDCl$_3$) δ (ppm) 0.87 (d, 6H, J=6.9 Hz), 1.2–1.3 (m, 2H), 1.37 (s, 9H), 1.38 (s, 9H), 1.5–1.7 (m, 3H), 3.53 (t, 2H, J=6.9 Hz), 4.75 (brs, 2H), 6.68 (s, 1H), 7.6–7.8 (m, 2H), 7.84 (d, 1H, J=4.0 Hz), 8.61 (t, 1H, J=8.4 Hz), 10.5 (s, 1H)

FAB-MS (M/Z) 589 (M$^+$+H)

Molecular formula $C_{32}H_{39}F_3N_2O_5$=588

(2) Substantially the same manner as that in EXAMPLE 150 (2) was repeated except that the above 6,8-difluoro-2-(3-fluoro-4-pivaloylaminophenyl)-7-hexyloxymethyl-5-pivaloylamino-4H-1-benzopyran-4-one was used to give Compound 152 (yield: 79%).

NMR (270 MHz, CDCl$_3$) δ (ppm) 0.87 (d, 6H, J=6.4 Hz), 1.1–1.3 (m, 2H), 1.5–1.7 (m, 3H), 3.51 (t, 2H, J=6.4 Hz), 4.68 (t, 2H, J=2.0 Hz), 6.48 (s, 1H), 6.83 (t, 1H, J=8.9 Hz), 7.5–7.6 (m, 2H)

FAB-MS (M/Z) 421 (M$^+$+H)

Molecular formula $C_{22}H_{23}F_3N_2O_3$=420

EXAMPLE 153

5-Amino-2-(4-amino-3-fluorophenyl)-7-(2-dimethylaminoethoxymethyl)-4H-1-benzopyran-4-one (Compound 153)

(1) 800 mg (1.37 mmol) of 6,8-difluoro-2-(3-fluoro-4-pivaloylaminophenyl)-7-methanesulfonyloxymethyl-5-pivaloylamino- 4H-1-benzopyran-4-one obtained in EXAMPLE 120 (1) was dissolved in 20 mL of dimethylformamide at 0° C., 0.28 mL (2.75 mmol) of 2-dimethylaminoethanol and 220 mg (5.20 mmol) of sodium hydride (60% oil dispersion) were added, and the mixture was stirred at room temperature for 80 minutes. Water was added to the reaction solution and the mixture was extracted with ethyl acetate. The organic layer was washed with an aqueous saturated solution of sodium chloride and dried over anhydrous sodium sulfate, and the solvent was distilled off under reduced pressure. The residue was purified by silica gel column chromatography (chloroform:methanol=9:1) to give 477 mg of 7-(2-dimethylaminoethoxymethyl)-6,8-difluoro-2-(3-fluoro-4-pivaloylaminophenyl)-5-pivaloylamino-4H-1-benzopyran-4-one (yield: 60%).

NMR (90 MHz, CDCl$_3$) δ (ppm) 1.36 (s, 9H), 1.38 (s, 9H), 2.35 (s, 6H), 2.63 (t, 2H, J=5.7 Hz), 3.71 (t, 2H, J=5.7 Hz), 4.79 (brs, 2H), 6.67 (s, 1H), 7.6–7.9 (m, 3H), 8.62 (t, 1H, J=8.4 Hz), 10.5 (s, 1H)

FAB-MS (M/Z) 576 (M$^+$+H)

Molecular formula $C_{30}H_{36}F_3N_3O_5$=575

(2) Substantially the same manner as that in EXAMPLE 85 (3) was repeated except that 454 mg (0.790 mmol) of the above 7-(2-dimethylaminoethoxymethyl)-6,8-difluoro-2-(3-fluoro-4-pivaloylaminophenyl)-5-pivaloylamino-4H-1-benzopyran-4-one was used and the resulting compound was purified by silica gel column chromatography (chloroform:methanol=9:1), to give 271 mg of Compound 153 (yield: 83%).

NMR (270 MHz, CDCl$_3$) δ (ppm) 2.30 (s, 6H), 2.58 (t, 2H, J=5.7 Hz), 3.67 (t, 2H, J=5.7 Hz), 4.20 (brs, 2H), 4.73 (t, 2H, J=1.8 Hz), 6.20 (brs, 2H), 6.48 (s, 1H), 6.83 (t, 1H, J=8.7 Hz), 7.5–7.6 (m, 2H)

FAB-MS (M/Z) 408 (M$^+$+H)

Molecular formula $C_{20}H_{20}F_3N_3O_3$=407

EXAMPLE 154

5-Amino-2-(4-amino-3-fluorophenyl)-7-(3-dimethylaminopropoxymethyl)-4H-1-benzopyran-4-one (Compound 154)

(1) Substantially the same manner as that in EXAMPLE 153 (1) was repeated except that 0.33 mL (2.75 mmol) of 3-dimethylaminopropanol was used instead of 2-dimethylaminoethanol, to give 151 mg of 7-(3-dimethylaminopropoxymethyl)-6,8-difluoro-2-(3-fluoro-4-pivaloylaminophenyl)-5-pivaloylamino-4H-1-benzopyran-4-one (yield: 19%).

NMR (90 MHz, CDCl$_3$) δ (ppm) 1.36 (s, 9H), 1.37 (s, 9H), 1.8–2.2 (m, 2H), 2.53 (s, 6H), 2.62 (t, 2H, J=5.7 Hz), 3.64 (t, 2H, J=5.7 Hz), 4.76 (brs, 2H), 6.68 (s, 1H), 7.5–7.8 (m, 3H), 8.61 (t, 1H, J=8.4 Hz), 10.5 (s, 1H)

FAB-MS (M/Z) 590 (M$^+$+H)

Molecular formula $C_{31}H_{38}F_3N_3O_5$=589

(2) Substantially the same manner as that in EXAMPLE 85 (3) was repeated except that 139 mg (0.236 mmol) of the above 7-(3-dimethylaminopropoxymethyl)-6,8-difluoro-2-(3-fluoro-4-pivaloylaminophenyl)-5-pivaloylamino-4H-1-benzopyran-4-one was used and the resulting compound was purified by silica gel column chromatography (chloroform:methanol=9:1), to give 30 mg of Compound 154 (yield: 30%).

NMR (270 MHz, CDCl$_3$) δ (ppm) 2.25 (s, 6H), 1.80 (q, 2H, J=6.4 Hz), 2.39 (t, 2H, J=6.9 Hz), 3.59 (t, 2H, J=6.4 Hz), 4.19 (brs, 2H), 4.69 (t, 2H, J=1.8 Hz), 6.20 (brs, H), 6.48 (s, 1H), 6.84 (t, 1H, J=8.7 Hz), 7.5–7.6 (m, 2H)

FAB-MS (M/Z) 422 (M$^+$+H)

Molecular formula $C_{21}H_{22}F_3N_3O_3$=421

EXAMPLE 155

5-Amino-2-(4-amino-3-fluorophenyl)-6,8-difluoro-7-(4-methylvaleryloxymethyl)-4H-1-benzopyran-4-one (Compound 155)

Substantially the same manner as that in EXAMPLE was repeated except that isocaproic acid was used instead of acetic acid, to give Compound 155 (yield: 51%).

NMR (270 MHz, CDCl$_3$) δ (ppm) 0.89 (d, 6H, J=6.4 Hz), 1.5–1.6 (m, 3H), 2.35 (t, 2H, J=7.4 Hz), 5.29 (s, 2H), 6.49 (s, 1H), 6.84 (t, 1H, J=8.4 Hz), 7.5–7.6 (m, 2H)

FAB-MS (M/Z) 435 (M$^+$+H)

Molecular formula $C_{22}H_{21}F_3N_2O_4$=434

EXAMPLE 156

5-Amino-2-(4-amino-3-fluorophenyl)-7-diethylcarbamoyloxymethyl-6,8-difluoro-4H-1-benzopyran-4-one (Compound 156)

(1) 303 mg (0.722 mmol) of Compound P obtained in Reference EXAMPLE 13 was dissolved in 15 mL of dimethylformamide, 0.30 mL (2.2 mmol) of triethylamine and 293 mg (1.44 mmol) of 4-nitrophenyl chloroformate were added under ice-cooling and the mixture was stirred at room temperature for 12 hours. The reaction solution was cooled on ice, 0.75 mL (7.2 mmol) of diethylamine was added and the mixture was stirred at the same temperature for 4.5 hours. Water was added to the reaction solution and the mixture was extracted with ethyl acetate. The organic layer was washed with water and an aqueous saturated solution of sodium chloride and dried over anhydrous sodium sulfate, and the solvent was distilled off under reduced pressure. The residue was purified by silica gel column chromatography (chloroform), to give 239 mg of 2-(4-allyloxycarbonylamino-3-fluorophenyl)-5-amino-7-diethylcarbamoyloxymethyl-6,8-difluoro-4H-1-benzopyran-4-one (yield: 64%).

NMR (90 MHz, CDCl$_3$) δ (ppm) 1.12 (t, 6H, J=7.3 Hz), 3.20 (q, 2H, J=7.3 Hz), 3.28 (q, 2H, J=7.3 Hz), 4.72 (d, 2H, J=5.7 Hz), 5.2–5.5 (m, 2H), 5.32 (s, 2H), 5.7–6.2 (m, 1H), 6.23 (brs, 2H), 6.57 (s, 1H), 7.09 (d, 1H, J=3.3 Hz), 7.5–7.8 (m, 2H), 8.32 (t, 1H, J=8.5 Hz)

FAB-MS (M/Z) 520 (M$^+$+H)

Molecular formula $C_{25}H_{24}F_3N_3O_6$=519

(2) 223 mg (0.429 mmol) of the above 2-(4-allyloxycarbonylamino-3-fluorophenyl)-5-amino-7-diethylcarbamoyloxymethyl-6,8-difluoro-4H-1-benzopyran-4-one was dissolved in 20 mL of tetrahydrofuran, 0.29 mL of formic acid-triethylamine and 50 mg (0.043 mmol) of tetrakis(triphenylphosphine)palladium were added and the mixture was stirred at room temperature for 40 minutes. Water was added to the reaction solution and the mixture was extracted with ethyl acetate. The organic layer was washed with water and an aqueous saturated solution of sodium chloride and dried over anhydrous sodium sulfate, and the solvent was distilled off under reduced pressure. The residue was purified by silica gel column chromatography (chloroform) and recrystallized from ethyl acetate/n-hexane, to give 105 mg of Compound 156 (yield: 56%).

NMR (270 MHz, CDCl$_3$) δ (ppm) 1.12 (brs, 6H), 3.2–3.4 (m, 4H), 5.30 (s, 2H), 6.58 (s, 1H), 6.83 (t, 1H, J=8.9 Hz), 7.5–7.6 (m, 2H)

FAB-MS (M/Z) 436 (M$^+$+H)

Molecular formula $C_{21}H_{20}F_3N_3O_4$=435

EXAMPLE 157

5-Amino-2-(4-amino-3-fluorophenyl)- 6,8-difluoro-7-(4-methylpiperazinyl)carbonyloxymethyl-4H-1-benzopyran-4-one (Compound 157)

(1) Substantially the same manner as that in EXAMPLE 156 (1) was repeated except that 420 mg (1.00 mmol) of Compound P obtained in Reference EXAMPLE 13 was used and 0.35 mL (3.0 mmol) of N-methylpiperazine was used instead of diethylamine, to give 294 mg of 2-(4-allyloxycarbonylamino-3-fluorophenyl)-5-amino-6,8-difluoro-7-(4-methylpiperazinyl)carbonyloxymethyl-4H-1-benzopyran-4-one (yield: 54%).

NMR (90 MHz, CDCl$_3$) δ (ppm) 2.31 (s, 3H), 2.38 (t, 4H, J=5.3 Hz), 3.52 (t, 4H, J=5.1 Hz), 4.72 (d, 2H, J=5.5 Hz), 5.2–5.5 (m, 2H), 5.33(s, 2H), 5.7–6.2 (m, 1H), 6.23 (brs, 1H), 6.56 (s, 2H), 7.15 (d, 1H, J=3.1 Hz), 7.5–7.7 (m, 2H), 8.30 (t, 1H, J=8.1 Hz)

FAB-MS (M/Z) 547 (M$^+$+H)

Molecular formula $C_{26}H_{25}F_3N_4O_6$=546

(2) Substantially the same manner as that in EXAMPLE 156 (2) was repeated except that 294 mg (0.539 mmol) of the above 2-(4-allyloxycarbonylamino-3-fluorophenyl)-5-amino-6,8-difluoro-7-(4-methylpiperazinyl)carbonyloxymethyl-4H-1-benzopyran-4-one was used, to give 232 mg of Compound 157 (yield: 93%).

NMR (270 MHz, CDCl$_3$) δ (ppm) 2.31 (s, 3H), 2.39 (brs, 4H), 3.52 (brs, 4H), 4.20 (brs, 2H), 5.32 (s, 2H), 6.22 (brs, 2H), 6.48 (s, 1H), 6.84 (t, 1H, J=8.4 Hz), 7.5–7.6 (m, 2H)

FAB-MS (M/Z) 463 (M$^+$+H)

Molecular formula $C_{22}H_{21}F_3N_4O_4$=462

EXAMPLE 158

5-Amino-2-(4-amino-3-fluorophenyl)-7-[N-(2-dimethylaminoethyl)carbamoyloxymethyl]-6,8-difluoro-4H-1-benzopyran-4-one (Compound 158)

(1) Substantially the, same manner as that in EXAMPLE 156 (1) was repeated except that 420 mg (1.00 mmol) of Compound P obtained in Reference EXAMPLE 13 was used and 0.33 mL (3.0 mmol) of N,N-dimethylethylenediamine was used instead of diethylamine, to give 265 mg of 2-(4-allyloxycarbonylamino-3-fluorophenyl)-5-amino-7-[N-(2-dimethylaminoethyl)carbamoyloxymethyl]-6,8-difluoro-4H-1-benzopyran-4-one (yield: 50%).

NMR (90 MHz, CDCl$_3$) δ (ppm) 2.23 (s, 6H), 2.42 (t, 2H, J=5.9 Hz), 3.28 (q, 2H, J=5.9 Hz), 4.72 (d, 2H, J=5.7 Hz), 5.1–5.5 (m, 2H), 5.30 (s, 2H), 5.7–6.2 (m, 1H), 6.22 (brs, 2H), 6.56 (s, 1H), 7.05 (brs, 2H), 7.5–7.7 (m, 2H), 8.31 (t, 1H, J=8.1 Hz)

FAB-MS (M/Z) 535 (M$^+$+H)

Molecular formula $C_{25}H_{25}F_3N_4O_6$=534

(2) Substantially the same manner as that in EXAMPLE 156 (2) was repeated except that 265 mg (0.496 mmol) of the above 2-(4-allyloxycarbonylamino-3-fluorophenyl)-5-amino-7-[N-(2-dimethylaminoethyl)carbamoyloxmethyl]-6,8-difluoro-4H-1-benzopyran-4-one was used, to give 176 mg of Compound 158 (yield: 79%).

NMR (270 MHz, CDCl$_3$) δ (ppm) 2.22 (s, 6H), 2.43 (t, 2H, J=5.4 Hz), 3.29 (q, 2H, J=5.4 Hz), 4.20 (brs, 2H), 5.29 (s, 2H), 5.38 (m, 1H), 6.21 (brs, 2H), 6.47 (s, 1H), 6.83 (t, 1H, J=8.9 Hz), 7.5–7.6 (m, 2H)

FAB-MS (M/Z) 451 (M$^+$+H)

Molecular formula $C_{21}H_{21}F_3N_4O_4$=450

EXAMPLE 159

5-Amino-2-(4-amino-3-fluorophenyl)-7-chloroacetoxymethyl-6,8-difluoro-4H-1-benzopyran-4-one (Compound 159)

100 g (1.06 mol) of chloroacetic acid and 30 mL of sulfuric acid were added to 10.8 g (20.0 mmol) of 6,8-difluoro-2-(3-fluoro-4-pivaloylaminophenyl)-7-hydroxymethyl-5-pivaloylamino-4H-1-benzopyran-4-one obtained in EXAMPLE 118 (4), and the mixture was stirred at 100° C. for 20 minutes. The reaction solution was poured into 1 L of ice-water and the mixture was extracted with ethyl acetate. The organic layer was washed with an aqueous saturated solution of sodium chloride and dried over anhydrous sodium sulfate, and the solvent was distilled off under reduced pressure. The residue was triturated with diisopropyl ether, to give 8.00 g of Compound 159 (yield: 97%).

NMR (90 MHz, DMSO-d$_6$) δ (ppm) 4.40 (s, 2H), 5.36 (s, 2H), 6.00 (brs, 2H), 6.66 (s, 1H), 6.87 (t, 1H, J=8.9 Hz), 7.06 (brs, 2H), 7.5–7.7 (m, 2H)

FAB-MS (M/Z) 413 (M$^+$+H)

Molecular formula $C_{18}H_{12}{}^{35}ClF_3N_2O_4$=412

EXAMPLE 160

5-Amino-2-(4-amino-3-fluorophenyl)-7-(3-bromopropanoyl)oxymethyl-6,8-difluoro-4H-1-benzopyran-4-one (Compound 160)

7.65 g (50.0 mmol) of 3-bromopropionic acid and 1.5 mL of sulfuric acid were added to 504 mg (1.00 mmol) of 6,8-difluoro-2-(3-fluoro-4-pivaloylaminophenyl)-7-hydroxymethyl-5-pivaloylamino-4H-1-benzopyran-4-one obtained in EXAMPLE 118 (4), and the mixture was stirred at 100° C. for 10 minutes. The reaction solution was poured into 100 mL of ice-water and the mixture was extracted with ethyl acetate. The organic layer was washed with an aqueous saturated solution of sodium chloride and dried over anhydrous sodium sulfate, and the solvent was distilled off under reduced pressure. The residue was purified by silica gel column chromatography (chloroform:acetonitrile=19:1), to give 163 mg of Compound 160 (yield: 35%).

NMR (90 MHz, CDCl$_3$) δ (ppm) 2.97 (t, 2H, J=6.8 Hz), 3.58 (t, 2H, J=6.8 Hz), 5.36(t, 2H, J=1.5 Hz), 6.49 (s, 1H), 6.83 (t, 1H, J=8.7 Hz), 7.4–7.7 (m, 2H)

FAB-MS (M/Z) 473, 471 (M$^+$+H)

Molecular formula C$_{19}$H$_{14}$$^{79}$BrF$_3$N$_2$O$_4$=470

EXAMPLE 161

5-Amino-2-(4-amino-3-fluorophenyl)-7-dimethylaminoacetoxymethyl-6,8-difluoro-4H-1-benzopyran-4-one (Compound 161)

1.50 g (3.63 mmol) of Compound 159 obtained in EXAMPLE 159 was dissolved in 30 mL of dimethylformamide, 1.48 g (18.2 mmol) of dimethylamine hydrochloride and 2.50 g (18.2 mmol) of potassium carbonate were added, and the mixture was stirred at 50° C. for 30 minutes. Water was added to the reaction solution and the mixture was extracted with ethyl acetate. The organic layer was washed with water and an aqueous saturated solution of sodium chloride and dried over anhydrous sodium sulfate, and the solvent was distilled off under reduced pressure. The residue was recrystallized from ethyl acetate/n-hexane, to give 1.18 g of Compound 161 (yield: 77%). This compound was dissolved in ethyl acetate, 3 mL of a 1N hydrochloric acid/2-propanol solution was added, and the precipitated crystals were collected by filtration, to give a hydrochloride of Compound 161.

NMR (270 MHz, DMSO-d$_6$) δ (ppm) 2.84 (s, 6H), 4.27 (s, 2H), 5.42 (s, 2H), 6.73 (s, 1H), 6.87 (t, 1H, J=8.9 Hz), 7.5–7.7 (m, 2H), 10.3 (brs, 1H)

FAB-MS (M/Z) 422 (M$^+$+H)

Molecular formula C$_{20}$H$_{18}$F$_3$N$_3$O$_4$=421

EXAMPLE 162

5-Amino-2-(4-amino-3-fluorophenyl)-7-(3-dimethylaminopropionyl)oxymethyl-6,8-difluoro-4H-1-benzopyran-4-one (Compound 162)

130 mg (0.276 mmol) of Compound 160 obtained in EXAMPLE 160 was dissolved in 5 mL of dimethylformamide, 112 mg (1.38 mmol) of dimethylamine hydrochloride and 0.24 mL (1.38 mmol) of diisopropylethylamine were added, and the mixture was stirred at 50° C. for 30 minutes. Water was added to the reaction solution and the mixture was extracted with ethyl acetate. The organic layer was washed with water and an aqueous saturated solution of sodium chloride and dried over anhydrous sodium sulfate, and the solvent was distilled off under reduced pressure. The residue was purified by silica gel column chromatography (chloroform:methanol=9:1), to give 122 mg of Compound 162 (yield: 86%), which was converted to a hydrochloride according to the same manner as that in EXAMPLE 161.

NMR (270 MHz, DMSO-d$_6$) δ (ppm) 2.75 (d, 6H, J=4.5 Hz), 2.93 (t, 2H, J=7.4 Hz), 3.31 (t, 2H, J=7.4 Hz), 5.31 (s, 2H), 6.10 (brs, 2H), 6.72 (s, 1H), 6.88 (t, 1H, J=8.9 Hz), 7.13 (brs, 2H), 7.60 (dd, 1H, J=8.4, 2.0 Hz), 7.66 (dd, 1H, J=12.9, 2.0 Hz), 10.2 (brs, 1H)

FAB-MS (M/Z) 436 (M$^+$+H)

Molecular formula C$_{21}$H$_{20}$F$_3$N$_3$O$_4$=435

EXAMPLE 163

5-Amino-2-(4-amino-3-fluorophenyl)-7-(4-dimethylaminobutyryl)oxymethyl-6,8-difluoro-4H-1-benzopyran-4-one (Compound 163)

(1) 3.99 g (23.8 mmol) of 4-dimethylaminobutyric acid hydrochloride was dissolved in 50 mL of dimethylformamide, 3.86 g (23.8 mmol) of N,N'-carbonyldiimidazole was added, and the mixture was stirred at 80° C. for 2.5 hours. 1.00 g (2.38 mmol) of Compound P obtained in Reference EXAMPLE 13 was added thereto and the mixture was stirred at the same temperature further for 2 hours. An aqueous saturated solution of sodium bicarbonate was added to the reaction solution and the mixture was extracted with ethyl acetate. The organic layer was washed with an aqueous saturated solution of sodium chloride and dried over anhydrous sodium sulfate, and the solvent was distilled off under reduced pressure. The residue was purified by silica gel column chromatography (chloroform:methanol=9:1), to give 1.27 g of 2-(4-allyloxycarbonylamino-3-fluorophenyl)-5-amino-7-(4-dimethylaminobutyryl)oxymethyl-6,8-difluoro-4H-1-benzopyran-4-one (yield: 100%).

NMR (90 MHz, CDCl$_3$) δ (ppm) 1.6–2.0 (m, 2H), 2.1–2.5 (m, 4H), 2.23 (s, 6H), 4.72 (d, 2H, J=5.7 Hz), 5.2–5.5 (m, 2H), 5.30 (s, 2H), 5.7–6.2 (m, 1H), 6.23 (brs, 2H), 6.56 (s, 1H), 7.10 (brs, 1H), 7.5–7.7 (m, 2H), 8.31 (t, 1H, J=7.9 Hz)

FAB-MS (M/Z) 534 (M$^+$+H)

Molecular formula C$_{26}$H$_{26}$F$_3$N$_3$O$_6$=533

(2) Substantially the same manner as that in EXAMPLE 156 (2) was repeated except that 1.27 g of the above 2-(4-allyloxycarbonylamino-3-fluorophenyl)-5-amino-7-(4-dimethylaminobutyryl)oxymethyl-6,8-difluoro-4H-1-benzopyran-4-one was used, to give 567 mg of Compound (yield: 53%).

NMR (270 MHz, DMSO-d$_6$) δ (ppm) 1.94 (q, 2H, J=7.9 Hz), 2.48 (t, 2H, J=7.9 Hz), 2.73 (s, 6H), 3.04 (m, 2H), 5.27 (s, 2H), 6.14 (brs, 2H), 6.72 (s, 1H), 6.87 (t, 1H, J=8.4 Hz), 7.13 (brs, 2H), 7.60 (dd, 1H, J=8.4, 2.0 Hz), 7.66 (dd, 1H, J=12.9, 2.0 Hz), 10.2 (brs, 1H)

FAB-MS (M/Z) 450 (M$^+$+H)

Molecular formula C$_{22}$H$_{22}$F$_3$N$_3$O$_4$=449

EXAMPLE 164

5-Amino-2-(4-amino-3-fluorophenyl)-6,8-difluoro-7-piperidinoacetoxymethyl-4H-1-benzopyran-4-one (Compound 164)

515 mg (1.25 mmol) of Compound 159 obtained in EXAMPLE 159 was dissolved in 10 mL of dimethylformamide, 0.62 mL (6.2 mmol) of piperidine and 0.22 mL (1.25 mmol) of diisopropylethylamine were added, and the mixture was stirred at 50° C. for 2 hours. Water was added to the reaction solution and the mixture was extracted with ethyl acetate. The organic layer was washed with water and an aqueous saturated solution of sodium chloride and dried over anhydrous sodium sulfate, and the solvent was distilled off under reduced pressure. The residue was purified by silica gel column chromatography (chloroform:acetonitrile= 4:1) and recrystallized from ethyl acetate, to give 441 mg of Compound 164 (yield: 77%).

NMR (270 MHz, CDCl$_3$) δ (ppm) 1.44 (quint., 2H, J=5.4 Hz), 1.64 (quint., 4H, J=5.4 Hz), 2.57 (t, 2H, J=5.4 Hz), 3.28 (s, 2H), 4.21 (brs, 2H), 5.34 (s, 2H), 6.23 (brs, 2H), 6.49 (s, 1H), 6.84 (t, 1H, J=8.9 Hz), 7.5–7.6 (m, 2H)

FAB-MS (M/Z) 462 (M$^+$+H)

Molecular formula $C_{23}H_{22}F_3N_3O_4$=461

EXAMPLE 165

5-Amino-2-(4-amino-3-fluorophenyl)-6,8-difluoro-7-(4-methylpiperazinyl)acetoxymethyl-4H-1-benzopyran-4-one (Compound 165)

Substantially the same manner as that in EXAMPLE 164 was repeated except that 0.69 mL (6.2 mmol) of methylpiperazine was used instead of piperidine, to give 408 mg of Compound 165 (yield: 69%).

NMR (270 MHz, CDCl$_3$) δ (ppm) 2.33 (s, 3H), 2.55 (brs, 4H), 2.66 (brs, 4H), 3.28 (s, 2H), 4.21 (brs, 2H), 5.34 (s, 2H), 6.23 (brs, 2H), 6.49 (s, 1H), 6.84 (t, 1H, J=8.4 Hz), 7.5–7.6 (m, 2H)

FAB-MS (M/Z) 477 (M$^+$+H)

Molecular formula $C_{23}H_{23}F_3N_3O_4$=476

EXAMPLE 166

5-Amino-2-(4-amino-3-fluorophenyl)-6,8-difluoro-7-morpholinoacetoxymethyl-4H-1-benzopyran-4-one (Compound 166)

Substantially the same manner as that in Example 164 was repeated except that 0.55 mL (6.2 mmol) of morpholine was used instead of piperidine, to give 350 mg of Compound 166 (yield: 61%).

NMR (270 MHz, DMSO-d$_6$) δ (ppm) 2.4–2.6 (m, 4H), 3.56 (t, 4H, J=4.7 Hz), 5.28 (s, 2H), 6.10 (brs, 2H), 6.71 (s, 1H), 6.87 (t, 1H, J=8.9 Hz), 7.12 (brs, 2H), 7.60 (dd, 1H, J=8.4, 2.0 Hz), 7.66 (dd, 1H, J=12.9, 2.0 Hz)

FAB-MS (M/Z) 464 (M$^+$+H)

Molecular formula $C_{22}H_{20}F_3N_3O_5$=463

EXAMPLE 167

5-Amino-2-(4-amino-3-fluorophenyl)-6,8-difluoro-7-(4-hydroxypiperidino)acetoxymethyl-4H-1-benzopyran-4-one (Compound 167)

Substantially the same manner as that in Example 164 was repeated except that 633 mg (6.2 mmol) of 4-hydroxypiperidine was used instead of piperidine, to give 518 mg of Compound 167 (yield: 89%).

NMR (270 MHz, DMSO-d$_6$) δ (ppm) 1.3–1.5 (m, 2H), 1.6–1.8 (m, 2H), 2.1–2.3 (m, 2H), 2.6–2.8 (m, 2H), 3.23 (s, 3H), 3.3–3.5 (m, 1H), 4.53 (d, 1H, J=4.0 Hz), 5.26 (brs, 2H), 6.12 (brs, 2H), 6.71 (s, 1H), 6.87 (t, 1H, J=8.9 Hz), 7.12 (brs, 2H), 7.60 (dd, 1H, J=8.4, 2.0 Hz), 7.67 (dd, 1H, J=12.9, 2.0 Hz)

FAB-MS (M/Z) 478 (M$^+$+H)

Molecular formula $C_{23}H_{22}F_3N_3O_5$=477

EXAMPLE 168

5-Amino-2-(4-amino-3-fluorophenyl)-7-[N-(2-dimethylaminoethyl)-N-methylamino]acetoxymethyl- 6,8-difluoro-4H-1-benzopyran-4-one (Compound 168)

Substantially the same manner as that in Example 164 was repeated except that 0.80 mL (6.2 mmol) of N,N,N'-trimethylethylenediamine was used instead of piperidine, to give 398 mg of Compound 168 (yield: 67%).

NMR (270 MHz, CDCl$_3$) δ (ppm) 2.33 (s, 6H), 2.43 (s, 3H), 2.51 (t, 2H, J=6.4 Hz), 2.74 (t, 2H, J=6.4 Hz), 3.41 (s, 2H), 4.20 (brs, 2H), 5.33 (s, 2H), 6.24 (brs, 1H), 6.49 (s, 1H), 6.85 (t, 1H, J=8.7 Hz), 7.5–7.6 (m, 2H)

FAB-MS (M/Z) 479 (M$^+$+H)

Molecular formula $C_{23}H_{25}F_3N_4O_4$=478

EXAMPLE 169

5-Amino-2-(4-amino-3-fluorophenyl)-6,8-difluoro-7-methoxycarbonylmethylaminoacetoxymethyl-4H-1-benzopyran-4-one (Compound 169)

Substantially the same manner as that in Example 164 was repeated except that 783 mg (6.2 mmol) of glycine methyl ester hydrochloride was used instead of piperidine, to give 291 mg of Compound 169 (yield: 50%).

NMR (270 MHz, CDCl$_3$) δ (ppm) 3.50 (s, 2H), 3.53 (s, 2H), 3.73 (s, 3H), 4.20 (brs, 2H), 5.36 (s, 2H), 5.41 (brs, 1H), 6.24 (brs, 2H), 6.49 (s, 1H), 6.84 (t, 1H, J=8.9 Hz), 7.5–7.6 (m, 2H)

FAB-MS (M/Z) 466 (M$^+$+H)

Molecular formula $C_{21}H_{18}F_3N_3O_6$=465

EXAMPLE 170

7-Allyloxycarbonyloxymethyl-5-amino-2-(4-amino-3-fluorophenyl)-6,8-difluoro-4H-1-benzopyran-4-one (Compound 170)

336 mg (1.00 mmol) of Compound 118 obtained in Example 118 was dissolved in 20 mL of pyridine, 1.0 mL (5.0 mmol) of diallyl pyrocarbonate and 27 mg (0.20 mmol) of 4-dimethylaminopyridine were added, and the mixture was stirred at room temperature for 4 hours. Water was added to the reaction solution and the mixture was extracted with ethyl acetate. The organic layer was washed twice with 1N HCl and each once with water and an aqueous saturated solution of sodium chloride and dried over anhydrous sodium sulfate, and the solvent was distilled off under the reduced pressure. The residue was purified by silica gel column chromatography (chloroform:methanol=200:1) and recrystallized from ethyl acetate/n-hexane, to give 172 mg of Compound 170 (yield: 41%).

NMR (270 MHz, CDCl$_3$) δ (ppm) 4.67 (d, 2H, J=5.9 Hz), 5.28 (dd, 1H, J=10.4, 1.0 Hz), 5.37 (dd, 1H, J=17.3, 1.0 Hz), 5.38 (2,2H), 5.95 (ddd, 1H, J=17.3, 10.4, 5.9 Hz), 6.49 (s, 1H), 6.84 (t, 1H, J=8.9 Hz), 7.5–7.6 (m, 2H)

FAB-MS (M/Z) 421 (M$^+$+H)

Molecular formula $C_{20}H_{15}F_3N_2O_5$=420

EXAMPLE 171

5-Amino-2-(4-amino-3,5-dichlorophenyl)-7-chloroacetoxymethyl-6,8-difluoro-4H-1-benzopyran-4-one (Compound 171)

26.7 g (283 mmol) of chloroacetic acid and 8.0 mL of sulfuric acid were added to 3.14 g (5.66 mmol) of Compound Q obtained in Reference Example 16, and the mixture was stirred at 100° C., for 20 minutes. The reaction solution was cooled at room temperature and poured into ice-water, and the precipitated crystals were collected by filtration, to give 2.40 g of Compound 171 (yield: 91%).

NMR (90 MHz, DMSO-$d_6$) δ (ppm) 4.44 (s, 2H), 5.36 (t, 2H, J=1.5 Hz), 6.84 (s, 1H), 7.88 (s, 2H)

FAB-MS (M/Z) 463 (M$^+$+H)

Molecular formula $C_{18}H_{11}{}^{35}Cl_3F_2N_2O_4$=462

EXAMPLE 172

5-Amino-2-(4-amino-3,5-dichlorophenyl)-7-dimethylaminoacetoxymethyl-6,8-difluoro-4H-1-benzopyran-4-one (Compound 172)

2.00 g (4.31 mmol) of Compound 171 obtained in Example 171 was dissolved in 80 mL of dimethylformamide, 1.76 g (21.6 mmol) of dimethylamine hydrochloride and 3.75 mL (21.6 mmol) of diisopropylethylamine were added, and the mixture was stirred at 50° C., for 3 hours. Water was added to the reaction solution and the precipitated crystals were collected by filtration. The crystals were purified by silica gel column chromatography (chloroform:methanol=9:1), to give 1.68 g of Compound 172 (yield: 83%).

NMR (270 MHz, DMSO-$d_6$) δ (ppm) 2.25 (s, 6H), 3.24 (s, 2H), 5.27 (brs, 2H), 6.37 (brs, 2H), 6.83 (s, 1H), 7.11 (brs, 2H), 7.87 (s, 2H)

FAB-MS (M/Z) 472 (M$^+$+H)

Molecular formula $C_{20}H_{17}{}^{35}Cl_2F_2N_3O_4$=471

REFERENCE EXAMPLE 1

Ethyl 2-(N-ethoxycarbonyl-N-pivaloylamino)-3-fluoro-6-methoxymethoxybenzoate (Compound A)

200 g of ethyl 6-(N-ethoxycarbonyl-N-pivaloylamino)-2-(2-tetrahydropyranyloxy)benzoate obtained according to the known method (U.S. Pat. No. 4,571,405) was dissolved in 900 ml of ethanol, 300 ml of concentrated hydrochloric acid was added and the mixture was heated at reflux for 3.5 hours. The reaction solution was cooled on ice, 500 ml of water was added and the precipitated crystals were collected by filtration to give 89.1 g (74%) of ethyl 6-(N-ethoxycarbonylamino)-2-hydroxybenzoate (Compound D).

NMR (90 MHz, CDCl$_3$) δ (ppm) 1.31 (3H, t, J=7.0), 1.50 (3H, t, J=7.0), 4.22 (2H, q, J=7.0), 4.53 (2H, q, J=7.0), 6.65 (1H, dd, J=8.2, 1.2), 7.37 (1H, t, J=8.4), 7.86 (1H, dd, J=8.4, 1.1), 9.48 (1H, brs), 10.74 (1H, s)

MS (M/Z) 253 (M$^+$)

Molecular formula $C_{12}H_{15}NO_5$=253

12.7 g of the above Compound D was dissolved in 100 ml of dichloroethane, 17.4 g of N-fluoro-3,5-pyridinium triflate [Onoda Florinate FP-T700 (Wako Pure Chemical Industries Ltd.)] was added and the mixture was stirred at 60° to 70° C. for two hours. Additional 4.74 g of FP-T700 was added and the mixture was stirred at the same temperature for 2.5 hours. The reaction solution was made acidic by addition of 1N hydrochloric acid thereto, the mixture was extracted with ether, the organic layer was washed with water and an aqueous saturated solution of sodium chloride and dried over anhydrous sodium sulfate, and the solvent was distilled off under reduced pressure. The residue was subjected to silica gel column chromatography (n-hexane:ethyl acetate= 8:1–4:1) to give 5.08 g (37%) of ethyl 2-(N-ethoxycarbonylamino)-3-fluoro-6-hydroxybenzoate.

NMR (90 MHz, CDCl$_3$) δ (ppm) 1.30 (3H, t, J=7.1), 1.42 (3H, t, J=7.1), 4.21 (2H, q, J=7.0), 4.44 (2H, q, J=7.1), 6.80 (1H, dd, J=9.2, 4.4), 7.05 (1H, brs), 7.20 (1H, t, J=9.3), 10.4 (1H, s)

MS (M/Z) 271 (M$^+$)

Molecular formula $C_{12}H_{14}FNO_5$=271

26.6 g of the resulting ethyl 2-(N-ethoxycarbonylamino)-3-fluoro-6-hydroxybenzoate was dissolved in 300 ml of dichloromethane under argon atmosphere, 20.5 ml of diisopropylethylamine and 9.0 ml of chloromethyl methyl ether were added under ice-cooling and the mixture was stirred at room temperature for 1.5 hours. Additional 20.5 ml of diisopropylethylamine and 9.0 ml of chloromethyl methyl ether were added and the mixture was stirred for 1.6 hours. Additional 5.1 ml of diisopropylethylamine and 2.2 ml of chloromethyl methyl ether were added and the mixture was stirred for 1 hour. An aqueous dilute solution of hydrochloric acid was added to the reaction solution, the mixture was extracted with dichloromethane, the organic layer was washed with water and an aqueous saturated solution of sodium chloride and dried over anhydrous sodium sulfate, and the solvent was distilled off under reduced pressure to give ethyl 2-(N-ethoxycarbonylamino)-3-fluoro-6-methoxymethoxybenzoate.

NMR (90 MHz, CDCl$_3$) δ (ppm) 1.28 (3H, t, J=7.2), 1.37 (3H, t, J=7.2), 3.48 (3H, s), 4.20 (2H, q, J=7.2), 4.38 (2H, q, J=7.1), 5.13 (2H, s), 6.71 (1H, brs), 6.97 (1H, dd, J=9.0, 4.6), 7.13 (1H, t, J=9.0)

MS (M/Z) 315 (M$^+$)

Molecular formula $C_{14}H_{18}FNO_6$=315

The resulting ethyl 2-(N-ethoxycarbonylamino)-3-fluoro-6-methoxymethoxybenzoate was dissolved in 200 ml of tetrahydrofuran under ice-cooling, 3.92 g of sodium hydride (60% oil dispersion) and 8.39 ml of pivaloyl chloride were added and the mixture was stirred at 0° C. for 45 minutes. Additional 785 mg of sodium hydride (60% oil dispersion) and 1.68 ml of pivaloyl chloride were added and the mixture was stirred at 0° C. for 40 minutes. An aqueous saturated solution of ammonium chloride was added to the reaction solution, the mixture was extracted with ether, the organic layer was washed with an aqueous saturated solution of sodium chloride and dried over sodium sulfate, and the solvent was distilled off under reduced pressure. The residue was subjected to silica gel column chromatography (n-hexane:ethyl acetate=4:1-3:1) to give 32.2 g (two stages 82%) of Compound A.

NMR (90 MHz, CDCl$_3$) δ (ppm) 1.20 (3H, t, J=7.0), 1.32 (3H, t, J=7.2), 1.39 (9H, s), 3.48 (3H, s), 4.19 (2H, q, J=6.8), 4.33 (2H, q, J=7.2), 5.14 (2H, s), 6.9–7.3 (2H, m)

MS (M/Z) 399 (M$^+$)

Molecular formula $C_{19}H_{26}FNO_7$32 399

REFERENCE EXAMPLE 2

Ethyl 6-(N-ethoxycarbonyl-N-pivaloylamino)-3-fluoro-2-methoxymethoxybenzoate (Compound B)

12.7 g of Compound D obtained in Reference Example 1 was dissolved in 100 ml of dichloroethane, 17.4 g of Onoda Florinate FP-T100 (Wako Pure Chemical Industries Ltd.) was added and the mixture was stirred at 60° to 70° C. for 2 hours. Additional 4.74 g of FP-T700 was added and the mixture was stirred at the same temperature for 2.5 hours. The solution was made acidic by addition of 1N hydrochloric acid thereto, the mixture was extracted with ether, the organic layer was washed with water and an aqueous saturated solution of sodium chloride and dried over sodium sulfate, and the solvent was distilled off under reduced pressure. The residue was subjected to silica gel column chromatography (n-hexane:ethyl acetate=8:1–4:1) to give 3.26 g (24%) of ethyl 6-(N-acethoxycarbonylamino)-3-fluoro-2-hydroxybenzoate.

NMR (90 MHz, CDCl$_3$) δ (ppm) 1.31 (3H, t, J=7.1), 1.51 (3H, t, J=7.1), 4.22 (2H, q, J=7.1), 4.56 (2H, q, J=7.2), 7.22 (1H, t, J=9.7), 7.79 (1H, dd, J=9.2, 4.4), 9.22 (1H, brs)

MS (M/Z) 271 (M$^+$)

Molecular formula C$_{12}$H$_{14}$FNO$_5$=271

11.2 g of the resulting ethyl 6-(N-ethoxycarbonylamino)-3-fluoro-2-hydroxybenzoate was dissolved in 100 ml of dichloromethane under argon atmosphere, 14.4 ml of diisopropylethylamine and 6.3 ml of chloromethyl methyl ether were added under ice-cooling and the mixture was stirred at room temperature for 40 minutes. An aqueous dilute solution of hydrochloric acid was added to the reaction solution, the mixture was extracted with dichloromethane, the organic layer was washed with water and an aqueous saturated solution of sodium chloride and dried over anhydrous sodium sulfate, and the solvent was distilled off under reduced pressure to give 6-(N-ethoxycarbonylamino)-3-fluoro-2-methoxymethoxybenzoate.

NMR (90 MHz, CDCl$_3$) δ (ppm) 1.30 (3H, t, J=7.1), 1.41 (3H, t, J=7.1), 3.55 (3H, s), 4.20 (2H, q, J=7.0), 4.43 (2H, q, J=7.0), 5.12 (2H, d, J=0.7), 7.18 (1H, t, J=9.8), 7.89 (1H, dd, J=9.3, 4.3), 8.45 (1H, brs)

Ms (M/z) 315 (M$^+$)

Molecular formula C$_{14}$H$_{18}$FNO$_6$=315

The resulting 6-(N-ethoxycarbonylamino)-3-fluoro-2-methoxymethoxybenzoate was dissolved in 80 ml of tetrahydrofuran under ice-cooling, 1.98 g of sodium hydride (60% oil dispersion) and 4.25 ml of pivaloyl chloride were added and the mixture was stirred at 0° C. for 3.8 hours. Additional 1.65 g of sodium hydride (60% oil dispersion) and 3.54 ml of pivaloyl chloride were added and the mixture was stirred at 0° C. for 35 minutes. An aqueous saturated solution of ammonium chloride was added to the reaction solution, the mixture was extracted with ether, the organic layer was washed with an aqueous saturated solution of sodium chloride and dried over anhydrous sodium sulfate, and the solvent was distilled off under reduced pressure. The residue was subjected to silica gel column chromatography (n-hexane:ethyl acetate=4:1) to give 15.7 g (two stages 95%) of Compound B.

NMR (90 MHz, CDCl$_3$) 67 (ppm) 1.19 (3H, t, J=7.0), 1.35 (3H, t, J=7.0), 1.35 (9H, s), 3.55 (3H, s), 4.17 (2H, q, J=7.1), 4.32 (2H, q, J=7.2), 5.17 (2H, s), 6.85 (1H, dd, J=8.8, 4.4), 7.16 (1H, dd, J=10.3, 9.0)

MS (M/Z) 399 (M$^+$)

Molecular formula C$_{19}$H$_{26}$FNO$_7$=399

REFERENCE EXAMPLE 3

Ethyl 3,5-difluoro-6-(N-ethoxycarbonyl-N-pivaloylamino)-2-methoxymethoxybenzoate (Compound C)

2.0 g of Compound D obtained in Reference Example 1 was dissolved in 30 ml of dichloroethane, 5.0 g of Onoda Florinate FP-T700 (Wako Pure Chemical Industries Ltd.) was added and the mixture was heated at reflux for 3.7 hours. Additional 1.25 g of FP-T700 was added and the mixture was heated at reflux for 50 minutes. Additional 1.25 g of FP-T700 was added and the mixture was heated at reflux for 1 hour. The reaction solution was made acidic by addition of 1N hydrochloric acid thereto, the mixture was extracted with ether, the organic layer was washed with water and an aqueous saturated solution of sodium chloride and dried over anhydrous sodium sulfate, and the solvent was distilled off under reduced pressure. The residue was subjected to silica gel column chromatography (n-hexane:ethyl acetate=9:1-3:1) to give 690 mg (30%) of ethyl 3,5-difluoro-6-(N-ethoxycarbonylamino)- 2-hydroxybenzoate.

NMR (90 MHz, CDCl$_3$) δ (ppm) 1.29 (3H, t, J=7.0), 1.43 (3H, t, J=7.1), 4.21 (2H, q, J=7.2), 4.47 (2H, q, J=7.1), 6.83 (1H, brs), 7.13 (1H, t, J=9.9), 10.54 (1H, s)

MS (M/Z) 289 (M$^+$)

Molecular formula C$_{12}$H$_{13}$F$_2$NO$_5$=289

5.72 g of the resulting ethyl 3,5-difluoro-6-(N-ethoxycarbonylamino)-2-hydroxybenzoate was dissolved in 70 ml of dichloromethane under argon atmosphere, 4.13 ml of diisopropylethylamine and 1.80 ml of chloromethyl methyl ether were added under ice-cooling and the mixture was stirred at 0° C. for 20 minutes. An aqueous dilute solution of hydrochloric acid was added to the reaction solution, the mixture was extracted with ether, the organic layer was washed with water and an aqueous saturated solution of sodium chloride and dried over anhydrous sodium sulfate, and the solvent was distilled off under reduced pressure to give ethyl 3,5-difluoro-6-(N-ethoxycarbonylamino)-2-methoxymethoxybenzoate.

NMR (90 MHz, CDCl$_3$) δ (ppm) 1.27 (3H, t, J=7.1), 1.38 (3H, t, J=7.3), 3.55 (3H, s), 4.19 (2H, q, J=7.1), 4.39 (2H, q, J=7.1), 5.11 (2H, s), 6.56 (1H, brs), 7.01 (1H, t, J=10.0)

MS (M/Z) 333 (M$^+$)

Molecular formula C$_{14}$H$_{17}$F$_2$NO$_6$=333

The resulting ethyl 3,5-difluoro-6-(N-ethoxycarbonylamino)-2-methoxymethoxybenzoate was dissolved in 35 ml of tetrahydrofuran under ice-cooling, 792 mg of sodium hydride (60% oil dispersion) and 1.69 ml of pivaloyl chloride were added and the mixture was stirred at 0° C. for 20 minutes. Additional 396 mg of sodium hydride (60% oil dispersion) and 0.85 ml of pivaloyl chloride were added and the mixture was stirred at 0° C. for 20 minutes. Additional 158 mg of sodium hydride (60% oil dispersion) and 0.34 ml of pivaloyl chloride were added and the mixture was stirred at 0° C. for 1.2 hours. An aqueous saturated solution of ammonium chloride was added to the reaction solution, the mixture was extracted with ether, the organic layer was washed with an aqueous saturated solution of sodium chloride and dried over anhydrous sodium sulfate, and the solvent was distilled off under reduced pressure to give 6.63 g (two stages 80%) of Compound C.

NMR (90 MHz, CDCl$_3$) δ (ppm) 1.20 (3H, t, J=7.0), 1.33 (3H, t, J=7.0), 1.39 (9H, s), 3.55 (3H, s), 4.18 (2H, q, J=7.0), 4.33 (2H, q, J=7.0), 5.12 (2H, s), 7.00 (1H, dd, J=10.2, 9.1)

MS (M/Z) 417 (M$^+$)

Molecular formula C$_{19}$H$_{25}$F$_2$NO$_7$=417

REFERENCE EXAMPLE 4

Ethyl 3,5-difluoro-6-pivaloylamino-2-(2-tetrahydropyranyloxy)benzoate (Compound E)

104 g (796 mmol) of 2,4-difluorophenol was dissolved in 800 ml of dichloromethane, 132 ml of triethylamine and 92.0 ml of ethyl chloroformate were added under ice-cooling and the mixture was stirred at −10° to 0° C. for 2 hours. The reaction solution was washed with an aqueous saturated solution of sodium chloride and dried over anhydrous magnesium sulfate and the solvent was distilled off under reduced pressure to give 156 g (97%) of 2,4-difluoro-O-ethoxycarbonylphenol.

NMR (90 MHz, CDCl$_3$) δ (ppm) 1.39 (3H, t, J=7.0), 4.33 (2H, q, J=7.0), 6.7–7.3 (3H, m)

MS (M/Z) 202 (M$^+$)

Molecular formula C$_9$H$_8$F$_2$O$_3$=202

50.5 g (250 mmol) of the resulting 2,4-difluoro-O-ethoxycarbonylphenol was dissolved in 115 ml of concentrated sulfuric acid, 15.9 ml of fuming nitric acid was added while maintaining the internal temperature at from 10° to 20° C. and the mixture was stirred at the same temperature for 1 hour. The reaction solution was poured into ice water and the mixture was extracted with 500 ml of ethyl acetate. The organic layer was washed twice with an aqueous saturated solution of sodium chloride and dried over anhydrous sodium sulfate and the solvent was distilled off under reduced pressure. The residue was dissolved in 1.0 liter of methanol, 50 ml of water and 40 g of sodium bicarbonate were added and the mixture was stirred at room temperature for 16 hours. The reaction solution was filtered, methanol was distilled off under reduced pressure, and the mixture was adjusted to pH 5 by addition of 200 ml of water thereto and extracted twice with 200 ml of ethyl acetate. The organic layer was washed once with 400 ml of water and once with 400 ml of an aqueous saturated solution of sodium chloride and dried over sodium sulfate. The solvent was distilled off under reduced pressure to give 41.6 g (95%) of 2,4-difluoro-5-nitrophenol.

NMR (90 MHz, CDCl$_3$) δ (ppm) 7.23 (1H, t, J=9.9), 7.76 (1H, dd, J=8.6, 7.3)

MS (M/Z) 175 (M$^+$)

Molecular formula C$_6$H$_3$F$_2$NO$_3$=175

24.9 g (142 mmol) of the resulting 2,4-difluoro-5-nitrophenol was dissolved in 150 ml of ethyl acetate, 5.0 g of 10% palladium-carbon was added and the mixture was stirred at 50° to 60° C. for 27 hours under a stream of hydrogen. The reaction vessel was filled with nitrogen, the reaction solution was filtered by means of suction, the solvent was distilled off under reduced pressure, and the residue was triturated with n-hexane to give 19.8 g (96%) of 5-amino-2,4-difluorophenol.

NMR (90 MHz, CDCl$_3$) δ (ppm) 4.75 (2H, brs), 6.37 (1H, t, J=9.1), 6.87 (1H, t, J=11.1), 9.21 (1H, s)

MS (M/Z) 145 (M$^+$)

Molecular formula C$_6$H$_5$F$_2$NO=145

18.9 g (130 mmol) of the resulting 5-amino-2,4-difluorophenol was dissolved in 45 ml of pyridine, 16.0 ml of pivaloyl chloride was added dropwise over 8 minutes under ice-cooling, and the mixture was stirred at the same temperature for 30 minutes. 1N hydrochloric acid was added to the reaction solution and the mixture was extracted with ether. The organic layer was washed once with a 1N aqueous solution of hydrochloric acid, water and an aqueous saturated solution of sodium chloride, respectively, and dried over magnesium sulfate. The solvent was distilled off under reduced pressure and the residue was triturated with n-hexane to give 27.0 g (91%) of 2,4-difluoro-5-pivaloylaminophenol.

NMR (90 MHz, CDCl$_3$) δ (ppm) 1.35 (9H, s), 6.90 (1H, t, J=10.4), 7.65 (1H, brs), 7.94 (1H, brs), 8.24 (1H, dd, J=9.1, 8.0)

MS (M/Z) 229 (M$^+$)

Molecular formula C$_{11}$H$_{13}$F$_2$NO$_2$=229

2.15 g (9.39 mmol) of the resulting 2,4-difluoro-5-pivaloylaminophenol was dissolved in 40 ml of dichloromethane, 4.3 ml of 3,4-dihydro-2H-pyrane and 44 mg of camphorsulfonic acid were added and the mixture was stirred at room temperature for 4.3 hours. The reaction solution was added to a 5% aqueous solution of potassium carbonate and the mixture was extracted with chloroform. The organic layer was washed once with water and once with an aqueous saturated solution of sodium chloride and dried over anhydrous magnesium sulfate. The solvent Was distilled off under reduced pressure and the residue was triturated with n-hexane to give 2.51 g (85%) of 2,4-difluoro-5-pivaloylamino-O-(2-tetrahydropyranyl)phenol.

NMR (90 MHz, CDCl$_3$) δ (ppm) 1.31 (9H, s), 1.4–2.2 (6H, m), 3.4–4.2 (2H, m), 5.43 (1H, brs), 6.89 (1H, t, J=10.4), 7.44 (1H, brs), 8.25 (1H, t, J=8.5)

MS (M/Z) 313 (M$^+$)

Molecular formula C$_{16}$H$_{21}$F$_2$NO$_3$=313

31.3 g (100 mmol) of the resulting 2,4-difluoro-5-pivaloylamino-O-(2-tetrahydropyranyl)phenol was dissolved in 300 ml of tetrahydrofuran under argon atmosphere, 40 ml of hexamethylphosphoric triamide was added and the mixture was cooled to −78° C. 140 ml of a 1.6M solution of n-butyl lithium in n-hexane was added to the reaction solution at an internal temperature of −60° C. or below and the mixture was stirred at the same temperature for 1 hour. 19 ml of ethyl chloroformate was added, and the mixture was stirred while raising the temperature gradually. After 2.2 hours when the internal temperature was raised up to −15° C., water was added and the mixture was extracted with ethyl acetate. The organic layer was washed once with water and once with an aqueous saturated solution of sodium chloride and dried over anhydrous magnesium sulfate. The solvent was distilled off under reduced pressure and the residue was triturated with n-hexane to give 23.4 g (61%) of Compound E.

NMR (90 MHz, CDCl$_3$) δ (ppm) 1.28 (9H, s), 1.38 (3H, t, J=7.0), 1.4–2.0 (6H, m), 3.3–4.1 (2H, m), 4.36 (2H, q, J=7.0), 5.32 (1H, brs), 7.00 (1H, dd, J=10.7, 9.6), 7,57 (1H, brs)

FAB-MS (M/Z) 386 (M$^+$+1)

Molecular formula C$_{19}$H$_{25}$F$_2$NO$_5$=385

REFERENCE EXAMPLE 5

Ethyl 3,5-difluoro-6-pivaloylamino-2-(2-tetrahydropyranyloxy)-4-trimethylsilylbenzoate (Compound F)

161 ml (1.15 mmol) of diisopropylamine was dissolved in 500 ml of tetrahydrofuran under a Stream of nitrogen, 690 ml of a 1.6M solution of 1.10 mol of n-butyl lithium in n-hexane was added over 30 minutes while maintaining an internal temperature at −20° to 0° C. and the mixture was cooled to an internal temperature of -60° C. or below. A solution of 156 g (0.50 mol) of 2,4-difluoro-5-pivaloylamino-O-(2-tetrahydropyranyl)phenol obtained in Reference Example 4 dissolved in 900 ml of tetrahydrofuran was added thereto over 40 minutes while maintaining an internal temperature at −55° C. or below and the mixture was stirred for 10 minutes. 114 ml (0.90 mol) of trimethylsilyl chloride was added thereto over 15 minutes while maintaining an internal temperature at −60° C. or below and the mixture was stirred at the same temperature for 1 hour. 50 ml of water was added to stop the reaction, the temperature was raised to room temperature, 1000 ml of water and 1000 ml of ethyl acetate were further added and the mixture was stirred vigorously. The organic layer was separated, washed once with water and once with an aqueous saturated solution of sodium chloride and dried over anhydrous magnesium sulfate. The solvent was distilled off under reduced pressure to give 189 g (98%) of 2,4-difluoro-5-pivaloylamino-3-trimethylsilyl-O-(2-tetrahydropyranyl)phenol.

NMR (90 MHz, CDCl$_3$) δ (ppm) 0.37 (9H, m), 1.31 (9H, s), 1.4–2.1 (6H, m), 3.4–3.8 (2H, m), 5.41 (1H, brs), 7.50 (1H, brs), 8.27 (1H, t, J=8.8)

FAB-MS (M/Z) 386 (M$^+$+1)

Molecular formula C$_{19}$H$_{29}$F$_2$NO$_3$Si=385

268 g (0.70 mmol) of the resulting 2,4-difluoro-5-pivaloylamino-3-trimethylsilyl-O-(2-tetrahydropyranyl)phenol was dissolved in 2 liter of tetrahydrofuran under a stream of nitrogen and the mixture was cooled to an internal temperature of −60° C. or below. 1.0 liter of a 1.6M solution of 1.6 mol of n-butyl lithium in N-hexane was added thereto at a temperature of −50° C. or below over 1 hour. The reaction solution was warmed to −45° C., stirred for 5 minutes and cooled again to −60° C. or below. 133 ml (1.4 mol) of ethyl chloroformate was added thereto at an internal temperature of −55° C. or below and the mixture was stirred at the same temperature for 10 minutes. 50 ml of water was added to stop the reaction, the mixture was warmed to room temperature, 1 liter of water and 1 liter of ethyl acetate were added and the mixture was stirred vigorously. The organic layer was separated, washed once with water and once with an aqueous saturated solution of sodium chloride and dried over magnesium sulfate, and the solvent was distilled off under reduced pressure. About 1 liter of petroleum ether (b.p.30°–60° C.) was added to the solidified residue to form slurry which was cooled on ice and collected by filtration to give 245 g (77%) of Compound F. The mother liquor was concentrated and the similar operations were carried out to give additional 11.4 g (3.6%) of Compound F.

NMR (90 MHz, CDCl$_3$) δ (ppm) 0.37 (9H, t, J=1.7), 1.28 (9H, s), 1.37 (3H, t, J=7.0), 1.4–2.1 (6H, m), 3.4–4.1 (2H, m), 4.33 (2H, q, J=7.0), 5.26 (1H, brs), 7.46 (1H, brs)

FAB-MS (M/z) 458 (M$^+$+H)

Molecular formula C$_{22}$H$_{33}$F$_2$NO$_5$Si=457

REFERENCE EXAMPLE 6

3'-Fluoro-4'-pivaloylaminoacetophenone (Compound G)

(1) 250 g (1.32 mol) of 4-bromo-2-fluoroaniline was dissolved in 500 mL of pyridine, 178 mL (1.45 mol) of pivaloyl chloride was added dropwise under ice-cooling and the mixture was stirred for 10 minutes. The reaction solution was poured into 1.5 L of ice water and the precipitated crystals were collected by filtration. The crystals were washed with 1N hydrochloric acid and water and dried by heating at 40° to 60° C. under reduced pressure to give 350 g of 4-bromo-2-fluoro-N-pivaloylaniline (yield: 97%).

(2) 70.6 g (258 mmol) of the above 4-bromo-2-fluoro-N-pivaloylaniline was dissolved in 500 mL of toluene under argon atmosphere, 108 mL (310 mmol) of 1-ethoxyvinyltributyltin and 1.80 g (2.57 mmol) of bis(triphenylphosphine)palladium (II) chloride were added and the mixture was stirred at 100° C. for 5 hours.

The reaction solution was cooled on ice, 500 mL of 2N hydrochloric acid was added, the mixture was stirred at room temperature for 2 hours and the insoluble matters were filtered off. The filtrate was extracted once with ethyl acetate, 500 mL of a 10% aqueous solution of ammonium fluoride was added to the organic layer and the mixture was stirred at room temperature for 3 hours. The insoluble matters were filtered off, and the organic layer was washed once with water and once with an aqueous saturated solution of sodium chloride and dried over anhydrous sodium sulfate. The solvent was distilled off under reduced pressure and the residue was purified by silica gel column chromatography (n-hexane:ethyl acetate=6:1-4:1) to give 60.8 g of a compound G (yield: 99%).

NMR (90 MHz, CDCl$_3$) δ (ppm) 1.35 (s, 9H), 2.57 (s, H), 7.6–7.9 (m, 3H), 8.53 (t, 1H, J=8.4 Hz)

EIMS (M/Z) 237 (M$^+$)

Molecular formula C$_{13}$H$_{16}$FNO$_2$=237

REFERENCE EXAMPLE 7

3'-Chloro-4'-pivaloylaminoacetophenone (Compound H)

(1) Substantially the same manner as that in Reference Example 6 (1) was repeated except that 20.6 g (100 mmol) of 4-bromo-2-chloroaniline was used, to give 27.8 g of 4-bromo-2-chloro-N-pivaloylaniline (yield: 96%).

(2) Substantially the same manner as that in Reference Example 6 (2) was repeated except that 2.91 g (10.0 mmol) of the above 4-bromo-2-chloro-N-pivaloylaniline was used, to give 1.64 g of compound H (yield: 65%).

NMR (90 MHz, CDCl$_3$) δ (ppm) 1.30 (t, 3H, J=7.7 Hz), 1.35 (s, 9H), 2.57 (s, 3H), 2.65 (q, 2H, J=7.7 Hz), 7.47 (brs, 1H), 7.7–7.9 (m, 2H), 8.25 (d, 1H, J=9.0 Hz)

EIMS (M/Z) 247 (M$^+$)

Molecular formula C$_{15}$H$_{21}$NO$_2$=247

REFERENCE EXAMPLE 8

3,-Ethyl-4'-pivaloylaminoacetophenone (Compound J)

(1) Substantially the same manner as that in Reference Example 6 (1) was repeated except that 4.68 g (19.8 mmol) of 4-bromo-2-ethylaniline was used, to give 5.10 g of 4-bromo-2-ethyl-N-pivaloylaniline (yield: 90%).

(2) Substantially the same manner as that in Reference Example 6 (2) was repeated except that 4.28 g (15.0 mmol) of the above 4-bromo-2-ethyl-N-pivaloylaniline was used, to give 3.23 g of compound J (yield: 87%).

NMR (90 MHz, CDCl$_3$) δ (ppm) 1.36 (s, 9H), 2.57 (s, 3H), 7.80 (dd, 1H, J=8.8, 2.0 Hz), 8.01 (d, 1H, J=2.0 Hz), 8.20 (brs, 1H), 8.58 (d, 1H, J=8.6 Hz)

EIMS (M/Z) 253 (M$^+$)

Molecular formula C$_{13}$H$_{16}$$^{35}$ClNO$_2$=253

REFERENCE EXAMPLE 9

3,5,-Dichloro-4'-pivaloylaminoacetophenone (Compound K)

(1) 12.0 g (50.0 mmol) of 4-bromo-2,6-dichloroaniline hydrochloride was dissolved in 50 mL of pyridine, 9.90 mL (80.0 mmol) of pivaloyl chloride and 0.61 g (5.0 mmol) of N,N-dimethylaminopyridine were added and the mixture was stirred at 40° C. for 28 hours. Thereafter, substantially the same manner as that in Reference Example (1) was repeated to give 15.7 g of 4-bromo-2,6-dichloro-N-pivaloylaniline (yield: 97%).

(2) Substantially the same manner as that in Reference Example 6 (2) was repeated except that 11.4 g (35.0 mmol) of the above 4-bromo-2,6-dichloro-N-pivaloylaniline was used and the recrystallization from toluene/n-hexane was carried out in place of purification by silica gel column chromatography, to give 8.93 g of compound K (yield: 89%).

NMR (90 MHz, CDCl$_3$) δ (ppm) 1.38 (s, 9H), 2.58 (s, 3H), 7.26 (brs, 1H), 7.90 (s, 2H)

EIMS (M/Z) 287 (M$^+$)

Molecular formula C$_{13}$H$_{15}$$^{35}$Cl$_2$NO$_2$=287

REFERENCE EXAMPLE 10

6,8-Difluoro-2-(3-fluoro-4-pivaloylaminophenyl)-5-pivaloylamino-4H-1-benzopyran-4-one (Compound L)

(1) 200 g of ethyl 6-(N-ethoxycarbonyl-N-pivaloylamino)-2-(2-tetrahydropyranyloxy)benzoate obtained according to the known method (JP-A-61-78) was dissolved in 900 mL of ethanol, 300 mL of concentrated hydrochloric acid was added and the mixture was heated at reflux for 3.5 hours. The reaction solution was cooled on ice, 500 mL of water was added and the resulting crystals were collected by filtration to give 89.1 g of ethyl 6-(N-ethoxycarbonylamino)-2-hydroxybenzoate (yield: 74%).

NMR (90 MHz, CDCl$_3$) δ (ppm) 1.31 (t, 3H, J=7.0 Hz), 1.50 (t, 3H, J=7.0 Hz), 4.22 (q, 2H, J=7.0 Hz), 4.53 (q, 2H, J=7.0 Hz), 6.65 (dd, 1H, J=8.2, 1.2 Hz), 7.37 (t, 1H, J=8.4 Hz), 7.86 (dd, 1H, J=8.4, 1.1 Hz), 9.48 (brs, 1H), 10.74 (s, 1H)

MS (M/Z) 253 (M$^+$)

Molecular formula C$_{12}$H$_{15}$NO$_5$=253

(2) 2.0 g of the above ethyl 6-(N-ethoxycarbonylamino)-2-hydroxybenzoate was dissolved in 30 mL of dichloroethane, 5.0 g of Onoda Florinate FP-T700 (Wako Pure Chemical Industries Ltd.) was added and the mixture was heated at reflux for 3.7 hours. 1.25 g of FP-T700 was further added and the mixture was heated at reflux for 50 minutes. 1.25 g of FP-T700 was further added and the mixture was heated at reflux for 1 hours. The reaction solution was made acidic by addition of 1N hydrochloric acid thereto, the mixture was extracted with ether, the organic layer was washed with water and an aqueous saturated solution of sodium chloride, and dried over anhydrous sodium sulfate, and the solvent was distilled off under reduced pressure. The residue was purified by silica gel column chromatography (n-hexane-:ethyl acetate=9:1-3:1) to give 690 mg of ethyl 3,5-difluoro-6-(N-ethoxycarbonylamino)-2-hydroxybenzoate (yield: 30%).

NMR (90 MHz, CDCl$_3$) δ (ppm) 1.29 (t, 3H, J=7.0 Hz), 1.43 (t, 3H, J=7.1 Hz), 4.21 (q, 2H, J=7.2 Hz), 4.47 (q, 2H, J=7.1 Hz), 6.83 (brs, 1H), 7.13 (t, 1H, J=9.9 Hz), 10.54 (s, 1H)

MS (M/Z) 289 (M$^+$)

Molecular formula C$_{12}$H$_{13}$F$_2$NO$_5$=289

(3) 5.72 g of the above ethyl 3,5-difluoro-6-(N-ethoxycarbonylamino)-2-hydroxybenzoate was dissolved in 70 mL of dichloromethane under argon atmosphere, 4.13 mL of diisopropylethylamine and 1.80 mL of chloromethyl methyl ether were added under ice-cooling and the mixture was stirred at 0° C. for 20 minutes. Dilute hydrochloric acid was added to the reaction solution and the mixture was extracted with ether. The organic layer was washed with water and an aqueous saturated solution of sodium chloride, and dried over anhydrous sodium sulfate, and the solvent was distilled off under reduced pressure to give ethyl 3,5-difluoro-6-(N-ethoxycarbonylamino)-2-methoxymethoxybenzoate.

NMR (90 MHz, CDCl$_3$) δ (ppm) 1.27 (t, 3H, J=7.1 Hz), 1.38 (t, 3H, J=7.3 Hz), 3.55 (s, 3H), 4.19 (q, 2 H, J=7.1 Hz), 4.39 (q, 2H, J=7.1 Hz), 5.11 (s, 2H), 6.56 (brs, 1H), 7.01 (t, 1H, J=10.0 Hz)

MS (M/Z) 333 (M$^+$)

Molecular formula C$_{14}$H$_{17}$F$_2$NO$_6$=333

(4) The above ethyl 3,5-difluoro-6-(N-ethoxycarbonylamino)-2-methoxymethoxybenzoate was dissolved in 35 mL of tetrahydrofuran under ice-cooling, 792 mg of sodium hydride (60% oil dispersion) and 1.69 mL of pivaloyl chloride were added and the mixture was stirred at 0° C. for 25 minutes. 396 mg of sodium hydride (60% oil dispersion) and 0.85 mL of pivaloyl chloride were further added and the mixture was stirred at 0° C. for 20 minutes. 158 mg of sodium hydride (60% oil dispersion) and 0.34 mL of pivaloyl chloride were further added and the mixture was stirred 0 ° C. for 1.2 hours. An aqueous saturated solution of ammonium chloride was added to the reaction solution and the mixture was extracted with ether. The organic layer was washed with an aqueous saturated solution of sodium chloride, and dried over anhydrous sodium sulfate, and the solvent was distilled off under reduced pressure to give 6.63 g of ethyl 3,5-difluoro-6-(N-ethoxycarbonyl-N-pivaloylamino)-2-methoxymethoxybenzoate (two stage yield: 80%).

NMR (90 MHz, CDCl$_3$) δ (ppm) 1.20 (t, 3H, J=7.0 Hz), 1.33 (t, 3H, J=7.0 Hz), 1.39 (s, 9H), 3.55 (s, 3 H), 4.18 (q, 2H, J=7.0 Hz), 4.33 (q, 2H, J=7.0 Hz), 5.12 (s, 2H), 7.00 (dd, 1H, J=10.2, 9.1 Hz)

MS (M/Z) 417 (M$^+$)

Molecular formula C$_{19}$H$_{25}$F$_2$NO$_7$=417

(5) A solution of 4.19 g of the above ethyl 3,5-difluoro-6-(N-ethoxycarbonyl-N-pivaloylamino)-2-methoxymethoxybenzoate and 1.98 g of 3'-fluoro-4'-pivaloylaminoacetophenone dissolved in 23 mL of dioxane was added dropwise to a suspension obtained by adding 10 mL of dioxane to 737 mg of sodium hydride (60% oil dispersion) and the mixture was heated at reflux for 2.3 hours. The reaction solution was cooled, water was added, the aqueous layer was washed with n-hexane and further extracted with ethyl acetate. The ethyl acetate layer was washed with an aqueous saturated solution of sodium chloride, dried over anhydrous sodium sulfate and purified by silica gel column chromatography (chloroform: acetone=40:1-30:1) to give 3.37 g of a 1,3-diketone compound (yield: 75%).

(6) 3.37 g of the above 1,3-diketone compound was dissolved in 80 mL of ethanol, 20 mL of concentrated hydrochloric acid was added and the mixture was stirred at room temperature for 6.6 hours. The reaction solution was cooled on ice, 100 mL of water was added, and the precipitated crystals were collected by filtration to give 2.72 g of compound L (yield: 91%).

NMR (90 MHz, CDCl$_3$) δ (ppm) 1.36 (s, 9H), 1.38 (s, 9H), 6.68 (s, 1H), 7.35 (t, 1H, J=9.5Hz), 7.5–7.9 (m, 2H), 8.60 (t, 1H, J=8.4 Hz)

MS (M/Z) 474 (M$^+$)

Molecular formula C$_{25}$H$_{25}$F$_3$N$_2$O$_4$=474

REFERENCE EXAMPLE 11

3',4',5'-Trifluoro-2'-hydroxy-6'-pivaloylaminoacetophenone (Compound M)

(1) 7.40 g (50.0 mmol) of 2,3,4-trifluorophenol was dissolved in 50 mL of dichloromethane, 8.30 mL (60.0 mmol) of triethylamine and 5.74 mL (60.0 mmol) of ethyl chloroformate were added under ice-cooling and the mixture was stirred at room temperature for 20 minutes. Water was added to the reaction solution and the mixture was extracted once with chloroform. The organic layer was washed once with an aqueous saturated solution of sodium chloride, and dried over anhydrous sodium sulfate, and the solvent was distilled off under reduced pressure to give 9.83 g of O-ethoxycarbonyl-2,3,4-trifluorophenol (yield: 89%).

NMR (90 MHz, CDCl$_3$) δ (ppm) 1.40 (t, 3H, J=7.0 Hz), 4.34 (q, 2H, J=7.0 Hz), 6.9–7.1 (m, 2H)

(2) 9.82 g (44.6 mmol) of the above O-ethoxycarbonyl-2,3,4-trifluorophenol was dissolved in 25 mL of concentrated sulfuric acid under ice-cooling, 8.0 mL of fuming nitric acid was added at an internal temperature of 50° C. or below and the mixture was further stirred for 2 hours. The reaction solution was poured into 300 mL of ice water and the mixture was extracted once with ethyl acetate. The organic layer was washed once with water and twice with an aqueous saturated solution of sodium chloride and dried over anhydrous sodium sulfate. The solvent was distilled off under reduced pressure and the residue was purified by silica gel column chromatography (n-hexane:ethyl acetate=20:1) to give 1.44 g of O-ethoxycarbonyl-2,3,4-trifluoro-5-nitrophenol (yield: 12%).

NMR (90 MHz, CDCl$_3$) δ (ppm) 1.42 (t, 3H, J=7.3 Hz), 4.39 (q, 2H, J=7.3 Hz), 7.92 (td, 1H, J=7.0, 2.4 Hz)

FAB-MS (Negative) (M/Z) 264 (M$^+$+H)

Molecular formula C$_9$H$_6$F$_3$NO$_5$=265

(3) 1.43 g (5.40 mmol) of the above O-ethoxycarbonyl-2,3,4-trifluoro-5-nitrophenol was dissolved in 20 mL of ethyl acetate under argon atmosphere, 200 mg of 10% palladium/carbon was added thereto, the gaseous phase in the reaction vessel was substituted with hydrogen and the mixture was stirred at room temperature for 4 hours. The reaction solution was filtered and the solvent was distilled off under reduced pressure to give 1.27 g of 5-amino-O-ethoxycarbonyl-2,3,4-trifluorophenol (yield: 100%).

NMR (90 MHz, CDCl$_3$) δ (ppm) 1.38 (t, 3H, J=7.3 Hz), 3.45 (brs, 2H), 4.34 (q, 2H, J=7.3 Hz), 6.3–6.5 (m, 1H)

EIMS (M/Z) 235 (M$^+$)

Molecular formula C$_9$H$_8$F$_3$NO$_3$=235

(4) 1.27 g (5.40 mmol) of the above 5-amino-O-ethoxycarbonyl-2,3,4-trifluorophenol was dissolved in 5 mL of pyridine, 0.80 mL (6.5 mmol) of pivaloyl chloride was added under ice-cooling and the mixture was stirred at the same temperature for 15 minutes. 1N hydrochloric acid was added to the reaction solution and the mixture was extracted once with ethyl acetate. The organic layer was washed once with water and once with an aqueous saturated solution of sodium chloride, dried over anhydrous sodium sulfate and the solvent was distilled off under reduced pressure. The residue was dissolved in 25 mL of methanol, 1.40 g (10.1 mmol) of potassium carbonate and 15 mL of water were added and the mixture was stirred at room temperature for 4 hours. The reaction solution was adjusted to pH 2 by addition of 2N hydrochloric acid thereto and the mixture was extracted once with ethyl acetate. The organic layer was washed once with water and once with an aqueous saturated solution of sodium chloride, and dried over anhydrous sodium sulfate, and the solvent was distilled off under reduced pressure to give 1.20 g of 2,3,4-trifluoro-5-pivaloylaminophenol (two stage yield: 90%).

NMR (90 MHz, CDCl$_3$) δ (ppm) 1.36 (s, 9H), 7.66 (brs, 1H), 8.02 (ddd, 1H, J=8.4, 7.3, 2.6 Hz), 8.45 (brs, 1H)

EIMS (M/Z) 247 (M$^+$)

Molecular formula C$_{11}$H$_{12}$F$_3$NO$_2$=247

(5) 1.19 g (4.82 mmol) of the above 2,3,4-trifluoro-5-pivaloylaminophenol was dissolved in 50 mL of dichloromethane, 0.88 mL (9.6 mmol) of 3,4-dihydro-2 H-pyran and 22 mg (0.095 mmol) of dl-camphorsulfonic acid were added and the mixture was stirred at room temperature for 1 hour. The reaction solution was poured into 100 mL of a 10% aqueous solution of potassium carbonate and the mixture was extracted once with chloroform. The organic layer was washed once with an aqueous saturated solution of sodium chloride and dried over anhydrous sodium sulfate. The solvent was distilled off under reduced pressure and the residue was triturated with n-hexane to give 1.25 g of 2,3,4-trifluoro-5-pivaloylamino-O-tetrahydropyranylphenol (yield: 78%).

(6) 3.60 g (10.9 mmol) of the above 2,3,4-trifluoro-5-pivaloylamino-O-tetrahydropyranylphenol was dissolved in 50 mL of tetrahydrofuran, 14 mL of a 1.6 M solution of n-butyl lithium in n-hexane was added dropwise to the solution at an internal temperature of −60° C. or below, the mixture was warmed to −35° C. and cooled again to −60° C. or below. About 2 mL of acetaldehyde was added thereto in a gaseous condition and the mixture was stirred for 20 minutes. Water was added to the reaction solution, the mixture was warmed to room temperature and extracted once with ethyl acetate. The organic layer was washed once with water and once with an aqueous saturated solution of sodium chloride and dried over anhydrous sodium sulfate. The solvent was distilled off under reduced pressure and the residue was purified by silica gel column chromatography (n-hexane:ethyl acetate=5:1-3:1) to give 2.45 g of a mixture of diastereomers of 2,3,4-trifluoro-6-(1-hydroxyethyl)-5-pivaloylamino-O-tetrahydropyranylphenol (yield: 60%).

FAB-MS (M/Z) 376 (M$^+$+H)

Molecular formula C$_{18}$H$_{24}$F$_3$NO$_4$=375

(7) 2.45 g (6.53 mmol) of the above 2,3,4-trifluoro-6-(1-hydroxyethyl)-5-pivaloylamino-O-tetrahydropyranylphenol was dissolved in 50 mL of acetone, a Jones reagent was added thereto under ice-cooling until a starting material was consumed and 2 mL of 2-propanol was added. Water was added to the reaction solution and the mixture was extracted twice with ethyl acetate. The organic layer was washed twice with water and once with an aqueous saturated solution of sodium chloride and dried over anhydrous sodium sulfate. The solvent was distilled off under reduced pressure, the residue was dissolved in 40 mL of tetrahydrofuran, 10 mL of 1N hydrochloric acid was added and the mixture was stirred at room temperature for 40 minutes. Water was added to the reaction solution and the mixture was extracted once with ethyl acetate. The organic layer was washed once with an aqueous saturated solution of sodium chloride and dried over anhydrous sodium sulfate. The solvent was distilled off under reduced pressure and the residue was purified by silica gel column chromatography (chloroform:ethyl acetate= 50:1) to give 1.26 g of compound M (two stage yield: 75%).

NMR (90 MHz, CDCl$_3$) δ (ppm) 1.34 (s, 9H), 2.50 (s, 3H), 7.55 (brs, 1H), 11.1 (brs, 1H)

FAB-MS (M/Z) 290 (M$^+$+H)

Molecular formula C$_{13}$H$_{14}$F$_3$NO$_3$=289

REFERENCE EXAMPLE 12

4-Acetylamino-3-fluorobenzoic acid (Compound N)

696 mg (3.0 mmol) of 4-bromo-2-fluoroacetanilide was dissolved in 12 mL of tetrahydrofuran under argon atmosphere and the solution was cooled to not higher than −60° C. 4.1 mL of a 1.6M solution of n-butyl lithium in n-hexane was added to the solution and the mixture was stirred for 20 minutes. About 2 g of dry ice was added thereto and the mixture was stirred for 1.5 hours. Water was added to the reaction solution, the mixture was warmed to room temperature, a 1N aqueous solution of sodium hydroxide was added to adjust the pH to 10 or above, ethyl acetate was added and the two layers were separated. 4N hydrochloric acid was added to the aqueous layer to adjust the pH to 1 and the mixture was stirred under ice-cooling. The precipitated crystals were collected by filtration to give 378 mg of a compound N (yield: 64%).

NMR (90 MHz, DMSO-$d_6$) δ (ppm) 2.14 (s, 3H), 7.6–7.8 (m, 2H), 8.19 (t, 1H, J=8.4 Hz), 9.90 (brs, 1H)

EIMS (M/Z) 197 (M$^+$)

Molecular formula $C_9H_8FNO_3$=197

REFERENCE EXAMPLE 13

2-(4-Allyloxycarbonylamino-3-fluorophenyl)-5-amino-6,8-difluoro-7-hydroxymethyl-4H-1-benzopyran-4-one (Compound P)

6.72 mg (20.0 mmol) of Compound 118 obtained in Example 118 was dissolved in 200 mL of pyridine, 10.6 mL (100 mmol) of allyl chloroformate was added dropwise under ice-cooling, and the mixture was stirred at room temperature for 1.5 hours. Water was added to the reaction solution and the precipitated crystals were collected by filtration. The crystals were dissolved in 500 mL of ethanol, 18 mL of a 2N aqueous solution of sodium hydroxide was added, and the mixture was stirred at room temperature for 1.5 hours. Water was added to the reaction solution and the precipitated crystals were collected by filtration, to give 6.92 g of Compound P (yield: 82%).

NMR (90 MHz, DMSO-$d_6$) δ (ppm) 4.5–4.7 (m, 4H), 5.1–5.5 (m, 2H), 5.7–6.2 (m, 1H), 6.90 (s, 1H), 7.01 (brs, 2H), 7.7–8.0 (m, 4H), 9.79 (brs, 1H)

FAB-MS (M/Z) 421 (M$^+$+H)

Molecular formula $C_{20}H_{15}F_3N_2O_5$=420

REFERENCE EXAMPLE 14

3'-Fluoro-4'-pivaloylaminoacetophenone 250 g (1.32 mol) of 4-bromo-2-fluoroaniline was dissolved in 500 mL of pyridine, 178 mL (1.45 mol) of pivaloyl chloride was added dropwise under ice-cooling, and the mixture was stirred for 10 minutes. The reaction solution was poured into 1.5 L of ice-water and the precipitated crystals were collected by filtration. The crystals were washed with 1N HCl and water, and dried under reduced pressure, to give 350 g of 4-bromo-2-fluoro-N-pivaloylaniline (yield: 97%).

70.6 g (258 mmol) of the above 4-bromo-2-fluoro-N-pivaloylaniline was dissolved in 500 mL of toluene under argon atmosphere, 108 mL (310 mmol) of 1-ethoxyvinyltributyltin and 1.80 g (2.57 mmol) of bis(triphenylphosphine)palladium (II) chloride were added, and the mixture was stirred at 100° C. for 5 hours. The reaction solution was cooled on ice, 500 mL of 2N HCL was added, and the mixture was stirred at room temperature for 2 hours. The insoluble matters were filtered off and the filtrate was extracted once with ethyl acetate. 500 mL of a 10% aqueous solutiuon of ammonium fluoride was added to the organic layer and the mixture was stirred at room temperature for 3 hours. The insoluble matters were filtered off and the organic layer was washed once with water and once with an aqueous saturated solution of sodium chloride and dried over anhydrous sodium sulfate. The solvent was distilled off under reduced pressure and the residue was purified by silica gel column chromatography (n-hexane:ethyl acetate=6:1-4:1), to give 60.8 g of 3'-fluoro-4'-pivaloylaminoacetophenone (yield: 99%).

NMR(90 MHz, CDCl$_3$) δ (ppm) 1.35 (s, 9H), 2.57 (s, 3H), 7.6–7.9 (m, 3H), 8.53 (t, 1H, J=8.4 Hz)

EI-MS (M/Z) 237(M$^+$)

Molecular formula $C_{13}H_{16}FNO_2$=237

REFERENCE EXAMPLE 15

3',5'-Dichloro-4'-pivaloylaminoacetophenone

Substantially the same manner as that in Reference Example 14 was repeated except that 4-bromo-2,6-dichloroaniline was used instead of 4-bromo- -fluoroaniline, to give 8.93 g of 3',5'-dichloro-4'-pivaloylaminoacetophenone (overall yield: 86%).

NMR (90 MHz, CDCl$_3$) δ (ppm) 1.38 (s, 9H), 2.58 (s, 3H), 7.26 (brs, 1H), 7.90 (s, 2H)

EI-MS (M/Z) 287 (M$^+$)

Molecular formula $C_{13}H_{15}{}^{35}C_{12}NO_2$=287

REFERENCE EXAMPLE 16

2-(3,5-Dichloro-4-pivaloylaminophenyl)-6,8-difluoro-7-hydroxymethyl-5-pivaloylamino-H-1-benzopyran-4-one (Compound Q)

Substantially the same manner as that in Example (4) was repeated except that 3',5'-dichloro-4'-pivaloylaminoacetophenone obtained in Reference Example was used instead of 3'-fluoro-4'-pivaloylaminoacetophenone, to give 3.34 g of Compound Q (overall yield: 64%).

NMR (90 MHz, DMSO-$d_6$) δ (ppm) 1.29 (s, 18H), 4.68 (brs, 2H), 7.22 (s, 1H), 8.16 (s, 2H), 9.51 (brs, 1H), 9.88 (brs, 1H)

FAB-MS (M/Z) 555 (M$^+$+H)

Molecular formula $C_{26}H_{26}{}^{35}Cl_2F_2N_2O_5$=554

What is claimed is:

1. 5-Aminoflavone derivatives represented by the formula (I):

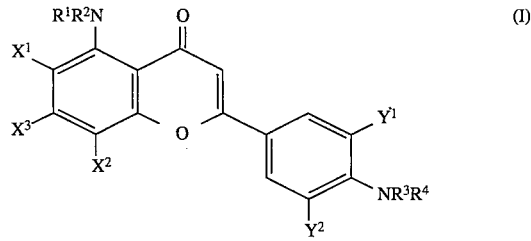

wherein $R^1$, $R^2$, $R^3$ and $R^4$ are the same or different and represent hydrogen, substituted or unsubstituted lower alkyl, lower alkenyl, halogen-substituted or unsubstituted lower alkanoyl or lower alkoxycarbonyl, $X^1$, $X^2$, $Y^1$ and $Y^2$ are the same or different and represent hydrogen, halogen or lower alkyl, at least one of $X^1$ and $X^2$ represents halogen $X^3$ represents hydrogen substituted or unsubstituted lower alkyl, lower alkenyl, lower alkynyl, halogen, hydroxy, substituted or unsubstituted lower alkoxy, $NR^5R^6$ (wherein $R^5$ and $R^6$ are the same or different and represent hydrogen, or substituted or unsubstituted lower alkyl, or $R^5$ and $R^6$ are taken together to form a heterocyclic group containing the nitrogen atom in the ring), lower alkylthio, lower alkylsulfinyl, lower alkylsulfonyl, carboxy, lower alkoxycarbonyl, lower alkanoyl, adizo, cyano, substituted or unsubstituted carbamoyl or lower alkylthiothiocarbonyl: or pharmaceutically acceptable salts thereof.

2. The 5-aminoflavone derivatives represented by the formula (IA):

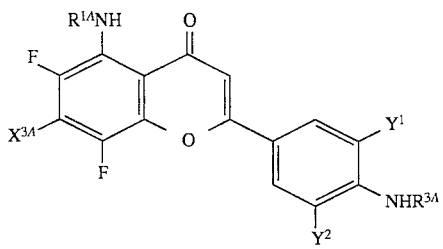

wherein $R^{1A}$ and $R^{3A}$ are the same or different and represent hydrogen, or substituted or unsubstituted lower alkyl, $X^{3A}$ represents substituted or unsubstituted lower alkyl, lower alkenyl, lower alkynyl, halogen, hydroxy, substituted or unsubstituted lower alkoxy, $NR^5R^6$ (wherein $R^5$ and $R^6$ are the same as defined above), lower alkylthio, lower alkylsulfinyl, lower alkylsulfonyl, carboxy, lower alkoxycarbamoyl, lower alkanoyl, azido, cyano, substituted or unsubstituted carbamoyl or lower alkylthiothiocarbonyl, $Y^1$ and $Y^2$ are the same as defined above: or pharmaceutically acceptable salts thereof.

3. The 5-aminoflavone derivatives according to claim 2, wherein $R^{1A}$ and $R^{3A}$ are hydrogen: or pharmaceutically acceptable salts thereof.

4. The 5-aminoflavone derivatives according to claim 3, wherein one of $Y^1$ and $Y^2$ is hydrogen and the other is fluorine: or pharmaceutically acceptable salts thereof.

5. The 5-aminoflavone derivatives according to claim 4, wherein $X^{3A}$ is substituted or unsubstituted lower alkyl: or pharmaceutically acceptable salts thereof.

6. The 5-aminoflavone derivatives according to claim 5 which is:

5-amino-2-(4-amino-3-fluorophenyl)-6,8-difluoro-1-methyl-4H-1-benzopyran-4-one, 5-amino-2-(4-amino-3-fluorophenyl)6,8-difluoro-1-hydroxymethyl-4H-1-benzopyran-4-one, 5-amino-2-(4-amino-3-fluorophenyl)-7-aminomethyl-6,8-difluoro-4H-1-benzopyran-4-one, hydrochloride of 5-amino-2-(4-amino-3-fluorophenyl)-7-dimethylaminomethyl-6,8-difluoro-4H-1-benzopyran-4-one, 7-acetoxymethyl-5-amino-2-(4-amino-3-fluorophenyl)-6,8-difluoro-4H-1-benzopyran-4-one, 5-amino-2-(4-amino-3-fluorophenyl)6,8-difluoro-1-(1-propanoyloxymethyl)-4H-1-benzopyran-4-one, or 5-amino-2-(4-amino-3-fluorophenyl)6,8-difluoro- -(1-hexanoyloxymethyl)-4H-1-benzopyran-4-one:

or pharmaceutically acceptable salts thereof.

7. The 5-aminoflavone derivatives according to claim 4, wherein $X^{3A}$ is $NR^5R^6$ (wherein $R^5$ and $R^6$ are the same as defined above) or azido: or pharmaceutically acceptable salts thereof.

8. The 5-aminoflavone derivatives according to claim 7 which is:

5-amino-2-(4-amino-3-fluorophenyl)-7-azido6,8-difluoro-4H-1-benzopyran-4-one, 5,7-diamino-2-(4-amino-3-fluorophenyl)-6,8-difluoro-4H-1-benzopyran-4-one, or 5-amino-2-(4-amino-3-fluorophenyl)-7-dimethylamino-6,8-difluoro-4H-1-benzopyran-4-one: or pharmaceutically acceptable salts thereof.

9. The 5-aminoflavone derivatives represented by the formula (IB):

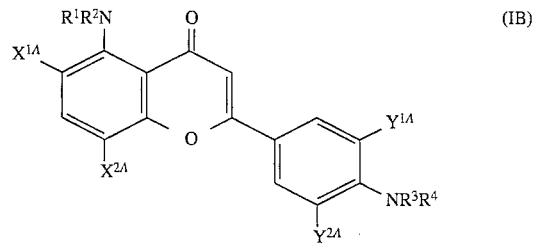

wherein $X^{1A}$ $X^{2A}$, $Y^{1A}$ and $Y^2A$ are the same or different and represent hydrogen or halogen, at least one of $X^{1A}$ and $X^{2A}$ represents halogen, and $R^1$, $R^2$, $R^3$ and $R^4$ are the same as defined above: or pharmaceutically acceptable salts thereof.

10. The 5-aminoflavone derivatives according to claim 9, wherein $X^{1A}$ and $X^{2A}$ are the same or different and represent hydrogen or fluorine provided that at least one of $X^{1A}$ and $X^{2A}$ represents fluorine: or pharmaceutically acceptable salts thereof.

11. The 5-aminoflavone derivatives according to claim 10, wherein $X^{1A}$ and $X^{2A}$ represent fluorine: or pharmaceutically acceptable salts thereof.

12. The 5-aminoflavone derivatives according to claim 11, wherein $R^1$, $R^2$ and $R^3$ are hydrogen: or pharmaceutically acceptable salts thereof.

13. The 5-aminoflavone derivatives according to claim 12 which is:

5-amino-2-[4-[(3-aminopropyl)amino]phenyl]-6,8-difluoro-4H-1-benzopyran-4-one, 5-amino-2-[4-(3-aminopropylamino)-3-fluorophenyl]-6,8-difluoro-4H-1-benzopyran-4-one, 5-amino6,8-difluoro-2-[3-fluoro-4-[2-(pyrrolidin-1-yl)ethylamino]phenyl]-4H-1-benzopyran-4-one, 5-amino6,8-difluoro-2-[3-fluoro-4-[2-morpholinoethylamino)phenyl]-4H-1-benzopyran-4-one, 5-amino6,8-difluoro-2-[4-[3-(N',N'-dimethylamino)propylamino]-3-fluorophenyl]-4H-1-benzopyran-4-one, 5-amino6,8-difluoro-2-[3-fluoro-4-[3-(pyrrolidin-1-yl)propylamino]phenyl]-4H-1-benzopyran-4-one, 5-amino6,8-difluoro-2-[3-fluoro-4-[3-(imidazol-1-yl)propylamino]phenyl]-4H-1-benzopyran-4-one, 5-amino6,8-difluoro-2-[3-fluoro-4-[6-(imidazol-1-yl)hexylamino]phenyl]-4H-1-benzopyran-4-one, 5-amino6,8-difluoro-2-[4-[6-(N',N'-dimethylamino)hexylamino]-3-fluorophenyl]-4H-1-benzopyran-4-one, 5-amino6,8-difluOro-2-[3-fluoro-4-[6-(pyrrolidin-1-yl)hexylamino]phenyl]-4H-1-benzopyran-4-one, or 5-amino6,8-difluoro-2-[3-fluoro-4-[6-morpholinohexylamino)phenyl]-4H-1-benzopyran-4-one:

or pharmaceutically acceptable salts thereof.

14. The 5-aminoflavone derivatives according to claim 12, wherein $R^4$ is hydrogen: or pharmaceutically acceptable salts thereof.

15. The 5-aminoflavone derivatives according to claim 14 which is:

5-amino-2-(4-aminophenyl)6,8-difluoro-4H-1-benzopyran-4-one, 5-amino-2-(4-amino-3-fluorophenyl)-6,8-difluoro-4H-1-benzopyran-4-one, 5-amino-2-(4-amino-3,5-difluorophenyl)-6,8-difluoro-4H-1-benzopyran-4-one, 5-amino-2-(4-amino-3,5-difluorophenyl)-6,8-difluoro-4H-1-benzopyran-4-one, or 5-amino-2-(4-amino-3,5-dibromophenyl)-6,8-difluoro-4H-1-benzopyran-4-one: or pharmaceutically acceptable salts thereof.

16. The 5-aminoflavone derivatives according to claim 11, wherein $R^1$, $R^3$ and $R^4$ are hydrogen; and one of Y1A and $Y^2$A is hydrogen and the other is fluorine: or pharmaceutically acceptable salts thereof.

17. The 5-aminoflavone derivatives according to claim 16 which is:

2-(4-amino-3-fluorophenyl)-6,8-difluoro-5-[3-(imidazol-1-yl)propylamino]-4H-1-benzopyran-4-one, 2-(4-amino-3-fluorophenyl)-5-(3-dimethylaminopropylamino)-6,8-difluoro-4H-1-benzopyran-4-one, 2-(4-amino-3-fluorophenyl)-5-(3-diethylaminopropylamino)-6,8-difluoro-4H-1-benzopyran-4-one, 2-(4-amino-3-fluorophenyl)-6,8-difluoro-5-[3-(pyrrolidin-1-yl)propylamino]-4H-1-benzopyran-4-one, 2-(4-amino-3-fluorophenyl)-6,8-difluoro-5-(4-dimethylaminobutylamino)-4H-1-benzopyran-4-one, 2-(4-amino-3-fluorophenyl)-6,8-difluoro-5-(4-methyl-3-pentenylamino)-4H-1-benzopyran-4-one, or 2-(4-amino-3-fluorophenyl)-5-(5-dimethylaminopentylamino)-6,8-difluoro-4H-1-benzopyran-4-one; or pharmaceutically acceptable salts thereof.

18. The 5-aminoflavone derivatives represented by the formula (IC):

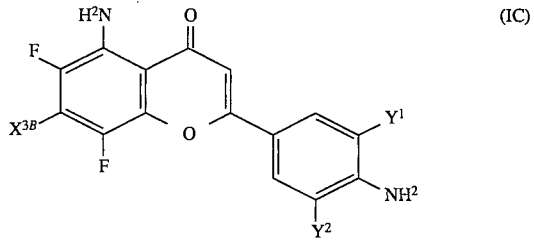

wherein $X^{3B}$ represents lower alkyl substituted by substituted or unsubstituted lower alkanoyloxy, substituted or unsubstituted lower alkoxycarbonyloxy or $R^9R^{10}NCO_2$ (wherein $R^9$ and $R^{10}$ are the same as defined above), and $Y^1$ and $Y^2$ are the same as defined above: or pharmaceutically acceptable salts thereof.

19. The 5-aminoflavone derivative according to claim 18 which is:

5-amino-2-(4-amino-3-fluorophenyl)-7-dimethylaminoacetoxymethyl-6,8-difluoro-4H-1-benzopyran-4-one; or pharmaceutically acceptable salts thereof.

* * * * *

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.  Page 1 of 13

It is certified that error appears in the above-identified patent and that said Letters Patent is hereby corrected as shown below:

ON TITLE PAGE

[56] Under References Cited
"al Proc. Ind. Acad. Sci.," should read --al ¶ Proc. Ind. Acad. Sci.,--.

COLUMN 15

Line 28, "n" should read --in--;
Line 41, "rahydro,utah," should read --rahydrofuran,--.

COLUMN 16

Line 39, "(XvII)" should read --(XVII)--.

COLUMN 17

Line 47, "obtaied" should read --obtained--.

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.

It is certified that error appears in the above-identified patent and that said Letters Patent is hereby corrected as shown below:

COLUMN 19

Line 34,    "above" should read --above.--.

COLUMN 20

Line 36,    "in" should read --in 1--.

COLUMN 23

Line 41,    "Compound (It)" should read --Compound (Ir)--.

COLUMN 41

Line 18,    "18." should read --18--;
   Line 59,    "C25H27FN2O4=438" should read --$C_{25}H_{27}FN_2O_4=438$--.

COLUMN 42

Line 2,    "(total" should read --(total 59%)--.

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.

It is certified that error appears in the above-identified patent and that said Letters Patent is hereby corrected as shown below:

COLUMN 47

Line 15, "EXAMPLE23" should read --EXAMPLE 23--;
Line 52, "8(ppm)" should read --$\delta$(ppm)--.

COLUMN 48

Line 16, "8(ppm)" should read --$\delta$(ppm)--;
Line 32, "4," should read --1484,--.

COLUMN 51

Line 48, "hydrochlo-ric" should read --hydrochloric--;
Line 53, "chloroformand" should read --chloroform and--.

COLUMN 52

Line 6, "$\delta$ ml" should read --6 ml--;
Line 43, "8(ppm)" should read --$\delta$(ppm)--.

COLUMN 54

Line 58, "$\delta$ hours." should read --6 hours--.

UNITED STATES PATENT AND TRADEMARK OFFICE
CERTIFICATE OF CORRECTION

PATENT NO. : 5,539,112
DATED     : July 23, 1996
INVENTORS : TSUTOMU AKAMA ET AL.

It is certified that error appears in the above-identified patent and that said Letters Patent is hereby corrected as shown below:

COLUMN 55

Line 41,   "8(ppm)" should read --$\delta$(ppm)--.

COLUMN 60

Line 26,   "3.81-(2H,t,J=7.4)," should read --3.81 (2H,t, J=7.4),--

COLUMN 61

Line 60,   "(10mmol) should read --(10 mmol)--.

COLUMN 62

Line 39,   "67 (ppm)" should read --$\delta$ (ppm)--;
   Line 55,   "(10mmol)" should read (10 mmol)--.

COLUMN 65

Line 55,   "(7.53mmol)" should read --(7.53 mmol)--.

UNITED STATES PATENT AND TRADEMARK OFFICE
CERTIFICATE OF CORRECTION

PATENT NO. : 5,539,112
DATED : July 23, 1996
INVENTORS : TSUTOMU AKAMA ET AL.

It is certified that error appears in the above-identified patent and that said Letters Patent is hereby corrected as shown below:

COLUMN 78

Line 54,   "Ms" should read --MS--.

COLUMN 79

Line 57,   "(2.03mmol)" should read --(2.03 mmol).

COLUMN 80

Line 18,   "(0.434mmol)" should read --(0.434 mmol)--,
   Line 57,   "Art" should read --An--.

COLUMN 83

Line 25,   "Ms" should read --MS--.
   Line 65,   "8 (ppm)" should read --$\delta$ (ppm)--.

COLUMN 84

Line 14,   "to0°C." should read --to 0°C.--.

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.

It is certified that error appears in the above-identified patent and that said Letters Patent is hereby corrected as shown below:

<u>COLUMN 85</u>

Line 37, "Example (2)" should read --Example 80(2)--;
  Line 66, "Example (1)" should read --Example 80(1) --.

<u>COLUMN 86</u>

Line 51, "H)," should read --9H),--.

<u>COLUMN 87</u>

Line 31, "$C_{19}H_{2479}BrF_2NO_5=463$" should read
           --$C_{19}H_{24}{}^{79}BrF_2NO_5=463$--.
  Line 41, "(s, H)," should read --(s, 9H),--;
  Line 45, "$C_{25}H_{2479}BrF_3N_2O_4=552$" should read
           --$C_{25}H_{24}{}^{79}BrF_3N_2O_4=552$--.
  Line 56, "$C_{15}H_{879}BrF_3N_2O_2=384$" should read
           --$C_{15}H_8{}^{79}BrF_3N_2O_2=384$--.

<u>COLUMN 88</u>

Line 2, Close up right margin;
  Line 6, "Example (2)" should read --Example 80(2)--;

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.

It is certified that error appears in the above-identified patent and that said Letters Patent is hereby corrected as shown below:

COLUMN 88

Line 29, "(yield:" should read --(yield: 89%).--;
   Line 45, "to0°C." should read --to 0°C--.

COLUMN 90

Line 29, "t" should be deleted.
   Line 49, "ι (ppm)" should read --δ (ppm)--.

COLUMN 95

Line 29, "(1.00mmol)" should read --(1.00 mmol)--.

COLUMN 96

Line 15, "for2" should read --for 2--.

COLUMN 97

Line 42, "(6.80mmol)" should read --(6.80 mmol)--.

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.

Page 8 of 13

It is certified that error appears in the above-identified patent and that said Letters Patent is hereby corrected as shown below:

COLUMN 98

Line 49, "($H^+$)" should read --($M^+$)--.

COLUMN 99

Line 53, "sodiumchloride" should read --sodium chloride--.

COLUMN 106

Line 5, "(0.054mmol)" should read --(0.054 mmol)--.

COLUMN 107

Line 19, "distilied" should read --distilled--.

COLUMN 111

Line 64, "(48.2mmol)" should read --(48.2 mmol)--.

COLUMN 116

Line 42, "-(3-azidoproy-" should read --(3-azidopro- --;
   Line 43, "plamino)-" should read --pylamino)- --.

UNITED STATES PATENT AND TRADEMARK OFFICE
CERTIFICATE OF CORRECTION

PATENT NO. : 5,539,112
DATED : July 23, 1996
INVENTORS : TSUTOMU AKAMA ET AL.

It is certified that error appears in the above-identified patent and that said Letters Patent is hereby corrected as shown below:

COLUMN 121

Line 48, "(m," should read --(m, 1H)--.

COLUMN 122

Line 50, "(1.16mmol)" should read --(1.16 mmol)--.

COLUMN 123

Line 3, "($M^{++H}$)" should read --($M^+$+H)--.

COLUMN 125

Line 40, "(2.19mmol)" should read --(2.19 mmol)--.

COLUMN 127

Line 13, "Ms" should read --MS--.

COLUMN 128

Line 39, "(2.62mmol)" should read --(2.62 mmol)--.

UNITED STATES PATENT AND TRADEMARK OFFICE
CERTIFICATE OF CORRECTION

PATENT NO. : 5,539,112
DATED : July 23, 1996
INVENTORS : TSUTOMU AKAMA ET AL.

It is certified that error appears in the above-identified patent and that said Letters Patent is hereby corrected as shown below:

COLUMN 130

Line 10, "(0.722mmol)" should read --(0.722 mmol)--.

COLUMN 131

Line 36, "$C_{29}-H_{34}F_3N_3O_4=545$" should read --$C_{29}H_{34}F_3N_3O_4=545$--.

COLUMN 136

Line 49, "EXAMPLE" should read --EXAMPLE 123--.

COLUMN 138

Line 15, "the," should read --the--.

COLUMN 139

Line 36, "laye," should read --layer--.

UNITED STATES PATENT AND TRADEMARK OFFICE
CERTIFICATE OF CORRECTION

PATENT NO. : 5,539,112
DATED : July 23, 1996
INVENTORS : TSUTOMU AKAMA ET AL.

It is certified that error appears in the above-identified patent and that said Letters Patent is hereby corrected as shown below:

COLUMN 144

Line 52, "$C_{19}H_{26}FNO_732$ 399" should read --$C_{19}H_{26}FNO_7=399$--.

COLUMN 145

Line 29, "Ms(M/z)" should read --MS (M/Z)--.
Line 48, "67 (ppm)" should read --$\delta$ (ppm)--.

COLUMN 146

Line 31, "J=10.0)." should read --J=10.0).--.

COLUMN 148

Line 10, "Was" should read --was--;
Line 50, "Stream" should read --stream--.

COLUMN 149

Line 60, Close up right margin.
Line 61, Close up right margin.

COLUMN 156

Line 26, "-H-1-" should read -- -4H-1- --;
Line 28, "Example (4)" should read --Example 118 (4)--.
Line 30, "Example" should read --Example 15--.

UNITED STATES PATENT AND TRADEMARK OFFICE
CERTIFICATE OF CORRECTION

PATENT NO. : 5,539,112
DATED : July 23, 1996
INVENTORS : TSUTOMU AKAMA ET AL.

It is certified that error appears in the above-identified patent and that said Letters Patent is hereby corrected as shown below:

COLUMN 156

Line 58, "hydrogen" should read --hydrogen,--;
Line 66, "adizo," should read --azido,--.

COLUMN 157

Line 46, "8-difluoro-1-(1-" should read --8-difluoro-7-(1- --;
Line 49, "8-difluoro- -(1-" should read --8-difluoro-7-(1- --;
Line 58, "7-azido6," should read --7-azido-6,--

COLUMN 158

Line 10, "$Y^2A$" should read --$Y^{2A}$--;
Line 32, "5-amino6," should read --5-amino-6,--;
Line 34, "5-amino6," should read --5-amino-6,--;
Line 36, "5-amino6," should read --5-amino-6,--;
Line 39, "5-amino6," should read --5-amino-6,--;
Line 41, "5-amino6," should read --5-amino-6,--;
Line 43, "5-amino6," should read --5-amino-6,--;
Line 45, "5-amino6," should read --5-amino-6,--;
Line 48, "5-amino6,8-difluOro-2-" should read --5-amino-6,8-difluoro-2- --;

UNITED STATES PATENT AND TRADEMARK OFFICE
CERTIFICATE OF CORRECTION

PATENT NO. : 5,539,112

DATED : July 23, 1996

INVENTORS : TSUTOMU AKAMA ET AL.

Page 13 of 13

It is certified that error appears in the above-identified patent and that said Letters Patent is hereby corrected as shown below:

COLUMN 158

Line 50,   "5-amino6," should read --5-amino-6,--;
   Line 59,   "(4-aminophenyl)6," should read --(4-aminophenyl)-6,--.

COLUMN 159

Line 5,   "Y1A" should read --$Y^{1A}$--;
   Line 6,   "Y²A" should read --$Y^{2A}$--.

COLUMN 160

Line 23, "one;" should read --one:--.

Signed and Sealed this

Third Day of June, 1997

Attest:

*Attesting Officer*

BRUCE LEHMAN

*Commissioner of Patents and Trademarks*